US012637686B2

(12) United States Patent
Payyavula et al.

(10) Patent No.: US 12,637,686 B2
(45) **Date of Patent: \*May 26, 2026**

(54) COMPOSITIONS AND METHODS FOR PRODUCING TOBACCO PLANTS AND PRODUCTS HAVING REDUCED OR ELIMINATED SUCKERS

(71) Applicant: ALTRIA CLIENT SERVICES LLC, Richmond, VA (US)

(72) Inventors: Raja S. Payyavula, Henrico, VA (US); Yanxin Shen, Henrico, VA (US); Chengalrayan Kudithipudi, Midlothian, VA (US); Rajanikanth Govindarajulu, Henrico, VA (US)

(73) Assignee: ALTRIA CLIENT SERVICES LLC, Richmond, VA (US)

( \* ) Notice: Subject to any disclaimer, the term of this patent is extended or adjusted under 35 U.S.C. 154(b) by 499 days.

This patent is subject to a terminal disclaimer.

(21) Appl. No.: 17/893,246

(22) Filed: Aug. 23, 2022

(65) Prior Publication Data

US 2023/0145103 A1     May 11, 2023

Related U.S. Application Data

(63) Continuation of application No. 16/886,118, filed on May 28, 2020, now Pat. No. 11,447,790.

(60) Provisional application No. 62/854,139, filed on May 29, 2019.

(51) Int. Cl.
*C12N 15/82* (2006.01)

(52) U.S. Cl.
CPC .............................. *C12N 15/8262* (2013.01)

(58) Field of Classification Search
None
See application file for complete search history.

(56) References Cited

U.S. PATENT DOCUMENTS

| | | | |
|---|---|---|---|
| 4,516,590 A | 5/1985 | Teng |
| 4,528,993 A | 7/1985 | Sensabaugh, Jr. et al. |
| 4,660,577 A | 4/1987 | Sensabaugh et al. |
| 4,848,373 A | 7/1989 | Lenkey |
| 4,897,355 A | 1/1990 | Eppstein et al. |
| 4,946,787 A | 8/1990 | Eppstein et al. |
| 4,987,907 A | 1/1991 | Townend |
| 5,049,386 A | 9/1991 | Eppstein et al. |
| 5,159,135 A | 10/1992 | Umbeck |
| 5,188,958 A | 2/1993 | Moloney et al. |
| 5,372,149 A | 12/1994 | Roth et al. |
| 5,463,174 A | 10/1995 | Moloney et al. |
| 5,538,880 A | 7/1996 | Lundquist et al. |
| 5,550,318 A | 8/1996 | Adams et al. |
| 5,591,616 A | 1/1997 | Hiei et al. |
| 5,750,871 A | 5/1998 | Moloney et al. |
| 5,824,877 A | 10/1998 | Hinchee et al. |

| | | | |
|---|---|---|---|
| 6,153,812 A | 11/2000 | Fry et al. |
| 6,160,208 A | 12/2000 | Lundquist et al. |
| 6,194,636 B1 | 2/2001 | McElroy et al. |
| 6,232,526 B1 | 5/2001 | McElroy et al. |
| 6,384,301 B1 | 5/2002 | Martinell et al. |
| 6,399,861 B1 | 6/2002 | Anderson et al. |
| 11,447,790 B2 * | 9/2022 | Payyavula ......... C12N 15/8262 |
| 2004/0118422 A1 | 6/2004 | Lundin et al. |
| 2004/0216189 A1 | 10/2004 | Houmard et al. |
| 2005/0178398 A1 | 8/2005 | Breslin et al. |
| 2006/0191548 A1 | 8/2006 | Strickland et al. |
| 2006/0200878 A1 | 9/2006 | Lutfiyya et al. |
| 2016/0281100 A1 | 9/2016 | Kudithipudi et al. |
| 2017/0260535 A1 | 9/2017 | Xu et al. |
| 2019/0218564 A1 | 7/2019 | Suzuki et al. |

FOREIGN PATENT DOCUMENTS

| | | | |
|---|---|---|---|
| CN | 108882689 A | 11/2018 |
| CN | 109715810 A | 5/2019 |
| EP | 3 437 465 A1 | 2/2019 |
| WO | WO 91/16024 A1 | 10/1991 |
| WO | WO 91/17424 A1 | 11/1991 |
| WO | WO 2004/041006 A1 | 5/2004 |
| WO | WO-2016057515 A2 * | 4/2016 ......... C12N 15/8295 |
| WO | WO 2017/121776 A1 | 7/2017 |
| WO | WO 2017/170796 A1 | 10/2017 |

OTHER PUBLICATIONS

Doerks, Tobias, Amos Bairoch, and Peer Bork. "Protein annotation: detective work for function prediction." Trends in Genetics 14.6 (1998): 248-250 (Year: 1998).*
Smith, Temple F., and Xiaolin Zhang. "The challenges of genome sequence annotation or "the devil is in the details"." Nature biotechnology 15.12 (1997): 1222-1223. (Year: 1997).*
Bork, Peer, and Amos Bairoch. "Go hunting in sequence databases but watch out for the traps." Trends in Genetics 12.10 (1996): 425-427. (Year: 1996).*
Kumar, Narender, and John C. Larkin. "Why do plants need so many cyclin-dependent kinase inhibitors ?. " Plant signaling & behavior 12.2 (2017): e1282021. (Year: 2017).*
Kano-Murakami, Yuriko, et al. "A rice homeotic gene, OSH1, causes unusual phenotypes in transgenic tobacco." FEBS letters 334.3 (1993): 365-368. (Year: 1993).*
Wells, James A. "Additivity of mutational effects in proteins." Biochemistry 29.37 (1990): 8509-8517. (Year: 1990).*
Guo, Haiwei H., Juno Choe, and Lawrence A. Loeb. "Protein tolerance to random amino acid change." Proceedings of the National Academy of Sciences 101.25 (2004): 9205-9210. (Year: 2004).*

(Continued)

*Primary Examiner* — Amjad Abraham
*Assistant Examiner* — Kelsey L McWilliams
(74) *Attorney, Agent, or Firm* — Arnold & Porter Kaye Scholer LLP; David R. Marsh

(57) ABSTRACT

The present disclosure provides methods and compositions for controlling sucker growth in tobacco by altering the expression of different target genes.

16 Claims, 6 Drawing Sheets

Specification includes a Sequence Listing.

(56)                    References Cited

OTHER PUBLICATIONS

Ng, Pauline C., and Steven Henikoff. "Predicting deleterious amino acid substitutions." Genome research 11.5 (2001): 863-874. (Year: 2001).*

Keskin, Ozlem, et al. "A new, structurally nonredundant, diverse data set of protein-protein interfaces and its implications." Protein Science 13.4 (2004): 1043-1055. (Year: 2004).*

Thornton, Janet M., et al. "From structure to function: approaches and limitations." nature structural biology 7.11 (2000): 991-994. (Year: 2000).*

Altschul, "Basic local alignment search tool," *Journal of Molecular Biology*, 215:403-410 (1990).

Altschul et al., "Gapped BLAST and PSI-BLAST: a new generation of protein database search programs," *Nucleic Acids Research*, 25:3389-3402 (1997).

Ambawat et al., "MYB transcription factor genes as regulators for plant responses: an overview," *Physiology and Molecular Biology of Plants*, 19:307-321 (2013).

Chenna et al., "Multiple sequence alignment with the Clustal series of programs," *Nucleic Acids Research*, 31: 3497-3500 (2003).

Davis et al., "Tobacco, Production, Chemistry and Technology," Blackwell Publishing, pp. 70-103 (1999).

Fisher et al., "Topping, Managing Suckers, and Using Ethephon," *2016 Flue-Cured Tobacco Information*, pp. 96-117 (2016).

Goldman et al., "Female sterile tobacco plants are produced by stigma-specific cell ablation," *EMBO Journal*, 13:2976-2984 (1994).

Griffiths-Jones et al., "Rfam: an RNA family database," *Nucleic Acids Research*, 31:439-441 (2003).

Horsch et al., "A simple and general method for transferring genes into plants," *Science*, 227:1229-1231 (1985).

International Search Report and Written Opinion issued in International Application No. PCT/US2020/034884 on Nov. 16, 2020.

Katoh et al., "Specific residues at every third position of siRNA shape its efficient RNAi activity;" *Nucleic Acids Research*, 35:e27 (2007).

Khvorova et al., "Functional siRNAs and miRNAs exhibit strand bias," *Cell*, 114:209-216 (2003).

Kumar et al., "Why do plants need so many cyclin-dependent kinase inhibitors?," *Plant Signaling & Behavior*, 12:e1282021 (2017).

Larkin et al., "Clustal W and Clustal X version 2.0," *Bioinformatics*, 23:2947-2948 (2007).

Mayo et al., "Genetic transformation of tobacco NT1 cells with agrobacterium tumefaciens," *Nature Protocols*, 1:1105-11 (2006).

Menges et al., "Genomic Organization and Evolutionary Conservation of Plant D-Type Cyclins," *Plant Physiology*, 145:1558-1576 (2007).

Mironov et al., "Cyclin-Dependent Kinases and Cell Division in Plants—The Nexus," *The Plant Cell*, 11:509-521 (1999).

Reynolds et al., "Rational siRNA design for RNA interference," *Nature Biotechnology*, 22:326-330 (2004).

Robinson et al., "A scaling normalization method for differential expression analysis of RNA-seq data," *Genome Biology*, 11:R25 (2010).

Robinson et al., "edgeR: a Bioconductor package for differential expression analysis of digital gene expression data," *Bioinformatics*, 26:139-140 (2010).

Rushton et al., "WRKY transcription factors," Trends in Plant Science, 15:247-258 (2010).

Sun et al., "Inhibition of tobacco axillary bud differentiation by silencing CUP-SHAPED COTYLEDON 3," African Journal of Biotechnology, 11(16):3919-3927 (2012) <http://www.academicjournals.org/AJB>.

Thompson et al.,"Clustal W: Improving the sensitivity of progressive multiple sequence alignment through sequence weighting, position-specific gap penalties and weight matrix choice," *Nucleic Acids Research*, 22: 4673-4680 (1994).

Wernsman et al., "Principles of Cultivar Development: Crop Species," Chapter Seventeen, pp. 669-698 (1987).

Yang et al., "Regulation of Axillary Meristem Initiation by Transcription Factors and Plan Hormones" Frontiers in Plan Science; 7(183) Feb. 18, 2016.

Zeng et al., "Both natural and designed micro RNAs can inhibit the expression of cognate mRNAs when expressed in human cells," *Molecular Cell*, 9:1327-1333 (2002).

Chapters 4B and 4C of Tobacco, Production, *Chemistry and Technology*, Davis & Nielsen, eds., Blackwell Publishing, pp. 70-103, (1999) (Oxford, UK).

Extended European Search Report issued in European Patent Application No. 22188330.9, dated Feb. 22, 2023, 8 pages.

Luo, et al. "Developmental analysis of the early steps in strigolactone-mediated axillary bud dormancy in rice," *The Plant Journal*, vol. 97, pp. 1006-1021 (Feb. 2019) (online publication), available at: https://onlinelibrary.wiley.com/doi/epdf/10.1111/tpj.14266.

Noble et al., "The cyclin box fold: protein recognition in cell-cycle and transcription control," *Trends Biochem Sci.* 22(12):482-487 (Dec. 1997). DOI: 10.1016/s0968-0004(97)01144-4.

Search Report issued in Chinese Patent Application No. 2020800482309, dated Nov. 22, 2023, with English translation (5 pages).

Tso "Seed to Smoke," Chapter 1 in Davis and Nielsen (ed.), *Tobacco: Production, Chemistry and Technology*, Blackwell Science Publishing, pp. 1-2 with cover page and table of contents (Oxford, UK).

Extended European Search Report issued in European Patent Application No. 22188330.9, dated Feb. 22, 2023.

Noble et al., "The cyclin box fold: protein recognition in cell-cycle and transcription control," *Trends Biochem Sci.* 22(12):482-487 (Dec. 1997). doi: 10.1016/s0968-0004(97)01144-4. PMID: 9433129.

Sierro et al., "The tobacco genome sequence and its comparison with those of tomato and potato," *Nat Commun.*, 5(3833), pp. 1-9 (May 2014).

Song et al., "Whole genome re-sequencing in 437 tobacco germplasms identifies plant height candidate genes," *Sci Rep.*, 15(4734), 10 pages (Feb. 2025).

* cited by examiner

PI_2.4::MYB Plants

P1_2.4::CDKI Plants amiRNA-2 Plants amiRNA-3 Plants

SEQUENCE LISTING

```
Sequence total quantity: 126
SEQ ID NO: 1              moltype = DNA  length = 912
FEATURE                  Location/Qualifiers
source                   1..912
                         mol_type = unassigned DNA
                         organism = Nicotiana tabacum
SEQUENCE: 1
atggagaaat acgagaaatt ggagaaagta ggagaaggaa cgtacggcaa agtatataaa  60
gcaaaggaca aagcaacggg tcaattggtg gcgctgaaga aaactcggct agaaatggac  120
gaagaaggga ttccacccac tgctttaaga gaaatatcac ttcttcaaat gctttccaat  180
tctctctaca tcgttcgtct cctctgtgtc gagcaaattg acaaaaatgg gaagcctctt  240
ctttacctag tttttgagta tttggatact gatctgaaga aattcgtcga ttctcatcgt  300
aaaggtccta atcctagacc tctccctcct tctctcatcc agagtttctt atatcaattg  360
tgcaaagggg tcgctcactg ccatagccat ggagttctcc acagagattt gaagccacag  420
aacctattag tggacaaaga gaagggcata cttaagattg ctgatttggg tcttggaagg  480
gctttcactg tcccaataaa gagctacacc catgagattg ttactctatg gtacagagct  540
cctgaagtct tgttgggatc tactcattac tcaactgcgg ttgatatgtg gtctgtggga  600
tgtatttttg ccgagatggt tcgaaggcag gccttatttc ctggtgactc tgagtttcag  660
caattgcttc acatattcag gttgttagga accccaactg agaagcagtg gcctggagtg  720
agttcactcc gcgactggca tgtttatcca aaatgggaac ctcagaactt ggcctctgct  780
gttccagcat tgggtcctga tggtgtggat ctcctcacga aaatgctcca atatgatccg  840
gcagatagga tttcagcaaa agctgcactt gatcatccat actttgatag cttggacaag  900
tcgcaattct ga                                                     912

SEQ ID NO: 2              moltype = DNA  length = 858
```

-continued

```
FEATURE            Location/Qualifiers
source             1..858
                   mol_type = unassigned DNA
                   organism = Nicotiana tabacum
SEQUENCE: 2
atggagactg taaaaaagag tgcatcggca atggaagcat tcgagaagct tgagaaggta   60
ggggaaggta cttacggaaa ggtgtacaga gcgagagata gggttactgg caaaatcgta  120
gcactgaaga agacgaggct tcacgaggac gaagaaggtg ttcctcccac tactctccgc  180
gagatctctc ttctgcggat gctctctagg gatcctcaca ttgtcaaact gatggatgtt  240
aaacaaggcc agaacaaaga aggaaagacg gttctctact tggtctttga gtacatggat  300
actgatgtca agaaatttat tcgtagtttc cgcgcaaatg gagaaaacat tcccctaaa  360
actgtcaaga gcttgatgta ccaactatgc aaaggagttg ctttctgcca tggtcatggc  420
gtgttacaca gggatctgaa accacacaat cttctgatgg accgtaagac gaatgtgctc  480
aaattagcag attttggact tggcagagct tatactctgc ccatcaagaa gtacacgcat  540
gagatattaa ccctatggta tagagcccct gaggttcttc ttggagctac tcattactcc  600
acagcagttg acatgtggtc tgttggttgt atctttgctg aactggtcac aaaacaagcc  660
ctcttcccag gagactctga gctgcaacaa ctgcttcaca tttttcagatt gctaggtact  720
cctaatgaag aactctggcc cggggtgagc aagctagtaa actggcatga atacccccaa  780
tggaaccccc agccactctc aactgctgtc cctggtctag atgaagatgg gctccacctt  840
ctaactgtaa gtgtttga                                                 858

SEQ ID NO: 3        moltype = DNA   length = 939
FEATURE            Location/Qualifiers
source             1..939
                   mol_type = unassigned DNA
                   organism = Nicotiana tabacum
SEQUENCE: 3
atggagactg taaaaaagag tgcatcggcc atggaggcat tcgagaagct tgagaaggta   60
ggggaaggta cttacggaaa ggtgtacaga gcgagagata gggttactgg caaaatcgta  120
gcactgaaga agacgaggct tcatgaggac gaagaaggtg tccctcctac tactctccgc  180
gagatctctc ttctgcggat gctttctagg gatcctcaca ttgtcaaact gatggatgtt  240
aaacaaggcc agaacaaaga aggaaagacg gtcctatact tggtgtttga gtacatggat  300
actgatgtca agaaatttat tcgtagtttc cgcgcaaatg gagaaaacat tcccctaaa  360
actgtcaaga gcttgatgta ccagctgtgc aaaggagttg ctttctgcca tggtcatggt  420
gtgttacaca gggatctgaa accacacaat cttctgatgg accgtaagac gaatgtgctc  480
aaattagcag attttggact tggcagagct tatactctgc ccatcaagaa gtatacgcat  540
gagatattaa ccctgtggta tagagcccct gaggttcttc ttggagctac tcattactcc  600
acagcagttg acatgtggtc tgttggttgt atatttgctg aactggtcac aaaacaagcc  660
ctcttcccag gagactctga gctgcaacaa ctacttcaca tttttcagatt gctaggtact  720
cctaatgaag aactctggcc cggggtgagc aagctagtta actggcatga atacccccaa  780
tggaaccccc agccactctc aactgctgtc cctggtctag atgaagatgg gctccacctt  840
ctatctgaga tgttgcatta tgagccagct aagaggattt cagcaaagaa agctatggaa  900
catccctatt tcgatgatct ggacaaaact cctctctga                          939

SEQ ID NO: 4        moltype = DNA   length = 912
FEATURE            Location/Qualifiers
source             1..912
                   mol_type = unassigned DNA
                   organism = Nicotiana tabacum
SEQUENCE: 4
atggagaaat acgagaaatt ggagaaagta ggagaaggaa cgtacggcaa agtatataaa   60
gcaaaggaca aggcgacggg acaattggtg gcgctgaaga aaactcggct agaaatggac  120
gaagaaggga tcccacccac tgccctaaga gaaatctcgc ttcttcaaat gctttcccat  180
tctctctaca tcgttcgtct cctctgtgtc gagcaaattg acaaaaatgg gaagcccctt  240
ctttacctag tttttgagta tttggatact gatctgaaga aattcgtcga ttctcatcgt  300
aaaggtccca atcctagacc tctccctcct tctctcatcc agagttttctt atatcaattg  360
tgcaaagggg tagctcactg ccatagccat ggagttctcc acagagattt gaagccacag  420
aacctattag tggacaaaga gaagggcata cttaagattg ctgatttggg ccttggaagg  480
gctttcactg tcccaataaa gagctacacc cacgagattg ttactctatg gtacagagct  540
cctgaggttt tgttgggatc tactcattac tcaactgcgg ttgatatgtc gtctgtggga  600
tgtatttttg ccgagatggt tcgaaggcaa gccttatttc ctggtgactc tgagtttcag  660
caactgcttc acatattcag gctgttagga accccaactg agaagcagtg gcctggagtc  720
agttcactcc gcgactggca tgtttatcca aaatgggaac ctcagaactt ggcctctgct  780
gttccagcat tgggtcctga tggcgtggac ctcctcacga aaatgctcca atatgatccg  840
gcagatagga tttcagcaaa agctgcactt gatcatccat acttcgatag cttggacaag  900
tctcagtttt ga                                                       912

SEQ ID NO: 5        moltype = DNA   length = 222
FEATURE            Location/Qualifiers
source             1..222
                   mol_type = unassigned DNA
                   organism = Nicotiana tabacum
SEQUENCE: 5
atggagggg tagatagtga ttgcgaggtg gtggaagaag gatgcatgac tccgaggcgt   60
gacacgtgta ggataatggt gaattctttg tgcccgccgc cgccgccgaa aaagaaacga  120
gtttatgtca aacaacagcg tcctccgcct aaggaaggtt attttcaacc acctgatctt  180
gagcttttct ttgccattgt aaggagagag gcttgtgctt aa                      222

SEQ ID NO: 6        moltype = DNA   length = 1602
```

```
FEATURE              Location/Qualifiers
source               1..1602
                     mol_type = unassigned DNA
                     organism = Nicotiana tabacum
SEQUENCE: 6
atgcaaagct tgattttctc tggcgagaag aacatgattg ctgcttattt atttatacct    60
ctagaactgc atcggaatgt aatacaggtg tgtcatcgag ttcaacgcac tttctgctcg   120
atgaggcatg caaatataaa acatggatct tttcatcttg aagagcacaa tatgcgaatc   180
acacgagcac gagcaagagt gtcgggttca tcaggacgat taccaccct acacccatcc   240
acaaaacagg ataagaagca ggcattggga gcagagtcca aaagatcgaa aagatctgcc   300
tcagatgaga acagacctgg tacctctagt attgctactg gtgttcagcc taagagaagg   360
gctgttctta aagacatgaa gaatgtactt catgagaact ctcacatgaa ttgcatcaac   420
ggaagcaaaa ttcaggttaa gaaaggctcc gataaaagga acaataaggc gaaacctgct   480
gtttctctaa aattgtcaca gctccaagag aaaggaaaag aggatatagc tgataaagta   540
aagaaagtga aggttgaggg atcacaagaa atcagttcgg gggcaaactg caaggaggat   600
atgttaccac agctaagtag atatgtcact ccagcacaat gtggtttagt ccatctagtg   660
cctgtgaaca gaagttcctg caaggccttc ccacttcaga atgtaatgaa aaaagatgaa   720
agcaaagttt gccagaaaca agaaggcttt gctaatctag gaattgctga tattgattca   780
agacacaagg atccactgat gtgtagtctg tatgctcctg atatttataa caacttgcat   840
gccattgagt ttgaccgtag gccttctgtt gattacctgg aaaagctgca gctggacatt   900
aacaagggta tgcgaggtat tctgattgat tggcttgtgg aggtttcaga agaatatagg   960
ctggttcctg acacacttta cctaactgtt aatcttattg accggttcct atctgaaaat  1020
tacattgaaa aacaaaagct gcaactactt ggagttacct gcatgctaat agcttccaaa  1080
tttgaagaga tttgtgcacc tcgtgttgaa gaatttgct tcattacaga taacacttac  1140
tcgaaggaag aggtaataaa aatggaaagc agagtcttga acctttgag ctttcaactt  1200
gcttctccaa ccactaagaa attcctgagg agattcattc aagcagctca agcttcttac  1260
aaggttccct ctgtcgaact ggaattcatg gcaaattatt tagcagagtt aacacttgtt  1320
gactatgggt ttcttaagtt tcttccatct cttactgctg catcagctgt atttctagct  1380
agatggacgc ttgatcaatc taaccaccca tggaatccaa ctttggaaca ctataccaga  1440
tacaaggtat cagagcttag aactacagtt tttgcactgc aagagttaca gatgaacacc  1500
agtggctgca ccctcaatgc catacgtgaa aaatatagac aaccaaagtt caagtccgtg  1560
gctactttag cagcttcaaa accagtccaa tcactgttct aa                     1602

SEQ ID NO: 7           moltype = DNA  length = 1245
FEATURE              Location/Qualifiers
source               1..1245
                     mol_type = unassigned DNA
                     organism = Nicotiana tabacum
SEQUENCE: 7
atggatatat ctgatgagaa tcagttcact aggaaatcac tggttggtga ggcaggaatg    60
ggaaacagca agattggagt ggagacaaga cacaacagaa gagcactgag agtgattaat   120
cagaatttat taggacctaa tccatatcgt tgtgttgtta acaagagaag attatcacat   180
gcaaatggaa tcatctacga caagaatcct acgaggaaat tgactgcaca aattgctagc   240
tcacaccagc attaccccga ggaaaccaag aaaccaaaac tagcagcgga agattttagg   300
atttgggaag aacatgtggc agctaaagac caacccatgt ctatgtcttt ggaacaagaa   360
gcaacatttt caaatgacaa gacagaaatg gaggttgaaa tggaggatat atttgaggag   420
gcactaatag atattgacag tgatgacact aacaatccgc ttgcagttgt tgactatgtg   480
gaagatctat atgccaacta cagaaaaatg gagggttata gctgtgtttc accaaactat   540
atgacacaac agtttgacat caatgaaagg atgagagcta cattagtaga ctggctcatt   600
gaggtaaatc acaagtttga gctcagggaa gagacgttat tcttgactgt taattcgata   660
gacagatttt tggagaagca aatagttgca agaaagaagt tgcagcttgt tgggcgtgtt   720
gctatgctat tagcatgcaa atatgaagag gtctctgtcc ctgtggtgga tgatttggtg   780
attatttcgg acaacgccta tacaaggaaa gaggttcttg aaatggaaac attaatgctc   840
gatacactgc agtttaatat gtcagttcca actgcatatg tttttatgag aagatttctc   900
aaggctgctc aagctgatag gaagcttgag gtcctgtctt tcttcttaat cgagctttgc   960
ctcgtggaat atgaaatgct taagtttcca ccatctttca tggctgctgc tgcaatttat  1020
acagctcagt gcacgctata tggtgtcatg caatggagta aaacatgtga atggcataca  1080
agttactcag aagatcaact tctgaaatgc tcgagatcta tcgtgatcta ccaccaaaag  1140
gcagcaacag ggaaactaac aggagtacat aggaagtata gcacatcaa atttggctat  1200
gcagcaaaat ttgagccagc acttttcctg gtgcagatca aataa                  1245

SEQ ID NO: 8           moltype = DNA  length = 1311
FEATURE              Location/Qualifiers
source               1..1311
                     mol_type = unassigned DNA
                     organism = Nicotiana tabacum
SEQUENCE: 8
atggccatat ctgatgagaa caatcctaca atggttaaac ccacaaatgt gcaaggtggg    60
gctggaatgg gtaccagaaa gtttggtgga gtggaaacaa gaaacaacag aagagcattg   120
ggagtgatta atcagaattt agtgggtggt actcatccat ttccttgtgt tgttaacaag   180
agaggattat ctgaagcaaa tggaatctgt gacaagaatc ttcaaattcc agctcataga   240
cctatcacga ggaaatttgc agctcaaatt gctagctctc agcaaaatcg ctccgaggaa   300
aacaagaaag ctaaaatagc agcagaagaa ttcagtatat gggaggatat ccctctgaca   360
gatgtggagg aaaatgaggc agctaaagat caacctgttc ctatgtcttt ggaacaaaca   420
gaaacagtga ctaatgacaa gaatcaaatg gaggtagaaa tggaggatat atttgaggaa   480
actattatag atattgatgg cgacgatgca aagaacccgc ttgcagttgt tgaatatgta   540
caagatttgt ttgcctccta tagaaaaatg gagggttgta gctgtgtttc ccgattat   600
atggcacaac agtttgacat caatgagaaa atgagatcca ttctaattga ctggctcatt   660
gaggtacatc acaagtttga gctcagagaa gagactttgt ttctgactgt taatttgata   720
```

-continued

```
gatagatttt tggagaagca aggtgttgtt aggaagaagt tgcagcttgt tgggttggtt   780
gccatgctat tagcatgcaa atatgaggaa gtttctgttc cattagtgga tgatttcgtg   840
tttatttcgg acaaagccta ttcaaggaag gaggttcttg aaatggaaag aatgatgctc   900
aacacactgc agtttaacat gtcagttcca actgcatatg tttttatgag aagatatctt   960
aaggctgctc aatctgatag gaagctcgag ctgctgtctt tcttcttggt tgagctttgt   1020
ctagtggaat atgaaatgct caagtttcca ccatcattca tagcagctgc agcaatctat   1080
acagctcaga ccacactcta cggtgtccag caatggagta agacatgcga gtggcatact   1140
agttactcgg aagatcaact tatggagtgt tcgagatcga ttgtgagcta tcaccagaag   1200
gcagcaacag gaaaactaac aggagtacat aggaagtaca gcacatcaa atttggttat   1260
gcagcaaagt gtgagcctgc ccattttctt gtgcagacac aacaacaata g          1311
```

SEQ ID NO: 9          moltype = DNA   length = 432
FEATURE               Location/Qualifiers
source                1..432
                      mol_type = unassigned DNA
                      organism = Nicotiana tabacum
SEQUENCE: 9

```
atggagaaaa ggattcttgg ccaattggag tggtacttaa cagttccaac accttacgtg   60
ttcctcgtcc gctacattaa agctgctgtt tccaatgcac agatggaaaa catggtttat   120
ttcctggctg aattggggtt aatgaattat gcaaccaata tatactgccc atcgatgatt   180
gctgcctcag cagtctatgt tgctcaacac acgctgaatt gcactccatt ttggaacgac   240
acactaaaat tgcatactgg tttctcagag tctcagctac tggttgtgc aaagttgctc   300
gtaagctatc acatggaagc tccagaacac aagctgaaag tgatttacaa gaagtattcc   360
aaaccagaga gaggtgctgt tgcactgcaa cctccagcca aatccctctt ggctgcttct   420
tcatatgaat ag                                                       432
```

SEQ ID NO: 10         moltype = DNA   length = 906
FEATURE               Location/Qualifiers
source                1..906
                      mol_type = unassigned DNA
                      organism = Nicotiana tabacum
SEQUENCE: 10

```
atggcttcaa gaaacgttct tcaacagcag aatataggtg aggcagtccc cggggcgtta   60
aagcagaaaa atatggcagc agcagcacaa gggagaaatc gcaaggcgt tggtgacatt   120
gggaataata tggtaactgt tcgtggtgtc gagggaaagc cacttcctca acgccccata   180
acgaggggct tttgtgcaca attgctcgct aatgcacaag cagcagctga aaaccaaaag   240
aaatctatgg ttgttaatgg ggatgcaccg atcgttgcta aaggagttct accggttaaa   300
ggtgcagcaa agaaaccagt tcaaaagaaa gctgctgtta aaccaaagcc tgatgttatt   360
gaaattagtc ctgatactga agaacaagtg aaggaaaata agcaaaagaa gaaggctggt   420
gatgattctt cagtaaagaa agcaactctt acttcaactc tcactgctag gagcaaggct   480
gcctgtggac tgagtcataa accaaaggtc cagattgtgg atattgatgc tgcagatgtg   540
aataatgagt tggctgtggt ggaatatgtt gaggatattt acaatttta taagatagct   600
gagaatgaga gcagaattca tgactacatg gattcacagc ctgagataac tgcaaggatg   660
agagctattc tgattgattg gttgattgaa gtgcatcaca aatttgagct tagtcaagag   720
actctttacc ttacaatcaa tatcgtcgat cgttacctcg ctgtgacaac tacatcaagg   780
agggaattgc agttagtagg catgagtgct atgctcattg cctctaaata tgaagaaatt   840
tgggctcctg aggtacattt caagtctaat tatgccaagt actttcccca ttttgaaagt   900
tgctaa                                                              906
```

SEQ ID NO: 11         moltype = DNA   length = 1422
FEATURE               Location/Qualifiers
source                1..1422
                      mol_type = unassigned DNA
                      organism = Nicotiana tabacum
SEQUENCE: 11

```
atggcttcaa gaatcgttct tcaacagcag aatagaggtg aggcagtccc tggggcagta   60
aagcagaaaa agaatatggc accagaaggg agaaatagga aagcacttgg cgatattggg   120
aatgtggcta caggtcgtgg gctcgaagga aaaaagccac ttcctcagaa acctgtggct   180
gttaaggtga aaggagcaaa tgttgctaaa gtacctgcac caaggaaacc agctcagaag   240
aaagccacag ttaagccaaa ccccgaggat attattgaaa ttagtcctga cacccaagaa   300
aaactgaagg agaagatgca aaggaagaag gctgataaag actcattaaa acagaaagca   360
actcttactt ctactctcac tgctcgaagc aaggctgcat gtggtctgag taaaaaacca   420
aaggagcagg tagtggacat tgatgctgca gatgtgaaca atgagttggc agttgtggaa   480
tatgttgaag acatttacag cttctacaaa cttgctgaga atgagacaag agttcatgac   540
tacatggact cacagcctga gataaatgat aggatgaggg cagttctgat agattggttg   600
gttgaagtcc accaaaaatt tgaacttaat ccagagactc tttacctcac aatcaacatt   660
gtggatcgtc accttgcggt gaagactaca tcaagaaggg aattgcagtt actgggcatt   720
agtgccatgc tcatagcctc caaatatgaa gaaatttggg ctcctgaggt caatgacttt   780
gtgtgcatct cagacaaaag ttacactcat gatcaggtgt tagctatgga gaaagaaatt   840
cttgggcaat tggaatggta cttaacagtc ccaacacctt acgtatttct cgcccgtttc   900
attaaagctt ctctacctga ttcagaaatt gagaacatgg tatattttct ggctgagctg   960
gggttgatga attatgcaac cattatctac tgccctcga tgattgctgc ctcagcggtc   1020
tatgctgctc gacacaccct caataggaca ccatttgga atgagacact taagctgcac   1080
actggtttct cagagtctca gctaatagag tgtgcaaggt tgttagtgag ctatcaatct   1140
gcggctgcga ctcacaagct aaaggtgata tacaagaagt actccagtcc ggagagaggt   1200
gttgtttcat tactaactcc ggccaaatcc ttgttggctg catcatcatc aagtgtgttg   1260
tcggagcaag ctgatttacg caaaagcaca gaagcagcag caacatcatc atccaaaatg   1320
gtggtggtgg gttgtcaaag gtgccacatg tatgtcatgg taactgaagc tgatccaaga   1380
tgcccccaat gcaagagcac tactactagg aagatgactt aa                     1422
```

```
SEQ ID NO: 12          moltype = DNA  length = 1608
FEATURE                Location/Qualifiers
source                 1..1608
                       mol_type = unassigned DNA
                       organism = Nicotiana tabacum
SEQUENCE: 12
atgagtaggg cttgttccct ggttcaagag tactatgact gttgcttctt atttatacaa   60
agctctagaa ttgtggtgga acgcaatgca gttgtagccc agataatagg catatccacca  120
cctggatcaa tgaggaatgc aaatatgaca attggatctt ctaatcttaa agagcccact   180
atgcgaatca caagatcacg ggcaaaagcc ttgggttcat caggaggatt accacctcga   240
cacccgtctg tcagacagga taacaaacag ggactgggag cacagggaac taagtacaaa   300
agatctgcct cggatgagaa taatccagtt actaatgcta gtacagcctg tcaacagcct   360
aagcgaaggg ccgttctcag ggatgtcacc aatgtgcttt gtgaaaattc atacatgaat   420
tgcatcaata gaagcaaatt tcaggttaag aaattctctg atacgaggaa ttcaaaggtg   480
acacctgcta ttttggtaaa aagaccgcat aatgaagata gaaaagaaaa cacgattgaa   540
gaagcaaaaa aagtaaagat cgagaaatca caagaacact gttcacaagc acgcttcaag   600
gaccttacat taactcaccc aagtaaatat atcactccag cacagtgtgg ttttgttgat   660
cttatgcctg tgaataggag tttacctaca gccattgcag tcccgaatac aacagaaaaa   720
gatgaaacca aggtttgcca gaaacaagaa ggctccgatt ctcttggtat agcagatata   780
gattcaaagc acaaggatcc actaatgtgt agtctatatg ctcctgatat atatagcaat   840
ttgcatgcca tggagcttga ccggcggcct tcatttaatt acatggaaaa gctgcagcgg   900
gacgttaaca agggtatgcg aggtattcta attgattggc tggtggaggt ttctgaagaa   960
tataggctgg ttccggacac actttacctg actgtacatc tcattgatag gttcctctct  1020
gagaattaca ttgaaaaaca aaagctgcag ctgctcggag ttacctgcat gctaattgct  1080
tccaaatatg aagaaatttg tgcccctcgt gtggaagaat tttgctttat tacagacaac  1140
acttactcaa aagaagaggt agtaagaatg gaaagtctag tattgaattt tttgggcttt  1200
caacttgctg ctccgaccac taaaaagttc ctgaggagat ttgttcaagc agcacaagct  1260
tcatatgagg ttccctctgt tgaactggaa ttcatggcaa actatttagc agagctaaca  1320
cttgttgact atagtttttct taagtttctt ccgtctatca ctgctgcatc ggctgtattt  1380
ctagccaaat ggacacttga tcaatctaac cacccatgga atccaacttt ggagcactac  1440
actagttata cagcgctaga gctgaaaacc acagttcttt tgctgcaaga tttacagctg  1500
aacaccagcg gaagcaccct gaatgccatt cgtgaaaagt atagacaacc aaagttcaag  1560
tccgtggcaa ctttatcatc tccggaacca gtccaatcac tgttctaa               1608

SEQ ID NO: 13          moltype = DNA  length = 2193
FEATURE                Location/Qualifiers
source                 1..2193
                       mol_type = unassigned DNA
                       organism = Nicotiana tabacum
SEQUENCE: 13
atgggtaaat tgaactcgca gaaacatata tccaccataa aagatggagt tacagaactc   60
aaggtttacg aagaggcaga taagataaaa atccaaagcc gtgattctct cagcaggcgc  120
tgcaagggaa tgtctggtgc gcctaacatg agtgatgtgc agaccagtcg gaagagctcg  180
gagagtgata tcaagcacat agagaggata aaagcaaaat gcagtacttc tgttaaggta  240
aatgtcaaaa gaaaagtatt gacagatatc agcaatatca ggggcaactc ttcgagaacc  300
aaatcatata atagctccaa actgctggtg tcaaatggta aatgcccaaa aaatgcaagc  360
aattcagcaa gaaaatttat catgggaaat gtgaggccaa acttgaacgg agctactggt  420
gacaagcaaa tcttgacacg ggcaccattc aaagatacaa aagcctcatt tgatggccga  480
aagaccagaa ttcaaggccg taaatcagtt accactggaa tcaggccaac tggaaggaat  540
gatttaccgc catcaaggag gtctttacct atactacagc aggtgaacat cgagggtaca  600
gacaataaag agaagggaaa ggtgagggcg aacttgaata aagctactga tgacaagcaa  660
atcttgacac aggcaccacg caaagatatg aaagcctcct ttgatggccc aaagaccaga  720
attcaagtcc gtaaatcagt taccactgga atcaggagaa ctggaaggaa tgctttaccg  780
ccatcaaggc ggtctttacc aatactacag caggtgaacg tagaggacac gaacaataaa  840
gagaaggtaa attccaaaaa gctggagaaa ggcaaaggaa taagtggtgt ttcagttttg  900
gcaaagccta aggccgcagg agatgtttta ccacagttaa gcaaccacag caacatacgg  960
agaaatcgag ttggtgatgc ctcggctaga atggctcccc ggggtcaagc taaggtggaa  1020
gttggagcat tgagaagaaa atcagtcagg acagttctga aaattactgc tagcagtctc  1080
aattcacaaa agtgttcaaa gtcgaactcc atgtcaggtg tgcacaaatg cacctctcga  1140
gtttccattc catgtaaaag gctggtggat gttaggacat cttccctatc aaaatatgca  1200
acatcagaga tttcagctga gcaacctcat caaaaggaag ttccttctag tagtagtggc  1260
agcttagcta caccggaatt gtcaattgcc aggaggaaat ctgatcgtag gaagtctttt  1320
acgtgtttac tgatggcaag atcaaagctt atgaaggagc tatttggaaa tgtagagctg  1380
gacaatttgt caaacatttta tgatagttgc aatcatcttg aagttactga atatgttgat  1440
gacatctatc aatattattg ggttatagag gcacagaatc agcctatcaa aaactacatg  1500
gagactcaga aggaaataac accccaaatg cgtggcatat tgatcaactg gcttattgaa  1560
gtccatctga aatttgattt gatgcaagaa actctatttc tcatggttac actcctggac  1620
tactacttat cattagcaag ggtcaagaag aatgatttgc agttagttgg ccttacttca  1680
ctgttgttgg catcaaaata tgaggacctt ttccatccga gggtcatgga cttactaagc  1740
atctctgctg agtcatacac aagagatcag atgctggaaa tggagaaaga tatcttaagg  1800
aaattgaagt ttcgccttaa tgcagcaact ccttatgtct tcatgctaag gcttcttaag  1860
gctgctcaag cagacacaag gtttgaacat ctggcatttt acctcatcga gttgtgcttg  1920
gttgaatacg aagctttgaa ctacaagcca tccatgtctt gtgcatgcac tatttatgtg  1980
gcaagatgta cgatgcaaat gacgccagcc tggacaccac tgctggggat tcatggacgt  2040
tatcaagaat cccaattcag acattgtgcg gaaatgatct tgaggtttca caaagctgca  2100
agcacagcac ttttgaaagt cacgcatgag aaatatatgc agtccagtaa cagcaaagtt  2160
gctgctataa aacctttgca gagtctccct taa                              2193
```

-continued

```
SEQ ID NO: 14        moltype = DNA   length = 1326
FEATURE              Location/Qualifiers
source               1..1326
                     mol_type = unassigned DNA
                     organism = Nicotiana tabacum
SEQUENCE: 14
atggttggat cagacgagaa cttttcaggt gtgatgaggg cttcaaatct tcaagggggg  60
ttaaggcctg gtgttggagg aggaaaattg actgcaggag tgggacaaaa taggagggca  120
ttaagtacaa tcaataggaa tgtaattggc gctccccctt taccctatgc tgtcaacaag  180
agaaatggca tttctgacaa caaagccaat gctgctaaca aaatcccttc tgttccgatt  240
catcgtccaa tcacaaggaa gttagctgca caaatcgcaa gcaaacagca gcaacctgca  300
gtcgaggtaa caaagccacc agtcccagtg gcaccaaata gaaatggatc agaagactgc  360
attattatcg atgctgaaga atacaaggcc gctggtgatt cttccgtgcc aatgtttgtg  420
caacatactg aagcaatgat ggaggaaatt gataggatgg atgaggagat agagatggaa  480
gatgtagaag actggccaat tgtggatata gacagtgctg ataaaaagaa cacgcttgca  540
gttgtggagt acatcgatga catctatgct tactacaaga agactgaagt tcttagctgt  600
gtccctccaa actatatgga acagcaaatt gatgttaatg aaaggatgag agccatcctc  660
attgactggc tgattgaggt acactacaag tttgaactgg tggaggagac cttgtactta  720
accgtgaatc tcatcgatag attcctggcg gttcagtcag tgattaggaa gaaacttcag  780
cttgtcggaa taacagctat gcttctcgcc tgcaaatatg aagaggtttc tgtacctgta  840
gtggaggatc taattttgat atctgacaag gcttacacca gaaaagaagt gcttgacatg  900
gaaaagttga tggttaatac cttacagttc aacgtaacag tgcctacagc atatgtgttt  960
attaggcgat ttcttaaagc cgctctgtct gataaaaagg tggagctcat gtctttcttc  1020
ttgatagagc tatgtttggt tgaatatgag atgcttaaat tcccaccatc aatgctagca  1080
gctgcttcca tctttactgc tcaatgcact cttggtgttt ctaaggagtg gaataaaacc  1140
tgtgagaagc atagtagcta tgctaaaaat cagctttttg aatgctcgaa attgatggtt  1200
tctttccatc agaaggcagc aagtgggaag cttactggcg tgcaccgcaa gtacagcact  1260
tgtaaatatg gctatgctgc tagatgtgaa ccagcttctt tcctgttaga agcagcatgg  1320
ttctag                                                              1326

SEQ ID NO: 15        moltype = DNA   length = 1452
FEATURE              Location/Qualifiers
source               1..1452
                     mol_type = unassigned DNA
                     organism = Nicotiana tabacum
SEQUENCE: 15
atggcgacga cccagaatag acgttcgtca gtttcgagtg cgacggcaaa gaggcaagcg  60
atgacggcta attcgtcgtt ggagaataat aatcatggga aattggtggc caagaaacga  120
ccagccctca ctaatatcag taatcataca actgcctccg ctcgtaactc gctctctcac  180
tcctccaaac tcgcaccatg tacatccaag gctgtaagca ttaagaagag caatagtaat  240
gcagcttcct cagttctgcc aacatcctcc tttgtcaaac caatcagcaa aactgtgtct  300
attccaagaa gtgatgcagc tatccctaag atcactgcca ttcctcttcc tgctacttgc  360
agcatggaca tttctccatc tcactcggac ggatcattgg tctccatgga tgaaactatg  420
tccacttctg actcactgag aagtccggat gttgagtaca ttgacgacaa ccaaacagct  480
gcattcgatt ccattgagaa gaaggcgttt agcaccctct acatctcaga agatgtcaaa  540
gcagcagata tatgcaagag agatgtactt gtagacatcg aatcagggga taaaattgcc  600
aacattgata acaattttgt tgatccacaa ttatgtgctc caatggcctg tgacatatac  660
aaacacttga gagccacaga ggtaaagaaa aggccttcca cagatttcat ggagaaagtt  720
cagaaggaca tcaacgctag catgcgtgct attttgattg actggcttgt tgaggttgcc  780
gaggaataca ggcttgtccc ggacacattg tatctgactg ttaactacat tgatcgatat  840
ctctccgtca atttgatgga caggcaacga ctacagttgc ttggagtagc ttgcatgatg  900
atcgcatcca aatatgagga gatctgtgcg cctcaagtag aagagttctg ctacatcaca  960
gacaacactt acttcaagga gggaggtttta caaatggagt ctaccgtttt aaattacttg  1020
aagtttgaaa tgacagcccc aacagccaaa tgttttctga ggaggttcgt tcgtgctgct  1080
caaggactta atgaggttct gtcactgcag ttggaacaat tggccagcta catagcagaa  1140
ctctctcttt tagagtacaa catgctttgt tatgctccat cagtcattgc tgcttctgca  1200
attttcttag ccaaatatat tcttctcccc tcaaagaaac cttggaactc taccttgagg  1260
cattatactc tgtatcaacc ctctgatcta cgagactgtg tcgtggcact acatagcctt  1320
tgttgcaaca caacaattc tagtttacca gcaatcaggg aaaaatacag ccagcacaag  1380
tacaaatttg ttgcaaagaa gtattgccct ccaacaatac ctgtagagtt cttccagaac  1440
ataagctgct aa                                                      1452

SEQ ID NO: 16        moltype = DNA   length = 1239
FEATURE              Location/Qualifiers
source               1..1239
                     mol_type = unassigned DNA
                     organism = Nicotiana tabacum
SEQUENCE: 16
atgggtgtat ctaatgagaa caatcctacc atgattaaac ccacaaatgt gcaaggtgag  60
gcagaattgg gttgcagaaa gtttggaatg gaaacaagga acaacagaag agcattaagt  120
gtgattaacc agaattttgt tggagctaag ccataccctt gtgttgttaa taagagagta  180
ttatctgaag ctaatgggat ctgtaacaag aatcctcctg ttccagctca tagacctatt  240
acaaggaaat ttgctgcaca aattgctaac tcaaagcagc attatcctga ggaaaacaag  300
aaaccaaaaa tagcagctga aggtttaagt gtgtatgagg atgtaccaat aatagatgtg  360
gaagaatatg aggcagcagc aaaagaccag ccagttccaa tgtctttgga acaaactcaa  420
atggaaattg agatggagga tatatttgag gagagtgtga tagatattga cagtaatgat  480
gcgaagaaca cgctcgcagt tgttgactat gtggaagatc tgtatgctta ctactcaaaa  540
atggaggggct gcaatcgtat cccgccagac tatataggac aacagtttga catcaacgag  600
aggatgagat ctatactaat tgactggctc attgaggtac accacaagtt tgatctcagg  660
```

```
gaggagacat tattcctgac tgttaatttg atagatagat ttttggagaa acaatccgtt   720
gtgagaaaga agctgcagct tgttggtctc gtcgccatgt tactagcgtg caaatacgag   780
gaagtttctc tccctgtggt ggatgatttg gtggtcattt cggataaagc atacacaagg   840
aaggaggttc ttgaaatgga aaaattgatg ctcaacacac tacagtttaa tatgtcactt   900
ccaactccat atgtttttat gagaaagattt ctcaaagctg ctcaatcgga tagaaagctt   960
gagctacttt cgttcttctt gatcgagctt tgcctcgtgg aatatgaaat gcttaaattc  1020
ccaccatcgt ttatcgctgc tgctgcaatc tatacagctc agtgcacact ttatggtgtt  1080
aaacaatgga gtaagacgtg cgagcttcac acaaaatact cggcagatca actcctggag  1140
tgttcaagat tgattgtgga attccaccaa aaggcagcga cagggaaact aacaggggat  1200
ctatattcta aacaaaatcc agaaaataaa gaagagtaa                         1239
```

SEQ ID NO: 17          moltype = DNA   length = 1320
FEATURE                Location/Qualifiers
source                 1..1320
                       mol_type = unassigned DNA
                       organism = Nicotiana tabacum
SEQUENCE: 17

```
atggtaggat cagacgagaa ttgccaaggt gttatcatgg cttcaaatgt tcaagggggct    60
ggaggaggaa aagtgacaat ggggcataat agaagggctc taagtacaat aaatgggaat   120
atagttgaag ctccagcata cccttgcaaa gtacacaaga gaaatggcat cactgacaag   180
agcgcgaatg gtgttaagaa tcctcccatt ccaattcatc gaccggtaac gagtatgggg   240
gattcttgct gcttcaggaa atttgctgca caaatggcta gcaaccaacg   300
gtaacaaagc agccagtcca aacagcaact gatagaaatg aatcagaaga ccgcatcatt   360
attgatgtag aagattacaa ggccacaagt gactatgatc ctgtgccaat gtttgtgcaa   420
catacagaag caatgatgga ggaaattgat aggatggacg cagagacgga gatggaagat   480
gtagagagaa cactaattgt ggacatagac agtgctgata aaaagaaccc acttgcagtt   540
gtggagtaca ttgatgacat gcatgcttac tacaagaaga ccgagagttc tagctgtgcc   600
cctccaaatt acatggaaca acaatttgat attaatgaga ggatgagagc tattctcatt   660
gactggctga ttgaggtaca ttacaagttt gatctgatgg aagagacttt gtatttgacc   720
gtaaatctta tcgatagatt cttggcagtc caacaagtga ttaggaaaaa actccagctt   780
gttggggtaa cagctatgct tctagcctgc aagtatgaag aagtttcagt tcctgtcgtt   840
gaggatctta ttttgatctc tgataaggct tacaccagaa aagaagtgct tgagatggag   900
aagttgatga tcaataccttt acagttcaac ctatcagtgc ctacagcata tgtgtttatg   960
atgcgatttc ttaaagctgc tcagtctgat aagaaggtgg agctcctgtc tttctttatg  1020
actgaactat gcctcgttga gtatgaaatg cttaggttcc caccttcaat gctagctgct  1080
gcggcaatat ttactgccca atgtgctcta agtgcgccta acgagttgag taaaacttgt  1140
gagaagtata gccactacac tcaagatcag cttttggagt gctcaagact gatggtttct  1200
ttccatcaga aggctgcaat tgggaagctt actggtgtat acagaaagta tagcatctct  1260
aaatatggat ttgttgcaaa atgcccacct gcttcttttc ttttagaggc atgctttttag  1320
```

SEQ ID NO: 18          moltype = DNA   length = 1104
FEATURE                Location/Qualifiers
source                 1..1104
                       mol_type = unassigned DNA
                       organism = Nicotiana tabacum
SEQUENCE: 18

```
atggcagacc aagaaaattg tgttagagtg actcgattag ccaagaaaag agcagcagaa    60
gcaatggttc agcacctgca acagcccaac aagaagagag tggtgttggg tgagattcgg   120
aatttgtcca atcagattca gatgtttgat tctgagcctc ttaagcccaa atgtaataag   180
cagactacta agaggaaggt gaaaaggtct gttagtgtga aagagagaga atttagggag   240
gaggatgttg attctaaatt ggatgatgat ccccagatgt gcagtgctta tgtttctgat   300
atatatgagt atcttcatca aatggagatt gagaaaaaga gaagaccatt gtctgattac   360
cttgagaaag ttcagaagga tgtaactgca aacatgagag gggtttttagt ggattggcta   420
gtggaagttg cagaggaata caagcttctt tcagacactt tatatctcgc tgtagcctac   480
atcgacagat acttatcgat aaaggtcatc cctagacaaa gacttcagct attgggtgtt   540
tcttcaatgc tcattgcctc gaagtatgag gagattaagc ctccacgtgt tgaggatttt   600
tgttacatta cagacaatac atatacaaag aaagatgtgg taaagatgga ggctgatgtg   660
ctacaatccc ttaaatttga aatgggcaat cctacaacca aaacatttct cagaagattt   720
actagggttg ctcaagaaga ttgtaaaaac tccaatttga agttagagtt cctggggtgt   780
tacctagcag agttaagttt attggattac aactgtgta agttcttacc ttctttggta   840
gcagctgctg tgatattcct ttcaagattc acattgcagc caaagttaca tccttggagt   900
gtgggcctcg aacaaaactc gggatataga gcagcagatc taaaggaatg tgttcttatc   960
atacatgact tgcaattaag tagaagagga ggctctttgg tagctgcgag gaacaaatac  1020
aagcaacata agttcaaata tgtgtcaaca ttgtcttctc ctctgggaaat accagattca  1080
ttctttgaag atacaagaca atga                                          1104
```

SEQ ID NO: 19          moltype = DNA   length = 1449
FEATURE                Location/Qualifiers
source                 1..1449
                       mol_type = unassigned DNA
                       organism = Nicotiana tabacum
SEQUENCE: 19

```
atggcgacga ctcagaatag acgtaattca gtttcgagtg cggtggcaaa gcggcaagcg    60
atggcggaga ataatcacgg gaaattgccg gcgggtgggg ccaagaaaag accagccctc   120
actaatatca gtaatcatac aactgcttcc gctcgtaact cgctctctca ctcctccaaa   180
ctcgcaccat gtacatctaa ggttgtaagc attaagaaga acaatagtaa tgcagcttcc   240
tcagttctgc caacatcctc ctcctttgtc aaaccaatca gcaaaactgt gtctcttcca   300
agaagtgatg cagctgtccc taagatcact gcaattcctc ctcttccttc cacttgcagc   360
atggacatttt ctccgtctca ctcggacgga tcattggtct ccatggatga aactatgtcc   420
```

-continued

```
acttctaact cactgagaag tccggatgtt gagtacattg acgacaacca aacagctgca   480
tttgattcca ttgagaagaa ggcttttagc accctctaca tctcagaaga tgttaaagca   540
gcagatatat gcaagagaga tgtactcgtg gatatggaat cagggggataa aattgccaac   600
attgataaca atcttgttga tccacaatta tgtgctacaa tggcctgtga catatacaaa   660
cacttgagag ccacagaggt aaagaaaagg ccttccacag atttcatgtg gaaagttcag   720
aaagacataa atgctagcat gcgtgctatc ttgattgact ggcttgttga ggttgccgag   780
gaatacaggc ttgtcccaga cacattgtat ctgactgtta actacattga tcgatatctc   840
tctggcaatt tgatggacag gcaacgacta cagttgcttg gagtagcttg catgatgatc   900
gcatccaaat atgaggagat ctgtgcgcct caagtagaag aattctgcta cataacagac   960
aacacttact tcaaggagga ggtcttgcaa atggagtcta ccgtttttaaa ttacttgaag  1020
tttgaaatga cagccccaac agccaaatgt tttctgagga ggttcgttcg cgctgctcaa  1080
ggacttaatg aggttctgtc actgcagttg gaacacttgg ccagctacat agcagaactc  1140
tctcttttag agtacaacat gctttgttat gctccatcag tcattgctgc ttctgcaatt  1200
ttcttagcca aatatattct tctcccctca aagaaacctt ggaactctac cttgaggcat  1260
tatactctgt atcaaccctc tgatttacga gactgtgtca tggcactaca tagcctttgc  1320
tgcaacaaca acaattctag tttaccagca atcagggaaa aatacagcca gcacaagtac  1380
aaatttgttg caaagaagta ttgtcctcca acaatacctg tagagttctt ccagaacata  1440
agctgctaa                                                          1449
```

```
SEQ ID NO: 20            moltype = DNA  length = 1155
FEATURE                  Location/Qualifiers
source                   1..1155
                         mol_type = unassigned DNA
                         organism = Nicotiana tabacum
SEQUENCE: 20
atgaagaagc aagagaaaga ggcaataatg gcggatttag aaaattgtgg cagagttaca   60
cggctagcca agaaaagggc agcagaggct atggcctcac atcaacaaca acaccctagt   120
aagaaacggg tggttttggg cgagattcag aattttttcta atctgggtgt gagtcaaatt   180
aagggtttga acactgagcc taaaaaacaa cccaaatcga agcagcagca atctaagagg   240
aaactgaaaa gggctgtgac tagtaaaatt gataaggagg agttgaatgt ggataatgtt   300
gatgctaatt acgatgaccc tcagatgtgt agtgcttatg tttctgatat atatgattat   360
cttcgtaaaa tggagattga ggaaaagagg agacctttgc ctgattactt agagaaagtt   420
cagaaggatt tgagcccaaa catgagaggg gtattagtcg attggctagt ggaagttgca   480
gaggaataca agctactttc agacacttta tatcttgctg tttcctacat cgatagattc   540
ttatcaacaa atgtcatcac caggcaaaaa cttcagcttt tgggtgtttc gtcaatgctc   600
atttctgcga agtatgagga gattagtcca ccacatgttg aagatttttg ttacataacg   660
gataacacat atactaagga agaggtggtg aaaatggaag ctgatgtgct taaaacactc   720
aactttgaga tgggaaatcc cacagtgaaa acatttctca gaagatttac tggggttgct   780
caagaagatt ataaaacccc caatttgcag ttggagtttt tgggctatta cctagcggag   840
ttaagcatat tggattatag ctgtgtgaaa tacgtacctt cttttgctggc tgctgctgtg   900
gtattccttt cgaggtttac actacaacct aatacacatc cttggagttt ggctcttcaa   960
caatactcgg gatataaagc agcggatttg aaggaatgta ttcttatctt acacgacttg  1020
caattaagta gaagaggagg ctctttagcg gctgtgaggg acaaatataa gcagcataag  1080
tttaagtgtg tgtcatcgtt gacctctcca gtggaaatac cagcttcatt ctttgaagat  1140
atgagacaat tgtaa                                                    1155
```

```
SEQ ID NO: 21            moltype = DNA  length = 1326
FEATURE                  Location/Qualifiers
source                   1..1326
                         mol_type = unassigned DNA
                         organism = Nicotiana tabacum
SEQUENCE: 21
atggttggat cagacgagaa cttttcaggt gtgatgaggg cttcaaatct tcaaggagga   60
ttaaggcctg ttgttggagg aggaaaattg actgcaggag ttggacaaaa tagaagggca   120
cttagtacaa tcaataggaa tgtaattgga gctcccccctt taccctatgc tgtcaacaag   180
agaaatggca tttctgacaa caaagccaat gctgctaaca aaatccctcc tgttccgatt   240
catcgtccaa tcacaaggaa gttagctgca caaatcgcaa gcaaacagca gcaacctgca   300
gtcgaggtaa caaagccacc agtcccattg gcaccaaata gaaatgaatc agaagactgc   360
attattatcg atgctgaaga atacaaggct actggtgatt cttccgtgcc aatgtttgtg   420
caacatactg aagcaatgat ggaggaaatt gataggatgg acgaggagat agagatggaa   480
gatgtagaag actgtccaat tgtggatata gacagcactg ataaaaagaa cacgcttgca   540
gttgtggagt acattgacga catctatgct tactacaaga agactgaggt tcttagctgt   600
gtccctccaa actacatgga acagcaaatt gatgttaatg aaaggatgag agccatccta   660
attgactggc tgattgaggt acactacaag tttgaactga tgggagagac cctgtatttg   720
actgtgaatc ttatcgatag attcctagca gttcagtcag tgattaggaa aaaacttcaa   780
cttgtcggaa taactgcatt gcttcttgcc tgcaaatatg aagaggtttc tgtacctgta   840
gtggaggatc taatttttaat ttctgacaag gcttacacca gaaatgaagt gcttgtgatg   900
gaaaagttga tggttaatac cttgcaattc aatgtaacag tgcctacagc atatgtgttt   960
atgaggcgat ttcttaaagc cgctcagtct gataaaaagg tggagctcat gtctttcttc  1020
ttgatagagc tatgtttggt tgaatatgag atgcttaaat tcccaccatc aatgctagca  1080
gctgctgcta tctttactgc tcaatgcact cttggtgttt ctaaggagtg gaataaaacc  1140
tgtgagaagc atagcagcta tgctaaagat cagcttccgg aatgctcgag attgatggt  1200
tctttccatc agaaggcagc aagtgggaag cttactggcg tgcaccgaaa gtacagcact  1260
tctaaatatg gctatgctgc tagatgtgaa ccagcttctt tcctgttaga agcagcatgg  1320
ttctag                                                             1326
```

```
SEQ ID NO: 22            moltype = DNA  length = 1215
FEATURE                  Location/Qualifiers
source                   1..1215
```

```
                        mol_type = unassigned DNA
                        organism = Nicotiana tabacum
SEQUENCE: 22
atgaaaggtg gtgaggcaga aatgggaaac aacaagtttg actttggagt ggagacaaga  60
cacaacagaa gagcactgag agtgattaat cagaatttgt taggacctaa tccatatcgt  120
tgtgttgtta acaagagagg attatcacat gcaaatggaa tcatctacga taagaatcct  180
acgaggaaat tgactgcacc aattgctagc tcacaccagc attaccccga ggaaacaaag  240
aaaccaaaac tagcagctga agattttagg atttgggagg aacatgtggc agctaaagac  300
caactcatgc ctatgtcttt ggaacaagaa gcaacatttt caaatgacaa gacagaaatg  360
gagattcaaa tggaggatat atttgaggag gcactaatag atattgacag tgatgatgca  420
aagaacccac ttgcagttgt tgactatgtg aatgatctgt accccaacta cagaaaaatg  480
gagggttata gctgtgtttc accaaactat atgacacaac agtttgatat caatgaaagg  540
atgagagcta tattagtaga ctggctcatt gaggtacatc acaagtttga gctcagggaa  600
gagacgttat tcttgaccgt taattcgata gacagatttt tggagaagca aacagttgca  660
agaaagaagt tgcagcttgt tgggctggtt gctatgctat tagcatgcaa atatgaagag  720
gtctctgtcc cagtagtgga tgatttggtg attatttcgg acaacgccta taggaggaaa  780
gaggttcttg aaatggaaac attaatgctc aatacactgc agtttaatat gtcagttcca  840
actgcgtatg tttttatgag aagatttctc aaggctgctc aagctgataa aaagcttgag  900
gtcctgtcct ttttcttaat cgagctttgc ctcgtggaat atgaaatgct taagtttcca  960
ccatctttca tggctgctgc ggtagtctat acagctcagt gcacgcttta tggtgtcaag  1020
caatggaata aaacctgtga atggcataca agttactcag aagatcaact tctggagtgc  1080
tcaagatcga tcgtgagcta ccaccgaaag gcagcaacag ggaaactaac aggagtacat  1140
aggaagtata gcacatctaa atatggctac gcagcaaaat atgagccagc actttttctg  1200
gtgcagatcc aataa                                                    1215

SEQ ID NO: 23         moltype = DNA   length = 1314
FEATURE               Location/Qualifiers
source                1..1314
                        mol_type = unassigned DNA
                        organism = Nicotiana tabacum
SEQUENCE: 23
atggccatat ctgatgagaa caatcctaca atgattaaac ctacaaatgt gcaaggtggg  60
gctggaatgg gtaccagaaa gtttggtgga gtggaaacaa gaaacaacag aagagcattg  120
ggagtgatta atcagaattt agtgggtggt gctcatcctt ttccttgtgt tgttaacaaa  180
agaggattat ctgaagcaaa tggaagatgt gacaagaatc tgcctattcc agctcataga  240
cctatcacga ggaaatttgc agcacaaatt gctagctctc atcaacatcg ctccgaggaa  300
aacaagaaag ctaaaatagc atcagaagaa ttcagtatat gggaggatat ccctctcaca  360
gatgtggagg aaaatgaagc agctaaagat caacctgttc ctatgtcttt ggaactaaca  420
gaaacagtcc caaatgacaa caagaatcaa atggaagtag aaatggagga tattattagg  480
gaaaatataa tagatatcga tggcgatgat gcaaagaacc cccttgcagt tgttgaatat  540
gtacaagatt tgtttgcctc ctatagaaaa atggagggt gtagctgtgt ttctccggac  600
tatatggcac aacagtttga catcaacgag agaatgagat ccattctaat cgactggctc  660
attgaggtac atcacaagtt cgagctcagg gaagagacgt tgttcctgac tgttaatttg  720
atagatagat ttttggagaa gcaaggtgtt gtcagaaaga agctgcagct tgttgggttg  780
gttgccatgc tattagcatg caaatatgag gaagtttctg ttccattggt ggaagatttg  840
gtgtttattt ctgacaaagc ctattcaagg aaggagattc ttgaaatgga aagaatgatg  900
cttaacacac tgcagtttaa catgtcagtt ccaactgcat atgtttttat ggaaagatat  960
cttaaggctg ctcaatctga taggaagctt gagctgctgt cttttcttctt ggttgagctt  1020
tgtctagtgg aatatgcaat gctcaagttt ccaccatcat tcatagctgc tgcagcaatc  1080
tatacagctc agaccacact ctacggtgtc cagcagtgga gtaagacatg cgagtggcat  1140
actagttact cggaagatca acttatggag tgctcgaagt cgattgtgag ctatcaccag  1200
aaggcagcaa caggaaaact aacaggggtg cataggaagt acagtacatc taaatttggt  1260
tatgcagcaa aatgtgagcc tgcccatttt cttgtgcaga cacaacaaca atag         1314

SEQ ID NO: 24         moltype = DNA   length = 2181
FEATURE               Location/Qualifiers
source                1..2181
                        mol_type = unassigned DNA
                        organism = Nicotiana tabacum
SEQUENCE: 24
atgggtaaat tgaactcgca gaaacatata tccaccataa aagatggagt tacagaactc  60
aaggtttacg aagaggtaga taagataaaa atccaaagcc gtgattctct cagcaggcgc  120
tgcaagggaa agtctggtgc gcctaacatg agtgatgtgc agaccagttg gaagagctcg  180
gagagggta tcaagcacat agagaggata aaagcaaagt gcaggacttg tgttaaggta  240
aatgtcaaaa gaaaagtatt gacggatatc agcaatatca gggcaactc ttcgagaacc  300
aaatcatata atagctccaa actgctggtg tcagatggta aatgcccaaa aaatgcaagc  360
aattcagcaa gaagatttat catgggaaat gtgaggacaa acttgaacgg agctactggt  420
gacaagcaaa tcttgacacg ggatatgaaa gcctcctttg atggcccaaa gaccagaatt  480
caaggccgta aatcagttac cactggaatc aggccaactg gaaggaatga tctaccgcca  540
tcaaggaggt ctttacctat actacagcag gtgaacatcg agggtacaaa caataaagag  600
aagggaaagg tgaggcgaa cttgaataaa gctactgatg acaagcaaat cttgacacag  660
gcaccacgca aagatatgaa agcctccttt gatggcccaa agaccagaat tcaagtccgt  720
aaaccagtta ccactggaat caggagaact ggaaggaatg ctctaccgcc atcaaggagg  780
tctttaccaa tactacagca ggtgaacgtc gaggacacaa acaataaaga gaaggaaaat  840
tccaaaaagt tggagaaagg caaaggaata agtggtgttt cagttttggc aaaagcctaag  900
gccgcaggag atgttttacc acagttaagc aaccacagca acatccggag aaatcgagtt  960
ggtgatgcct cggctagaat ggctcccgg ggtcaagcta aggtggaagt tggagcattg  1020
agaagaaaat cagtcaggac agttctgaaa attactgcta gtggtctcaa ttcacaaaag  1080
agttcaaagt cgaactccat gtcaggtgtg cacaaatgca cctctcgatt tgccagtcca  1140
```

```
tgtaaaaggc tggtggatgt taggacatct tccctatcaa aatctgcaac atcagagatt   1200
tcagctgagc aacctcatca aaaggaagtt ccttctagta gtagtggcag cttagctaca   1260
ccggaattgt caattgccag gaagaaatct gaccgtagga agtctttac gtgtttactg    1320
atggcaagat caaagcttat gaaggagcta tgtggaactg tagagctgga caatttgtca   1380
aacatttatg atagttgcaa tcatcttgaa gttacagaat atgttgatga catctatcag   1440
tattattggg ttatagaggc acagaatcag cctatcaaaa actacatgga gactcagaag   1500
gaaataacac cccaaatgcg tggcatattg atcaactggc ttattgaagt ccatttgaaa   1560
tttgatttga tgcaagaaac tctatttctc atggttacac tcctggacta ctacttaaca   1620
ttagcaaggg tcaagaagaa tgatttgcag ttagttggcc ttacttcact gttgttggca   1680
tcaaaatatg aggacctttt ccatccgagg gtcatggact tactaagcat ctctgcagag   1740
tcatacacaa gagatcagat gctggaaatg gaaaaagata tcttaaggaa attgaagttt   1800
cgccttaatg cagcaactcc ttatgtcttc atgctaaggc ttcttaaggc tgctcaagca   1860
gacacaagga ttgaacatct ggcattttac ctcatcgagt tgtgcttggt tgaatatgaa   1920
gctttgaact acaagccatc catgctttgt gcatcagtca tttatgtggc aagatgtacg   1980
atgcaaatga cgccagcctg gacaccactg ctggggatgc atgcacgtta tcaagaatcc   2040
caactcagac attgcgcgga aatgatcttg aggtttcaca aagctgcaag cacagcactt   2100
ttgaaagtca cgcatgagaa atatatgcag tccagtaaca gcaaagttgc tgctataaaa   2160
cctttgcaga gtctcccctta a                                            2181
```

SEQ ID NO: 25          moltype = DNA  length = 1278
FEATURE                Location/Qualifiers
source                 1..1278
                       mol_type = unassigned DNA
                       organism = Nicotiana tabacum
SEQUENCE: 25

```
atggataaca atagtgttgg tgttcctcac aatttaccca gaggagaaat gggaggaaaa    60
cagaaaaatg cacaagccga tggaagaaat aggcgtgctc tcggagacat tggcaacctt   120
gtgcctgctc ctgctgcaga aggaaagcct aaagcagctc agatttctcg ccctgtgact   180
aggagctttt gtgcacagtt gctagctaat gcacaagaag agaagaacaa gaaaccacta   240
gcagaagttg tcaataaaga tgtaccagcc aagaagaagg catcagataa ggaaatgaag   300
actgttgggg gaagtccatt gagcaaaaga aaagcaaaga agtctggaaa gactctcact   360
tctactctca ctgctagaag caaggctgct tgtggacttt ccaatagacc aaagtatgag   420
attgaggaca tcgatgtcgc tgatgctgat aatcatttgg ctgctgtaga gtatgttgag   480
gatatctaca acttctacaa gctcactgag ggtgaaagtc gagtggatga cgactacatg   540
aactttcaac cagacctgaa tcataagatg agagccattt tagtggactg gttaatagaa   600
gttcacagga aatttgagct tatgcctgag agcctttacc ttacaattac catactggac   660
cgtttcctct cgctgaagac ggttccaagg aaggaacttc agttagttgg cattagctca   720
atgctaattg cttgcaagta tgaagagatt tgggcaccag aggtgaatga tttcattcat   780
atatcagaca atgcatatgc cagagagcaa atacttcaga tggagaaagc aattcttggg   840
aagttggaat ggtatttgac agttccaaca ccatatgttt ttctggttag gtacattaaa   900
gctgcaacac catctgataa tcaggagatg gagaacatga cattcttttt tgctgaactt   960
ggtcttatga actacaagat cacaaatatca taccgcccat caatgctagc agcatcgtcc  1020
gtttatgctg ctcgtagcac tctcaacaaa actccactat ggctcaaac tctgcagcac   1080
catactggct actcagaaga tcagttgatg gaatgtgcaa agatattggt tagttatcac   1140
ttggatgctg cagaaagtaa gctgaaagca atttacagga agtttcgag tccagataga    1200
ggtgctgttg cattcttccc accagcaaga aatctcctac ctactactac tactgatgct  1260
gcttcctcct cttcttga                                                 1278
```

SEQ ID NO: 26          moltype = DNA  length = 1311
FEATURE                Location/Qualifiers
source                 1..1311
                       mol_type = unassigned DNA
                       organism = Nicotiana tabacum
SEQUENCE: 26

```
atggttggat caaacgagaa ttgccaaggt gttataatgg cttcaaatgt tcaaggggga    60
ttaggggctg gaggaggaaa ggtgacaatg gggcctaata gaagggctct aagcacaata   120
aatgggaata tagttgaagc tccagcatac ccttgtaaag tacacaagag aaatggcatc   180
actgacaaga gcgcgaatgg tgttaagaat cctcccattc caattcatcg accaatcaca   240
aggaaatttg ctgcacaaat ggctaccaag cagcagcaac caacggttga ggtaacaaag   300
cagccagtcc aaacagcacc tgctaaaaat gaatcagaag actgcatcat tattgatgca   360
gaagattaca aggccacaag cgactatgat cctgtgccaa tgtttgtgca acatacagaa   420
gcaatgatga aggaaattga tcggatggac gctgagatgg agatggaaga tgtagaagag   480
acactaattg tggacataga tagtgctgat aaaaagaacc cacttgcagt agcggagtac   540
attgatgaca tgcatgctta ctacaagaag accgaagatt ctagctgcac ccctccaaat   600
tatatggaac aacaatttga tattaatgag aggatgagag ctattctcat tgactggctg   660
attgaggtac attacaagtt tgatctgatg gaagagactt gtatttgac cgtaaatctt    720
atcgatagat tcttagcagt ccaacaagtg attaggaaaa aactccagct tgttgggggta  780
acagctatgc ttctagcctg caagtatgaa gaagtttcag ttcctgtcgt tgaggatctt   840
attttgatct ctgataaggc ttacaccaga aaagaggtgc ttgagatgga gaagttgatg   900
atcaatacct tacagttcaa cctaccagtg cctacagcat atgtgtttat gatgcgattt   960
cttaaagctg ctcagtctga taagaaggtg gagctcctgt cttttttcat gactgaacta  1020
tgcctcgttg agtatgaaat gcttaggttc ccaccttcaa tgctagctgc tgcagcaata  1080
tttacagccc aatgtactct aggtgtgctt aacgagtgga gtaaaacttg tgagaagtat  1140
agcactata ctcgaagatca gcttttggag tgctcaagac tgatggtttc tttccatcag   1200
aatgctgcaa ctgggaagct tgctggtgtg catagaaagt atagcactc taaatatggc   1260
tttgttgcaa aatgcccacc tgcttctttt cttttagagg caagctttta g            1311
```

SEQ ID NO: 27          moltype = DNA  length = 1269
FEATURE                Location/Qualifiers -continued

```
source                  1..1269
                        mol_type = unassigned DNA
                        organism = Nicotiana tabacum
SEQUENCE: 27
atgggtgtat ctaatgagaa caatcctagc atgattaaac ccagaaatgt gcaaggtggg   60
gcagaattag gttacagaaa gtttggagtg gagacaagga ataacagaag agcattaagt  120
gtgattaatc agaattttgt tggagctaag ccataccctt gtgttgttaa taagagagga  180
ttatctgata ctaacaagaa tcctcctgtt ccagctcata gacctatcac aaggaaattt  240
gctgcacaaa ttgccaactc aaagcagcat tatcctgagg aaaacaagaa accaaagata  300
gcagctgaag gtttaagtgt atatgaggat gtagctatag tagatgtgga agaatatgag  360
gcagcagcaa aagaccagcc agttccaatg tctttggaac aaaactcaaat ggagattgag  420
atggaggata catttgagga gagtgtgata gatattgaca gtaacgatgc gaagaacccg  480
ctcgcagttg ttgactatgt ggaagatctc tatgcctact actcaaaaat ggagggctgc  540
agtcgtatct cgccagacta tataggacaa cagtttgaca tcaacgagag gatgagatct  600
atactaatcg actggctcat tgaggtacac cacaagtttg atctcaagga agagacatta  660
ttcctaactg ttaatttgat agatagattt ttggagaaac aatctgttgt gagaaagaaa  720
ctgcagcttg ttggtctcgt cgccatgtta ctagcgtgca aatatgagga agtttctctc  780
cctgtggtgg atgatttggt ggtcatttcg gataaagcat acacaaggaa ggaggttgct  840
gaaatggaaa aattgatgct caatacgctg cagtttaata tgtcggttcc aactccatat  900
gtttttatga gaagatttct caaagctgct caatcggata aaaagcttga gctactttcg  960
ttcttcttga tcgaactttg cctcgtggaa tatgaaatgc ttaaatttcc accatcattt 1020
atcgctgctg ctgcaatcta cacagctcag tgcacatttt atggtgttaa acaatggagt 1080
aagacgtgcg agctgcacac taaatactcg gaagatcaac ttctggagtg ttccagattg 1140
attacgggat tccaccaaaa ggcagcaaca gggaaattaa ccggggtaca tagaaagtac 1200
aatacatcta aatttggtta tgtggcaaaa tgtgagcctg ctcattttct tcttgtgcag 1260
acccgataa                                                         1269

SEQ ID NO: 28          moltype = DNA  length = 1479
FEATURE                Location/Qualifiers
source                 1..1479
                       mol_type = unassigned DNA
                       organism = Nicotiana tabacum
SEQUENCE: 28
atgaggaatg caaatatgac aattggatct tctaatctta aagagcccac tatgcgaatc   60
acaagatcac gggcaaaagc cttgggttca tcaggaggat taccacctcg acacccatct  120
gtcagacagg ataacaaaca gggactggga gcaaagggaa ctaagtacaa aagatctgcc  180
tcggatgaga ataatccagt tactaatgct agtacagcct gtcaacagcc taagcgaagg  240
gctgttctca gggatgtcac caatgtgctt tgtgaaaatt catatatgaa ttgcatcaat  300
agaagcaaat ttcaggttaa gaaattctct gataagagga attcaaaggt gacacctgct  360
attttggcaa aaagaccgca tcatgaagat acaaaagaga acacgattga agaagcaaaa  420
aaagtaaaga tcgagaaatc acaagaacac tgttcacaag cacgcttcaa ggaccataca  480
ttaactcagc caagtaaata tatcactcca gcacagtgtg gtttttgttga tcttatgcct  540
gtgaatagga gtttacctac agccattgca gtcctgaata caacagaaaa agatgaaacc  600
aaggtttgcc agaaacaaga aggctccgat tctcttggta tagcagatat agattcaaag  660
cacaaggatc cactaatgtg tagtctatat gctcctgata tatatagcaa tttgcatgcc  720
atggagcttg accggcggcc ttcatttaat tacatggaaa agctgcagcg ggacgttaac  780
aagggtatgc gaggtattct aattgattgg cttgtggagg tttctgaaga atataggctg  840
gttccggaca cactttacct gactgtacat ctcattgatc ggttcctctc tgagaattac  900
attgaaaaac aaaaagctgca gctgctcgga gttacctgca tgctaattgc ttccaaatat  960
gaagaaattt gtgcccctcg tgtggaagaa ttttgcttta ttacagacaa cacttactca 1020
aaagaagagg tagtaagaat ggaaagtcta gtattgaatt ttttgggctt tcaacttgct 1080
gctccgacca ctaaaaagtt cctgaggaga tttgttcaag cagcacaagc ttcatatgag 1140
gttccctctg ttgaactgga attcatggca aactatttag cagagctaac acttgttgac 1200
tatagttttc ttaagtttct tccgtctatt actgctgcat cggctgtatt tctagccaaa 1260
tggacacttg atcaatctaa ccacccatgg aatccaactt tggagcacta cactaggtat 1320
acagcgctag agctgaaaac catagttctt ttgctgcaag atttacagct gaacaccagc 1380
ggaagcaccc tgaatgccat tcgtgaaaag tatagacaac caaagttcaa gtccgtggca 1440
actttatcgt ctccgcagcc agtccaatca ctgttctaa                        1479

SEQ ID NO: 29          moltype = DNA  length = 1269
FEATURE                Location/Qualifiers
source                 1..1269
                       mol_type = unassigned DNA
                       organism = Nicotiana tabacum
SEQUENCE: 29
atggataaca aaactgttgt tgttcctcac aatttaccca aaggagaaat gggaggaaaa   60
cagaaaaatg gacaagccga tggaagaaat aggcgtgctc tcggtgacat ggcaaccttt  120
gtgcctgctc ctgctgtaga aggaaagcct aaagcagctc agatttctcg ccctgtgact  180
cggagctttt gtgcacagtt gctagctaat gcacaagcag agaagaacaa gaaagcacta  240
gcagaaattg tcaataaaga tgcaccagcc aagaagaagg catcagataa ggaaataaag  300
actgttgagg gaagttcatt gagcaaaaga aaagcaaaga gagcggaaa gactctcact  360
tctactctca ctgctagaag caaggctgct tgtggacttt ccaatagacc aaagtatgag  420
attgatgaca tcgatgtcgt ggatgctgat aatcatttgg ctgctgtaga gtatgttgag  480
gatatctaca acttctacaa gctcactgag ggtgaaagtc gagtggatga ttacatgaac  540
tttcagccag acctgaatca aagatgagaa gccattttag tggactggtt gatagaagtt  600
cacaggaaat ttgagcttat gcctgagagc ctttaccttg caattaacat actgaccgg   660
ttcctctcgc tgaagacggt tccaaggaag gaacttcagt tagttggcat tagctcaatg  720
ctaattgctt gcaaatatga agagatttgg gcaccagagt gaatgatttt cattcatata  780
tcagacaatg catatgccag agagcaaata cttcagatgg agaaagctat tcttgggaaa  840
```

-continued

```
ttggaatggt atttgactgt tccaacacca tatgtttttc tggttagata cattaaagct    900
gcaacaccat ctgataatca ggagatggag aacatgacat tcttttttgc tgaacttggt    960
cttatgaact acaagaccac aatatcatac tgcccatcaa tgctagcagc atcgtccgtt   1020
tatgctgctc gtagcactct caacaaaact ccattatgga ctcaaactct gcagcaccat   1080
actggctact cagaagatca gttgatggaa tgtgcaaagc aattggttag ttatcacttg   1140
ggtgctgcag aaagtaagct gaaagcaatt tacaggaagt tttcgagtcc ggatagaggt   1200
gctgttgcct tcttcccgcc agcaagaaat ctcctaccta ctactactga tgctgcttcc   1260
tgttcttga                                                           1269
```

SEQ ID NO: 30          moltype = DNA  length = 1488
FEATURE                Location/Qualifiers
source                 1..1488
                       mol_type = unassigned DNA
                       organism = Nicotiana tabacum
SEQUENCE: 30

```
atgaggcatg caaatataaa acatggatct tttcatcttg aagagcacaa tatgcgaatc     60
acacgagcac gagcaagagc aagtgtgttg ggttcatcag gacgattacc accctcacac    120
ccatccacaa aacaggataa gaagcatgta ttgggagcag agtccaaaag atcgaaaaga    180
tctgcctcag atgagaacag acctggtacc tctagtactg ctactggtgt tcagcctaag    240
agaagggctg ttcttaaaga catgacgaat gtacttcatg agaactctca catgaattgc    300
atcaacggaa gcaaaattca ggttaaaaaa ggctccgata gaggaacaa taaggcgaaa    360
cctgctgttt cggtaaaatt gtcacagctc caagagaaag gaaaagagga tatagctgat    420
aaagtaaaga aagtgaaggt tgagggatca caagaaataa gttcgggggc aaactgcaag    480
gaggatatgt tacctcagct aagtagatat gtcactccag cacaatgtgg tttagtccat    540
ctagtgcctg tgaacagaag ttcctgtaag gccatcccac ttcaggatat aatgaaaaaa    600
gatgaaagca aagtttgccg gaaacaagaa ggctttgcta atctaggagt tgctgatatt    660
gattcaagac acaaggatcc actgatgtgt agtctgtatg ctcctgatat ttataacaat    720
ttgcatgcca ttgagtttga ccgtaggcct tctgttgatt acctggaaaa gctgcagctg    780
gacattaaca agggtatgcg aggtattctg attgattggc ttgtggaggt ttcagaagaa    840
tataggctgg ttccagacac actttaccta actgttaatt ttattgaccg tttcctatct    900
gaaaattaca ttgaaaaaca aaagctgcaa ctacttggag ttacctgcat gctaatagct    960
tccaaatttg aagagatttg tgcacctcgt gttgaagaat tttgcttcat tacagataac   1020
acttactcga aggaagaggt aataaaaatg gaaagcagag tcttgaacct tttgagcttt   1080
caacttgctt ctccaaccac taagaaattc ctgaggagat tcattcaagc agctcaagct   1140
tcttacaagg ttccctctgt cgaactggaa ttcatggcaa attatttagc tgagttaaca   1200
cttgttgact atgggtttct taagtttctt ccatctctta ctgctgcatc agctgtattt   1260
ctagctagat ggacgcttga tcaatctaac cacccatgga atccaacttt ggagcactat   1320
accagataca aggtatcaga gcttagaact acagtttttg cactgcaaga gttacagatg   1380
aacaccagtg gctgcaccct caatgccata cgtgaaaaat atagacaacc aaagttcaag   1440
tccgtggcta ctttagcagc ttcaaaacca gtccaatcac tgttctaa               1488
```

SEQ ID NO: 31          moltype = DNA  length = 1341
FEATURE                Location/Qualifiers
source                 1..1341
                       mol_type = unassigned DNA
                       organism = Nicotiana tabacum
SEQUENCE: 31

```
atggcttcaa gaaacgttct tcaacagcag aatataggtg aggcagtacc cggggcacta     60
aaacagaaga atatggcagc agcagcacaa ggtagaaacc gaaaggcgct tggtgatatt    120
gggaataatg tggtaactgt tcgtggcgtc gagggaaagc cacttcctca acgccccata    180
acaaggagct tttgtgcaca attgctcgct aatgcacaag cagcagctga aaaccaaaga    240
aaatctttgg tggttaatgg ggatgcaccg atcgttgcta aaggagctct agcggttaaa    300
gctgcagcca aaaaaccagc tcataagaaa gttgctgtaa aaccaaagcc tgatgtgatt    360
gaaattagtc ctggtactga agaacaagtg aaggaaaata agcaaaagaa gaaggctggt    420
gatgactctt cactaaagaa agcaactctt acttcaactc tcactgctag gagcaaggct    480
gcttgtggac tgagtcataa accaaaggtc cagattgtgg acattgatgc tgttgatgtg    540
aataatgagt tggctgtggt ggaatatgtt gaggatattt acaattttta taagatagct    600
gagaatgaga gcagaattca tgattacatg gattcacagc ttgagataac tgaaagaatg    660
agagctattc tgattgattg gttgattgaa gtgcatcaca aatttgagct tagtcaagag    720
actctttacc tcacaatcaa tatcgtcgat cgttatctcg cggtcacaac tacatcaagg    780
agggaattgc agttagtagg catgagtgct atgctcattg cctctaaata tgaagaaatc    840
tgggctcccg aggtgaatga ctttgtgtgc atctcagata aagcttacag tcatgagcag    900
gtgttgggaa tggagaaaag gattcttggc caattggagt ggtacttaac agttccaaca    960
cctatgtgt cctcgttcg ctttatcaaa gctgctgttt ctaatgcaca aatggaaaac   1020
atggtttatt tcctggctga attggggtta atgaattatg caacaaatat ctactgccca   1080
tcgatgattg ctgcctcagc agtctatgtt gctcaacaca cactgaattg cactccgttt   1140
tggaacgaca cactaaaatt gcatactggt ttctcagagt ctcagctact gggttgtgca   1200
aagttgctgg taagctatca catggaagct ccagaacaca agctgaaagt gatttacaag   1260
aagtattcga gacctgagag aggtgctgtt gcactgcaac ctccagccaa atccctgttg   1320
gctgcttctt tatatgaata a                                             1341
```

SEQ ID NO: 32          moltype = DNA  length = 1422
FEATURE                Location/Qualifiers
source                 1..1422
                       mol_type = unassigned DNA
                       organism = Nicotiana tabacum
SEQUENCE: 32

```
atggcttcaa gaatcgtcct tcaacagcag aatagaggtg aggcagtccc tggggcatta     60
aagcagaaaa agaatgtggc agcagaagga agaaatagga aagcgcttgg tgatattggg    120
```

-continued

```
aatgtggcta caggtcgtgg ggtcgaagga aaaaagccac ttcctcagaa acctgttgct    180
gttattgtaa aaggagcaaa tgttgctaaa gtacctgcag taaggaaacc agctcagaag    240
aaaagccacag ttaaaccaaa acctgaggag attattgaaa ttagtccgga cactcaagaa    300
aaaactgaagg agaagatgca aaggaagaag gctgataaag actcattaaa acagaaagca    360
actcttactt caactctcac tgctcgaagc aaggctgcat gtggtctgaa taaaaaacca    420
aaggagcaga tagtggatat tgatgctgca gatgtgaaca atgagttggc agttgtggaa    480
tatgttgaag acatttacag cttctacaaa cttgctgaga atgagacaag agtccatgac    540
tacatggatt cacagcctga aataaatgat aggatgagag cagttctgat tgattggttg    600
gttgaagtcc accaaaaatt tgaacttaat ccagagactc tttacctcac aatcaacatt    660
gtcgatcgct accttgctgt gaagagtaca tcaagaaggg acttgcagct agtgggtgtc    720
agtgccatgc tcatagcctc caaatatgaa gaaatttggg ctcctgaggt caatgacttt    780
gtgtgcatct cagacaaaag ttacactcat gatcaggtgt taactatgga gaaagaaatt    840
cttgggcaat tggaatggta cttaacagtt ccaacacctt atgtgttcct agcacgtttc    900
attaaagctt ctccacctga ttcagaaact gagaacatgg tatattttct ggctgagctg    960
gggttgatga attatccaac cattatctac tgcccttcaa tgattgctgc ctcagcggtc   1020
tatgctgctc gacacaccct caataggaca ccattttgga atgagacact taagctgcac   1080
actggtttct cagaatctca gctaatagag tgtgcaaggt tgttagtgag ctatcaatcc   1140
gcggctgcaa ctcacaagct aaaggtgata tacaagaagt actccagtcc ggaaagaggt   1200
gttgttgcat tgctaactcc agccaaatcc ctgttggctg catcatcatt acgtgtgtcg   1260
tcggagcaag ctgatttagg caaaagcaca gaagcagcag caacatcatc atcccctatg   1320
gtggtggtgg gttgtcaaag gtgccacatg tatgtcatgg taactgaagc tgatccaaga   1380
tgcccccaat gcaagaacac tactactagg aagatgactc aa                       1422
```

SEQ ID NO: 33          moltype = DNA   length = 1767
FEATURE                Location/Qualifiers
source                 1..1767
                       mol_type = unassigned DNA
                       organism = Nicotiana tabacum
SEQUENCE: 33

```
atgatacaag ttaaggagga atctcagact ctggactttg gtggatttgc ttcttgttca    60
tctttctctg atagcagtta cgaggctagc actccaagat actcctccga acctggttct   120
agttatcgaa ggagctcagg tccaactaaa cgttcttccc aggcaggctg gacagaagaa   180
gaggataatc tgttgactga cgtggtgaaa aggttcaaag ggagaaactg gaaaaaaata   240
gctgagtgca tgaatggaag gactgatgtg cagtgcttgc atcgctggca gaaagttctg   300
aatcctgagc ttgtaaaggg tccttggtca aaggaggagg atgacctgat tattgagtta   360
gttgagaaat atggctgtaa gaagtggtct tttattgcca agtctttgcc tggtcgcatt   420
ggtaagcaat gtagggaaag gtggcacaac catcttgacc caaccataaa aagagatgct   480
tggactgaac aggaagaatc agtcctatgc cactatcacc aaatatatgg gaacaagtgg   540
gcagaaattg cgaggtttct gcctggaagg actgataatg caattaaaaa tcattggaat   600
tcctcagtta agaaaagatc gaacttgaat ttgccaagtg ggttagtgct ggataccgaa   660
agtgaggaat ctcctaattt ctctagtgac aagaaaaaac tagagatcca gaagcatcca   720
ttacaagctc aaaatgcaga acaaacaatc tttttaggcg agcagacagg attggataat   780
gctgctgttg ctttgtcaac tgatctgaga attggatatg cttattctgc tggaaatgct   840
ttgcataagg atacttcttt atttggagcc tgtatatcag cagaagaaaa tgtgagggat   900
ctgataaagc cacttggtgg aataccattt ggcaaggcag atgttcttcc aattggtgag   960
acagataaac catgtcaatc caatttaagt cgcactaaaa tatcatatcc actctcagcc  1020
tcttcttcag attttccttt ggatcagttg caccacacaa gatggagtac ttctcaagtt  1080
gaggctgttc atcctactac ttttgggagc atgtatgaat ctcccaagag gtctaggcac  1140
gacactgtta acgatcctga ccatgatttt ttgagtttgt cattggctag ctttactgag  1200
gttcgttccc aaagtaacaa gaagaataaa gcatatgaca cacaatcttc tttgggtctc  1260
aagcagcagg gctccttgta ttatgaacca ccacagttaa aggacatgct gattccttta  1320
acagatgaaa accttagtag agacaacctt atcacggaaa aaaatggtca tccattttgc  1380
tctactcctc ctagtcttaa attaacagtc tctgctaatg gtagcagtcc agaatctgtc  1440
ttaaggaatt ctgcaatgag ttacacagga actccttcaa tcataagaaa gaagaattcc  1500
agatttcccg aagctgcgac gcattctagt tgcacaggca ccaccactcc cacacataat  1560
ttcccaagag cttctgacag ggaagacacc tcaaacctga aggacagatt ttctgggtgt  1620
aaatcatcag tttcgggaaa atctcttgga agacggttgg aatatgcctt tgatatggaa  1680
tgggatgcct ctagatgttg cacaccagtt tctgcagctt caccttgtgc acttagactt  1740
ggtgctaata cgatgctgac accataa                                       1767
```

SEQ ID NO: 34          moltype = DNA   length = 3132
FEATURE                Location/Qualifiers
source                 1..3132
                       mol_type = unassigned DNA
                       organism = Nicotiana tabacum
SEQUENCE: 34

```
atggaaagtg atagaataag cactccttca gatggcacta gcagtagtct ccaaagagtt    60
cggcctttgc atgggagaac tagtggtcct acgagacgtt cgacaaaggg gcagtggact   120
actgaagaag acgagatcct acgcaaagct gtccaacgtt ttaaggacaa aaactggaaa   180
aaaatagcgg aatgttttaa agaccggact gatgtacaat gcttgcaccg gtggcagaaa   240
gttcttaatc ctgaacttgt caaaggtcca tggtctaaag aggaggatga agtaatagtt   300
gaattagtta agaaatatgg ccccaaaaag tggtccacca tcgctcaaca tttgccggga   360
cgtattggaa aacaatgtcg agaaaggtgg cacaatcatc tgaatcctgg aataaacaag   420
gaagcttgga cgcaggagga ggagttgact ctgattcgcg cccaccaaat ttacgggaat   480
aaatgggcag agttaacaaa gtatttgcct ggaaggacga ataatgcaat aaaaaatcac   540
tggaatagtt ctgtcaaaaa gaaattggac tcgtatttgg catccggttt acttgcacag   600
ttcccttctc tgcctaatgt caaccgtcag aaccaatcaa tcccttcttc gacgaagttg   660
caacagagta gtgaagatga cagtgttcgt aaagaaggaa tcgaaatgga ggaagcttca   720
gaatgcagtc aagggtcaaa tcttgcaggc tgttcccagt ctacaagtga catgggcaat   780
```

```
acatttgtac atacaagaga ggagggcaag ttgctggagg attcaaatta taggaaggac   840
ccaagctcca gttcagcacc atgctctgaa tactataccc cagcctttga agatattacc   900
tttttcaatgg cagaagtgcc tagtgaactt gacgaatcca agctcctgga gcataacttc  960
tcacatgact gggcagcatc catgggaaaa gaatggcagt ttaatccaga tgacatacct   1020
aatatttctc cgctggagtt gatgcaggat tcttcaggge tcttcatcga gtgtttaact   1080
ggtaatggga atcacgaaat ggttaccttt ccacagcaaa atgcagtgaa gtatgaaatg   1140
actaatgtcg gaagcatggt tgtgggttta gataagccca atgagatgtt tacctctgtg   1200
gagggttgcg ggatggtata ccctgaggca ggaattccac aatacattcc ctctgaaact   1260
ggtatgaacg gtgctgatga aactgcagat tctttgattt gccaatcgtc gaactatcag   1320
atctctgaag gtggaaatat gtctatagag aattgctgca accctctgtg ttcacatgtt   1380
atgggaactt catccggtca accattttct attccttcac agttttcttc agagcaaagc   1440
tcactcatgt ttggtactgc cgcaaatcac tttcataatc catcgcaggg aaacccagca   1500
caggagtccc acacaagtaa ctctgatggt tttctatatc cctttgaatc tggtactgct   1560
tgtgacaaca taatggacga tcctctcctg gaagagcaac tggatcaaac taaagattct   1620
ctacagctag tttctgtcaa tgattttcgc tcaactcctt caaatactat tcaaacatgt   1680
ccattggtga acgaaaattc gagcgtacca gaagagcaga aggatggagg agccttatac   1740
tatgagcctc ctcgttttcc gagcttggac attccatttt tcagttgtga tcttatacaa   1800
tctggtgcag atgcacagca agagtatagc cctcttggca tccgccagtt gatgatgact   1860
tctgtgaact gtcttactcc atttaggctg tgggattcac catctagaga tggaagtcca   1920
gatgctgtcc tgagaagtgc tgccaaaact ttcaccagca cacttccat attaaagaag    1980
cgacaccgtg atttggtgtc acctttgtca gaaaagagat gtgaaagaa gcttggaagt   2040
gatctccgtc aagaatcatt ctctgatctg tctaaggatt tttctcgact agatgttatg   2100
tttgacgagg ctgcaaatga aaaagcaaca aagtcttctc taactatgag tcagacgttg   2160
gaacttcaag cttcatctga agataaagaa aacataaatc caactgaaga tggaagtaag   2220
gaggaggaca aggtacgcaa tggactttcc agcgagagac agttagatgg aggtgaagtt   2280
cactataaag agaaagtaac aaggaagggc acaaagggtg tgcaattgga tgcaattgaa   2340
aagataaaac aaccttctgg agttctggtt gaactgaacg caagtgacct gttcttctct   2400
cctgatcgtt ttggagccaa gtctggtaga gctacaaatc tctgcagtaa agctctagga   2460
aatcagtatg ctagacgact cgaagctgca tcaaatcaag gttctgtttc atcttcattt   2520
gagacttcat gtttttctgt tatttgctct cctcgtatac gtggaaagaa agacggaagt   2580
agttttgtca tcactacatc aatgcaatct gctccagcac caacagcctt ggacaactca   2640
gctgaaactt caggaaatgg agttggcgct gagactgtaa gcatatctgg agaaacgcct   2700
tataaaagga gtattgaatc tccttcagct tggaaatctc catggttcat caactctttt   2760
ctgtcaagcc caagacttga taatgaactt aattttgagg atcttgcgct gtttatgagc   2820
ccaggtgaca gaagctatga tgctattgga ttaatgaact aattgagtga gcagactgca   2880
ggggcatttg cagatgccca ggaggtcttg ggaggtgaaa ctccagagtc gatcctacgg   2940
gggaggaact ccaaaaacca gaaagcagat gaaaatcatt ctcttttgtc agcaaatgtt   3000
atgagtgaga ggcgtactct tgatttcagt gaatgtggat cccctggaaa gggaaaggaa   3060
actgaaattt tttgcaccag caacaacagt tttgcaagtc cttcctccta cctattgaaa   3120
ggctgcaggt ag                                                       3132

SEQ ID NO: 35              moltype = DNA  length = 474
FEATURE                    Location/Qualifiers
source                     1..474
                           mol_type = unassigned DNA
                           organism = Nicotiana tabacum
SEQUENCE: 35
atgggcatga aaatgatgc cttactgaag tctaaggcaa gacgcaaaag ggtggagaaa    60
ccccagaaaa gtgttgggaa gataaatgca gaaaaagctc aagaaagacc cgtattattt   120
ctggctatta ataatctaac gataggaaaa tccagcaaca acagcttgac atcacctgat   180
gtttcttcat cctgcagcag cagcattatt acattcggtg aaaaccaaaa gatgaatatt   240
gaaatggaaa acacggttat cttggagagc aatcctgaaa tttatcagtc tgattgtttg   300
agtattgagt cattggatca gttcgatacg agttcattct ggtttatcta cttaatgatg   360
cccatcgtct tattttatga aagattaatt agaatctgcg acctccagag acagatccaa   420
aatttgatct ttatgggttc gagttcacga ctttactgca gcctattgtt ttag          474

SEQ ID NO: 36              moltype = DNA  length = 879
FEATURE                    Location/Qualifiers
source                     1..879
                           mol_type = unassigned DNA
                           organism = Nicotiana tabacum
SEQUENCE: 36
atggaaacag acatgtcttt cttgtctaaa agttcaagta gctctagtga tgaagaaatt    60
ggattgagga gaggtccatg gactgttgaa gaagacagtc tcctcgtaaa ttacatttcc   120
caacatggcg aaggccgatg gaacatgctt gcacaccgtg ctggattgaa gagaacaggc   180
aagagttgca gattgagatg gctgaattac ctgaaccgg acgttaaaag agggaatctc    240
actcctcagg aacaactcct gattcttgaa cttcatttca agttgggtaa cagatggtca   300
aagattcgc aatatctacc aggaagaaca gataatgaaa tcaagaatta ctggagaaca    360
agggtgcaaa aacaagctaa gcatttgaag attgactcca atagtgcagc atttcaacac   420
atgattcgat gtatttggat acctcggctt ctacaaaaga tacaaggttc atctgctatt   480
ccatcaattc agacttcaca atcaacttca ttattggatt cacaatatgg tcctttaaat   540
atcacagaaa ttacacaaac cccacaagtt ttaagcttag agaaacag catcagcagc     600
agcagatgct gcagttcgag atcaccttcg tcagaatcca tgagtatcta taaatctccc   660
aacattattt cggaatgtcc taaaattcca cctcgtgaga tgggtgattc tgttgtcaat   720
gttcatttc catttgacga caacagttat gatatggata ctttcagccc agcaactggc    780
aacttttga caaattatga tcaaatggtg ggtggagaaa acaatatgat gaatggtgat    840
attttagcta cacagcttctg gagcatggat caatttttag                        879

SEQ ID NO: 37              moltype = DNA  length = 738
```

```
FEATURE                  Location/Qualifiers
source                   1..738
                         mol_type = unassigned DNA
                         organism = Nicotiana tabacum
SEQUENCE: 37
atggcaagga cacgttgcta tgacaaaagt ggattgaaga agggaacttg gacacctgat    60
gaagatagga aattagcagc ttatgttagt aaatatggtt gctggaattg gcgtcaactt   120
cccaagtttg ctggattagc taggtgtggg aagagctgca gactgagatg gctgaattat   180
ctccaaccaa atatcaaaag aggaaactat actaaagaag aagatgaaat tatcatgaag   240
ctccacgcag aaattggaaa caaatggtcg gtaattgctc ctcacttacc tggaagatca   300
gacaatgaca taaagaatca ttggcacacc tctctcaaaa agagatcaac tcgggaatat   360
tcaacttcaa ctgactcaat aaagagatca tctaacaaca gttatcaagc caacagtcaa   420
aaaaagagac gtgaaaatga aactcaacta aatgcaaatg agagtttttca attgtcaccg   480
atgcaatcat gcagtactga ggtttcttct tgtgctacaa ttgatcaaaa tgtggaaaat   540
atacatggcg aacgcgaggt tttttcaagaa gaaatatttg aagtatctag cggaagtttt   600
tggacagaac cattttttagt agatagtttt aacactgcta gtgattgttt tgtaccatca   660
ttcgatgatc atggagtatt tgtatctcca ttttcccctg ttatgagcta tggtgaatta   720
ctatgctcat attattaa                                                 738

SEQ ID NO: 38           moltype = DNA   length = 708
FEATURE                  Location/Qualifiers
source                   1..708
                         mol_type = unassigned DNA
                         organism = Nicotiana tabacum
SEQUENCE: 38
atggtgagaa ctccttctgt tgacaaaaat ggaataaaga gaggtgcatg gagtgaagaa    60
gaagacaaca aactaaaagc ttttgttgaa agattcggtc atccgaattg gaggcaattg   120
cctaaacatg ctggtttaat gagatgtgga aagagctgca gactgagatg gatgaattac   180
ttgaggcctg gtttgaagaa agggaattat agccttgaag aagaggaact cattattaaa   240
ctacacaagg aacatggaaa cagatggtca gtcattgctg caagattacc cggaagatcc   300
gacaacgatg tcaaaaacca gtggcatgct catctcaaga aacgtgccaa aacaaatact   360
aataacaatt caccaattat ggagcaattt tctgagtctt cgcagtctgg atctcaaagt   420
gagcaatatt ctcataaagt atcagaacag gaagctggct gtgatacggc tagtgtaaat   480
gccgttgata cttcagtaga ggtttcatca actgatttat attcgagttt ttcccttttta   540
aatggaatgg attggattga agaagatcat atcaggtcaa tggaacaact tccagcagat   600
ttctttaact tttgttggac aaatcccatc gacaattttc agacagaacc ctttgacaat   660
tttcagacgg aaccccttaga caatttctgg agacaaccat tcttttttaa                708

SEQ ID NO: 39           moltype = DNA   length = 846
FEATURE                  Location/Qualifiers
source                   1..846
                         mol_type = unassigned DNA
                         organism = Nicotiana tabacum
SEQUENCE: 39
atggtgagag ctccttgttg tgagaagatg gggttgaaaa aaggaccatg gactcctgaa    60
gaagatcaaa ttcttgtttc ttatattcaa acaaatggcc atggcaattg gagagccctc   120
cctaaactag ctggactttt gagatgtgga aagagttgca gattgcgttg gactaactat   180
ttgcgtccag atataaagag gggaaacttt actagagaag aagaagactc cattattcag   240
ttacatgaaa tgcttggcaa tagatggtct gcaatagcag cgagattacc gggacgaacg   300
gacaatgaaa ttaaaaatgt atggcacacc cacttgaaaa agaggcttaa aaattaccag   360
cctcctcaaa actccaaaag acactccaaa aacaaccttg attccaaagc tcctagtact   420
tctcaaacct tcaataattc agacaatttt agcaatatcc aagaagatat taatgggccc   480
gtgaccggcc cgaactcgcc acaacgatcg tctagtgaga tgtcgactgt cacggttgat   540
tcaacagcca tgacgaccat cacaatcgat gatcagaata tgtttaagca attagatgag   600
atggactcgt ctgaaaattt tattccagag attgatgaga gtttttggac ggatgattta   660
tccacaagcg ataactcgac ttttggtatg gagggtaccg gtggagaatt acaagtccaa   720
tttccatttt cttcggtgaa gcaagaaagt atggacatgg ttggagcaaa attagaggac   780
gacatggact tttggtacaa tgtttttcata aagtccgggg acttactaga tttaccggaa   840
ttttga                                                              846

SEQ ID NO: 40           moltype = DNA   length = 1002
FEATURE                  Location/Qualifiers
source                   1..1002
                         mol_type = unassigned DNA
                         organism = Nicotiana tabacum
SEQUENCE: 40
atgggaaggc ctccttgttg tgataaagca aatgtgaaaa gaggcccttg gactgctgag    60
gaagatgcaa aaattcttgc ttatgtagcc agtcatggaa ttggcaactg gaccttggtc   120
cctcagaaag caggtctgaa taggtgtgga aaaagctgca ggctcagatg gaccaattat   180
ctacgtcctg atcttaagca tgacaacttc acacctcaag aagaagagtg catcattgag   240
cttcacaaaa ccattggtag caggtggtct ttaaatagcaa agcaattacc tgggagaaca   300
gacaatgatg tcaaaaatta ttggaacaca aaactgaaga aaaagcttgt gaacatggga   360
attgaccctg taacacataa accatttgct caagtctttg ctgagtatgg aaaaatcagt   420
ggtctcccaa ttcaaaatgc aagaaatcat atctgtttgc ccaacaatac tactgaaata   480
tcaaagcaac ttccattctc attacgagaa aactactcca ctcaaaaata cacatgggat   540
cctaaggctc agtatcaagt catccatgag gagactcttc aaacacacag ttttagtgaa   600
gtctcccct tgatttcatc agcaacttat tttaacccaa cagtattcag ctcatcgtct   660
tcttacgctt ccgtgcaatc tcaggttcat accacggcat cttcttcgtc aacatctact   720
tggaacgagt ttgtatttgg agatctgtgt acatccacag atacagaaca aaaacaggaa   780
```

-continued

```
taccaactcc aagctgggat atatttgtca aaggatctgt caaattcagt tcacaaggac    840
aatcctactt gtggggaagt gactgaagtt gaggaaaacc aatctgttga agaagccact    900
tgttcctctg ctgtggattc gttcgtggac accatcttgg ctcgcgacaa gcaaatgcta    960
atggattttc ctccactttt agatgtatac cttgattatt ga                     1002

SEQ ID NO: 41           moltype = DNA   length = 2997
FEATURE                 Location/Qualifiers
source                  1..2997
                        mol_type = unassigned DNA
                        organism = Nicotiana tabacum
SEQUENCE: 41
atggaaagtg ataaaaccag cacgactcct tcagatgata tcagtagtct gcaaagagtt    60
cagcctttga acgggaggac gagtggtcct aagagacgtt ccagtcagtg gactcctgag    120
gaggatgaaa tcttgcgtca agctgtccaa ctgtttaagg ggaaaagctg gaaaaggatt    180
gcggaatgtt ttaaggaccg gacagatgtg caatgcttgc acaggtggca gaaagttctt    240
gatcccgaac ttgtcaaagg ctcatggact aaggaggagg atgataaact aatcgaatta    300
gtgaacagat atggcccaa aaaatggtcc accattgcac aagagttagc aggacgtatt    360
ggaaagcaat gtcgggaaag gtggcacaat catctgaatc cttcaataaa caaagaacct    420
tggacacaag aggaggaatt gactctaatt cgtgcccatc aagtttatgg aaacaagtgg    480
gcagagttag caaaagtttt gcatggaagg tctgacaatg caataaagaa tcattggcat    540
agttctgtta aaaagaaact ggactcgtat ttggcatcag gtttacttgc acagttccct    600
gctctaccta atgtcaacca tcagaaccaa tcagtccctt cttcttctat gacgttgcaa    660
caaaatagtg aagatgaaag cgttcacaaa caaggaacag aagcggagga tagtttgtt     720
aaaaagaaac tggactcata tttggcatca ggtctacttg gacagttccc tgctctgcct    780
aatgtcaacc atcagaacca atcagtccct tcttcttcta tgacgttgca acaaaatagt    840
gaagatgaaa gcgttcacaa agaaggaacg gaagcagagg aagtgcctga atgcagtcaa    900
ggctctactt ttgctggctg ttctcagtct acaagtgact tgggcaacac atttgtgcat    960
gtaagagaga atggtgggat gtcggaggaa tcaatttgta aaaaggatgc aacctccagc   1020
actgctccat gttgtaggaa ctataacccg gtttttcaag atgtttcttg ttcaatgcta   1080
aaagttccta gtgaacttgt ggattccaag ttccttgagc ataatttatc acatgactgg   1140
ggcaattcca tggaagaaga ttggcagttt aataggatg acatacctaa tatttctcct    1200
cccgagctaa ttcaggaatc ttcagggatt tccgtgcact gtttaaatgg caatgaaaac   1260
catgacatgg aagcaactac taatgtagga aacgtggttg agggtccata taatcccaac   1320
gaaatgtttg tttgtgtgga cggttgcatg atggtatacc ctgaggaagg aattcctcaa   1380
tgctcctctg aaactggggt taatggctgt ggtcaacctg catattcttt attttaccga   1440
tcatcaaact atcagatccc tgaagtagga gatatggttc cacaaaactg caatgcttta   1500
agttttgatg attttgaagc ttcatcccat cagccttttt ctgttccttt acaattttct   1560
tcagaggata gatcgcctgt gtttgacctt gttttaaatc agttccataa tcctccgctt   1620
gaaagcccag atcatatgaa agattcctca aggatagttc cctgtgaatga tcttggctca   1680
actacatcaa acactgttca aacatgtctg ctgaatgaaa aatcatttgt acaagaaaag   1740
cagaaagatg gaggaggttt atgctacgac cctcctcgtt ttccaagctc agatgttcct   1800
ttcttttgtt gtgatcttat gcaatctggt tcagatacac aggaagagta tagccctttt   1860
ggcatccggc agttgatgat gacttcagcc aactgcctta ctccattaag gttgtgggat   1920
tcaccatcaa gagatgatag tccagatgct atcttgaaaa gtgctgccaa aacttttaca   1980
gggacaccctt ctatactaaa gaagcgacat cgtcatttac tgtcgccttt gtcagaaaag   2040
agatgtgaga aaaggcttga aagcgatctc aatcaggaat cattctctaa tatgacttca   2100
aacttttccc gactagacga tatgtttgat gagtcagcaa atgaaaaagc gtctatggaa   2160
gacggagaaa atctaccatc ctcagaagat ggaagaaaag aggagggtga aattctggga   2220
gccaatgatg caatgggaaa ggtaaaacag cctcctggag ttctggttga gcttagctca   2280
aatgacctgt tcttatctcc tgatagtttc ttgatcaagt gtgatagagc tacaagtcta   2340
agtaataaag ctctgggtaa gcagtatgct agacgacttg aagctgcatc aaatcaagtt   2400
actgtttcgt cctctttcga gacttcatgc ttttctgttg tttgctctcc tgacatacgt   2460
gggaagcgta gaagcagtgt tgtcctagct acatcagctg cattgggcgaa tacagctgaa   2520
gattctgaaa atagatttgg tactgagact ttaagcatat ctggagagac accttataaa   2580
aggagttttg aatctccttc agcatggaaa tctccatggt tcatgaattc ttttccgcca   2640
agcacaagat atgatataga acttgcattt gaggatcttg cgcgttttat gagccctggt   2700
gacagaagct atgatgctat tgggttaatg aagcaattaa gtgagcagac agcagcttca   2760
attgcagatg cccatcagat cttgggaagt gaaactccag aaacaaattt gtcgaaaagg   2820
aattccaaaa aacagaaagc agatgaaatt tgtaaggctt caaatgcaac gagtgagaga   2880
cgcacactcg atttcaatga atgtggaaca ccaggaaagg gaaaggaaac taccaaattt   2940
ggcagcaaca acagtttttc aagtccttcc tcctacctgt tgaaatattg cagataa       2997

SEQ ID NO: 42           moltype = DNA   length = 3048
FEATURE                 Location/Qualifiers
source                  1..3048
                        mol_type = unassigned DNA
                        organism = Nicotiana tabacum
SEQUENCE: 42
atgttggatt atccagattt gcctttgtct ttgaccatgg aaagtgataa aaccagcacg    60
acgccttcag atgatatcag tagtctgcaa agagttcagc cttcgcacgg gaggacgagt    120
ggtcctaaga cgttccag tcagtggact cccgaggagg atgaaatctt gcgccaagct     180
gtccaacagt ttaagggga aagctggaaa aggattgcgg aatgttttaa ggaccggaca    240
gatgtgcaat gcttgcacag gtggcagaaa gttcttgatc ctgaacttgt caaaggctca    300
tggactaagg aggaggatga taaactaatc gaattagtga acagatatgg ccccaaaaaa    360
tggtccacca ttgcacaaga gttagcagga cgtattggaa agcaatgccg ggaaaggtg     420
cacaatcatc tgaatcctgc aataaacaaa gaacttggga cacaagagga ggaattgact    480
ctaattcgtc cccaccaagt ttatggaaac aagtgggcag agttagcaaa agttttgcat    540
ggaaggagtg acaatgcaat aaagaatcat tggcatagtt ctgttaaaaa gaaactggac    600
tcatatttgg catcaggttt acttgcacag ttccctgctc tacctaatgt caaccatcag    660
```

```
aaccaatcag tcccttcttc ttctatgacg ttgcaacaaa atagtgaaga tgaaagcgtt   720
cacaaagaag gaacagaagc ggaggatagt tctgttaaaa agaaactgga ctcatattcg   780
gcatcaggtc tacttggaca gttctctgct ctgcctaatg tcaaccatca gaaccaatca   840
gtcccttctt cttctatgac gttgcaacaa aatagtgaag atgaaagcgt tcacaaagaa   900
ggaatggaag cggaggaagt gcctgaatgc agtcaaggct cgaattttgc tggctgttct   960
cagtctacaa gtgacttggg caacacattt gtgcatataa gagagaacgg tgggatgtcg  1020
gaggaatcaa tttgtaaaaa ggatgcaacc tccagcactg ctccatgttg taggaactat  1080
agcccagttt ttcaagatgt ttcttgttca atgttaaaag ttcctagtga acttgcggat  1140
tccaagttcc ttgagcataa tttatcacat gactggggca attccatgga agaagattgg  1200
cagtttaata gggatgacat acctaatatt tctcctccgg agtttattca ggaatcttca  1260
gggatttccg tgcactgttt aactggcaac gacaaccatg acatggtagc aactgctaat  1320
gtaggaaacg tggttgagga tccatataag cccaacgaaa tgtttgtttc tgtggacggt  1380
tccatgatgg tataccccga ggaaggaatt cctcaatgct ctccgtctga aactgggggtt  1440
aatggctgtg gtcaaccttc atattctttat ttttaccaat catcaaacta tcagatccct  1500
gaagcaggag atatggttcc acaaaactgc aatgctttaa attttgatga ttttgaagct  1560
tcattccatc agccattttc tgttccttca caatttttctt cagaggatag atcgtctgtg  1620
tttgacattg tttttaaatca gttccataat cctccgcttg aaggcccaga tcatatgaaa  1680
gattcctcaa ggatagttcc cgtgaatgat attggctcaa ctacatcaaa cactgttcaa  1740
acatgtctgc tgaatgaaaa ttcatttgta caagaagagc agaaagatgg aggagcttta  1800
tgctatgacc ctcctcgttt tccaagctcg gatgttcctt tcttttgttg tgatcttata  1860
caatctggtt cagatacaca ggaagagtat agcccttttg gcatccggca gttgatgatg  1920
acttcggcga actgccttac tccattaagg ttgtgggatt caccatcaag agatgatagt  1980
ccagatgcta tcttgaaaag tgctgccaaa acttttacag ggacaccttc tatactaaag  2040
aagcgacatc gtcatttact gtcgcctttg tcagaaaaga gatgtgagaa aaagcttgaa  2100
agcaatctca atcaggaatc attctataat atgtctacaa acttttcccg accagacgat  2160
atgtttgatg agtcagcaaa tgaaaaagca tctatggaag acaaagaaaa tctacatcca  2220
tcctcagaag atggaagaaa agaggagggc gaaatttctg gagccaatga tgcaacggga  2280
atggtaaaac agcatcctgg agtgctggtt gagcttagct caaatgactt gttctttttct  2340
cctgatcgtt tcttaatcaa gtgtgataga gctacaagtc taagtaataa agctctgggt  2400
aggcagtatg ctagacgact tgaagctgca tcaaatcaag ttactgtttc gtcctcttttt  2460
gaaacttcat gcttgtctgt tgtatgctct cctgacatat gtgggaagca tagaggcagt  2520
gttgtcatag ctacatcaac tgctttggag aatacagctg aagattctga aaatggatttt  2580
ggtgctgaga ctttaagcat atttggagag acaccttttta aaaggagttt tgaatctcct  2640
tcagcatgga aatctccatg gttcatgagt tcttttccgc caagcacaag atatgataca  2700
gaacttgaat ttgaggatct tgcccttttt atgagcccgg gtgacagaag ctatgatgct  2760
attgggttaa tgaagcaatt aagtgagcag acagcacctt caattgcaga tgcccatcag  2820
atcttgggaa gtgaaactcc agaaacaaac ttgtcgaaaa ggaattccaa aaaaccgaaa  2880
gcagatgaaa attgtaccct tctggcttca aatgctacga gtgagagacg aacactcgat  2940
tttaatgaat gtggaattcc aggaaaggga aaggaaacta ccaaatttgg cagcaacaac  3000
aacagctttt caagtccttc ctcctacctg ttgaaatatt gcagataa            3048
```

```
SEQ ID NO: 43              moltype = DNA  length = 3129
FEATURE                    Location/Qualifiers
source                     1..3129
                           mol_type = unassigned DNA
                           organism = Nicotiana tabacum
SEQUENCE: 43
atggaaagtg atagaataag cactccttca gatggcacta gcagtagtct ccaaagagtt   60
cggcctttgc atgggagaac tagtggtcct acgagacgtt caacaaaggg gcagtggact  120
actgaagaag acgagatcct acgcaaagct gtccaacgtt ttaagggcaa aaactggaaa  180
aaaatagcgg aatgttttaa agaccggact gatgtacaat gcttgcaccg gtggcagaaa  240
gttcttaatc ctgaacttgt caaaggtcca tggtctaaag aggaggatga agtaatagtt  300
gaattagtta agaaatatgg ccccaaaaag tggtccacca tcgctcaaca tttgccggga  360
cgtattggaa aacaatgtcg agaaaggtgg cacaatcatc tgaatcctgg aataaacaag  420
gaagcttgga cgcaggagga ggagttgact ctgattcgtg cccatcaaat ttacgggaat  480
aaatgggcag agttaacgaa gtatttgcct ggaaggacag ataatgcaat aaaaaatcac  540
tggaatagtt ccgtcaaaaa gaaattggac tcgtatttgg catcaggttt acttgcacag  600
ttccctgctt tgcctaatgt caaccgtcag aaccaatcaa tcccttcttc ggcgaagttg  660
caacagagta gtgaagatga tagtgttcgt aaagaaggaa ccgaaatgga ggaagcttca  720
gaatgcagtc aagggtcaaa tcttgctggc tgttcccagt ctacaagtga catgggcaac  780
aaatttgtac atacaagaga ggagggcaag ttgctggagg attcaaatta taggaaggac  840
ccaagctcca gttcagcacc atgctctgaa tactataccc cagcctttga agatattacc  900
tttttcaatgg cagaagtgcc tagtgaactt gacgaatcca agctcctgga gcataccttc  960
tcacatgact gggcagcatc cattggaaaa gaatggcaat ttaatccaga tgacatacct 1020
aatatttctc cgctggagtt gatgcaggat tcttcagggc tcttcatgca gtgtttaact 1080
ggtaatggga tcacgatat ggttacctttt ccacagcaaa atgcagtgaa gtttgaaacg 1140
actaatgtcg ggagcatggt tgtgggtttt gataagccca tgagatgtt tacctctgtg 1200
gagggttgca ggatggtata ccctgaggca ggaattccac aatacattcc ctctgaagct 1260
ggtacgaacg gtgctgatga aactgcagat tctttgattt gccaatcatc gaactatcag 1320
atctctgaag gtgaaatat gtctatagag aattgcaacc ctctctgttc agatgttatg 1380
ggaacttcat ccggccaacc attttccatt ccttcacagt tttcttcaga gcaaagctca 1440
ctcatgtttg gtactgccgc aaatcagttt cataatccat tgcagggaaa cccagcacag 1500
gagtcccaca caagtaactc tgatggtttt ctatatccct ttgaatctgg tactccttgt 1560
gacaacataa tggacgatcc tctcctggaa gagcaactgg atcaaactaa agattctcta 1620
cagctagttt ctgtcaatga ttttcgcaca actccttcaa atactattca aacatgtcca 1680
ttggtgaacg aaaattcgag catcccagta gagcagaagg atggaggagc cttatactat 1740
gagcctcctc gttttccgag cttggacatt ccattttttca gttgtgatct tatacaatct 1800
ggtacagatg cacagcaaga gtacagccct cttggcatcc gccagttgat gatgacttct 1860
gtgaactgtc ttactccatt taggctgtgg gattcaccat ctagagatgg aagtacagat 1920
```

-continued

```
gccgtcctga gaagtgctgc caaaactttc accagcacac cttctatatt aaagaagcga  1980
caccgtgatt tggtgtcacc tttgtcagaa aagagatgtg aaaagaagct tggaagtgat  2040
ttccgtcaag aatcattctc tgatctgtct aaggattttt ctcgactaga tgttatgttt  2100
gacgaggctg caaatgaaaa agcaacaaag tcttctctaa ctacggatca aacattggaa  2160
cttgaagctt catctgaaga taaagaaaac ataaatccaa ctgaagatgg aagtaaggag  2220
gaggacaagg tacgtaatgg actttccaac gagagacagt tagatggagg tgaagttcac  2280
tataaagaga aaggaacaag ggagggcaca aagggtggag ccaatagtgc aattggaaag  2340
ataaaacaac cttctggagt tctggttgaa ctgaacgcaa gtgacctgtt cttctctcct  2400
gatcgttttg gagccaagtc tggtagagct acatatctca gcactaaagc tctaggaaat  2460
cagtacgcta gacgactcga agctgcatca aatcaaggtt ctgtttcatc ttcatttgag  2520
acttcatgtt tttctgttat ttgctctcct cgtatacgtg gaaagaaaga cggaagtagt  2580
tttatcatca ctacatcaat gcaatctgct ccagcaccaa cagccttgga caactcagct  2640
gaaacttcag gaaatggagt tggcgcggag actgtaagca tatctggaga aacgccttat  2700
aaaaggagta ttgaatctcc ttcagcttgg aaatctccat ggttcatcaa ctctcttctg  2760
tcaagcccaa gacttgataa tgaacttaat tttgaggatc ttgcactgtt tatgagtcca  2820
ggtgacagaa gctatgatgc tattggattg atgaagcaat tgagtgagca gactgcaggg  2880
gcatttgcag acgcacagga ggtcttggga ggtgaaactc cagagtcaat cctacggggg  2940
aggaactcca aaaaccagaa agcagatgaa aatcattcac ttttgtctgc aaatgttatg  3000
agtgagaggc gtactcttga tttcagtgaa tgtggatcac ctggaaaggg aaaggaaact  3060
gaaaatttt gcacgagcaa caacagcttt tcaagtcctt cctcctacct attgaaaggc  3120
tgcaggtag                                                          3129
```

```
SEQ ID NO: 44             moltype = DNA   length = 954
FEATURE                   Location/Qualifiers
source                    1..954
                          mol_type = unassigned DNA
                          organism = Nicotiana tabacum
SEQUENCE: 44
atgggaagag ctccttgctg tgacaaaaac aacgttaaga gagggccatg gtcgcctgaa  60
gaagattcta agttgaagtc atatattgaa cagaatggga caggtggcaa ctggattgct  120
ttgcctccaa aaattggcct aaatagatgt ggaaagagct gtaggcttag atggttaaat  180
tatctgcgtc caaatattaa gcatggaggg ttctcagaag aagaagatag aatcatttgc  240
agcctctaca taagtattgg aagcaggtgg tcaataattg cagcacaact ccctggaaga  300
acagataatg atataaagaa ctactggaac actaggctga agaagaagct atttggaaag  360
cagcgccaaa agcaaggatc aagaaaagga aaagaaatca actccaatat ggtaatttcc  420
aataacaata caacaaccca attcccatgt tggcctgagc ttcccatctt gcagccaata  480
ccatactcta atgatgaacc aagatttaat gaccattctt ccataagaaa actgttgata  540
aaacttggag gtaaattttc agacgaagat caaccgataa atgaagcaac aaatcctcaa  600
tatcctatgg ataattcatt attgatgcag ccgatatatc agaatattcc tatcaatatg  660
atctcttctg ctccaataga taatgtcttg ggaaatgctc aatacaacat ggataggca  720
gctagcagtt ttacagctga gcttgagcat atgattcaaa ataatcaaca aaaattggac  780
ggtcttgaat ttttatatga ggattatatg cttattgata aatctgcgtc tacttctgga  840
ggaaacttgg actgggaatc gatgaatcct tttgtacttc ctcttcctcc tataaatgat  900
gaaggttttc aacaaggtgt tatatttcaa gagaataata ctatggcaca ataa         954
```

```
SEQ ID NO: 45             moltype = AA   length = 303
FEATURE                   Location/Qualifiers
source                    1..303
                          mol_type = protein
                          organism = Nicotiana tabacum
SEQUENCE: 45
MEKYEKLEKV GEGTYGKVYK AKDKATGQLV ALKKTRLEMD EEGIPPTALR EISLLQMLSN  60
SLYIVRLLCV EQIDKNGKPL LYLVFEYLDT DLKKFVDSHR KGPNPRPLPP SLIQSFLYQL  120
CKGVAHCHSH GVLHRDLKPQ NLLVDKEKGI LKIADLGLGR AFTVPIKSYT HEIVTLWYRA  180
PEVLLGSTHY STAVDMWSVG CIFAEMVRRQ ALFPGDSEFQ QLLHIFRLLG TPTEKQWPGV  240
SSLRDWHVYP KWEPQNLASA VPALGPDGVD LLTKMLQYDP ADRISAKAAL DHPYFDSLDK  300
SQF                                                                303
```

```
SEQ ID NO: 46             moltype = AA   length = 285
FEATURE                   Location/Qualifiers
source                    1..285
                          mol_type = protein
                          organism = Nicotiana tabacum
SEQUENCE: 46
METVKKSASA MEAFEKLEKV GEGTYGKVYR ARDRVTGKIV ALKKTRLHED EEGVPPTTLR  60
EISLLRMLSR DPHIVKLMDV KQGQNKEGKT VLYLVFEYMD TDVKKFIRSF RANGENIPPK  120
TVKSLMYQLC KGVAFCHGHG VLHRDLKPHN LLMDRKTNVL KLADFGLGRA YTLPIKKYTH  180
EILTLWYRAP EVLLGATHYS TAVDMWSVGC IFAELVTKQA LFPGDSELQQ LLHIFRLLGT  240
PNEELWPGVS KLVNWHEYPQ WNPQPLSTAV PGLDEDGLHL LTVSV                   285
```

```
SEQ ID NO: 47             moltype = AA   length = 312
FEATURE                   Location/Qualifiers
source                    1..312
                          mol_type = protein
                          organism = Nicotiana tabacum
SEQUENCE: 47
METVKKSASA MEAFEKLEKV GEGTYGKVYR ARDRVTGKIV ALKKTRLHED EEGVPPTTLR  60
EISLLRMLSR DPHIVKLMDV KQGQNKEGKT VLYLVFEYMD TDVKKFIRSF RANGENIPPK  120
TVKSLMYQLC KGVAFCHGHG VLHRDLKPHN LLMDRKTNVL KLADFGLGRA YTLPIKKYTH  180
```

```
EILTLWYRAP EVLLGATHYS TAVDMWSVGC IFAELVTKQA LFPGDSELQQ LLHIFRLLGT   240
PNEELWPGVS KLVNWHEYPQ WNPQPLSTAV PGLDEDGLHL LSEMLHYEPA KRISAKKAME   300
HPYFDDLDKT PL                                                       312

SEQ ID NO: 48              moltype = AA   length = 303
FEATURE                    Location/Qualifiers
source                     1..303
                           mol_type = protein
                           organism = Nicotiana tabacum
SEQUENCE: 48
MEKYEKLEKV GEGTYGKVYK AKDKATGQLV ALKKTRLEMD EEGIPPTALR EISLLQMLSH   60
SLYIVRLLCV EQIDKNGKPL LYLVFEYLDT DLKKFVDSHR KGPNPRPLPP SLIQSFLYQL   120
CKGVAHCHSH GVLHRDLKPQ NLLVDKEKGI LKIADLGLGR AFTVPIKSYT HEIVTLWYRA   180
PEVLLGSTHY STAVDMWSVG CIFAEMVRRQ ALFPGDSEFQ QLLHIFRLLG TPTEKQWPGV   240
SSLRDWHVYP KWEPQNLASA VPALGPDGVD LLTKMLQYDP ADRISAKAAL DHPYFDSLDK   300
SQF                                                                303

SEQ ID NO: 49              moltype = AA   length = 73
FEATURE                    Location/Qualifiers
source                     1..73
                           mol_type = protein
                           organism = Nicotiana tabacum
SEQUENCE: 49
MEGVDSDCEV VEEGCMTPRR DTCRIMVNSL CPPPPPKKKR VYVKQQRPPP KEGYFQPPDL   60
ELFFAIVRRE ACA                                                     73

SEQ ID NO: 50              moltype = AA   length = 533
FEATURE                    Location/Qualifiers
source                     1..533
                           mol_type = protein
                           organism = Nicotiana tabacum
SEQUENCE: 50
MQSLIFSGEK NMIAAYLFIP LELHRNVIQV CHRVQRTFCS MRHANIKHGS FHLEEHNMRI   60
TRARARVSGS SGRLPPLHPS TKQDKKQALG AESKRSKRSA SDENRPGTSS IATGVQPKRR   120
AVLKDMKNVL HENSHMNCIN GSKIQVKKGS DKRNNKAKPA VSLKLSQLQE KGKEDIADKV   180
KKVKVEGSQE ISSGANCKED MLPQLSRYVT PAQCGLVHLV PVNRSSCKAF PLQNVMKKDE   240
SKVCQKQEGF ANLGIADIDS RHKDPLMCSL YAPDIYNNLH AIEFDRRPSV DYLEKLQLDI   300
NKGMRGILID WLVEVSEEYR LVPDTLYLTV NLIDRFLSEN YIEKQKLQLL GVTCMLIASK   360
FEEICAPRVE EFCFITDNTY SKEEVIKMES RVLNLLSFQL ASPTTKKFLR RFIQAAQASY   420
KVPSVELEFM ANYLAELTLV DYGFLKFLPS LTAASAVFLA RWTLDQSNHP WNPTLEHYTR   480
YKVSELRTTV FALQELQMNT SGCTLNAIRE KYRQPKFKSV ATLAASKPVQ SLF          533

SEQ ID NO: 51              moltype = AA   length = 414
FEATURE                    Location/Qualifiers
source                     1..414
                           mol_type = protein
                           organism = Nicotiana tabacum
SEQUENCE: 51
MDISDENQFT RKSLVGEAGM GNSKIGVETR HNRRALRVIN QNLLGPNPYR CVVNKRRLSH   60
ANGIIYDKNP TRKLTAQIAS SHQHYPEETK KPKLAAEDFR IWEEHVAAKD QPMSMSLEQE   120
ATFSNDKTEM EVEMEDIFEE ALIDIDSDDT NNPLAVVDYV EDLYANYRKM EGYSCVSPNY   180
MTQQFDINER MRATLVDWLI EVNHKFELRE ETLFLTVNSI DRFLEKQIVA RKKLQLVGLV   240
AMLLACKYEE VSVPVVDDLV IISDNAYTRK EVLEMETLML DTLQFNMSVP TAYVFMRRFL   300
KAAQADRKLE VLSFFLIELC LVEYEMLKFP PSFMAAAAIY TAQCTLYGVM QWSKTCEWHT   360
SYSEDQLLKC SRSIVIYHQK AATGKLTGVH RKYSTSKFGY AAKFEPALFL VQIK          414

SEQ ID NO: 52              moltype = AA   length = 436
FEATURE                    Location/Qualifiers
source                     1..436
                           mol_type = protein
                           organism = Nicotiana tabacum
SEQUENCE: 52
MAISDENNPT MVKPTNVQGG AGMGTRKFGG VETRNNRRAL GVINQNLVGG THPFPCVVNK   60
RGLSEANGIC DKNLQIPAHR PITRKFAAQI ASSQQNRSEE NKKAKIAAEE FSIWEDIPLT   120
DVEENEAAKD QPVPMSLEQT ETVTNDKNQM EVEMEDIFEE TIIDIDGDDA KNPLAVVEYV   180
QDLFASYRKM EGCSCVSPDY MAQQFDINEK MRSILIDWLI EVHHKFELRE ETLFLTVNLI   240
DRFLEKQGVV RKKLQLVGLV AMLLACKYEE VSVPLVDDFV FISDKAYSRK EVLEMERMML   300
NTLQFNMSVP TAYVFMRRYL KAAQSDRKLE LLSFFLVELC LVEYEMLKFP PSFIAAAAIY   360
TAQTTLYGVQ QWSKTCEWHT SYSEDQLMEC SRSIVSYHQK AATGKLTGVH RKYSTSKFGY   420
AAKCEPAHFL VQTQQQ                                                   436

SEQ ID NO: 53              moltype = AA   length = 143
FEATURE                    Location/Qualifiers
source                     1..143
                           mol_type = protein
                           organism = Nicotiana tabacum
SEQUENCE: 53
MEKRILGQLE WYLTVPTPYV FLVRYIKAAV SNAQMENMVY FLAELGLMNY ATNIYCPSMI   60
AASAVYVAQH TLNCTPFWND TLKLHTGFSE SQLLGCAKLL VSYHMEAPEH KLKVIYKKYS   120
```

```
KPERGAVALQ PPAKSLLAAS SYE                                              143

SEQ ID NO: 54            moltype = AA  length = 301
FEATURE                  Location/Qualifiers
source                   1..301
                         mol_type = protein
                         organism = Nicotiana tabacum
SEQUENCE: 54
MASRNVLQQQ NIGEAVPGAL KQKNMAAAAQ GRNRKALGDI GNNMVTVRGV EGKPLPQRPI       60
TRGFCAQLLA NAQAAAENQK KSMVVNGDAP IVAKGVLPVK GAAKKPVQKK AAVKPKPDVI      120
EISPDTEEQV KENKQKKKAG DDSSVKKATL TSTLTARSKA ACGLSHKPKV QIVDIDAADV      180
NNELAVVEYV EDIYNFYKIA ENESRIHDYM DSQPEITARM RAILIDWLIE VHHKFELSQE      240
TLYLTINIVD RYLAVTTTSR RELQLVGMSA MLIASKYEEI WAPEVHFKSN YAKLLSHFES      300
C                                                                     301

SEQ ID NO: 55            moltype = AA  length = 473
FEATURE                  Location/Qualifiers
source                   1..473
                         mol_type = protein
                         organism = Nicotiana tabacum
SEQUENCE: 55
MASRIVLQQQ NRGEAVPGAV KQKKNMAPEG RNRKALGDIG NVATGRGLEG KKPLPQKPVA       60
VKVKGANVAK VPAARKPAQK KATVKPNPED IIEISPDTQE KLKEKMQRKK ADKDSLKQKA      120
TLTSTLTARS KAACGLSKKP KEQVVDIDAA DVNNELAVVE YVEDIYSFYK LAENETRVHD      180
YMDSQPEIND RMRAVLIDWL VEVHQKFELN PETLYLTINI VDRYLAVKTT SRRELQLLGI      240
SAMLIASKYE EIWAPEVNDF VCISDKSYTH DQVLAMEKEI LGQLEWYLTV PTPYVFLARF      300
IKASLPDSEI ENMVYFLAEL GLMNYATIIY CPSMIAASAV YAARHTLNRT PFWNETLKLH      360
TGFSESQLIE CARLLVSYQS AAATHKLKVI YKKYSSPERG VVSLLTPAKS LLAASSSSVL      420
SEQADLRKST EAAATSSSKM VVVGCQRCHM YVMVTEADPR CPQCKSTTTR KMT            473

SEQ ID NO: 56            moltype = AA  length = 535
FEATURE                  Location/Qualifiers
source                   1..535
                         mol_type = protein
                         organism = Nicotiana tabacum
SEQUENCE: 56
MSRACSLVQE YYDCCFLFIQ SSRIVVERNA VVAQIIGISP PGSMRNANMT IGSSNLKEPT       60
MRITRSRAKA LGSSGGLPPR HPSVRQDNKQ GLGAQGTKYK RSASDENNPV TNASTACQQP      120
KRRAVLRDVT NVLCENSYMN CINRSKFQVK KFSDTRNSKV TPAILVKRPH NEDRKENTIE      180
EAKKVKIEKS QEHCSQARFK DLTLTHPSKY ITPAQCGFVD LMPVNRSLPT AIAVPNTTEK      240
DETKVCQKQE GSDSLGIADI DSKHKDPLMC SLYAPDIYSN LHAMELDRRP SFNYMEKLQR      300
DVNKGMRGIL IDWLVEVSEE YRLVPDTLYL TVHLIDRFLS ENYIEKQKLQ LLGVTCMLIA      360
SKYEEICAPR VEEFCFITDN TYSKEEVVRM ESLVLNFLGF QLAAPTTKKF LRRFVQAAQA      420
SYEVPSVELE FMANYLAELT LVDYSFLKFL PSITAASAVF LAKWTLDQSN HPWNPTLEHY      480
TSYTALELKT TVLLLQDLQL NTSGSTLNAI REKYRQPKFK SVATLSSPEP VQSLF          535

SEQ ID NO: 57            moltype = AA  length = 730
FEATURE                  Location/Qualifiers
source                   1..730
                         mol_type = protein
                         organism = Nicotiana tabacum
SEQUENCE: 57
MGKLNSQKHI STIKDGVTEL KVYEEADKIK IQSRDSLSRR CKGMSGAPNM SDVQTSRKSS       60
ESDIKHIERI KAKCSTSVKV NVKRKVLTDI SNIRGNSSRT KSYNSSKLLV SNGKCPKNAS      120
NSARKFIMGN VRPNLNGATG DKQILTRAPF KDTKASFDGR KTRIQGRKSV TTGIRPTGRN      180
DLPPSRRSLP ILQQVNIEGT DNKEKGKVRA NLNKATDDKQ ILTQAPRKDM KASFDGPKTR      240
IQVRKSVTTG IRRTGRNALP PSRRSLPILQ QVNVEDTNNK EKVNSKKLEK GKGISGVSVL      300
AKPKAAGDVL PQLSNHSNIR RNRVGDASAR MAPRGQAKVE VGALRRKSVR TVLKITASSL      360
NSQKCSKSNS MSGVHKCTSR VSIPCKRLVD VRTSSLSKYA TSEISAEQPH QKEVPSSSSG      420
SLATPELSIA RRKSDRRKSF TCLLMARSKL MKELCGNVEL DNLSNIYDSC NHLEVTEYVD      480
DIYQYYWVIE AQNQPIKNYM ETQKEITPQM RGILINWLIE VHLKFDLMQE TLFLMVTLLD      540
YYLSLARVKK NDLQLVGLTS LLLASKYEDL FHPRVMDLLS ISAESYTRDQ MLEMEKDILR      600
KLKFRLNAAT PYVFMLRLLK AAQADTRFEH LAFYLIELCL VEYEALNYKP SMLCASAIYV      660
ARCTMQMTPA WTPLLGIHGR YQESQFRHCA EMILRFHKAA STALLKVTHE KYMQSSNSKV      720
AAIKPLQSLP                                                            730

SEQ ID NO: 58            moltype = AA  length = 441
FEATURE                  Location/Qualifiers
source                   1..441
                         mol_type = protein
                         organism = Nicotiana tabacum
SEQUENCE: 58
MVGSDENFSG VMRASNLQGG LRPGVGGGKL TAGVGQNRRA LSTINRNVIG APPLPYAVNK       60
RNGISDNKAN AANKIPSVPI HRPITRKLAA QIASKQQQPA VEVTKPPVPV APNRNGSEDC      120
IIIDAEEYKA AGDSSVPMFV QHTEAMMEEI DRMDEEIEME DVEDWPIVDI DSADKKNTLA      180
VVEYIDDIYA YYKKTEVLSC VPPNYMEQQI DVNERMRAIL IDWLIEVHYK FELMEETLYL      240
TVNLIDRFLA VQSVIRKKLQ LVGITAMLLA CKYEEVSVPV VEDLILISDK AYTRKEVLDM      300
EKLMVNTLQF NVTVPTAYVF IRRFLKAALS DKKVELMSFF LIELCLVEYE MLKFPPSMLA      360
AASIFTAQCT LGVSKEWNKT CEKHSSYAKN QLLECSRLMV SFHQKAASGK LTGVHRKYST      420
```

```
CKYGYAARCE PASFLLEAAW F                                              441

SEQ ID NO: 59              moltype = AA  length = 483
FEATURE                    Location/Qualifiers
source                     1..483
                           mol_type = protein
                           organism = Nicotiana tabacum
SEQUENCE: 59
MATTQNRRSS VSSATAKRQA MTANSSLENN NHGKLVAKKR PALTNISNHT TASARNSLSH   60
SSKLAPCTSK AVSIKKSNSN AASSVLPTSS FVKPISKTVS IPRSDAAIPK ITAIPLPATC   120
SMDISPSHSD GSLVSMDETM STSDSLRSPD VEYIDDNQTA AFDSIEKKAF STLYISEDVK   180
AADICKRDVL VDIESGDKIA NIDNNFVDPQ LCATMACDIY KHLRATEVKK RPSTDFMEKV   240
QKDINASMRA ILIDWLVEVA EEYRLVPDTL YLTVNYIDRY LSGNLMDRQR LQLLGVACMM   300
IASKYEEICA PQVEEFCYIT DNTYFKEEVL QMESTVLNYL KFEMTAPTAK CFLRRFVRAA   360
QGLNEVLSLQ LEHLASYIAE LSLLEYNMLC YAPSVIAASA IFLAKYILLP SKKPWNSTLR   420
HYTLYQPSDL RDCVVALHSL CCNNNNSSLP AIREKYSQHK YKFVAKKYCP PTIPVEFFQN   480
ISC                                                                 483

SEQ ID NO: 60              moltype = AA  length = 412
FEATURE                    Location/Qualifiers
source                     1..412
                           mol_type = protein
                           organism = Nicotiana tabacum
SEQUENCE: 60
MGVSNENNPT MIKPTNVQGE AELGCRKFGM ETRNNRRALS VINQNFVGAK PYPCVVNKRV   60
LSEANGICNK NPPVPAHRPI TRKFAAQIAN SKQHYPEENK KPKIAAEGLS VYEDVPIIDV   120
EEYEAAAKDQ PVPMSLEQTQ MEIEMEDIFE ESVIDIDSND AKNTLAVVDY VEDLYAYYSK   180
MEGCNRIPPD YIGQQFDINE RMRSILIDWL IEVHHKFDLR EETLFLTVNL IDRFLEKQSV   240
VRKKLQLVGL VAMLLACKYE EVSLPVVDDL VVISDKAYTR KEVLEMEKLM LNTLQFNMSL   300
PTPYVFMRRF LKAAQSDRKL ELLSFFLIEL CLVEYEMLKF PPSFIAAAAI YTAQCTLYGV   360
KQWSKTCELH TKYSADQLLE CSRLIVEFHQ KAATGKLTGD LYSKQNPENK EE           412

SEQ ID NO: 61              moltype = AA  length = 439
FEATURE                    Location/Qualifiers
source                     1..439
                           mol_type = protein
                           organism = Nicotiana tabacum
SEQUENCE: 61
MVGSDENCQG VIMASNVQGA GGGKVTMGHN RRALSTINGN IVEAPAYPCK VHKRNGITDK   60
SANGVKNPPI PIHRPVTSMG DSCCFRKFAA QMATKLQQPT VTKQPVQTAT DRNESEDRII   120
IDVEDYKATS DYDPVPMFVQ HTEAMMEEID RMDAETEMED VEETLIVDID SADKKNPLAV   180
VEYIDDMHAY YKKTESSSCA PPNYMEQQFD INERMRAILI DWLIEVHYKF DLMEETLYLT   240
VNLIDRFLAV QQVIRKKLQL VGVTAMLLAC KYEEVSVPVV EDLILISDKA YTRKEVLEME   300
KLMINTLQFN LSVPTAYVFM MRFLKAAQSD KKVELLSFFM TELCLVEYEM LRFPPSMLAA   360
AAIFTAQCAL SAPNELSKTC EKYSHYTQDQ LLECSRLMVS FHQKAAIGKL TGVYRKYSIS   420
KYGFVAKCPP ASFLLEACF                                                439

SEQ ID NO: 62              moltype = AA  length = 367
FEATURE                    Location/Qualifiers
source                     1..367
                           mol_type = protein
                           organism = Nicotiana tabacum
SEQUENCE: 62
MADQENCVRV TRLAKKRAAE AMVQHLQQPN KKRVVLGEIR NLSNQIQMFD SEPLKPKCNK   60
QTTKRKVKRS VSVKEREFRE EDVDSKLDDD PQMCSAYVSD IYEYLHQMEI EKKRRPLSDY   120
LEKVQKDVTA NMRGVLVDWL VEVAEEYKLL SDTLYLAVAY IDRYLSIKVI PRQRLQLLGV   180
SSMLIASKYE EIKPPRVEDF CYITDNTYTK KDVVKMEADV LQSLKFEMGN PTTKTFLRRF   240
TRVAQEDCKN SNLKLEFLGC YLAELSLLDY NCVKFLPSLV AAAVIFLSRF TLQPKLHPWS   300
VGLEQNSGYR AADLKECVLI IHDLQLSRRG GSLVAARNKY KQHKFKYVST LSSPLEIPDS   360
FFEDTRQ                                                             367

SEQ ID NO: 63              moltype = AA  length = 482
FEATURE                    Location/Qualifiers
source                     1..482
                           mol_type = protein
                           organism = Nicotiana tabacum
SEQUENCE: 63
MATTQNRRNS VSSAVAKRQA MAENNHGKLP AGGAKKRPAL TNISNHTTAS ARNSLSHSSK   60
LAPCTSKVVS IKKNNSNAAS SVLPTSSSFV KPISKTVSLP RSDAAVPKIT AIPPLPSTCS   120
MDISPSHSDG SLVSMDETMS TSNSLRSPDV EYIDDNQTAA FDSIEKKAFS TLYISEDVKA   180
ADICKRDVLV DMESGDKIAN IDNNLVDPQL CATMACDIYK HLRATEVKKR PSTDFMEKVQ   240
KDINASMRAI LIDWLVEVAE EYRLVPDTLY LTVNYIDRYL SGNLMDRQRL QLLGVACMMI   300
ASKYEEICAP QVEEFCYITD NTYFKEEVLQ MESTVLNYLK FEMTAPTAKC FLRRFVRAAQ   360
GLNEVLSLQL EHLASYIAEL SLLEYNMLCY APSVIAASAI FLAKYILLPS KKPWNSTLRH   420
YTLYQPSDLR DCVMALHSLC CNNNNSSLPA IREKYSQHKY KFVAKKYCPP TIPVEFFQNI   480
SC                                                                  482

SEQ ID NO: 64              moltype = AA  length = 384
FEATURE                    Location/Qualifiers
```

```
source                    1..384
                          mol_type = protein
                          organism = Nicotiana tabacum
SEQUENCE: 64
MKKQEKEAIM ADLENCGRVT RLAKKRAAEA MASHQQQHPS KKRVVLGEIQ NFSNLGVSQI    60
KGLNTEPKKQ PKSKQQQSKR KLKRAVTSKI DKEELNVDNV DANYDDPQMC SAYVSDIYDY   120
LRKMEIEEKR RPLPDYLEKV QKDLSPNMRG VLVDWLVEVA EEYKLLSDTL YLAVSYIDRF   180
LSTNVITRQK LQLLGVSSML ISAKYEEISP PHVEDFCYIT DNTYTKEEVV KMEADVLKTL   240
NFEMGNPTVK TFLRRFTGVA QEDYKTPNLQ LEFLGYYLAE LSILDYSCVK YVPSLLAAAV   300
VFLSRFTLQP NTHPWSLALQ QYSGYKAADL KECILILHDL QLSRRGGSLA AVRDKYKQHK   360
FKCVSSLTSP VEIPASFFED MRQL                                          384

SEQ ID NO: 65             moltype = AA   length = 441
FEATURE                   Location/Qualifiers
source                    1..441
                          mol_type = protein
                          organism = Nicotiana tabacum
SEQUENCE: 65
MVGSDENFSG VMRASNLQGG LRPVVGGGKL TAGVGQNRRA LSTINRNVIG APPLPYAVNK    60
RNGISDNKAN AANKIPPVPI HRPITRKLAA QIASKQQQPA VEVTKPPVPL APNRNESEDC   120
IIIDAEEYKA TGDSSVPMFV QHTEAMMEEI DRMDEEIEME DVEDCPIVDI DSTDKKNTLA   180
VVEYIDDIYA YYKKTEVLSC VPPNYMEQQI DVNERMRAIL IDWLIEVHYK FELMEETLYL   240
TVNLIDRFLA VQSVIRKKLQ LVGITALLLA CKYEEVSVPV VEDLILISDK AYTRNEVLVM   300
EKLMVNTLQF NVTVPTAYVF MRRFLKAAQS DKKVELMSFF LIELCLVEYE MLKFPPSMLA   360
AAAIFTAQCT LGVSKEWNKT CEKHSSYAKD QLSECSRLMV SFHQKAASGK LTGVHRKYST   420
SKYGYAARCE PASFLLEAAW F                                             441

SEQ ID NO: 66             moltype = AA   length = 404
FEATURE                   Location/Qualifiers
source                    1..404
                          mol_type = protein
                          organism = Nicotiana tabacum
SEQUENCE: 66
MKGGEAEMGN NKFDFGVETR HNRRALRVIN QNLLGPNPYR CVVNKRGLSH ANGIIYDKNP    60
TRKLTAPIAS SHQHYPEETK KPKLAAEDFR IWEEHVAAKD QLMPMSLEQE ATFSNDKTEM   120
EIQMEDIFEE ALIDIDSDDA KNPLAVVDYV NDLYPNYRKM EGYSCVSPNY MTQQFDINER   180
MRAILVDWLI EVHHKFELRE ETLFLTVNSI DRFLEKQTVA RKKLQLVGLV AMLLACKYEE   240
VSVPVVDDLV IISDNAYRRK EVLEMETLML NTLQFNMSVP TAYVFMRRFL KAAQADKKLE   300
VLSFFLIELC LVEYEMLKFP PSFMAAAVVY TAQCTLYGVK QWNKTCEWHT SYSEDQLLEC   360
SRSIVSYHRK AATGKLTGVH RKYSTSKYGY AAKYEPALFL VQIQ                    404

SEQ ID NO: 67             moltype = AA   length = 437
FEATURE                   Location/Qualifiers
source                    1..437
                          mol_type = protein
                          organism = Nicotiana tabacum
SEQUENCE: 67
MAISDENNPT MIKPTNVQGG AGMGTRKFGG VETRNNRRAL GVINQNLVGG AHPFPCVVNK    60
RGLSEANGRC DKNLPIPAHR PITRKFAAQI ASSHQHRSEE NKKAKIASEE FSIWEDIPLT   120
DVEENEAAKD QPVPMSLELT ETVPNDNKNQ MEVEMEDILE ENIIDIDGDD AKNPLAVVEY   180
VQDLFASYRK MEGCSCVSPD YMAQQFDINE RMRSILIDWL IEVHHKFELR EETLFLTVNL   240
IDRFLEKQGV VRKKLQLVGL VAMLLACKYE EVSVPLVEDL VFISDKAYSR KEILEMERMM   300
LNTLQFNMSV PTAYVFMRRY LKAAQSDRKL ELLSFFLVEL CLVEYAMLKF PPSFIAAAAI   360
YTAQTTLYGV QQWSKTCEWH TSYSEDQLME CSRSIVSYHQ KAATGKLTGV HRKYSTSKFG   420
YAAKCEPAHF LVQTQQQ                                                  437

SEQ ID NO: 68             moltype = AA   length = 726
FEATURE                   Location/Qualifiers
source                    1..726
                          mol_type = protein
                          organism = Nicotiana tabacum
SEQUENCE: 68
MGKLNSQKHI STIKDGVTEL KVYEEVDKIK IQSRDSLSRR CKGKSGAPNM SDVQTSWKSS    60
ERGIKHIERI KAKCRTCVKV NVKRKVLTDI SNIRGNSSRT KSYNSSKLLV SDGKCPKNAS   120
NSARRFIMGN VRTNLNGATG DKQILTRDMK ASFDGPKTRI QGRKSVTTGI RPTGRNDLPP   180
SRRSLPILQQ VNIEGTNNKE KGKVRANLNK ATDDKQILTQ APRKDMKASF DGPKTRIQVR   240
KPVTTGIRRT GRNALPPSRR SLPILQQVNV EDTNNKEKEN SKKLEKGKGI SGVSVLAKPK   300
AAGDVLPQLS NHSNIRRNRV GDASARMAPR GQAKVEVGAL RRKSVRTVLK ITASGLNSQK   360
SSKSNSMSGV HKCTSRFASP CKRLVDVRTS SLSKSATSEI SAEQPHQKEV PSSSSGSLAT   420
PELSIARKKS DRRKSFTCLL MARSKLMKEL CGTVELDNLS NIYDSCNHLE VTEYVDDIYQ   480
YYWVIEAQNQ PIKNYMETQK EITPQMRGIL INWLIEVHLK FDLMQETLFL MVTLLDDYYLT  540
LARVKKNDLQ LVGLTSLLLA SKYEDLFHPR VMDLLSISAE SYTRDQMLEM EKDILRKLKF   600
RLNAATPYVF MLRLLKAAQA DTRIEHLAFY LIELCLVEYE ALNYKPSMLC ASAIYVARCT   660
MQMTPAWTPL LGMHARYQES QLRHCAEMIL RFHKAASTAL LKVTHEKYMQ SSNSKVAAIK   720
PLQSLP                                                              726

SEQ ID NO: 69             moltype = AA   length = 425
FEATURE                   Location/Qualifiers
source                    1..425
```

```
                           mol_type = protein
                           organism = Nicotiana tabacum
SEQUENCE: 69
MDNNSVGVPH NLPRGEMGGK QKNAQADGRN RRALGDIGNL VPAPAAEGKP KAAQISRPVT     60
RSFCAQLLAN AQEEKNKKPL AEVVNKDVPA KKKASDKEMK TVGGSPLSKR KAKKSGKTLT    120
STLTARSKAA CGLSNRPKYE IEDIDVADAD NHLAAVEYVE DIYNFYKLTE GESRVDDDYM    180
NFQPDLNHKM RAILVDWLIE VHRKFELMPE SLYLTITILD RFLSLKTVPR KELQLVGISS    240
MLIACKYEEI WAPEVNDFIH ISDNAYAREQ ILQMEKAILG KLEWYLTVPT PYVFLVRYIK    300
AATPSDNQEM ENMTFFFAEL GLMNYKITIS YRPSMLAASS VYAARSTLNK TPLWTQTLQH    360
HTGYSEDQLM ECAKILVSYH LDAAESKLKA IYRKFSSPDR GAVAFFPPAR NLLPTTTTDA    420
ASSSS                                                                425

SEQ ID NO: 70              moltype = AA   length = 436
FEATURE                    Location/Qualifiers
source                     1..436
                           mol_type = protein
                           organism = Nicotiana tabacum
SEQUENCE: 70
MVGSNENCQG VIMASNVQGG LGAGGGKVTM GPNRRALSTI NGNIVEAPAY PCKVHKRNGI     60
TDKSANGVKN PPIPIHRPIT RKFAAQMATK QQQPTVEVTK QPVQTAPAKN ESEDCIIIDA    120
EDYKATSDYD PVPMFVQHTE AMMEEIDRMD AEMEMEDVEE TLIVDIDSAD KKNPLAVAEY    180
IDDMHAYYKK TESSSCAPPN YMEQQFDINE RMRAILIDWL IEVHYKFDLM EETLYLTVNL    240
IDRFLAVQQV IRKKLQLVGV TAMLLACKYE EVSVPVVEDL ILISDKAYTR KEVLEMEKLM    300
INTLQFNLPV PTAYVFMMRF LKAAQSDKKV ELLSFFMTEL CLVEYEMLRF PPSMLAAAAI    360
FTAQCTLGVL NEWSKTCEKY SHYTRDQLLE CSRLMVSFHQ NAATGKLAGV HRKYSISKYG    420
FVAKCPPASF LLEASF                                                    436

SEQ ID NO: 71              moltype = AA   length = 422
FEATURE                    Location/Qualifiers
source                     1..422
                           mol_type = protein
                           organism = Nicotiana tabacum
SEQUENCE: 71
MGVSNENNPS MIKPRNVQGG AELGYRKFGV ETRNNRRALS VINQNFVGAK PYPCVVNKRG     60
LSDTNKNPPV PAHRPITRKF AAQIANSKQH YPEENKKPKI AAEGLSVYED VAIVDVEEYE    120
AAAKDQPVPM SLEQTQMEIE MEDTFEESVI DIDSNDAKNP LAVVDYVEDL YAYYSKMEGC    180
SRISPDYIGQ QFDINERMRS ILIDWLIEVH HKFDLKEETL FLTVNLIDRF LEKQSVVRKK    240
LQLVGLVAML LACKYEEVSL PVVDDLVVIS DKAYTRKEVL EMEKLMLNTL QFNMSVPTPY    300
VFMRRFLKAA QSDKKLELLS FFLIELCLVE YEMLKFPPSF IAAAAIYTAQ CTFYGVKQWS    360
KTCELHTKYS EDQLLECSRL ITGFHQKAAT GKLTGVHRKY NTSKFGYVAK CEPAHFLLVQ    420
TR                                                                  422

SEQ ID NO: 72              moltype = AA   length = 492
FEATURE                    Location/Qualifiers
source                     1..492
                           mol_type = protein
                           organism = Nicotiana tabacum
SEQUENCE: 72
MRNANMTIGS SNLKEPTMRI TRSRAKALGS SGGLPPRHPS VRQDNKQGLG AKGTKYKRSA     60
SDENNPVTNA STACQQPKRR AVLRDVTNVL CENSYMNCIN RSKFQVKKFS DKRNSKVTPA    120
ILAKRPHHED TKENTIEEAK KVKIEKSQEH CSQARFKDHT LTQPSKYITP AQCGFVDLMP    180
VNRSLPTAIA VLNTTEKDET KVCQKQEGSD SLGIADIDSK HKDPLMCSLY APDIYSNLHA    240
MELDRRPSFN YMEKLQRDVN KGMRGILIDW LVEVSEEYRL VPDTLYLTVH LIDRFLSENY    300
IEKQKLQLLG VTCMLIASKY EEICAPRVEE FCFITDNTYS KEEVVRMESL VLNFLGFQLA    360
APTTKKFLRR FVQAAQASYE VPSVELEFMA NYLAELTLVD YSFLKFLPSI TAASAVFLAK    420
WTLDQSNHPW NPTLEHYTRY TALELKTIVL LLQDLQLNTS GSTLNAIREK YRQPKFKSVA    480
TLSSPQPVQS LF                                                       492

SEQ ID NO: 73              moltype = AA   length = 422
FEATURE                    Location/Qualifiers
source                     1..422
                           mol_type = protein
                           organism = Nicotiana tabacum
SEQUENCE: 73
MDNKTVVVPH NLPKGEMGGK QKNGQADGRN RRALGDIGNL VPAPAVEGKP KAAQISRPVT     60
RSFCAQLLAN AQAEKNKKAL AEIVNKDAPA KKKASDKEIK TVEGSSLSKR KAKKSGKTLT    120
STLTARSKAA CGLSNRPKYE IDDIDVVDAD NHLAAVEYVE DIYNFYKLTE GESRVDDYMN    180
FQPDLNHKMR AILVDWLIEV HRKFELMPES LYLAINILDR FLSLKTVPRK ELQLVGISSM    240
LIACKYEEIW APEVNDFIHI SDNAYAREQI LQMEKAILGK LEWYLTVPTP YVFLVRYIKA    300
ATPSDNQEME NMTFFFAELG LMNYKTTISY CPSMLAASSV YAARSTLNKT PLWTQTLQHH    360
TGYSEDQLME CAKQLVSYHL GAAESKLKAI YRKFSSPDRG AVAFFPPARN LLPTTTDAAS    420
CS                                                                  422

SEQ ID NO: 74              moltype = AA   length = 495
FEATURE                    Location/Qualifiers
source                     1..495
                           mol_type = protein
                           organism = Nicotiana tabacum
SEQUENCE: 74
```

-continued

```
MRHANIKHGS FHLEEHNMRI TRARARASVL GSSGRLPPLH PSTKQDKKHV LGAESKRSKR  60
SASDENRPGT SSTATGVQPK RRAVLKDMTN VLHENSHMNC INGSKIQVKK GSDKRNNKAK  120
PAVSVKLSQL QEKGKEDIAD KVKKVKVEGS QEISSGANCK EDMLPQLSRY VTPAQCGLVH  180
LVPVNRSSCK AIPLQDIMKK DESKVCRKQE GFANLGVADI DSRHKDPLMC SLYAPDIYNN  240
LHAIEFDRRP SVDYLEKLQL DINKGMRGIL IDWLVEVSEE YRLVPDTLYL TVNLIDRFLS  300
ENYIEKQKLQ LLGVTCMLIA SKFEEICAPR VEEFCFITDN TYSKEEVIKM ESRVLNLLSF  360
QLASPTTKKF LRRFIQAAQA SYKVPSVELE FMANYLAELT LVDYGFLKFL PSLTAASAVF  420
LARWTLDQSN HPWNPTLEHY TRYKVSELRT TVFALQELQM NTSGCTLNAI REKYRQPKFK  480
SVATLAASKP VQSLF                                                 495

SEQ ID NO: 75          moltype = AA  length = 446
FEATURE                Location/Qualifiers
source                 1..446
                       mol_type = protein
                       organism = Nicotiana tabacum
SEQUENCE: 75
MASRNVLQQQ NIGEAVPGAL KQKNMAAAAQ GRNRKALGDI GNNVVTVRGV EGKPLPQRPI  60
TRSFCAQLLA NAQAAAENQK KSLVVNGDAP IVAKGALAVK AAAKKPAHKK VAVKPKPDVI  120
EISPGTEEQV KENKQKKKAG DDSSLKKATL TSTLTARSKA ACGLSHKPKV QIVDIDAVDV  180
NNELAVVEYV EDIYNFYKIA ENESRIHDYM DSQLEITERM RAILIDWLIE VHHKFELSQE  240
TLYLTINIVD RYLAVTTTSR RELQLVGMSA MLIASKYEEI WAPEVNDFVC ISDKAYSHEQ  300
VLGMEKRILG QLEWYLTVPT PYVFLVRFIK AAVSNAQMEN MVYFLAELGL MNYATNIYCP  360
SMIAASAVYV AQHTLNCTPF WNDTLKLHTG FSESQLLGCA KLLVSYHMEA PEHKLKVIYK  420
KYSRPERGAV ALQPPAKSLL AASLYE                                     446

SEQ ID NO: 76          moltype = AA  length = 473
FEATURE                Location/Qualifiers
source                 1..473
                       mol_type = protein
                       organism = Nicotiana tabacum
SEQUENCE: 76
MASRIVLQQQ NRGEAVPGAL KQKKNVAAEG RNRKALGDIG NVATGRGVEG KKPLPQKPVA  60
VIVKGANVAK VPAVRKPAQK KATVKPKPEE IIEISPDTQE KLKEKMQRKK ADKDSLKQKA  120
TLTSTLTARS KAACGLSKKP KEQIVDIDAA DVNNELAVVE YVEDIYSFYK LAENETRVHD  180
YMDSQPEIND RMRAVLIDWL VEVHQKFELN PETLYLTINI VDRYLAVKST SRRDLQLVGV  240
SAMLIASKYE EIWAPEVNDF VCISDKSYTH DQVLTMEKEI LGQLEWYLTV PTPYVFLARF  300
IKASPPDSET ENMVYFLAEL GLMNYPTIIY CPSMIAASAV YAARHTLNRT PFWNETLKLH  360
TGFSESQLIE CARLLVSYQS AAATHKLKVI YKKYSSPERG VVALLTPAKS LLAASSLRVS  420
SEQADLGKST EAAATSSSPM VVVGCQRCHM YVMVTEADPR CPQCKNTTTR KMT        473

SEQ ID NO: 77          moltype = AA  length = 588
FEATURE                Location/Qualifiers
source                 1..588
                       mol_type = protein
                       organism = Nicotiana tabacum
SEQUENCE: 77
MIQVKEESQT LDFGGFASCS SFSDSSYEAS TPRYSSEPGS SYRRSSGPTK RSSQAGWTEE  60
EDNLLTDVVK RFKGRNWKKI AECMNGRTDV QCLHRWQKVL NPELVKGPWS KEEDDLIIEL  120
VEKYGCKKWS FIAKSLPGRI GKQCRERWHN HLDPTIKRDA WTEQEESVLC HYHQIYGNKW  180
AEIARFLPGR TDNAIKNHWN SSVKKRSNLN LPSGLVLDTE SEESPNFSSD KKKLEIQKHP  240
LQAQNAEQTI FLGEQTGLDN AAVALSTDLR IGYAYSAGNA LHKDTSLFGA CISAEENVRD  300
LIKPLGGIPF GKADVLPIGE TDKPCQSNLS RTKISYPLSA SSSDFPLDQL HHTRWSTSQV  360
EAVHPTTFGS MYESPKRSRH DTVNDPDHDF LSLSLASFTE VRSQSNKKNK AYDTQSSLGL  420
KQQGSLYYEP PQLKDMLIPL TDENLSRDNL ITEKNGHPFC STPPSLKLTV SANGSSPESV  480
LRNSAMSYTG TPSIIRKKNS RFPEAATHSS CTGTTTPTHN FPRASDREDT SNLKDRFSGC  540
KSSVSGKSLG RRLEYAFDME WDASRCCTPV SAASPCALRL GANTMLTP             588

SEQ ID NO: 78          moltype = AA  length = 1043
FEATURE                Location/Qualifiers
source                 1..1043
                       mol_type = protein
                       organism = Nicotiana tabacum
SEQUENCE: 78
MESDRISTPS DGTSSSLQRV RPLHGRTSGP TRRSTKGQWT TEEDEILRKA VQRFKGKNWK  60
KIAECFKDRT DVQCLHRWQK VLNPELVKGP WSKEEDEVIV ELVKKYGPKK WSTIAQHLPG  120
RIGKQCRERW HNHLNPGINK EAWTQEEELT LIRAHQIYGN KWAELTKYLP GRTDNAIKNH  180
WNSSVKKKLD SYLASGLLAQ FPSLPNVNRQ NQSIPSSTKL QQSSEDDSVR KEGIEMEEAS  240
ECSQGSNLAG CSQSTSDMGN TFVHTREEGK LLEDSNYRKD PSSSSAPCSE YYTPAFEDIT  300
FSMAEVPSEL DESKLLEHNF SHDWAASMGK EWQFNPDDIP NISPLELMQD SSGLFMQCLT  360
GNGNHEMVTF PQQNAVKYEM TNVGSMVVGL DKPNEMFTSV EGCGMVYPEA GIPQYIPSET  420
GMNGADETAD SLICQSSNYQ ISEGGNMSIE NCCNPLCSHV MGTSSGQPFS IPSQFSSEQS  480
SLMFGTAANH FHNPSQGNPA QESHTSNSDG FLYPFESGTP CDNIMDDPLL EEQLDQTKDS  540
LQLVSVNDFR STPSNTIQTC PLVNENSSVP EEQKDGGALY YEPPRFPSLD IPFFSCDLIQ  600
SGADAQQEYS PLGIRQLMMT SVNCLTPFRL WDSPSRDGSP DAVLRSAAKT FTSTPSILKK  660
RHRDLVSPLS EKRCEKKLGS DLRQESFSDL SKDFSRLDVM FDEAANEKAT KSSLTMDQTL  720
ELQASSEDKE NINPTEDGSK EEDKVRNGLS SERQLDGGEV HYKEKVTRKG TKGGANSAIG  780
KIKQPSGVLV ELNASDLFFS PDRFGAKSGR ATNLCSKALG NQYARRLEAA SNQGSVSSSF  840
ETSCFSVICS PRIRGKKDGS SFVITTSMQS APAPTALDNS AETSGNGVGA ETVSISGETP  900
YKRSIESPSA WKSPWFINSF LSSPRLDNEL NFEDLALFMS PGDRSYDAIG LMKQLSEQTA  960
```

```
GAFADAQEVL GGETPESILR GRNSKNQKAD ENHSLLSANV MSERRTLDFS ECGSPGKGKE   1020
TEIFCTSNNS FASPSSYLLK GCR                                          1043

SEQ ID NO: 79            moltype = AA  length = 157
FEATURE                  Location/Qualifiers
source                   1..157
                         mol_type = protein
                         organism = Nicotiana tabacum
SEQUENCE: 79
MGMKNDALLK SKARRKRVEK PQKSVGKINA EKAQERPVLF LAINNLTIGK SSNNSLTSPD   60
VSSSCSSSII TFGENQKMNI EMENTVILES NPEIYQSDCL SIESLDQFDT SSFWFIYLMM   120
PIVLFYERLI RICDLQRQIQ NLIFMGSSSR LYCSLLF                           157

SEQ ID NO: 80            moltype = AA  length = 292
FEATURE                  Location/Qualifiers
source                   1..292
                         mol_type = protein
                         organism = Nicotiana tabacum
SEQUENCE: 80
METDMSFLSK SSSSSSDEEI GLRRGPWTVE EDSLLVNYIS QHGEGRWNML AHRAGLKRTG   60
KSCRLRWLNY LKPDVKRGNL TPQEQLLILE LHFKLGNRWS KIAQYLPGRT DNEIKNYWRT   120
RVQKQAKHLK IDSNSAAFQH MIRCIWIPRL LQKIQGSSAI PSIQTSQSTS LLDSQYGPLN   180
ITEITQTPQV LSLERNSISS SRCCSSRSPS SESMSIYKSP NIISECPKIP PREMGDSVVN   240
VHFPFDDNSY DMDTFSPATG NFLTNYDQMV GGENNMMNGD ILADSFWSMD QF           292

SEQ ID NO: 81            moltype = AA  length = 245
FEATURE                  Location/Qualifiers
source                   1..245
                         mol_type = protein
                         organism = Nicotiana tabacum
SEQUENCE: 81
MARTRCYDKS GLKKGTWTPD EDRKLAAYVS KYGCWNWRQL PKFAGLARCG KSCRLRWLNY   60
LQPNIKRGNY TKEEDEIIMK LHAEIGNKWS VIAAHLPGRS DNDIKNHWHT SLKKRSTREY   120
STSTDSIKRS SNNSYQANSQ KKRRENETQL NANESFQLSP MQSCSTEVSS CATIDQNVEN   180
IHGEREVFQE EIFEVSSGSF WTEPFLVDSF NTASDCFVPS FDDHGVFVSP FSPVMSYGEL   240
LCSYY                                                              245

SEQ ID NO: 82            moltype = AA  length = 235
FEATURE                  Location/Qualifiers
source                   1..235
                         mol_type = protein
                         organism = Nicotiana tabacum
SEQUENCE: 82
MVRTPSVDKN GIKRGAWSEE EDNKLKAFVE RFGHPNWRQL PKHAGLMRCG KSCRLRWMNY   60
LRPGLKKGNY SLEEEELIIK LHKEHGNRWS VIAARLPGRS DNDVKNQWHA HLKKRAKTNT   120
NNNSPIMEQF SESSQSGSQS EQYSHKVSEQ EAGCDTASVN AVDTSVEVSS TDLYSSFSLL   180
NGMDWIEEDH IRSMEQLPAD FFNFCWTNPI DNFQTEPFDN FQTEPLDNFW RQPFF        235

SEQ ID NO: 83            moltype = AA  length = 281
FEATURE                  Location/Qualifiers
source                   1..281
                         mol_type = protein
                         organism = Nicotiana tabacum
SEQUENCE: 83
MVRAPCCEKM GLKKGPWTPE EDQILVSYIQ TNGHGNWRAL PKLAGLLRCG KSCRLRWTNY   60
LRPDIKRGNF TREEEDSIIQ LHEMLGNRWS AIAARLPGRT DNEIKNVWHT HLKKRLKNYQ   120
PPQNSKRHSK NNLDSKAPST SQTFNNSDNF SNIQEDINGP VTGPNSPQRS SSEMSTVTVD   180
STAMTTITID DQNMFKQLDE MDSSENFIPE IDESFWTDDL STSDNSTFGM EGTGGELQVQ   240
FPFSSVKQES MDMVGAKLED DMDFWYNVFI KSGDLLDLPE F                       281

SEQ ID NO: 84            moltype = AA  length = 333
FEATURE                  Location/Qualifiers
source                   1..333
                         mol_type = protein
                         organism = Nicotiana tabacum
SEQUENCE: 84
MGRPPCCDKA NVKRGPWTAE EDAKILAYVA SHGIGNWTLV PQKAGLNRCG KSCRLRWTNY   60
LRPDLKHDNF TPQEEECIIE LHKTIGSRWS LIAKQLPGRT DNDVKNYWNT KLKKKLVNMG   120
IDPVTHKPFA QVFAEYGKIS GLPIQNARNH ICLPNNTTEI SKQLPFSLRE NYSTQKYTWD   180
PKAQYQVIHE ETLQTHSFSE VSPLISSATY FNPTVFSSSS SYASVQSQVH TTASSSSTST   240
WNEFVFGDLC TSTDTEQKQE YQLQAGIYLS KDLSNSVHKD NPTCGEVTEV EENQSVEEAT   300
CSSAVDSFVD TILARDKQML MDFPPLLDVY LDY                               333

SEQ ID NO: 85            moltype = AA  length = 998
FEATURE                  Location/Qualifiers
source                   1..998
                         mol_type = protein
                         organism = Nicotiana tabacum
SEQUENCE: 85
```

```
MESDKTSTTP SDDISSLQRV QPLNGRTSGP KRRSSQWTPE EDEILRQAVQ LFKGKSWKRI  60
AECFKDRTDV QCLHRWQKVL DPELVKGSWT KEEDDKLIEL VNRYGPKKWS TIAQELAGRI  120
GKQCRERWHN HLNPSINKEP WTQEEELTLI RAHQVYGNKW AELAKVLHGR SDNAIKNHWH  180
SSVKKKLDSY LASGLLAQFP ALPNVNHQNQ SVPSSSMTLQ QNSEDESVHK QGTEAEDSFV  240
KKKLDSYLAS GLLGQFPALP NVNHQNQSVP SSSMTLQQNS EDESVHKEGT EAEEVPECSQ  300
GSTFAGCSQS TSDLGNTFVH VRENGGMSEE SICKKDATSS TAPCCRNYNP VFQDVSCSML  360
KVPSELVDSK FLEHNLSHDW GNSMEEDWQF NRDDIPNISP PELIQESSGI SVHCLNGNEN  420
HDMEATTNVG NVVEGPYNPN EMFVCVDGCM MVYPEEGIPQ CSSETGVNGC GQPAYSLFYR  480
SSNYQIPEVG DMVPQNCNAL SFDDFEASSH QPFSVPLQFS SEDRSPVFDL VLNQFHNPPL  540
ESPDHMKDSS RIVPVNDLGS TTSNTVQTCL LNEKSFVQEK QKDGGGLCYD PPRFPSSDVP  600
FFCCDLMQSG SDTQEEYSPF GIRQLMMTSA NCLTPLRLWD SPSRDDSPDA ILKSAAKTFT  660
GTPSILKKRH RHLLSPLSEK RCEKRLESDL NQESFSNMTS NFSRLDDMFD ESANEKASME  720
DGENLPSSED GRKEEGEISG ANDAMGKVKQ PPGVLVELSS NDLFLSPDSF LIKCDRATSL  780
SNKALGKQYA RRLEAASNQV TVSSSFETSC FSVVCSPDIR GKRRSSVVLA TSAALGNTAE  840
DSENRFGTET LSISGETPYK RSFESPSAWK SPWFMNSFPP STRYDIELAF EDLARFMSPG  900
DRSYDAIGLM KQLSEQTAAS IADAHQILGS ETPETNLSKR NSKKQKADEI CKASNATSER  960
RTLDFNECGT PGKGKETTKF GSNNSFSSPS SYLLKYCR                          998

SEQ ID NO: 86          moltype = AA  length = 1015
FEATURE                Location/Qualifiers
source                 1..1015
                       mol_type = protein
                       organism = Nicotiana tabacum
SEQUENCE: 86
MLDYPDLPLS LTMESDKTST TPSDDISSLQ RVQPSHGRTS GPKRRSSQWT PEEDEILRQA  60
VQQFKGKSWK RIAECFKDRT DVQCLHRWQK VLDPELVKGS WTKEEDDKLI ELVNRYGPKK  120
WSTIAQELAG RIGKQCRERW HNHLNPAINK EPWTQEEELT LIRAHQVYGN KWAELAKVLH  180
GRSDNAIKNH WHSSVKKKLD SYLASGLLAQ FPALPNVNHQ NQSVPSSSMT LQQNSEDESV  240
HKEGTEAEDS SVKKKLDSYS ASGLLGQFSA LPNVNHQNQS VPSSSMTLQQ NSEDESVHKE  300
GMEAEEVPEC SQGSNFAGCS QSTSDLGNTF VHIRENGGMS EESICKKDAT SSTAPCCRNY  360
SPVFQDVSCS MLKVPSELAD SKFLEHNLSH DWGNSMEEDW QFNRDDIPNI SPPEFIQESS  420
GISVHCLTGN DNHDMVATAN VGNVVEDPYK PNEMFVSVDG SMMVYPEEGI PQCSPSETGV  480
NGCGQPSYSL FYQSSNYQIP EAGDMVPQNC NALNFDDFEA SFHQPFSVPS QFSSEDRSSV  540
FDIVLNQFHN PPLEGPDHMK DSSRIVPVND IGSTTSNTVQ TCLLNENSFV QEEQKDGGAL  600
CYDPPRFPSS DVPFFCCDLI QSGSDTQEEY SPFGIRQLMM TSANCLTPLR LWDSPSRDDS  660
PDAILKSAAK TFTGTPSILK KRHRHLLSPL SEKRCEKKLE SNLNQESFYN MSTNFSRPDD  720
MFDESANEKA SMEDKENLHP SSEDGRKEEG EISGANDATG MVKQHPGVLV ELSSNDLFFS  780
PDRFLIKCDR ATSLSNKALG RQYARRLEAA SNQVTVSSSF ETSCLSVVCS PDICGKHRGS  840
VVIATSTALE NTAEDSENGF GAETLSIFGE TPFKRSFESP SAWKSPWFMS SFPPSTRYDT  900
ELEFEDLALF MSPGDRSYDA IGLMKQLSEQ TAPSIADAHQ ILGSETPETN LSKRNSKKPK  960
ADENCTLLAS NATSERRTLD FNECGIPGKG KETTKFGSNN NSFSSPSSYL LKYCR       1015

SEQ ID NO: 87          moltype = AA  length = 1042
FEATURE                Location/Qualifiers
source                 1..1042
                       mol_type = protein
                       organism = Nicotiana tabacum
SEQUENCE: 87
MESDRISTPS DGTSSSLQRV RPLHGRTSGP TRRSTKGQWT TEEDEILRKA VQRFKGKNWK  60
KIAECFKDRT DVQCLHRWQK VLNPELVKGP WSKEEDEVIV ELVKKYGPKK WSTIAQHLPG  120
RIGKQCRERW HNHLNPGINK EAWTQEEELT LIRAHQIYGN KWAELTKYLP GRTDNAIKNH  180
WNSSVKKKLD SYLASGLLAQ FPALPNVNRQ NQSIPSSAKL QQSSEDDSVR KEGTEMEEAS  240
ECSQGSNLAG CSQSTSDMGN KFVHTREEGK LLEDSNYRKD PSSSSAPCSE YYTPAFEDIT  300
FSMAEVPSEL DESKLLEHTF SHDWAASIGK EWQFNPDDIP NISPLELMQD SSGLFMQCLT  360
GNGNHDMVTF PQQNAVKFET TNVGSMVVGF DKPNEMFTSV EGCRMVYPEA GIPQYIPSEA  420
GTNGADETAD SLICQSSNYQ ISEGGNMSIE NCNPLCSDVM GTSSGQPFSI PSQFSSEQSS  480
LMFGTAANQF HNPLQGNPAQ ESHTSNSDGF LYPPESGTPC DNIMDDPLLE EQLDQTKDSL  540
QLVSVNDFRT TPSNTIQTCP LVNENSSIPV EQKDGGALYY EPPRFPSLDI PFFSCDLIQS  600
GTDAQQEYSP LGIRQLMMTS VNCLTPFRLW DSPSRDGSTD AVLRSAAKTF TSTPSILKKR  660
HRDLVSPLSE KRCEKKLGSD FRQESFSDLS KDFSRLDVMF DEAANEKATK SSLTTDQTLE  720
LEASSEDKEN INPTEDGSKE EDKVRNGLSN ERQLDGGEVH YKEKGTREGT KGGANSAIGK  780
IKQPSGVLVE LNASDLFFSP DRFGAKSGRA TYLSSKALGN QYARRLEAAS NQGSVSSSFE  840
TSCFSVICSP RIRGKKDGSS FIITTSMQSA PAPTALDNSA ETSGNGVGAE TVSISGETPY  900
KRSIESPSAW KSPWFINSLL SSPRLDNELN FEDLALFMSP GDRSYDAIGL MKQLSEQTAG  960
AFADAQEVLG GETPESILRG RNSKNQKADE NHSLLSANVM SERRTLDFSE CGSPGKGKET  1020
ENFCTSNNSF SSPSSYLLKG CR                                           1042

SEQ ID NO: 88          moltype = AA  length = 317
FEATURE                Location/Qualifiers
source                 1..317
                       mol_type = protein
                       organism = Nicotiana tabacum
SEQUENCE: 88
MGRAPCCDKN NVKRGPWSPE EDSKLKSYIE QNGTGGNWIA LPPKIGLNRC GKSCRLRWLN  60
YLRPNIKHGG FSEEEDRIIC SLYISIGSRW SIIAAQLPGR TDNDIKNYWN TRLKKKLFGK  120
QRQKQGSRKG KEINSNMVIS NNNNNNQFPC WPELPILQPI PYSNDEPRFN DHSSIRKLLI  180
KLGGKFSDED QPINEATNPQ YPMDNSLLMQ PIYQNIPINM ISSAPIDNVL GNAQYNMDRA  240
ASSFTAELEH MIQNNQQKLD GLEFLYEDYM LIDKSASTSG GNLDWESMNP FVLPLPPIND  300
EGFQQGVIFQ ENNTMAQ                                                 317
```

```
SEQ ID NO: 89          moltype = DNA  length = 2499
FEATURE                Location/Qualifiers
source                 1..2499
                       mol_type = unassigned DNA
                       organism = Nicotiana tabacum
SEQUENCE: 89
tctaggagca aaaaaaaaa aaaaaaaaa aacaagtagt agtagtagta gtaaatggaa   60
aaatagagag gcaatttttt ttagtatctt actttatcca ttagcactta aaaaacatag  120
gtttacatgc tctcattgtc acgccaggcc gctaattaaa tggtacattt catcatcccc  180
attttttggc ctcatagtta attatcacaa tttctgaaag caacatcaga acaaccccac  240
atttcttgtg gtcctataat tactgctaga tagtccaaac ccatctgcct atttagggct  300
tgtgaatgag gattgaaaat ggtagagaat atttgcaaag gcatcatgca tatatggaaa  360
agactaaaga gagagttagt gccttgcaaa gcggattctc acagttgtag aaaaggactc  420
accattttca agaatactcc cggcatgaag atggacaatt taatataaaa aacaaagaaa  480
atagtaatta agtgcgttga gatgaatgaa atttatccgc tcttaattga atatgggga   540
ttgaaagaaa tttctgataa taaattaatg agtcttacat gacgtggatc cgacttaatc  600
tagtctattt aaactaagaa tagataagaa tagagaatat agacaaaaga gaggctcatt  660
ggctagggtt tcaagggagt tccttgaaca taagtggcaa gtacaagcac aaagccaatt  720
tccatggact aaagatgaat aagatgtgtc gtgtggtatg gtgggaaggt gaggaggtat  780
ggggtaattg gagatgctaa acctctctaa aagctctttt gctccaaata tctaaatcca  840
tctctatcac ttttggcgac tgccccaaaa tttgcaactt atgaattaaa gttttaatat  900
ttttaagtta ataaattctg aattaataat ttaacatatt caataaactt tttaaaacaa  960
attacgtata taccatcaaa ctggctgcac catgatcact ttctaaactc acaatgacat 1020
atggatttaa tcaggcacaa agtcatgttg atagaaagag atagtacgga gaatgaagaa 1080
aaaagttagg ggagagagat ggggtgagtg gggaaaagat agggttctct ttttagtgaa 1140
agcgacaggg tctgagaacc ctaggtcaaa agttgcataa acctctatac aggcttcttc 1200
actcccttac tactaatata ctctcattaa ggcttgaggt ttaattcatt aaaattgtgg 1260
tttaattatt gtatcccctc aaacgaaata attgtccttg tcgaggttag acaatgttgc 1320
gtactatttt caaacgcagt cagccattat tctcctatcc tttacagtcg agattcaaag 1380
acagaaagta gcatgcaagc tgttattaat ttactttgat taggactttg ccaagaaaat 1440
gaagaacctt ttcttttttc ttttaattta gttatcttac aacatgtaat ttttcctagc 1500
aagcaaatac ggtaactttt tttttattc tcatttaatt tgttggagct attgctactt 1560
tgatgacttc aaccaaatcc tggttggtag gcggaggggtg ctgacgatgg aaactacccc 1620
tcttgtccaa atacgataac ctaaaaaata gaataatagc ttattgtact gtgctgcaaa 1680
aattgcattg tcagtataca taattaaaat ctattttgaa tgtgtggagg gcaaagaggg 1740
gtgactggtc tagggttgta gaaatcaggt gggagagaga atggtatttg tctctgtgtc 1800
agctgatatc acgtgaagag gcacaataag aagtccttcg tatccattca cttcccaaaa 1860
ataccggcat tactacaaat atagtactag cacttgcttt ctctatcccc atctttgcta 1920
tttccttttcc ctttccaact ttttggcttt agaattgcaa agatggaggg aattgtggtt 1980
ctttgtatct gtaaaatttt tcctccaagc tccagttgta gctagcttaa tgcgtggacg 2040
cgcgcgcaca cactagaaat ctgcaatcta tatatatt cacaaggcac tcacatatca 2100
aaaaccacat agacattgta tagagagagc tgtcgttcto agcagaaaa aatgatatga 2160
tttcatcagc atgtggtcaa ccaaatagtt caattctagt ctttgcttcc tctttctaat 2220
tactgtataa atagagccac aaggacatag aattgagaaa ataaaagaca ataaaaacaa 2280
atctagctac ttaagcgaat gatgatgact ctctctcagt agtcttaact cttaataccc 2340
ttgttttcct tcttgtgctg cagtttgatt ggttaattaa cctaatcaaa agatgtttta 2400
actgtgtttt atccgtcttt ctcaagatct atcttagtcc caccacatag ctccctcaag 2460
ctacagctgc aaaatatata ctatatatat atataacaa                        2499

SEQ ID NO: 90          moltype = DNA  length = 2500
FEATURE                Location/Qualifiers
source                 1..2500
                       mol_type = unassigned DNA
                       organism = Nicotiana tabacum
SEQUENCE: 90
tgacattgct ttggtggttt aagttctcag ccagtatatg cattgtccta ataggtctca   60
catggaagca gcactgagag ttgtaagata cataaaagaa gctcctggct taggtctctt  120
cttgcctgta aaatcttcag atcaactaag tgctttttgt gactcagatt ggggagcatg  180
tatacaaatt agaaggttag ttacagggta cttggtaaag tttgaaagtg ctcttatatc  240
ctggaagtct aagaagcaga gtactgtgtc taggagctct aatgaagctg agtttataag  300
tatggcttca tgtgcagcag aagttacctg gccggtagga ctgttcagtg aacttggtgt  360
caaggttaaa cttcctataa acttggtatg tgatagtaaa gctgcaatcc aaattgcagc  420
aaatccaatc ttccatgaaa gaacaaaaca tattgatata gactgtcact ttgtaaagga  480
aaagctaagt ctaaggatgc taaaaactga gtatgtcaac atgaggatca actggcagat  540
atacttacaa aaggattgtg aagagctcaa catgtacatt tgctgaacaa gctaggggttg  600
aagaatctgt atcaaccatc agcttgagag ggagtgttaa tcaacatggt taccactagt  660
ttatttataa agtgtaaatg ctaaaccata gctagtgagt tagttaatag ttagttgagt  720
ttgttataaa tattagtcag ctgtacagtt taacatagct tctcttttcag aaatgaaaat  780
tgctcttctc tcatttcctc tcttctagat tcttcttctc cctccttctc ttagctcaga  840
tctctcttat gacagctaac aataaatacg aatatttctt gtaacggttg ctcattgaat  900
gttgtctttc tcaaccgata tctttctttc aagtttccc cccgattcga gtattttga   960
aactcactca gcaccggtca catattcgta atcggtgcca gctatttgct tactcatatc 1020
ttatttgact tcattgtcac gtgtcagaca gaagtatgtg cgcatatacc atcaagtctc 1080
aatttgaaat aaaatcaact taagcagtta aaagtcaaat ctcttttagt tcggtcttta 1140
aaataataat ttaaataatg aacctataaa acacgcaact cacactgaat ataggggcag 1200
acataaaagc cgaaagactg aattccgaac cggaccgaat tatttcggta tttcgatatc 1260
ggtttattca gtatttcggt actatttcgg tataggattt ttagttattc ggtatttcgg 1320
tacgatcctc ggtattgaaa tttcgatatt tcggtatacc gaaataccga ataatttaag 1380
```

```
tacaccttcc ttcactgccc agcccgttat caattttcag cccaagtttc taacttgtta   1440
tttcttccc ttagccagta gcctactaag attaagccca acgccccaac ctaacattag    1500
aaattattat aattagaaaa gtataaagaa agtactcaca ttctactgct atgctcatgt   1560
agtgatttct attagaaatt attagaagtg aaggtactgc ccacatttc ttgttgctat    1620
actcattatc acgcaattag aaattttcta atgaattaga attcagtagt tcagcacaga   1680
ggcggatgta gcgtattacc tacgggttca actgaaccta taactttcga cacagagtaa   1740
aaatttatat gtaaaaattc tttaaaattg taaaaatcgt agatatgaac ccataacttt   1800
aaaaatataa tgggtaacat taaaattgaa cccatagaat ttaaatcctg gattcgcctc   1860
tggttcagca ttgtttagtt cacaaaaata tggtacgatg ccgaaccgta tcgaaaccat   1920
accgaaccaa acaagaagat atcgaacaat accgaactac tttggtacag tatttggtat   1980
gcacacttga tatatcgaat accgaaatac cgaaccgtaa ttttcgaata ccgtaccgaa   2040
ataccgaaca ctcacccata actaaacatt aaaaagctag aactcaggtg tttaatgact   2100
aaacggaagt aagatctaga taatccgtca ctctgttgat ttgtaaggct atcgacatgc   2160
aaaagtggaa gcaaaatgga gccgaaattt taacaaaaat gctgaaccaa taccatgaaa   2220
ttgatgaatg gtgggaccct atttcactct tttagaattt gcgtaagacc agaaaataac   2280
ttcaatcgaa atcaaaataa ataccaaccc ttttaggccc caaatcacta cgtgtgattt   2340
gcaaacgtca ttagccttat gtaaacagtg acctcatgcc aacatattat cgcagcctat   2400
aaatcttagt ttacatttca tttttcttca aacacacaca cctcacaata gaactaagtt   2460
gtaagagttt cattttcttt gttctttctc acaaaccaaa                        2500
```

```
SEQ ID NO: 91          moltype = DNA  length = 2499
FEATURE                Location/Qualifiers
source                 1..2499
                       mol_type = unassigned DNA
                       organism = Nicotiana tabacum
SEQUENCE: 91
tgccagacag tctaaaattc aaaaatagga cagcccacat cccctccacc ccactagatc   60
tcactacttc ttaattagga cttgtggggg ggagtagagg gatttgcaaa ggcggccgcg   120
gcatgcatat acgaaaaga gaagttagtg gtttgcaaa atgattgtgg aaaagggctt     180
acctaacaat gaagaagagg aagagggtag atggataata ataactcaaa aatagaaaga   240
agagggacaa gtgggggctc aatggctaag gtttttaaggg aggtcttgga aacatcatta   300
gcaagtacat gcagtattac caccctacat cagactgtgg ggtctgatgg aatattcttc   360
tactatactc ttttaaatag agggaattaa tgagccttta taatgttgaa atttataaga   420
aaatagtata acttttaaa tctcttaatt atgtatcaaa tcaaatctca tatttaccct   480
ttagtggatc tattcactga agtctgaata aatcgtacca gtaattcata ccgaatgtgt   540
aaataatttg aaagaaagat agacaaggcc tcaatgctag ggatttgtta gcatcaatag   600
caagtataag cagaaatata taccaccaag gagtgaggtg gaagaattaa gatttactct   660
aatgaaatat atatatcaag attgagtcat gtgaatgaag aatttcttag taccttaaat   720
taagcgaata tcacataaca gaggtgtaaa aaaacgaaag atggacaagc taagtggctc   780
tcaatggctg gggttttaag ggatcggagg tcttgttaac atcagacgga agtacaatta   840
gagtatatat gctactctaa taatacttgg ctacaaacat aaaaaaatat ctctatcact   900
atctctcaac tcgccatata gacttaattg gcacaaagtc atgctgatgg aaagagatat   960
aaggagaatg ggaagacaaa aaaaaaagtg gggatagaaa gagtgtccaa gtagctagaa   1020
gggggtgggg gtgggggtgg gggagttgt tgttttagtt gtggaagaga taggtttctc    1080
tttttagtga aagtgacata tatagctaga ctgagaaccc tggtcaaaag ttgctttgcc   1140
ttaacgtttc taaatgcctg acctctgaga ggctatcttc tcctctcatt ctctcgaccc   1200
ttactgttca tataccccca aatttgaggt ctaatttatc cacactatgg tttcttactg   1260
ttgtcttctt ctctgaaaca atattgcttg tcgatcttgg acttggccac gtcaacgtgt   1320
aacttcagca actagggtga ctccaagtca tagacagatc taggtcgact tctgtgaatt   1380
taactaaaca aattatttaa tttcgactca aaatagatat gtactatata tatatatagt   1440
aaacttattg tgaacttact aacttaaaat tttcaagttt gcagtatttt ttggaataag   1500
aaaggggaaa aagaggcaga aaaccccata tttcttcctc tttggagttg acgctaaagg   1560
gataaagcta acatgcaagc tcttaacaaa taacatactc agtataatct cacaaatggg   1620
gtatagagag gataaaacgt acacaaatct taacaatata cacagtgtaa ttccataagt   1680
gagttctgtg gacggtagta gcttacccct tgcctttaac atgcaagctc ttaagctttg   1740
tatttttatt ttgttctttc tttttggaga ggaagaagtg gtggttgaag actagagata   1800
aggaagaaaa gagaaggatt tttgtcagtt gctatcacgt gaactgaagg ggcacaatta   1860
gagagaagtc tatatgcttc acttcccata aaatcagttg taactacaac aagtactaag   1920
agtgtcccct ccattttctt tctttccctc aattcccttt catacttttta aagcttaatt   1980
ccacagctag aaaaagaagc ctttcttttt ctctagaggt atttagcaaa gatggaagga   2040
caatattaca gctctctttg tctctacagg taacaaacca ttgcctgtct ttctcaatct   2100
ccagtatttc cagctatctt ataatgcttt gagtactccc acaaaacaca tgcattatag   2160
ccactagcta catatatata tatatttgta aaaccacaca ttaatttagc tgtcattctc   2220
aaccaaaaag ctatgttatc atcaacatat tgacaaatta cctataattc cttcccctct   2280
agctatatga tctatctcac tttattatgc acttaaaaag ttatgttgtc cctctcaaaa   2340
gtcttaatta attaaccttg ttttgcatct tgctgcagct agctagctta ttaaattgac   2400
aaactcagaa gatgttgtgg ttctttcaac ttcaataaaa agctaagagt agtacttgtg   2460
cttgtatatc cgtccttctc aagctcaagt cccacttca                        2499
```

```
SEQ ID NO: 92          moltype = DNA  length = 3425
FEATURE                Location/Qualifiers
source                 1..3425
                       mol_type = unassigned DNA
                       organism = Nicotiana tabacum
SEQUENCE: 92
gttggagcta aaaataagag aaatggacaa gtgtcaaatt ctagcgtcca tggtagcgcg   60
acgcactatt gtggcgctag aaatagaaga ccaaaatttc caatgttggc gtcgaccttg   120
cgttgcggta ttttttctat ttcgctaggg acaagattat ttcaacaaaa ggggttctaa   180
acctaatttg gaggatatct aacatacttt gaaggcgaat tcacgtaagg gaatacaaac   240
```

```
cacgcttgga  aggggctttc  aactagtttt  tcttctcttc  ttttctcttc  ctttcatctc   300
attatgtatt  agttctaggg  ttgttggtac  ttacattaac  gttatagttt  gaagcttgga   360
ttatcttatt  attttatcat  attggtttat  ttattcaatc  ttgcgcttga  taatttaatt   420
ttaattgatt  gatcaccaat  taaatactat  ctacgaattt  aggattgaaa  tcgggagaga   480
aaattttaga  ttgcatatag  gattgagtag  agtaagatct  tgaacctgaa  ttacgaggga   540
acgaatttgc  gattaggata  taaggatata  cctaatcgtc  ttgcttggtt  actatacggg   600
aattattaat  acgttcttat  taatcctaat  ccactggaat  ataggcgttg  agttagcttg   660
aacaggcgag  tagtacttcg  ggagaatact  acgagtaata  ttaaattgtc  aatcaataaa   720
ctagataaat  ttataagata  gtttaagtaa  aaaactcaat  gagattgtta  gttgacccat   780
aactctgaaa  tattttctcc  cattagattg  tctttaagct  tgccggcata  gtttttctag   840
ttttctagtt  tacaactcta  gattagttat  agttaacaat  cacactttag  aaaatcgctt   900
gagtagatta  attgttaatt  tagttgatag  ttaatcataa  gtcatcgagg  gaacgatact   960
ctacttatca  ctttattact  tatcgaccac  gtatacttga  gtgcgtttgg  gagcaacaaa  1020
tttttgacgc  cgttgccggg  acgttagttg  atgttttcaa  ctagtgaaca  aaatgcaaat  1080
atgttatgca  attcggtgcc  atttacacgt  ctatgaggag  ttatattaaa  gaactttatg  1140
taggatgttg  gttggatcct  acaagctaaa  attatggcta  agaaaattgt  gaattactaa  1200
taaacttgta  ataagataaa  aaataatttc  ctagaacgta  atagaattga  agtgagatta  1260
gaccgacacc  tcttcgtcgg  aaaactatgt  tatatatgta  ggttatttta  tatatatata  1320
tatatatata  tataattttc  ttggcgttta  attttttata  ttttgattct  tcctactaat  1380
aattctaact  ctatcactga  attaaacgta  caggattcat  ttcttataca  aaagaggttg  1440
atcattatta  ggtctgggca  ctgtcagagg  ctgaccgata  tgagtagttc  ttcacatgct  1500
tggcagcaat  ttgaactgtg  attgcttgag  gggcgaaaaa  gagataagaa  tctaagttcg  1560
gtaattttta  tctgaattct  gtatttgtct  taaaaattta  ttgagtatgc  ataaaattat  1620
tattttaaac  tcagtaattt  aaaaaattta  gaattcgaac  tcataaattt  caaattggga  1680
ctccacctct  gattgtttgt  aagtggagtt  tagggggcaga  actagctcaa  aaagttcggg  1740
ttcgattgaa  ctcagtaaat  ttgattcaaa  gtctatatat  ttattgaaaa  atcaactaaa  1800
tatgtatata  tacaataaat  ttcaaattca  taaaaatta   aatcctgaat  taacctaata  1860
gtaaaaccgc  agactctaac  tagtggtcta  gtttagagag  tcaaattatg  gtttttaaca  1920
accttaaaca  agcacaaata  cttttccact  attggttcaa  ttttggttgt  taacaacctt  1980
gattggtaat  tacgtacttg  catgggcatt  tgaaaattaa  gttacgtacg  tgtaaaacgt  2040
tttagagtag  tccgtactaa  ttaagaacac  aaacactgct  tgagattttg  tggcggaagt  2100
ttgtttttgac ttagcatggg  taggcccacg  aattccccat  tttgaataaa  agacaacctg  2160
tgctagtcga  ttagctatta  tttaattact  agaatattac  ttactccctc  ctttttaatt  2220
tagacgattt  agtttgactt  ggcacaaagt  ttaaagaaaa  aaaaaagact  tttgaaatat  2280
gtggtgttaa  aatcttaatg  ggcaaaagct  aagtggagtc  atgatatttg  tgtgactata  2340
aaaacttctc  attaagaata  aagtgagtaa  aataaaaaat  taaagtcaaa  ttatttctaa  2400
atatagaaat  atatcattct  tttttgaacg  gactaatacg  gaaagtgtgt  catttaaatt  2460
aaaataaata  aagtaatatt  tatcatatga  ttttaacatg  taaatatcat  acaagtaatc  2520
taatcgtcaa  gcgcggatct  aataaataag  ggacgggtat  tttgtttagg  ctgtgtatat  2580
ataatttttt  aaaatctact  aaaaaagaac  aaataaataga  tttgtaaatt  agagggatat  2640
ggtagaatct  aactataaac  ccttaaagtt  caaatcttgt  atctgcttgt  ggtaatagtg  2700
tatatatatt  ttttacacgt  ttttgttgta  tagaactcaa  actaaaaagg  gcattccagt  2760
gcacaaagca  tctcctattc  acacacaatt  cggtgaaggg  ccgcactgta  tgcaaggggt  2820
gtgatatcgg  cagtctatcc  tgatgcaagc  atcaatggtt  gattccacgg  ctcgaatccg  2880
ttacctatag  gtcatacgga  gataacttta  ccgttactcc  aagtccccct  tctacataaa  2940
acttgcatca  atagctgatt  tcacgactcg  aacccataac  ctagttgata  cgaagataac  3000
tttaccgttg  cttcaaggtc  cgtctcacaca aaactgatca  aattattttc  ataaataaag  3060
aagctatcat  ttctctataa  atagaactag  agtccttgca  tattccaaca  taagtatcag  3120
ttccaggaaa  atcaagacat  aatctgttag  cttttctctt  tgccattctc  atggattcct  3180
taccagtctc  ctccattgaa  tctctagtca  ttgagatcaa  gaaagagatg  ttctcaaacc  3240
aagaatttaa  cacttttgtc  accccaatat  ctgcctatga  cactgcttgg  ttggccatga  3300
tttcttataa  taatcaagaa  gaagccatta  atggtcattc  tttttctggc  cctatgttta  3360
agagttgttt  aaattggatt  ctcaacaacc  aaaatgagca  aggattttgg  ggagaatcca  3420
atggt                                                             3425
```

```
SEQ ID NO: 93              moltype = DNA   length = 2512
FEATURE                    Location/Qualifiers
source                     1..2512
                           mol_type = unassigned DNA
                           organism = Nicotiana tabacum
SEQUENCE: 93
aagctggtac  ccttatgttt  agtccaagaa  aaataaccat  acccaaatat  aagggtttgt   60
tgaagacgga  aatatataaa  caaataaaca  aatatcatca  tatctccgat  agtttaaaat  120
tttagattgg  atatttcaca  caatttatca  aaattttcaa  aaaaaattc  tacttttttct  180
tgcttggaac  ttggaagggg  aaggggtggt  ggtggagata  gggcgggggca tcttctatct  240
agtctatgtg  attaatataa  caaaacaaaa  agggcgaggc  aaaaacatgg  atgaatggtg  300
gtccttttct  atatttatat  ggattgttac  gatacgtcga  tttcactttg  caaaatacca  360
attagattca  tttagttatc  ttttttgatca ctctgctttt  actatcatat  atatatagga  420
gtccttccac  gtttcgcatg  tgtcattgtt  tatattttcc  atggtcttcc  ttccaaatgg  480
ctaaaaaaat  ttgacacagt  ggtcccaaaa  gtttataaa   atagaattca  acagtgaggc  540
atatacctat  gaattctatt  ttacatcttc  atcgtataaa  atagaatgtg  ttataaactt  600
tacctcgtga  tgcttacaag  gggtgaaaat  ataaaagcac  tttatagatt  tacaagagtc  660
acaccttgat  ttatcctaag  attttatttt  tttcatgcc   aaacaatgaa  gtatgggaga  720
tccaattgga  ataacatcaa  atttaataaa  attcgaaata  gtcagagagc  tgtctactga  780
ggtatattga  aacttatttt  tttttaatag  aaaatatcaa  atacttagca  atatatttaaa  840
atgtttcata  aattacattg  tttaaaccaa  gcgttgaaac  atatgctgat  acgaggtagg  900
cttattgatg  aaatttataag ggcctcattg  gaaaagacga  tccaaagcaa  tgggctaaaa  960
aattggccca  ttttctgcca  cccagtgtat  ggttattact  agtttcacc   acacagattt  1020
gcacttcatt  agaggacaat  gttgctgaat  ttgaaacata  agtccattta  tctccactgt  1080
```

```
acagtccttc ctggagtcca atcctgacca tatcttcatg attttatgta atgtggtgaa    1140
taagcaaagt ttcatgttat gctttgtctc attttatagc aaaattcattt cctcataaaa   1200
tttacttcaa aaaagtttcg tttgattttc agaaatcaaa atatgctttt cggtaaccaa    1260
atggttttca attttgttta cgaagaactt aaaactttcc aacaccctac atctatgatt    1320
gcaagttaaa attgcagaaa tatgcacactt tttggagtgg tctttatcgt ttaacttcac   1380
ttgcactttta agggcaaaag ttaaaagtgt ttccatgaag caagcgaggg ataacactta   1440
ttaaacttga aattctactc atagaccaaa acaaggacaa aaattcaaga ctatctatgt     1500
gggtaaacgt acgaaaattg ggcttctcca gattagagcc ggaccttgtg gaaagacaga    1560
gaaattcgag gcccacttcc agtttctaag gagattaagc ctatcaaacg atggtccaga    1620
acgaaatatg tctttcttta ttctctacta tatagctgac tcagaatcgt tagaatttgc    1680
aatttcctca taataaaatg tgaggcagta tagattcgaa aacctttgtt gaagattatt    1740
gactcagcta cgcgaaacaa actgtagtat ccaatgtacc gattaacaag cgactggtta    1800
actatgaatt tgttagctcg acaaaatcac cggttaataa tgagtttgtg agttcgataa    1860
aatctaattt tctgatagaa atttatata ttatgcagaa atttaataaa agtagactta     1920
acttatatat tttagcattg actctttga agtaaaatcc attccatcta aattatgact      1980
tccctacatc gagtaagtaa gttgcgtctg tatcctcatt ttacccactt ttcgctatgc    2040
aattattcaa ggatctttac acaaatagca agccaatatt aattatttat tttttttagt    2100
catatatata aattatacat atattatata cccattaatt atttttaatt taagtgatag    2160
attggacgac tatttggatt aattcttcgt tattcaagat aatagatgtc gtctctaata    2220
catgagctag aagataataa ggattactag gccgaaaggc tgatggaaat gaacaagaag    2280
ataagctcct aaatggaaac agtacggaaa aagtcaaaga gcagtgcatg ggaggaatca    2340
tcagtcagaa aaggaagcca cgtgtcaagt agaaacaagc acgtgtccat gcaaaagcca    2400
cgtaactccc ttccatcaca tcttccttct tcaaaacctc gtgtttttact ctctcttttc   2460
tcactgccag tgatcgtcag gactgtgcat gtttgtttaa aaactaaagg ca            2512
```

```
SEQ ID NO: 94              moltype = DNA  length = 941
FEATURE                    Location/Qualifiers
source                     1..941
                           mol_type = unassigned DNA
                           organism = Nicotiana tabacum
SEQUENCE: 94
tttaaaacgc caaaaaataa gggacggcca tggcgtagca atgactattg ttccgtaggt      60
catttgtgaa ggaccgacaa aattttaggc gatccgggtc cgatttttcg gttctgctca    120
agaaaactcg atctgcacga atagcttata atcaaaccct tttttttttt tcaagaatgt    180
ctaattgatc ctaaaaagac aaccttatat gttccaccat ggcaggatcg gccttattac    240
taagggtttg ccaatagaca cgttttttaac attcaagtaa aaaaaacatt tattcttaat   300
aacccaccta ctatagtacg ttatttggca gtagactacg ttgtacattt gggaccattt    360
ggaacactcg tctttcacga gtcactaatt tttgtgttga atgcataaaa tttgttttt      420
tctttttcga aattgaacaa tttttatcttc gatcacacct atagtatatt attaccttat    480
tgttagaaaa tattttattt tattattgac tcctaataaa aagtggggta aatttgggtc    540
tttttttttaa agaatgtgaa ctactcattt cactttggtt agaacaaata tgagaagatt    600
tgctaatgac agcaaaatga atagaccaaa agcgtaacga atattaaaaa taaacaattc    660
cgaataactg gttactgaaa attgtggaac tctacatagc cgttgtgagt atggtattgt    720
ttgttcttgt gggcagaata actagttacg gaaaatttat gaatttgctt cacattattt     780
ttttcatttt cttttttgct tcaaaagata agtacaagtt tttatactct tatttcattg    840
cctataaata cctctattga gttactgctc attcacaact ctaaatagca atctttctta    900
ttattaaaat tcctatcctt ttttactcat tcagagaaac g                        941
```

```
SEQ ID NO: 95              moltype = DNA  length = 5000
FEATURE                    Location/Qualifiers
source                     1..5000
                           mol_type = unassigned DNA
                           organism = Nicotiana tabacum
SEQUENCE: 95
aaaaaatga gaatcgtgcg gaatttcagt tttatggaac taaaacgcca aaaatggagg      60
aacggtcatg gagaggcgat aactaatgtt ccttaggttt ttttagatgg gccgaaaaaa    120
tttttaggcga tacgggtaag gcgtccgaaa cacacgaaaa tttgaaaatc gggcgaattc    180
ttgtttttatg acactacaac accaaaaagt atggaagatt atggcgatgc gatgcgatga    240
ataatgttcc ttaggttatt tttgatgggt gacaacattt taggttatac gagaccgggt    300
tcccgggccc acaccagtgg cgtgggctat attgcacacg aaaatatagg aatcgagcga    360
atttctacat ttatggcact aaaatgcaaa acaaaaagga acagtcatgg cgaggcaatg    420
actaatgttc ctagggttat ttagatgggc cggaaaagtt ttaggtgatc ctggtcgtgg    480
cgctcgagcc cacgatggta gtgtgggcac acgaaaatct gggaaccgtg ctgaattcta    540
gtttatggc cttaaaacac caaaaccaac aaagagaat tctcatggag gggcgatgaa      600
taatgttcct taggttgttt tagatattcc agaaagatt taggtgatcc gggttgcggt    660
gcctgggccc acacccagtg gggtgggcta tagcgcatgc aaatgtggga atcgagcgga    720
attctaattt tatagcccta aaacaccaaa taatgttgaa cggtcatgac acgatgatga    780
ctaatgttcc ttaggttatt tttgatgggc tagcaaaatg ttagaagatt cgggtccggc    840
tgcccgggcc catgccagca caagaaaatc tgggaatcag gcaaattcca tattatggcg    900
attatggcga ggcgatgaat aatattactt agattgtttt ttacaggctg gcagaatttt    960
aggttatcca ggtgcgggcg tctgggcctc tgccggtggc gtgggctgta gtacacaaaa   1020
attagggaat caggtagaat tttagtttta tggccctaaa ataccaaaaa aggaggaaaa    1080
gtcatggcga ggtgatgact aatgtgcctt aggtaatatt ttatgttccg aaaaaaattt   1140
atgtgattca ggtccgggag ctcgtgccca tgcagatggc gtgggctata gcacccgaaa    1200
atctcaaaat catgtggaat tccatttta tggccataaa atgctaaaca taaggaacgu    1260
tcatggagag gcgatggcta atgttcattg ggtcgtattt gataggacgg caaaattata   1320
ggcgattcag gtccggcgcc gggcccatgc agatggcgtg ggctaataat agcacacgaa    1380
aatctgagaa tcgggtggaa ttcatgtttt atggccctaa aacgcaaaaa acaaatgaga    1440
aacggtcatg gcgaggcgat gacaaatgtt ccatgagtca ttttttgatgg gccagcaaaa   1500
```

-continued

```
gtttaggcga ttcggtttcg ggggcccggg cccatgcaga tggcctgggc tattgcacac   1560
gaacaactag gaatctggtg gaattccact tttacagcaa taaaatacca aacaatgaga   1620
aacggttatg gcgaggcgac gactagtgtt ccttaggtcg gtttagatgt ccggaaaaat   1680
aataggcgat cgggtccagg cgtccgggcc tgcgccaatt gcgtgggcca tagcatatga   1740
aaatatggga atcgggtgaa attcgagttt tatggcccta aaatactaaa aaggaggacg   1800
gtcatggcga ggcgatgatt aatgttcctt aggtcacttt ttatgggcag acataatttt   1860
tggcgatctg tgtctgggag accgaggcca tgtaggtagc gtaagctata gcacacgaca   1920
taattccagg tttatggacc taaaacatca aaaatggagg aacggtcatg gtgagccgat   1980
tactaatatt ccttaggtcg ttttggatgg gccgaaaaaa tttagggcga ttcgggtgcg   2040
gacgcccgag cacatacaaa tggtgtgggc tataccacac gaaaatctga ttacctgaca   2100
gaattccagt tttatggccc taaaatgcca aaatcgaaga acggtcatgg tgaggcgatg   2160
actaatgttc ctaaggtcgt tcttgatggg ccgacaaaat tttaggcgat tcgggtgcgg   2220
acgcccaagc acatgtagat ggcgtgggct ataccacacg taaagcaggg aatcgggcgg   2280
aattcaagtt ttatggccct aaaacgccat aaacgaagaa cggttatggc gaggcgatga   2340
ctaatgttcc ttaaatcatt tttgatgggc cgtcaaaatt ttaagcgatt cgggtcaggg   2400
cgccctggtc catgcagatg gcgtagcaca cgaaaatcta agaattgagc agaattctag   2460
ttttatggcc ttaaaacgcc aaggaacgag gaacggtcat gtgaaggcta tgattaatgt   2520
tccttaggtc gtttttaagg gcaggcaaaa ctttaggcta ttcagttctg gacgcccaga   2580
cccatgtaga tggcgtggct atagaacacg aaaatctagg aatcaggcgg aattccagtt   2640
ttatggtcat aaaatgctaa aaatgaggaa ctgtcatgga gaggcgacaa ctaatattcg   2700
ttgggtcatt tttgatggtc cagcaatatt ttagatgatt cgggtttggg cgcccgggcc   2760
catgcagatg gcatgtgcta ttgcatacac aaatctgatg accgggtgga attcaagttt   2820
tatggcccta aaatacaaaa aaatagagaa acggtcatgg cgatgcgatg gatatgttcc   2880
ataaggcatt tttgatggga tagcaaactt ttaggtgatt ctggtccggg agctagggtc   2940
tatgcagatg gcgtgggcta ttgcacacga aaatttaggt atcggtggaa tttcagtttt   3000
atggccataa aatgcataaa atgagaaacg gttatggcgc tatgacc agtgtgtcct   3060
taggtcgttt tagatgggct ggcaaaatgt taggcgattc gagtccgggt gcccgggcct   3120
gcgccaattg cgtgggtcat agcatacgaa aatataggaa tcggacgaaa ttctagtttt   3180
atggccctaa aatactaaaa aggaggaact gtcatgacga ggcgatgact aatgtttctt   3240
aggtcgtgtt tgttaggccg gcataatttt aggcgatctg ggctggacg cccagggtca   3300
tgcaggtagc ataggctgta gcacacgaaa attttgaaat cgggcgaaat tctagtttta   3360
tggccttaaa acgcgaaaaa caaaatgaat ggtcatggag atgcgatgac taatgttcct   3420
taggtcgttc ttgatgggac ggcaaaatgt taggcgattc gggtgtgggc gcctgggcac   3480
atgcatatgg cgtgggccat catagcatat gaaaatatgg gaatcgggca gaatttcagt   3540
tttatggccc taaaacgcca aaaacgaaaa acggccatgg cgaggcgatg actaatattc   3600
cttaggtcat ttctgatagg ccggcaaaat tttagacgat tcgggtaagg acgccctggc   3660
ccatgcagat ggcgtagcac acgaaaatct gggaatcgag aagaattcca gttttatggc   3720
cctaaaatgc gaaataacat ggaacggtca tgtcaaggcg atgattaatt tttcttaggt   3780
ttttttgat gggcaggaaa aatattaggt tatgcccatg cagatggcgt ggctatagca   3840
cacgaaaatc tgggaatcgg gcggaattct agttttatgg ccctaaaacg ccaaaatgtg   3900
aggaacggtc atgtcaaagc aatgattatt attccttagt tcatttttga ttgtcggaca   3960
aaatgttagg caattcgggt ccgttcaccc ggatggatgc atatggtgtg ggctagtaca   4020
cgaaaatctt ggaatcggac ggaattccag ttttatggct ttaaaacgcc aaaaaataag   4080
ggacggccat ggcgtagcaa tgactattgt tccgtaggtc atttgtgaag gaccgacaaa   4140
attttaggcg atccgggtcc gattttttcgg ttctgctcaa gaaaactcga tctgcacgaa   4200
tagcttataa tcaaacccttt tttttttttt caagaatgtc taattgatcc taaaaagaca   4260
accttatatg ttccaccatg gcaggatcgg ccttattact aagggtttgc caatagacac   4320
gtttttaaca ttcaagtaaa aaaaacattt attcttaata acccacctac tatagtacgt   4380
tatttggcag tagactacgt tgtacatttg ggaccatttg gaacactcgt ctttcacgag   4440
tcactaattt ttgtgttgaa tgcataaaat ttgtttttttt cttttttcgaa attgaacaat   4500
tttatcttcg atcacaccta tagtatatta ttaccttatt gttagaaaat attttatttt   4560
attattgact cctaataaaa agtgggtaa atttgggtct tttttttaaa gaatgtgaac   4620
tactcatttc actttggtta gaacaaatat gagaagattt gctaatgaca gcaaaatgaa   4680
tagaccaaaa gcgtaacgaa tattaaaaat aaacaattcc gaataactgg ttactgaaaa   4740
ttgtggaact ctacatagcc gttgtgagta tggtattgtt tgttcttgtg ggcagaataa   4800
ctagttacgg aaaatttatg aatttgcttc acattatttt tttcatttttc tttttttgctt   4860
caaaagataa gtacaagttt ttatactctt atttcattgc ctataaatac ctctattgag   4920
ttactgctca ttcacaactc taaatagcaa tctttcttat tattaaaatt cctatcctttt   4980
tttactcatt cagagaaacg                                                5000
```

```
SEQ ID NO: 96         moltype = DNA   length = 5000
FEATURE               Location/Qualifiers
source                1..5000
                      mol_type = unassigned DNA
                      organism = Nicotiana tabacum
SEQUENCE: 96
gctgatctac aaagggctta gaaagaagta agaaaagaaa tggataaagg aaagggaaag   60
attgcagaat cctcagagct gttgaggaag aggagatgga actggtccat caagaaaggg   120
gtacatcagt ggaggttcct accccaagcc aaaaagccca agacttcctc caagaagtct   180
tcctctgtgt ctgaggctgt tgaacctaca ctagccaaga ggacaagatc tgcagtgaaa   240
acaacaatca aaaatttctg aagatgatga ctggagtgga gaagaagaag aaaatgattc   300
tgagaaggaa caggatagct tgccagtttg gcaaagaaa gatttttaaag ggtagactgc   360
tgaaagacct ggtggaacca ggaatgatga gatgtggatg ctttagctgc tcaggatgga   420
aggacatggt ccttcagatg gatggtaggc tagccagaaa tgagctaatt gaatttatgg   480
caatgtctgg ttaaggatgg catgttagta gcctggtgaa aggagttcaa gtgcagtttg   540
atgcaaagaa actgggagag atcctggaca taccctctga agggtttgat gactatacaa   600
ggcaaaggtg gccctgcctg gactccctcc ctactgctct tgtaattacc aggaggtttt   660
gtgattctga agatgtgaat gaagccaggc tgtgcagaa aagtgaaatg aggcctgagc   720
acaaggactt gtttgaattt gtcaacaagt gtttattgcc cagacaggag agaagtcaca   780
```

-continued

```
ttgccaatta catggatcta gttcttatag agtgcctgga gagaggaaag caaatcaatt   840
gtctgccttc attatcaagc tgctcgacag ggttatataat ggctccaagg ctcatgctac   900
tctttatggc tttattctaa ccacagttct ggatagtctc aatgtgcctc taaagaaatg   960
ggaaatgatc tcgagaaagg atcactttgg catcaatact cttcttgctt gtgactatgc  1020
agtcaatgac atcccaaatg aacctggtac atcctagaag acaccatca acagcaaagt  1080
caggactctg gttcaggaat atgtagccaa ggatgctgaa atagctaggc ttttggctcg  1140
tgtgattgaa gtgaaatttg agagggatgg tctcagaact gagcttgaca aagaaaagga  1200
gaaaaatgat ggaattcttc ataacatgct gaaccttctc caagcccaaa cccaaccata  1260
tagttcttcc aagccttagg actcctagct tttgtctcct gaacttgttt agtacctcag  1320
tgacccagat tagggatttt tctatctttt atttttgctc atgatttgga tgttttcttt  1380
tcttttgtg gattgttggt ggcaacatat ctctgtcaat gataactact attttgctct  1440
tgtttaatgt taatttgtcc ttgatatttt aaatatattt tcttgattac tgatgattac  1500
tccatgatta catttgcagt tgccgcagtg gccatgggta cttattaaaa tctgggaatc  1560
acactttgta tgtaacattt cgatgatgcc aaaagggaga agagagttgt gcttacaca  1620
cattctgaaa taagtaatat ttataaccta attaacctgg tccttgatgt taagtgaatt  1680
ttctaagttt agtattgatg gttaagctga gttcttacag gtcccaaata agtaaaaagc  1740
acagagtttg tcatcatcaa aaaggggaat ttgttggccc aagaacaggt gaagttttga  1800
agatgacaaa agaactcaga catggaccag gtccatcttg gaagcacag tcatgatcaa  1860
cctatacatg tgagatgcac gtgaaagaga taagtcttac tgattaagca acaatatctc  1920
ttgatctgat cgaaaaggat gaagatagtg ttagagtttg agatcatcat gaactcttcc  1980
acgatagaag agcagcaatt gagtcacaat caaactctga ttactaacct attaaatgtc  2040
agtttgttct cttttacagg aaatacacat acgcaaaagt taaactaaat tgagagcaaa  2100
agagcaaggc gattttgcaa gcaatttatg tggatttgag tgtgcactcc tgaagctact  2160
tgaacgagat agaagaacca gttccatcgt gtctatcttt ttctagttca attgtagtag  2220
gtggtttaaa ttataccttt cagctttcat agaagcaatt gtattagata cctagagtgt  2280
tcaagttata gctaacttga agttgtcgca acagttgagg ttgtgtgcca caacgggatt  2340
agagttaatc cttaggttta taaagagttt ttgtaaaagc tattttggct cagtgatttt  2400
agtggaagtt tgggaaaatc ctactgagtt gtaggtcatg gttttttcac cttttgagcc  2460
aggtgttttc cacgtaaaaa tctccgtgtt ctttatttct gtatttatta ttccgcaatt  2520
agtagtagtt ggaacaccta gaaaaccaag ttcttctata gagtagttaa gcgaaaattg  2580
ggtgccacac aaacacccct ctagtgtggg attgacgctt aaacatcaat tagttaattt  2640
ctggagcaac tagctactag ttgttattaa aatagttagt ttctttgtta gctaatatgt  2700
tgttttggtt gtaaattagt tccggtgtgt agtttggact ttggaagaag acttgtacca  2760
attgtgtttg ttattttctt tggtcttatg aatgctcaca ctaaacatca agttggtatt  2820
tgattttgca tttgaattag aagtagtatt gagacgtgtt gttgctatgc ataagtagta  2880
aaagattggt ttgagcttag ttggtttcgt gataagattg gaaataaaag aaatgtgtca  2940
aagtatgta aaaatcagta aaataggctg ctacctttta atattaccac aagtccacat  3000
ttatttagt tttaaacaat ataaatttgt taaggtaatc ttcttacaat agtctcaact  3060
tttaatttag taacagataa ttgcaaagtc aatccaacta atcatacact acccatatgt  3120
aaaaaaaaaa aaaaaaaaaa aaaaaaaaaa aagtgaacaa tcaatgcaca aaaagaaaaa  3180
aaaatatttt tcttctttaa ttaattccat aacatagtcc ttaaaattag ttaattcttg  3240
ttttagaaaa attgtaacag tctagttaat tctccaaaat gaagcaaaag attttttttc  3300
ttaagtatta cgtcactttt tttattaatc caccaaataa attaaattag atttagttca  3360
ctaaataaac tcaataagat cagatgtttt atttattttta aaaataactc aattacttaa  3420
tcacaaatga tcatgactaa ctcaaaagta atttgtttta acaaaaataa ttaatttcgt  3480
cttaaccgat gtcgggacga ctcattttgg aataaataca taaataaaat ggccaggtcg  3540
cgaggacacg tcatattcca attctttcaa ataagcttgt tatttattaa cttgagtagg  3600
ctccaatttt aggtgcggcg cacgaactaa ggtcggagat attcatcttg gttagcgtaa  3660
gctaggggttg gggatattcg tcctagtttg agattaatta agtcatcaac agtaaaagtg  3720
gacataggca aaacatgaaa accgaataaa gcacaattta tccataatta attcatgcca  3780
aatttaagtt aataaagcaa ctgtgctaga accacggact cggagaatgc tttacacttc  3840
tccccgatca acaaaaatct ttattcggac tttattttttg cagaccgata ataatagagt  3900
caaatcttcc tttgactagg gattcaaata aaaagtgact tggaacatgc aaaaatcaat  3960
tccaagcggg cgaatctgta aacaaaaaat ccttattcaa atttgtcact ttaattgaaa  4020
aactctttaa cccactattc ataacatata tatttttggg gtagaaaagg gggtgacagt  4080
tatgacctac tttatgcatc agtgttcgaa tttattttga tcaacaccct tttggaagag  4140
cgtttgatag aaatggttgg cttaataaac aatcatatta tcatcacctg cggaatcata  4200
tcattaactt ttgaaaatta aaatggtttt caaagacgtt ttgataaaag aattcctatt  4260
gtcgcagttg gaatctacaa gaccaagatg ttgatctagt gctatatttg gagaaagtgc  4320
cttaattaaa aaaaattgtt cattagttgt cttaagattt tttattattt aaaaaaaaat  4380
taagacacaa agaaacacat ttacgagtat atgtcggccg actaatgtga agttcccacg  4440
gacaacccac acatattgtg gtcaagatgg attctatcat aatcaaaagt catcatcaat  4500
tcaattctca tatttggcat ctcaagtaca tgcacaaaag caacttagga tgtaagttta  4560
tatgcacatt cttgaaatag aacctattta tacgtagtac ttatttagtt acagtagtat  4620
tatttattct ctgctacaga gctatggttt atcaaatata tcagattatc atttgttgtg  4680
taggccattt ccttatttgt acttggtatt aattctggca aaagcacaaa actgggaaat  4740
gaggttcttc ttccttaata tgagtcacag attagtacca ctactatagc caagaaaatg  4800
tgaaatcata tagtactaaa tattaatttc agatgccaaa accataaatt tcccctcctc  4860
catcattgaa aacccctctg tcctttcccc tagagagacc ccttttttcct ctctctctcc  4920
ttctcttttt attagacgca tatattctct cttctttctc tttctagggt tttcacctga  4980
aatagtttta tttcggtgat                                             5000
```

SEQ ID NO: 97          moltype = DNA   length = 5000
FEATURE                Location/Qualifiers
source                 1..5000
                       mol_type = unassigned DNA
                       organism = Nicotiana tabacum
SEQUENCE: 97
atttaaaacc ctaaaaaaca agatttttat ctatctgcat ggtgaaggac aaagaggtct   60

-continued

```
tcaatctcag gttctttttt tttttttttt ttatatatat atcttgtttg ggtttaaggt   120
tattgggctg atgaatgttt taattttaac ataggtctac ttacgtagta gttataggtt   180
gataatgaga tataattaac taagtctttg tataatgcag atcctgaact taatctttat   240
ttgtattatt ttttttttgtt actgaaagat tctgttacca aattttatca gtctatttaa   300
ttagaggcca acgattgtta ggtatgtggc acttcgagtg ggaaatgata tattcccatt   360
aaaggtgtta attaaccacc aaattgttct ttaggtctgt ttgtcatttt gtattaaggt   420
ggatggttta ttatatatat cttctcttta atgctaatca tgcttaactt tttcatttag   480
taccagcaag catatttgtt tactttattg gttattcctt atcaaagtct tcatcttgtt   540
gctttttttt attgtacttt acaaaagatt tctagtatta atggaaagtg ctcatatttg   600
gaaaaagaca tggccaacaa gaaatgtcta tatacccat ttcttcttct tcttctttt   660
ttccgaaaat ttcttatttt tgttttattt tctgtttctt gttgagtgct ttcatggtag   720
aagaagaagt aggagattct tggacatggc tgcatgagaa ttgttaaata acccccgtata   780
catacacaag tagtgttggc tgtctttgat atcaaaccat ttattgccct aatttctgcc   840
ttttgtcccc tcaacaaaac catcaaagtt ctcaaagagg gtttattctt gtttcccact   900
ttgcccccca cctattaggg ccaccccacc aaagggatct ctctcgtgtc tagtgttttt   960
tcccaaggac caccactcct tttttttttct ctaccataac ttcgtccaca ccatcttatt   1020
gtgatatttt cgtttaatga atttgcagcc atgccttcat tcatcatcag aactcagtca   1080
taagcacaga ttctgagaga gtaattaatg aatgaatcag tggtgatttg acgtaaagta   1140
tacatgatta tggttttttag ctgaataagc agagggagaa aatatatatca tatataaaca   1200
agtagagtaa aagaatgacg caagattagt accaaaagag tgaaggaaga gatttaatat   1260
tatagggaaa agggaagtag taggtgatac ttgacaggtt gataagatgg ttattactac   1320
aagttgatgt attgacgcta actcacgcaa gagagaccta ctcactgtac aatattttta   1380
caagaataag cgattctttc tctctttact tgcaagaatt gtgtgttgtg tgagttgtat   1440
ggcgcatttt ctaggagcct gtggtagtga tggatgtatt catataatac aatacaatac   1500
atatggaata gatagataga taagatggtg cacgcatgag aggcaattat gcaacttacg   1560
tcaactactt ccatccatcc atcttttctt ccttctgttt ctgtctgata tagtgagtat   1620
atgcttgtgc tggtgttgtg tgcttttctg gcctgggatt ttcctaacac tttagataat   1680
ttaggttccc atcaataata atgtcttttt agaggagcat catcgataga tattcaaata   1740
ttaaacctgg cctagctact atctaggcg tctgctaggt ttttccatta cctttgtat   1800
atctcttatg tgggaccttt tgtttatgga agaatatgga gtactttat tcatctcgta   1860
gggtcttgaa tacaagatt tatatatatc actctttaaa aatgaccatc ctaaaattct   1920
tcctctttca tttgcattta ccagaattga tattagtacc taaactagta ctcttcactg   1980
aggccttttg tatttagtcc tattatattt gaatttggca ctatttaaat taaaaaaata   2040
atctacaata aaaaattctt ccctaaacat tacccatcaa atcctcacca cctaaggtaa   2100
ctctaccatg tattaatttt ttggatcaaa tctagtgagg attaattctc cacttatgtt   2160
ctttcggaac tggctaagta atcttcaaaa gctagggcat ctccgcagtc atatcgtgcc   2220
ctcccaagta tagcgaccgc ttctatattt tccctgaatt tcatctgtgc tagggcttgt   2280
tttcacgttg atttcaaaca aaggctaaca atttcattga gtaacttttt ctcatttcag   2340
gactcgaacc ttaaacctct gttcaaataa cttctaagaa gtatatatgt atacaatgtt   2400
tgtattcatt gtgacaaagt attatgagtt gtacaacttt cttgtgaaga tagagcataa   2460
tgttaaacaa ggatctatat agagcataat gtcaacaaaa caacaacatc aacccagtaa   2520
tcatcctact aataggattt ggggagggta gagtgtacgt aaaccttacc catacagggg   2580
aggggtaaa gaggttattt tcgggagacc ctcggctcag agacaaaaaa atctataata   2640
acaacagaaa ccagacaaat aatatcagca tcataagaga caacaaataa gtggaatgac   2700
aataattatg ccaataataa cattgaaaaa aataaaatta aaaattaaaa ataaaaatag   2760
tgtgatgaac aaaaatcgct agcagtctta gacaaaacac tatcagacta gctggaacaa   2820
cgaggaaaaa cgctgaagta cccctaacc tacaacccta atgctcgaca tccacacctc   2880
cctatccagg gtcatgtcct cggaaatctc aaatcgcgtc atgtcctgcc tgatcaccotc   2940
gccccattac ttcttaggtc gccctctacc tcttctcata cctgtcaaag ccaaccgtca   3000
cacctcctaa ctgggcatc taggcttctc ggggccggcc agcccgtaga tctaaaagga   3060
tccatccata gcgcccgaac catccacgcc tcgctttccg catcttgtcg tccatgggag   3120
ccacgcccac cttatccagc cttatccagc ctagtgtgcc cccacatcat ctcaacatcc   3180
tcatttcgac tactttcatc ttctggatac aagaattctt gactggccaa cattcagctc   3240
catacaacat ggtcgatcta accaccactc tataaaactt gcctttaaat ttcagtggca   3300
tgttagtatg tttactttag atacaatgtt ttttagagtc ttatagtctt gttagaatac   3360
tatatattat aaaatatgga gacttctggg cactttttgtt ttattttata taagatagga   3420
ttggaatgaa ttcaattgga gggacatgca tgataaatga atattcatgt agccgatata   3480
tgtttgggac tgaaacgaca ttattattgt gaaatatttt acaattgcat ttcacactca   3540
ctgaagtgaa actttgattc cacgtcggtc aatacttagg tgttacggtt tggctgcgag   3600
gggaatcgaa gagagcaaat taattaaagt atttaatgag gaatcatgag ttagttggtg   3660
gaattataat agtcaaatga atgagttatt cgcctgataa tatagttgat agtagtatat   3720
actatatatg ttgatactag ttattggtgg tgacctaatt aagtaaagag aagagaagag   3780
tggttatgta aaggaatcta ggtatagtgg gggatggggg gaggcaaggt taaaagaaag   3840
gtggaaaatc caagaatcct gcttcctcta gtaacatagc atatcctgca attcgtgctt   3900
ttgtttcctc tcacaagata actacttttt tgattaatta ttacatttga cacatacata   3960
caaacctata aaattagaca tccttatgga atcttacgac tccgaacttg tcatatatcc   4020
tttaattatg cttagctttt tgctaaaaac aaaaaggata tccttattcc aaaatgcaac   4080
taggagcatc ttcccacatt tcttttttat gcctctgcat catcaaatcc cataatgccg   4140
cacaacaatt tcttttttact taagtatatt ctagcttagc tatttcatac gaataatggg   4200
tatacaaatt tgcttattt aggttttaaa taccgattta aatatattgg atgggttcaa   4260
cttttaaaat tcttacactg atatacatgc atagaatatg tggaaaactt taatattaat   4320
tacaactgct aaacatttga atggattctt catgccgtgt gctcctttgt tgaagaacac   4380
gtactccctc cgttcgcatt tatttggcac gttttgactt ttcacgcccc ttaagaaata   4440
ataaataaaa tgcataattt atcatgataa acatatcaat ttatgcatat tttattagat   4500
ttgagaaaat aatttgaaat gagtaataaa tactgtgagt ataacaggaa attttttttt   4560
gtcttctctt gatatgcata aaatagcaag taaaaataaa aatctatttt taatataaat   4620
gtcaagtaaa agtgaatgga ggaagtattt ggaaggcga tatcgaataa aaaagttata   4680
ctaataacaa acagcaacaa ttacaagaaa ctgtagagtt ggccagtacc aggtatatat   4740
gtagaatttt ttttatgagg aatttagtga aacgctagct atttcaacac ttcagacata   4800
```

```
tcaataccaa ttttatggtt tctcttaggt gttgatagat tctcttttgt cagcaaacat  4860
tatttatgaa atttataata aaatgctgct cttttcgagt ttacattctc cgtcccaata  4920
caatatatac ttgatttgac gaaagaaatg taacaataga atcttaagtc ggaaaaagtc  4980
aaatcaaatt tgaaaaaaat                                             5000

SEQ ID NO: 98        moltype = DNA   length = 5000
FEATURE              Location/Qualifiers
source               1..5000
                     mol_type = unassigned DNA
                     organism = Nicotiana tabacum
SEQUENCE: 98
gaaaactaaa aaaagaacta aggcatttac actaggtctt caccggggct cgtcccatca   60
ccagaacccg ttggcctcag gtctcttggc ttctttaatc ttggccgaca ggtcaaaacc  120
tcgggaatgg atatcctcga gggtctctct ctggtatagc cgctttacgt actcggtctt  180
catctttaag cgggcctcag ctatctccac atcagcctta tactgggcca gcatttcctc  240
gacgtcggag gaatcaatag aagttgcctc caacttggat ctcagcgcgt tatattcttg  300
gtcgagggca tcccattccg tgacggctga gttcagctgt gctcggagtt catcatttag  360
ccgagatcac ttgtcggcct tgtcctttgc cacccggagt tggtccttta tcgatgtcaa  420
ctcctctttt gcagcctctt tttccgaagc cagtaggtcc atcctgccct tctacgcctc  480
ggtcgtggcc ttgacctcat ccatctcagc ccgaagccgg tcgatcaggt ctaccttctc  540
ttggacctgg gaagttgcgt tgttagtcac cacgagtagc ttctcatttt tagcctcaaa  600
gatccttacc ttctcgacca agtcagcgtg ctcccacttc atggacaagg cctccttctg  660
agccttttcc agctcggctc agagaattgg gaggtacttg agggcctcgt cttattgttc  720
gctgagagac ctgtaaatgt ccttctcccg gatcagttct ttaagctcga actcaagctg  780
actgatttgc aagagagacc gaaggaagct ttcatgatga agcattcaaa tctgaaatat  840
aataaggtca ttagaaatatg cggagcaaat attcgcaaag gatacaaagg atagacgtct  900
tacccggttc aatgcctatt gcacctcgtt gaagaggctc tacgtgccta cttcattcat  960
ctttgcctaa tccttatcgg tcaccaggca acgaaggtag ctggctatgc cgaccggagc  1020
ggacagggct cgggcgtcca tcgggatagt aagaatgacc attctcttac ggtcggggtc  1080
aacacccggg gggagggaac ttcttcacta gtttcgggct caagctcgag ctcggcttgc  1140
tcgctcccga tgacacatcc ttttttggga cctccaggtg accaagcctg gagaagtcct  1200
ccaatgcgac catgtccatg ccatcaaaga acgtgttgag ggcattatct ggacccgacg  1260
ctatctcatt taatttctct ttattagctt gaacctcttc gagcatggac tcagtatagg  1320
acggcgtctc tgcgatgtca atgatactag ctacatcctt cgggacagga gcggcttctc  1380
gataggccat ggactccgtc tctccctctg gttctcgagc tagaggggga tcgacctctt  1440
ggtcaccttt cctggttgcc accttctccc tctcgttgag ggtcgactca tgagcaatga  1500
actcaaggtc gtcatcctca ggataatccc taagccggta gagggaatca gatttcggta  1560
ccctcgactt ggtgctcttt ttgtttttct ggacctggac gaccaccctc ttcttcttca  1620
cctcgacatc cggggagcct gtggatttcc tttattctt cttttctct tcccttacgg  1680
cggcctcggg ctgtcccgaa gcggagggt cagcgagcga ggacggatcc tcgtcctcat  1740
ccaatggctt gagctcggtg gtcatgggtg aacctgtgag aagaaagaag acttagcgat  1800
atattcatca agtatatgaa tgtaatcatt cgggagagag actcactatg ggaacgagcc  1860
tcccatttgc ccttcgagag cttgcgccat acgctcgaag taggacatct atttgcacat  1920
cccctcgatt cactccttga agcaggggaa tgtattagga acctgggcaa ctgctacata  1980
atggcaaata caggcaatta gaaaaaagaa taaaaggaaa tgccagatac tcgagaggga  2040
aaagacttac gggatgcgtt tcactttttg aggaatggta gaaattcgga gaggatgagg  2100
tcttcggttt tcacccgaac gaacctcccc taccaacctc gatctcggtc ctcgtcgatg  2160
ctcgagaacg gagccttgct tgctcggcga acgatcttaa tcaacccctc tcggaagatt  2220
cgaggactgt atagatgaag tagatgttcg agggtgaact gaggtgcttc agttttgttt  2280
acaaagtgtt ggaggaggat tacgatcctc caaaaggaca ggtgaaggca gaccttgcac  2340
cttttataga tgtcgaggac tatggggtcc accgggacga gcgtgaagga gtaagtgaa  2400
acacttaggt acccctccac gtgagtggtg atgtctttgt tgggcccggg gacgaccacc  2460
tcctttccct cccagttaca ctctacccga actatgggta gtgtctcctc agtaacagag  2520
catatgtacc tccatgctcc ctcgtctcgg tcctgttgac tggaggcttt ctcgacgttg  2580
aagtcattct cgatagagca gcccccgagt acgaagctct tcaagggagg ctcatgggct  2640
acctcaggaa tggccacctc ggcatttatg gccagattgg aaaataaagg agcggtttgt  2700
tgaggaacga atttgaaagt ttttgctatc gggttctgaa aaatatgaag gtttgaagaa  2760
aaaatatgaa gatttgaaga tagaatgaa atatgaaggt ctgggttgaa gattgaaaga  2820
gaatgtatga agattgagga tgaaggtatg aaaatctaag gagcaatcta tgaagatttg  2880
aaggagttaa aggtatgtaa agaattcaag ggtaaatcaa ggagctctag aatcgaaaag  2940
tggagaagtg aaaaaggggt cggagctttt atagaggaag gacaatcaat gcatgacgtt  3000
tcacattcga ggacagtcaa tcaacggccg atacgtgtcc gatgttagaa cgatgcgact  3060
aatgggacgt ttcattgatc cgtcatctcg gttgtaacgt acgaagaaag gaatcggggt  3120
tcatttatcg cttcccgtcg tttcgataaa tctatcctcc gaaaaacaag gggactatct  3180
gtatacgggt aaaatcaggc aatgtctacc ctgattctcc tataagaaa taaaggggga  3240
gcgcggatcc gcgagattgt aatcgaggac agagacccat cgtatcaaga tccaagaaga  3300
gtgaacgata tatctaacat cagacacggc aaagcgatgt accccggacc gaatataact  3360
cctagacctc gggagaagcg ggggacggtt atgcatgaca gataggagac tgtatactcg  3420
ccctcaatcg gatattacga cgcgaatctc gtcagtaaca attatggatc aataattact  3480
ggaaaaagaa gattttttacc tttttttagac ttatactagg actgaaattc tcgtactata  3540
taaaggtaaa gttttttcttt gatctgacac attgtaacac gcaattcaaa gaaataaaaa  3600
tttgtttttg ccttctaact aatgttaaaa attttgctca cttgttctgt tcttcattca  3660
cgactggact cgaaccgagg gtccaatcga gtacgaggtc actgttcaat ctaagatcat  3720
gcttggtcat aacattgcga ttggtttgat catttatttc gtctttaatt catttatctg  3780
ttattttttaa ttattcgtgt tgaattaaat cacgtatcat ttaaaccgcg tacaaattta  3840
attgttaccc atttttaagg taaacaacta tagacgaaaa aaaaaatata aatattaaat  3900
attatgtttc gaaagataca caatagacaa gaaaagaaaa gaaaaatccc ttataaaatt  3960
tggatttagc ccaccagttt tattgagacg tctttgtgtg ttagttaccc ggcaaaggtt  4020
atgaacctac tttatgcgtc aatgtccgaa tttatttta tcaacatcct tttggaagag  4080
```

```
cttttgatag aaatggttgg cttaattagc aatcatatta tcatcacctg cgctttggtg   4140
ttatatcatt cggaatcata tcattacctt ttgaaattta aaatggtttt caaagacgtt   4200
tcgataaaaa aattcctatt gtcgcagttg gaatctacaa gacgaagatg ttgatctagt   4260
gctatatttg gagaaagtgc cttaattaaa aataaaaaat tgttgatcag ttgtcttaag   4320
attttttatt attaaaaaaa aaaaattaag atacaaagaa acacatttac gagtatatgt   4380
cggccgacta attaatgtga agttccacac ggtcaaccca cacatattgt ggtcaagata   4440
gattctatca taatcaaaag tcattatcga ctcaattttc atatttggca tcttaagtac   4500
atgcacaaaa gctacttagg atgtaagttt ataatcattc attcttgaaa tagaacctat   4560
ttaatagtac ttaattagtt acagtagtat aatttattct ctgctaaaga gctattgttc   4620
atcaaaatata tcagattatc ctttgtggtg tagaccattt ccttatttgt acttagtatt   4680
aattctggca aaagcacaaa actgggaaat gaggttcttc ttcattaatg ttgagtcaag   4740
attagtacta ctactatagc caagaaaatg tgaaatcata tagtactaac tttcccttct   4800
ccctagctac tgataactct aattaatttc agatgccaaa accataaatt tcccctcctc   4860
catcattgaa aacccctttg tcctttcccc ccagacccc ttttcctctc tctctctctc   4920
ctttctcttt ttattagacg catattctct cttctttctc tttctagggt tttcacctga   4980
aatagtttta tttcgttgat                                              5000

SEQ ID NO: 99          moltype = DNA   length = 5000
FEATURE                Location/Qualifiers
source                 1..5000
                       mol_type = unassigned DNA
                       organism = Nicotiana tabacum
SEQUENCE: 99
attataaggg aaattaaaac cctaaaaaca agattttatc tatctgcatg gtgaaggaca   60
aagaggtctt caatctcagg ttcttttttgt ttttttaact tgtttggata tgaggttatt   120
gagctgatga atgttttaat tttaacatag gcctacttac gtagtagtta taggttgata   180
atgatatata tttaactaag tctttgtata atgcagatcc tgaacttaat tttttatttt   240
attattttgt tgttaatgaa agattctgtt accaaatttt atcagtctat ttaattagag   300
gccaaagatt gttaggtatg tggcacttgg agtgggaaat gatatattcc cattaaaggt   360
gttaattaac caccaaattg ttctttaggt ctgtttgtca ttttgtatta aggtggatgg   420
ttcattatct tctctcttaat gctaatcatg cttcaccttt tcatttagta ctagcaagca   480
tatttgttta ctttattggt tattccttat caaagtcttt atcttgttgc tttttttttt   540
attgtacttt acaaaagatt tctggtatta atggaaagtg ctcatatttg gaaaaagaca   600
tggccaacaa gaaaggtgta tacccccattt cttttttctt ttctccaaat tttttttttt   660
ttttttttctg tttcttgttg agttcttcca tggaagaaga agaagagtag gagattcttg   720
gacatggctg catgagaatt gttattgttt tgtgcactta aataacccg tatacataca   780
caagtagtgt tggctgtctt tgatattgca ccatttattg ccctaatttc tgccttttgt   840
cccctcaaca aaaccatcaa agttctcaaa taggtttat tcttgtttcc cactttgccc   900
cccacccatt agggccaccc caccaaaggg atctctctcg tgtctagtgt tttttcccaa   960
ggaccaccac tactttttt tttttctcta ccataacttc cacaccatct tgtgatcttt   1020
cgtttaataa tgattttgca gccatgcctt cgttcatcag aactcggtca taagcacaga   1080
ttctgagaga gtaattaatg aatgaatcag tggtgatttg acttatacat gattatggtt   1140
tttagctcaa taagcagagg gagaaaatat atataaacaa gtaaatctag tagaagaagt   1200
agaagtttta tagctagagt agtgggaaag aatgacgcaa gattagtacc aaaagagtga   1260
aggaagagct ttaatatagg gaaaaggaa gtagtaggtg atacttgaca ggttgataag   1320
atggttacta ctacaagttg atgtattgac gctaactcac gcaagagacc tactcactgt   1380
gcaatattta caagaagcga ttctttctct ctttacttgc aagagttgtg tgttccgagt   1440
tgtatggcgc atatgaacct ttttttcatc aatacaatac atatggaata gatagataag   1500
acggtgcacg catgaggcaa ttatgcaact taacatcaac tacttccatc atctttttctt   1560
ccctctgttt ctgtttctgt ttctgtttct gtctgatata ctatatgctt ctctggcctg   1620
gatttttccta actctttttga taatttaggt tcccatcaat aatgtctttt tagaggagca   1680
tcatatcgat agatattcaa atattaaacc tggcctaggg ctaggcgtc tgctaggttt   1740
ttgcattact ctttgtatat ctcatctgtg ggaccttttg tttatggaag aatatacttt   1800
tattcatctt gttgggtctt aaattcaaga tttaatatta ctctttaaaa attaatgact   1860
atcctaaaat tcttcctctt ttatttgcat ttacaagaat tgatattagt acctaaaact   1920
cttctctggg gccttttgta tttagtcctt ttatgtttga aattgacact atttaaataa   1980
aacataatct acaataagat gttcttcacc cttcgggttg cccggttggt ttggatggga   2040
tcgattcccc cgatatcttc tgggttgagc atatcgcaca gggcttgtct agtgcggttt   2100
gcattcccta tgtggtttgc attccctatg tggtttgcat gctattatac atgggtttac   2160
ccagtggaca caaagtattc aatacagagt gttcacccga agaacagagg ctgtggcaaa   2220
gattgtaacg gccgcgggtt tcccctctta caaaaaaaaa aatgtcttc cttaaacatt   2280
acccatcaaa gactcaccaa agatagctct accaagtatt attttggat caaatggcat   2340
ttccacggtc atatctcctc cccccccct caccccccc cccaaagcta gtgatcactt   2400
ccatattttt tcctgatttc atcggtgctc aaatacttgt tcattcatct tcattccaaa   2460
caaaggcgaa aaacttcact attgagtgct ttttttcctat tccaagtgtc aaaccctaaa   2520
cttcagtca aataatatct aagatgtata ctcttatact atgtttgtat tcattatgac   2580
aaagtatgat gagttgtaca attttcttgc ggacttagtg aaaatagagc ataatgttaa   2640
aaaaatattt acatgatatt aattagccgg attaagttta taacgttagt atatatgtct   2700
actttaggta caatacaagt cttatactct tgtcagaatt tatatgtcac aaaatataga   2760
aacttctagc tactttttttt taattttata taatataata ttggaatgaa tttaagtgga   2820
gcaaagtga atattcatgt agtcgatata ttctaatctg tttggggctg agatgacatg   2880
attgtagtga aatattgtac cattgcattt cacactcact gaactgaaac tttggttcca   2940
cgtcggtgat catttgcatg tttcattagt caatactgtg gctgttatga tttggctgcg   3000
aggggggatcg aagagagcac attaaagtat ttaatcagta ttatgagtt gaatgctgtt   3060
agttggcgga attaatagtc aaataatgaa tgagttactc gctgatatag ttaatagtac   3120
tccgtatata tgttgattct agttattggt ggtgacctaa gtaaagagaa tagatgagag   3180
gagtggtggt atgtaaagga atctaggtaa aggggtgggg gtgggggag gcaaagttga   3240
aaagaaaggt ggaaaatcca agaatcctgc ttcctccagt aacatagcat atcctgctat   3300
tcgtgctttt gtttcctctc acaagataac tactttttga ttaattatta catttgacgc   3360
```

-continued

```
atacaaacct ataaaattaa actaatcaac gacatcctta tggaatctta cgagtccgaa   3420
cttgtcatat atataacttt aaagtacttt gtcacttctt aatatgctcc tttaattgtg   3480
cttagctttt tgctaaaaaa caaaaaggat atccttattc caaaatgcaa ctgggagcat   3540
cttctcactt ttcttttta tgcctctgca tcatcaaatc ccacaatgcc gcacaacaaa   3600
ctcttgttac ttaagtatat attctacttc ataagaataa tgggtataaa aatttgctta   3660
ttttatgttt taaataccac cgaaaattca taagcaaatt caggatttaa atatattaaa   3720
tgaattcaac ttttaaaatt gttgcactta tatatatata tatatatata tatgcatatc   3780
caagttgagg gatacgggtt cacatgaact catattactt tctctaaacc atgtataaca   3840
atgttatatt ttttcaaaat tatttaaata tatgtgtgtg aacccattct caaaatctct   3900
tatggtgcaa ttattattgg gtgcacatct acaagtgaaa tttgcagctc aaaacctcat   3960
ctgggcggtc ttgttttccg catggagtat aactatatat gtgaaaatta ctagaatttc   4020
aaaatgaata taattttgaa atgttgtggg ttcctggtaa gagactaaag ttaaactcgt   4080
caaatataaa ttctagatcc acctcttcac aatagtgcac ccattctttt gaaattctgg   4140
atctgcctct gttaataata tatatatata tatatatata tatatatata tatatatata   4200
tatatatata taaacacaaa aaaatatgtg gaaaacttta ctattaatta ccactgctaa   4260
acatttgaat ggattcttca tgccgtgtgc tcctttgttg aagaacacgt acttgggagg   4320
gcgagatttc gaataaaaaa gttatactaa taacaaacag caacaattat aagaaaatga   4380
aaataaaagg gaaagagcac tcacataaac tagaaactgt agagttggca agtaccaggt   4440
atatatgtcc ttgaatgttt tttacgagga attgagtaaa acgctagcta tttcaacaca   4500
tatataaaaa gcatcaatac caattttatg gtttctctta ggtgttgata gattctcttt   4560
tgtcagcaaa gttcttgcat taactatatg aaatttataa taaaaatgct gctcttttaa   4620
ttgagtatac atgcagtctc ctaacatata cattctccgt cccgatatat acttgatttg   4680
atgcatttca aaaattaaat gtttgagtgt tttggtgaat tgtgcttgat atagaagtat   4740
ttaaaataag aaagaaatgt aacggcagaa tcttaagtcg aaagtcaaat taaatttgaa   4800
aaataaaaaa taatactctt gatacttact agtactagtc aatgggcagc tctttcggga   4860
ctaaccaaaa gcattattct tattgtttcc ggcatagtat taaaatgtaa caatgcttaa   4920
ttatgttaca aaattaatgt ttttgtggac ttcggaataa tttatttctg aattcgccgg   4980
tgttatcgaa aacatgggga                                              5000

SEQ ID NO: 100        moltype = DNA  length = 5007
FEATURE               Location/Qualifiers
source                1..5007
                      mol_type = unassigned DNA
                      organism = Nicotiana tabacum
SEQUENCE: 100
tggggggccct ccgcacaagg gaggagctag gggaggcaag aaaattacat gtgtatataa   60
gattaaattt tcttcttctt ttttgtgtat aggataaata tttaatttc ttaatttttt   120
tgcgtagtta ctcttttaat tattttaac tcctctgaac gcaagtctta cctccgccgc   180
tgactcctct agagaggagg ggtctaaatg catgcaactc aaacgacgaa agggtctttg   240
cctaactaaa ggttccttat tctaatatat ccttctagaa aaggtaatag aagttgattc   300
gaatatcaaa gagagataca tgtcggttac aaaaataatt ctcaagataa tcaatagaca   360
tctctagatt ctcggactta aaagatccat ttagacacat aatcatattt tttttccaaa   420
caatcgtcga aggcagcttg ttgcacaaaa tatttcgtat ttacataagg tttaaggaaa   480
aatcgtactt caaagagtat gatgtagata atacattcta attagggtcg gctctatagg   540
tgtaaggcaa gtgtcttagg ccccaatttt gggaggcccc attttttagt aatactatat   600
attttagagg tttataattt tttttttaaat aattaaataa tatatatagt attttttttac   660
ttttcatata taaaaaagaa aaacttttaa tatattaaaa agataaagat taaaatagta   720
ctaaaaaata gttgtcactt tgatttgatt tgacaacttt actttttgct cttcttccca   780
aataattcct agacccaatc caacatttca attttcatat agaaggatga gacatagtaa   840
catacctttc tcctttcttt tgattcgtgc tcattttgtt tctactagat ttctttcttt   900
ctccaaaact ccaacaagcc aacaactaca tattttgaaa tcaaagtctt caaatttttt   960
gaatcagtta gtcgggtaat atcattctaa cttttttagta ttattttttat ttattatttta   1020
ttatttttatt aattttacca tgtacatatt gtttaatttt tttagaatat aaatatgtct   1080
acaagaaaat atgcatccgg atattcaaaa atccaaaaga aaagaaaagt tgaaaattta   1140
ataaaatctc aaaaaggagt tctcgagaat ttttgacaaa taataaaaaa actaaatcgc   1200
aaaatgtagg agaatattct gtagatgaac aagtcactaa ctttgagtca gatgataaca   1260
aaattcaaat tgaagaagat gtttatgaga aatctgacga agaaacaaac tttagcctta   1320
ggccctatat taaactttgg ccctaggcct catatgagct tgagtcgccc ctaattctaa   1380
tacaagtatt agtggctact ttcacggctt gtgacttatg gattacaaac aactttacag   1440
ttacgtcaag gctccacgta gttctcaatt tatggagcat atattagatg attaacgcag   1500
ggaaagattc tgctctcctc tgatacatgg ctattattcc tcgtttagtt caaaaaggaa   1560
aaagagggta gtcttgttat attattgggg aatgaattat ggtttcaaac ttttcaaact   1620
taaaggattt tgtacatggt aaaacctaaa ttgacacgta acttggtact ttcaaagaca   1680
cgatctttta cgcgatattt taaataaaga aagatcaag tcaaaacatg ggccaaaaag   1740
aaaaacccca tgattttttc tgataaaaag ctgctaactt ttagtttgtt ttatccaata   1800
aaacatcttt aacggtctgc ctgctttagt ttaatcctct ttttaagatg taattaagca   1860
taaaatagaa aagggaaaaa aaggtccat tggattttgg aagaaatttt aagaaagtac   1920
aagaactagt aaagtcattt tgtatagagt atgttaaaaa ggtgagtgac aattcgaaaa   1980
agaaagcatt gataagtcaa tcactaaata aaaaagcaca cctaataatc attcattcaa   2040
aaaaacaaat ttctatgaaa gataatcatt atcataagtc actgcagaaa tcccatatac   2100
agtagagtac caggatttta cgataaggtg ttagcaaact atctattcat tttttgacaa   2160
gcattttatg tttggtcatt tgttgggaaa aattagggag aaatttaaaa atagttagat   2220
ttacaactgg tcattaaaaa tagcccaatt tcaaaagtaa tcgaaattta gccactttc   2280
atgtaaagat aaatctgagc gaaaatattg ttcaaaaccg gaaaatacg cccgtatatt   2340
atactggagt tccagcataa gtatgcttga actccagcat attatacggg agttctagga   2400
taactatgtt ggaactccag cataatatgt tggagttcca gcataagtac actagaactc   2460
cagcatatta tacgggagtt ccaacaagta taactgtccc gtataatata ttggagtttg   2520
gagcaccggt gctccagtct cccgtatatt atacaggagt cagcaaagta taccggtcca   2580
gcataatatg ctggagttcg tacacagatg caccgaactc acgtatatta tgcggaaccg   2640
```

```
gtctctgttg cagcaaaata gtggctattt ttcattgact tcgtaaacgg tggctatttt   2700
tgaatgacca gtccgaaaac tggctatacc gtgctatttt gacgaaaaat tatcccccca   2760
cccacccacc cacccaaacg caccttacac acattagtgc acatctttta actagttttt   2820
ggttatttt ttatttgatg cccgatattc gtatatggat ttcgattaat tagaattcac    2880
accgaaacat tctttcttag gattttgtac atacttaata tgcgaataca aaacctatgc    2940
ggaaaggtaa gggaacctat tcatccctct cagtacttg tgataatgtt atactttttt    3000
gaatttaatt tgggagacat gtcaatcttt attttgaaaa aaaaatagaa taaaaccata    3060
gggaaatgaa caatttatct ttcactccta tctcatttta tttgtcttga attttttcaaa   3120
attttgaatt atattttgaa acttcttcaa tttattttct tggaatcttc agaattcaat    3180
ttaaaattcc aaaattccaa ggatttagct cccgtttggc cacagatttt ggcttcattt    3240
ttttaaaaaa aattttgaaa acattctttg tttatgcaat atgatcatgt tttaggggaa    3300
aaaaattaaa aaaaataaaa aaaatcaaa ttcccaaaaa ctggttaggc aattttttgga    3360
tgatatttt tcttccactc acaaaacttt aacatgtcca aacacaactt caacttcaaa     3420
aattattttc aacacaattt taaaaactct tttttcaagt ttcaatcaaa tctatatcca    3480
aatgttagct tagtatcaaa taagtgattg aaatcaaatt aaaatcgagt ggtaaataaa    3540
atagaggaga gctcggtaaa ttacaagagt gcggtaaatc ttttctcctt tactctcact   3600
gtagcctatt ctatctgttg taactaataa gtaactgagc tacggaaaaa gtgcctagac    3660
ttttaacttc acaagtataa taaatagaag tcaattcttt cataatattg tttccatcct    3720
atcaaacaga ctttgtctca ctgaccttcc ttctgagtgt gtcttttata tgtcattttt    3780
agtgaatcca tatgatttag agactctaat attccacatg cgggtcttaa tttggtgtat    3840
atgtatatgg taataatttt tgttaggtag ctgtagtatt ctattattgt tatgtattga    3900
ctcatcatgt aaataaagcc ggttagataa ggctagaaaa atatgagtat acctagaaat    3960
tattagcata ttgtttggaa catgtcaaaa atttcaatga cctagctaga gctgtcaatt    4020
agtcaaataa ctttattaat atttacttat gaaaacactt tgaaattctt ggagtttaag    4080
ggaaagacta ctgactaaaa aacaaagcaa aagtctatgc attactatac tatacacagc    4140
acagcatttt ccaatagtat ttgagatgaa tctccaatca gctactgttg ttcttttctt    4200
ttctttattt agtttaagtt ttatgtgttg atggtataca aattatttgc acaatcaaat    4260
ggcttatctg gataatatag gtaaacctct tgtaatcact aattggtaat ctggtaaaaa    4320
taacactatt tctattccaa tttatgtgat caatttcact agacaaaaat ttaagaaaga    4380
aataaatttt ttagaacttg tagtcataaa caagttgtaa caagttgtaa gctataattt    4440
ttttaacttg tgatgttaaa catgtcagat tgtttgtgta gctataaaag tttttcatta    4500
ggcgtaaaat taaaaattta gattaaatta ttattaaatt tagaaagagg tcattttttt    4560
tagcgaagta aaaaagaaat cggttcacat aaaccgaaac atagagtaag taatctgtta    4620
tgacaaatta aaaattactt gtagtgtaaa aaaatctttta caacattcgt gtatatactt   4680
aaatctttt tattttttgg caagagatag ttgttcagca aaagtaagtt agaaataggt      4740
ctgtccttct gactttgtaa ctctgaaatg aaaatttcaa aatcccttct attttttcttt   4800
tcccccccc cccccctcac aaaccccaac tcactcttat ttaataaaaa gctctactta     4860
gaaaagacac ccttgtccat ctgtctatat aggtagaatg agagtaaagg agaaaacata     4920
tcctcctctc catttctgta gacaaagatt ctcaaagaga aacaaattaa acactagaga     4980
gtgagagagt gctataagaa aaagaat                                        5007

SEQ ID NO: 101         moltype = DNA   length = 5000
FEATURE                Location/Qualifiers
source                 1..5000
                       mol_type = unassigned DNA
                       organism = Nicotiana tabacum
SEQUENCE: 101
agaagaaatg actgttgaaa agaaaacaaa tgcaagtacc attaggaaga tttgaaaggg    60
cgtttgggta tggggggttgc caagaagatt cagactttt ttggggtttt gtgtagttgt     120
ggtagaatta ttattgaatg aaaaaaaaaa acttcctgta ctttaattcg tcagtacata    180
ctacatacta ctacaaagta gttaaaagcc tattctattc gtgctttttt tttcactcga   240
tgttcaataa ttatattggt ttttgattaa atttgaattt gagcaaggaa gatcaacatt    300
ggagggataa attgtttcct aacgaaggcg attacatact tagaacttga actcaatatc    360
tctaattaaa aatgaagtaa tacttataat aactccacca caattcttat tgttgtgcat    420
ttctttataa aatatgtaaa taatgggtca tatatattgt ttacctttc tattcatata    480
catagatttt aaaattaatta tacacatata tataatacat taattattca tatattatat   540
ttttgctagc tattttttagt ttaagcgatt tggtaggcga ctacttgggt taattctttt   600
tttttaatat atatatcaaa ataatgaagc tgtataatac acttaaaaat catatttgaa    660
aggtattaaa tacgacttag gagagttctt aaaccatttt ggaaccttgt ctacgtactt    720
ttatgcaata gctgtttttg tttgtctctg ctaaaaccta tgctccccaa ccgtgcacca    780
atcaacttag aagttagaac tcagaaataa atgtaactat actccacaga aagttaaaaa    840
gttttactgt taccattcac tcaaggatca gaaactgaaa gacaaatgaa tcagtgcttc    900
actgttcttc actaaaagaa atactgttta cattagtttc aaaagagttt aatcataaaa    960
acaaatgtac cataaaaagg ggagattatc aacctgaaaa tgaaacagaa catacgttat    1020
atatcaatct atatacggtc gagatcggac tcgtctatta cacgacagat cgggattgaa    1080
acgtaacagt tttgaagatc aaccccgggt tcgtcggac cgaggtacaa ggtcagaatg     1140
cccgttctcg agaacatcga gtccatgacc ccagaatcaa ccctgacccc aaatgagctc    1200
gaggaaacat ccgggataacg gaaggcgaaa tatccgtaac cggtcgggta tcacggcatg   1260
aatttcggca cgtaacaatg agaaaccggc taattagcaa atcatggaat tttttacctt    1320
ttatagaatt gtaactaaag tgggattccc ctactatgta aaggggggtct gactatttgt   1380
acgggacatt cattaaacgc atcccaaagt aatataatat tattttcttt ttgtaagcta   1440
ttgttctcct gtatctgata ctatttgaat tgcatcaagt tcaagtgaga ctcattttt    1500
caaggctata attgttcaag tcgcacggtt tgaatttatt cgatcattgt tcgctttaat    1560
tacaattcaa ttcatcgctt tatgtcaaat taatccacat atccttaaaa ccacttacaa    1620
atttaattgt tatcaaattt taagggtaaa cagtttggcg ctcaccgtgg agctaaggat    1680
aatagtggtt gtttgatata gattttcata acacacacta ttttacaatt gttcttcgaa    1740
gtgtctctca tttcaggttt aagctcaaaa tgtcaaactc acaattggca cccctacctg    1800
cacacaatga gtctggtcac catggtgaaa ataacaaacat agcacctggt aacgaggtac    1860
cgcccgctga tcccatcaga atttcaatcg cggaccgtt ggacgctaac tcgcatgtgg     1920
```

```
ctatcgacat gttacagtct caacaggcga cgatagctca gttacaaaac caaagccgca   1980
caccgagcag agttgaactc gatccgtccc ggaaaatcac ctgcagggaa gaaccgtccg   2040
cggagaggtc aaatggagat gagtcgggga ctaaccccga gatcataaaa atgcttgagg   2100
aaccgatgat acggattgaa tcaggggaaa agaaaatcga ggcaaatgac aagaaggtaa   2160
aaacttacaa tttcacggtc aaccaaatcc cgggagcacc gccggtactg aaaagcttgg   2220
attccaagaa gttcgtgcaa aaacatttcc ctccgagtgt ggccccgaaa tcgatcccaa   2280
aaacatttat atgcccgaga ttcttaagta taatgggaca accgacccaa acgagtatgt   2340
cacttcttac acatgcccta tcaaagggaa caacttagag gttgatgaga tcgagtctgt   2400
tttgttgaag aaattcggag agaccctgtc aaatggagct atgatatggt atcacttacc   2460
tcctaattct attgactcat ttgcaatgct tgcaaactct ttcgtgaaag cacacgccag   2520
ggctatcaag gtcgagaccc agaagtcgga cctcttcaaa gtaagacaga aggataatga   2580
gatgctcaaa gagtccgtgt cctagtttca aatgaaacag aaggacctac caccggtcgc   2640
tgatgattgg gccgttcaag ctttcaccca aggactcaat gttcgaagct cggtggcttc   2700
acagcagttg aagcaaaatc tgataaagta cccaactgtt atttgggcca atgtgcataa   2760
ccgctatcaa tcaaaaatca aagtcgaaga tgatcaactt gaggctcttt ccgggtcggt   2820
ttaccctgtc agactcgtcg acagaatcaa gagagatatc gaccgtgaac caaggtcaaa   2880
cgtagatcat tactagccat atgatggaga ttggaaaagc aataggtctg ggtgaagttc   2940
tacacagaat gaaaagagaa atgatccagg tcagagcact cgaggactcg caagcaagaa   3000
cgacttcgac aggcctatca ggcctaaaga agcaccaagg ttatcgaaat ataactttaa   3060
tattgatgcg gctgccatcg tatcagctat cagacgcatc aaagatacca aatggcctcg   3120
acctttacaa tccgatccag cccaaaggga tcctaaccaa atgtgcaaat atcatggcac   3180
ttctggccac agaataaagg attgtcgacg gttaagagag gaagtagccc ggttgttcaa   3240
taacgggcac cttcaagaat ttctgagcga ccgagccaag aatcatttta gaaataggga   3300
ttctaacaaa tagaccgaac cagaagaacc tcaacacgtc attaacatga tcatcggtgg   3360
agtcgatgcc cctcaagtgc tgatgttgaa gcgcaccaaa gtgtccatta caagggaaaa   3420
acggactcga gattacatat tagaaggaac cttgtctttc aacgacgagg atgcagaagg   3480
gatcgtgcag cctcacaatg atgcattggt aatatctgta ctcataaata aatctcgagt   3540
taagcgtgtg ttaattgatc caggtagctc aaccaacatc atccgattga gggtcctaga   3600
atggcttggc ctacaagatc aaatcatgcc tgcagtccga gttctaaatg gattcaacat   3660
agcatgcaaa accactaagg gagaaataac attgccggtg aataccacca gaaccatcca   3720
ggaaaccaag ttttatgtga tcgaaggaga catggaggtac aacgctctgt tcgggaggct   3780
aaggatctac agcatgaggg cagcaccctc gactcttcac caagtgttaa agttcccaac   3840
gtcgggaggg atcaaaacaa tctacgggga gcaaccggcc gcaaaagaaa tatttgcagt   3900
cgaagaagag atcccggtat agacactagc aacatcaaag gaaccgagtt cggataagaa   3960
ataataggct aaaatagcaat tatcgacacc agccacgacc caatcggata aaaaggggac   4020
tgatgaagat gatgattatg gggttccag atctttata gtccctgatg attctgacgc   4080
caccaaatca atggtcgagg agctggaaca ggtcacatta atcgaacgtc tacccaatca   4140
gaaggtatac ctgggcacga ggttaacccc cgagcttagg aaaaactcat tcaatttctt   4200
atagctaaca tagactattt tgcttggtcc catattgata tgacagggat cccaccggag   4260
ataatcattc aaaagctgag cctggacttg aaattctacc cagtcaagca gaaaaggaga   4320
ccccagtcaa aaatcaaaca tgctttcatc aaggacgagt atttgcacaa aactttcaac   4380
atattgaaga agtacaatat gaagctaaac ccggagaaat gtgcattcag agtcggatca   4440
ggtaaattcc tcggattcat ggtatccaat cggggaattg agtcaaccc cgacaagatc   4500
aaatccatca aagatatcac gatcgtggac aacgtgaagg ccgtgcaaag attaatcggc   4560
cgcatagccg ccttggggca atttatctcg agattctcag ataaaagtca ccggttcatt   4620
tcgctactaa agaagaagca caacttttcg tggaccccgg agtgtcaccg ggacttggag   4680
gaactcaagc ggagatagct gcttcacaca acaaaggcaa acgaacaact atacctatac   4740
ttggcagtat cggagatagc ggtaagtgga gtcttggtcc gggaagaaca aggtacacaa   4800
tttccaattt actatgttag caggacccta ggtgaggccg aaactaggta ccctcaccta   4860
gaaatattgg cattcacttt gctaagcgcg tctaggaaac tgaaaccata tttctagtga   4920
catcccatat gtgttgtgat taccaaccaa ttgtggaata taatgtataa acggctactc   4980
tcgggatgat tggccaaatg                                                5000
```

```
SEQ ID NO: 102          moltype = DNA   length = 5002
FEATURE                 Location/Qualifiers
source                  1..5002
                        mol_type = unassigned DNA
                        organism = Nicotiana tabacum
SEQUENCE: 102
aatgcagcct cagtcttcaa cataaaaaat cacatgagta tataagatta atttttttt    60
ttttgtatat atgttagatg ttgaatttct tagttgtttt gcgtgtgttt tttttttttt   120
ttttgtacct ccctcggtaa aagtcttacc tccggcaact gtctccgcga gagagagggg   180
gtctaaacgc atgtaattat tcaatgattg aaggatggtc tttgcctaaa tactaaaggt   240
tccttattgt ataggtcata ggtgttgatt cgaatatcaa agagagattc ctgtgggtta   300
taaaagtaat tctaagataa taaatactct ttttagaggt gttgttttac tgtaaaatac   360
gtatttggtt aaagtgatag acatatctag attctcagac ataaaagatc catttagaca   420
cataatcata tttttgccag atagttgttg cagctgaaaa ttggagcata tatacttaga   480
agtagcataa cactttactt ccatatagtc ggatggaaaa ttggagtatc atatcttctt   540
ttaattcaca gttaaatctt taaacatatt taataattt tttaatacaa atataaagtc   600
tatgcaaaag ttattgggtt ggtccaagcc cttaatttcg atctctagct ccgtcccgc    660
atataattct aaaacttctg cttctcctat gatacatggc taatgtttat cgtttagttc   720
aacaagaaaa agagggtagt cttattatat tatgaacggc aaaggtccaa atatgccctt   780
gtactatacg aaattgagta cattgtgccat ttgttaatac tttagctcaa atatacccttt  840
accgtcacgt agttggtcca tatacactac tagaaatccg tcaaaaaaac caaaaaaaac   900
cgaccaactt tggtcggtaa tggccaataa ccgtccaaaa cacgaccatt acgtgtggac   960
ggtattttag gggtcggaaa ggcataccga ccaaagttgg tgtaaattac cgaccaattt   1020
tggtcggtca attaaaattaa aaaaaaaccg accaaagttg atcggtattt taattatgta   1080
atcaaaagat tgaccatctg ggaatcgaac cggggtttgt attgtggcag gatactattc   1140
taccactagg ccattagtgc attttgtttt aagactgttt tttatttgat ttatactctt   1200
```

-continued

```
taattgtatt ttcgcacgaa aataaccgat caaagttagt cgattttatt aaaaaataaa   1260
attaccgacc aaagttggtc ggttttttaa aatgaccggc cgaattaacc gaccaatttt   1320
ggtcggtttt ttaatattaa ttttttattta ttttaattaa aactgaccaa aattggtcgg   1380
tttcttgaaa aaaatttccg ggactcgaaa atagttttc gcattttct ccaaagaaaa      1440
ccgaccaaag ttggtcgatt tcgtaaaaaa aaattaaaa taaaatattt taaaaaaccg     1500
accaactttt gtcggttttt tggtcggtgt tttgaccgac caaagttggt cggtcgacct     1560
tggtcggttt ttgccgaatt tctagtagtg atatacccct agagttacac aattggcaca    1620
tatatgccct tctcaaaacg aaattcaccc aaaaattatg gtttaaactt taaaataata    1680
aaaacatctc aaactttaac aatactcaaa agaccaaaat atttaaatta tttctaaaaa    1740
gataatttaa tgattaaaag cctagagttc aagttgtagt gttataaaatt tgagttgtta   1800
gtcttttttca tctttttcag ctggacattt tctatttttt ttattaacta tgtaaattag   1860
gggtgtacat ggaacgggtt ggatcgattt ttatcaaaac taaaccaaac cgattatatc    1920
ggtttgaatt gttcggtttt attggttttt tcagattttt tgttacataa atattatttc    1980
aatcttgctt tgttaaattt tttagaacta aatatatgtt cagtaaaact taaaaaattg    2040
acaaacatat gatctatctt gattacctta tgggagaatt ttcttagtaa ttggaattca    2100
tgagttttgt caagtgaaat tggtgacgaa aatagagaag acatcagtaa ttgaggaaat    2160
cggataaggg agaaagaaaa agaaaaaaag aaaaaaagaa gaaagaaaag agaaaggtaa    2220
agaaaaaagc actaataaaa aggaaatagt atttgtaata tactttaata caattaacgt    2280
aagagctaat tagtttgagt ggattccgtt ttgaaaaggg catacatgtg ccaattatat    2340
aactctaagg gcatatatgg accaactatc tgacggtaag ggcatatttg agttaatata    2400
ttaacgaatg acaaatgtgc tcaatttcgt ataatacaag gacatattac attttcccta    2460
ttatgaaatg gttcaaactt aaggattttg tacatggtaa aacctaaatt gacatgtaac    2520
ttggtacttt ccattgggca aagacacgat cttttacgtg atattttaaa tcaagtaaag    2580
atcaagtcgg gccaaaaaga aaaaaaccca tgattttta agataaaaag ctgctaactt     2640
ttagtttgtt tcatccaata aaacatcttt aacgatctgt ctgctttagt ttaatcctct    2700
ttttaagatg taactaagca tgaaatagaa aaggggaaaa aaaggacca ttggattttg     2760
gaagaagttt taagaaagta caagaactag taaagtcatt ttgtatagag tatgttaaaa    2820
aggtgagtga caattcgaaa aagagagagc attgataagt caatcaataa aataaaagca    2880
cacctgataa tcattcattc agaaaacaaa tttctatgaa tgataatcat tatcataagt    2940
cactgcagaa atcccatata cagtagagta ccaggatttt acgataaggt gttagcagac    3000
tatctattca ttttttgaca accatttac gtttggtcat tttttgggaa acgaactctc     3060
ccaacattct tccaaattac cccacgcacc ttactgtgca catcttttaa ccaacttctg    3120
gttatttttt cttttgatgt ccgatattcg tatatgaatt cccattaatt ctaagttgca    3180
ccgaaatggt ttttatcaag attttgtata tatttaatat tcgaattcaa aactaatggt   3240
cgaaggtgga agatcgtatc catcccatca taatatttgg ttggtaatat cacacctttt    3300
tgaatttggg agacttgtca attttttattt tgaaaaaaga aaaaaaaaag aaatagaaac   3360
taaaaccata gggaaatgaa caattttatt ttcactccta cctcatttta tttgtcttga    3420
attttttcaat tttgtttttga aacttcttca gtttattttc ttggaatctt cagaatttaa   3480
tttgaaattc caaaattcca aggatttagt gtcaaatcag tgcttgaaat taaatttaaa    3540
acgagtggta aataaaatag aggagaactc ggtaaattac aggagtgcgg taaatctttt    3600
ctcctttttct ctctttggag cctactctat tctattgtaa ctaagtaact taactacgaa    3660
aaacgtgcct agactttaa cttcacaagt ataaaaata gaagtcaaat tctttcataa      3720
tattgtttcc atcctatcaa acagactttg cctcactgac tctccttctg agtgtgtctt    3780
ttttatgtca tttttagtga atccaattga tttagagact caaatattcc acatgcgtgt    3840
cttaatttgg tgtatatatg gtaataattt ttgttaggta gctgtagtat tctattattg    3900
ttatgtatta actcatgtaa ataaaagccg gttagataag actagaaaaa atagagtcta    3960
cttagaaatt attagcctat tgtttggaac atgtcaaaaa ttcagtgact cagctagagc    4020
tgtcaattag tcaaataact ttattaatat taacttatga aaacacttgg ggattccttgt   4080
agtttaaggg aaagactact gactgaaaaa caaagcaaaa gtctatgcat tactatatta   4140
tacacaatac agcattttcc aatagtattt tagataaatc tccaatcagc tactgttgtt    4200
cttttctttt cttttttagt ttaagttgta tgtgttgacg gtatacaaat tatttgcaca    4260
attagatggc ttatctagat aatacgtgta aatctattga taatcattaa ttagtaatct    4320
ggtaaaaata atattgcttt tgttctaata taatgtgata tatttgactg ggtacgaaat    4380
ttaaaaaaaa ataagacata tagaacttgt tgtcttaaac aattcataac atttgtgtgg    4440
ctataattct tttgaaactt atggtgttaa acatgtctaa ttgtttgtgt atgtataaaa    4500
gattctcatt aagcgtagga aaatttgaat taaattattt ttttaattta aaaagagatc    4560
actccttttta gagctgactt aaaaagaaat tgattcacat aaactcgcac ggagggaata   4620
agtaatatac tatcaaaaat taaaaatcac ttgtagtgta aaaaaatctt tacaccaatc    4680
gtgtatattc tcaattttttt ttttttttttt ggcgagaggt agttgttcag caaaagtaag   4740
ttagaaatag gtctgtactt ttgactttgt aactctgaaa tgaaaaattc aaaatctctt    4800
ctttttttact gttttaaaaa ctccaactca ctcttattaa tataaagctc tagttagcaa   4860
agacaccctt gtccacttgt ctatatagca agaaagagag taaaggagaa aacatattct    4920
cctctccatt tctgtagaca agattctcaa aaagaaacaa attaaacact agagagtgag    4980
agagaactat aagaaaaaga at                                             5002
```

```
SEQ ID NO: 103          moltype = DNA  length = 5000
FEATURE                 Location/Qualifiers
source                  1..5000
                        mol_type = unassigned DNA
                        organism = Nicotiana tabacum
SEQUENCE: 103
agaagaaatg actagctgtt gaaaagagaa aacaaatgta agtacaccat taggaagatt   60
tgaaagggcg tttgggtatg ggggttggca agaagattca aacttttttct gggggttttgt  120
gtaattgtgg tggaattatt attattgaaa cttctttact tcaatttaaa tcgtcggtac   180
atattacgta gttgtagtaa aagcctttttc cttttttgtgc tttttttttttt ttttcgtgtt  240
cgtattaaga cttcattaaa tccaaatttg cataggacg gtcaacatta gaggaataaa    300
ttgcttccta acaaagacga ttttatactc aagagttcga gcccgaaaaa cgacctctgg   360
ttaagggtaa aaatagtaat tacaataact ccaccacaat ccttattggt gtgcatttct     420
tcattaaata ctccctccaa tccactttaa ttgatttgtt tttggctatt tttatatata     480
```

-continued

```
ttaaggaatt atctttttagc attaatcaat aatgaaattg accatattaa ccttttagtt   540
cattggaaat ataacaaata ctcctaggct ttttaattca agagcaactt ttaaatccga   600
atttgggcta agaatacaag cttgttcttt tttatctgtt tttcactcgg tgtacgagga   660
ctcaattaaa tccgaatttg agctaagaat acagacatta gaggtaatat gctttctaac   720
aaatgtgact caatgttcag actcagaact cgatatctct ggtaaggatg acatagtact   780
tacaataact ccatcataat ctttataggt atgtatttct ttataaaata tgtaaatagt   840
gttatgattt tttgtatcaa aaatgatgaa gtataatact cttaaaaatc atactccatc   900
cgtttcaatt tatgtgaacg tattttcttt ttagtctgtg ccaaaaagaa tgacctattt   960
ccttatttgg aaataaattta ccttttatgca atgatttata gtcacacaaa atatatgtgt  1020
ctcatttta accacaagtt caaaagtctt ctatcttttt ttaaactctg tgcccagtca   1080
aatgagttca cataaaattaa aacggaggga ataataaaaa tgtattaaag actacttagg   1140
agagttctta aaaaaccatt ttggaaccttt gtctacgtac ttttatgcaa taactgctta   1200
agtttgtctc tgctaaaacc tatgctcccc aaccgtgcac caatcagctt agaaatttga   1260
actcaggaat aaatgtaact acactccaca gaaacttaaa aagttttact gttaccattc   1320
actcaaggat cagaactgaa aaacaaaaga atcagtgctt cactaaaaga aatactgttt   1380
acattatttt caaaagagtt taatcattaa aatagatgta ccatcagatt agctaaaaga   1440
taaataatcg ttaaaaaaag gagattatca acttgaaaat gaaacaaatt atatgttata   1500
atatgtcaaa atatactgac agtataaaaa ctcgttaaat gtgttaaatc ctatgaaaaa   1560
actgcccaaa taaatatttg agcttaggtg tcaaatgttg tactcaacaa caataacaac   1620
aacgcattag gatcctacta gtggggtgtc caatgttgta ctattgaaca ttattcaact   1680
aacttttgtt aggtgttcct gtagtttagt gaaattaaag tccactgttc ccctatatat   1740
taatcccaaa ttaattaatc aagtgcagat aaaaatttct cattttctat taatttatta   1800
agtgtaacaa actaaagaaa ttcaagaatc ttgaatgatg agaaagagtc atgcatgtag   1860
aaaaatagat aataatacat ggaaatatat atgtatttgg ggatttgcat ggtagctcaa   1920
agattattgg aaagtgacag gaagataaat caaaatctca gtgttatttc aaaaataaaa   1980
ggcacagatt atttaaataa ttgacagcca gttttataat actatgtggg aggggacaga   2040
gatcaatcca tgtacgtgca tggctaatat taaagtaagg gagaaaaaaa tattaagtta   2100
attgatgatt aaaaatagta aaatttcaga cgtatatcac ggcaatgaag agtttgatct   2160
ttaatatctg tataatggtc cataaatatga tggataggcg ttgtttatga tatgattgat   2220
tgatcattga tcattgacta ttgtttcttg aataattaat cagtatggga aagggtccca   2280
ttaaagttga ccatttgctt agcaatatta tcttaggtaa gctccatatt agtttaatcc   2340
acttgcgaat atattccgtc ctcgcaaatc aatatttaca attcttttttt ttcagttttc   2400
tatccggtat ctgatacttg cattggtgtt cgacaaaatc tgtattcgcg tcaaaaaatt   2460
tcatattatg gggcaaaatg ctccataata aaagcgactc aatattaggg ctcgaaccaa   2520
tggcggaaac aagattttta ctaagggaat tcaaaaaata aaaacgaaaa cacatgaaga   2580
acctcaggga attcaacatc taatataaat atatgaaata aaaatttgat tctattgtaa   2640
tttgatatac agtgtaattt acaccgtagg ggatttggct aaacctcctt ccgcgtacct   2700
agctccgtcc ctgactcgaa tccgaggtat ttggttaaaa atgaaagagt acttctcata   2760
acctcgtcgg tttttgtttc taatcaatct ttatattgtt aaaacataaa acgtttactt   2820
cctttcttct tcttttaagt tttgaaaatg ataactactt ttgtttgact aatattttgt   2880
agtttttgat gctaatcaat tttgtaaaaa ttactgtact tcaactagcg tttactaccc   2940
cacctcactt taaaaaattc cctaaagaga taacttttttg attaattcat aaactaaatt   3000
gaagaacttt tcaaatgaga gtaagttgaa aatgcatatt atattgtagt atataattgc   3060
aattttgcat aacttaccgt aaaatgttct tcctttttaat gatttgttaa tatgggaaat   3120
ttgaacttttt cttttctttga aattgtattc ttgtcccatg gtttctatgc aatctcaatc   3180
atcaaattgc aattatttttt ttttgttttt tgttggcaaa ttcaggagag cttaggtcag   3240
tgatatatga aaaactattt tttactctta tttattttac cctttactta ttaaagaata   3300
aagtccaaga cgaatagacg atgtacaacg caaatgtaaa aatacaaaaa aatgtttacg   3360
acttcttctc tatttatttt ctacttaatt tacttattaa acaagtactt acttgttaaa   3420
ctagctaatc tgaccaacaa tgtgaaaatg tttgacatta tacatcttga cttttttattt   3480
ctctattatt ttctcgatgg ttacttcaaa tcatagattt gctaatctga ccaatatcgt   3540
ttaacttcaa gtagaacgaa atgaacattt caaggtttta gaaaacagtt gaaattggac   3600
cctaaaataa ataaaatgaa gttattaata ggtttacacc ccaatcttat ctaatgctta   3660
aaacacatag tgtggagcgg aattcattgt cttcacatta ttgtacatta atcatatttt   3720
cttaactaat tctgacgatt atttgtgttc atctaataga aaatgcaaaa gtcattttcc   3780
ttaatacttg gcatctttat agtcaaaata taactcatat ccaatgcaaa agtacagtca   3840
tgcacaacaa tttaaagtat taggagcatt tattagtttc acttgtttat taatgtaaaa   3900
gtacgtagta aaatgaaagg taaactcaaa aatatcacat acatatttta atttgatcga   3960
tcaagtcagc ttgagttctt gaactttgtg aaagcaatat atatatatg aatgaaacac   4020
ttatgcattg cgacattgag agttaattta agaaaatttt accccacaag ttctagcttt   4080
gattgacagg cctagccaca aagtaagata tgcacaattt atcttagtgc ttctatgttg   4140
tgtatcaaaa ctcaacaagt tatgtttagt actcctatga tgtttatcct aatttaaaag   4200
tcaatattaa gtaaataaaa ataaaaataa attaaagtct atgtatgtat tctcttacca   4260
atgcctatag tttaggccca gaacctacca tctccctgcc aacccactac tcttactggt   4320
tttcagaaa tagttgctga tcaaatcatt tatccaaaga tctagtttca accttaaaga   4380
tggaaggttc gagtcacttg attttgaagt attgacttaa tgatgtactt tctttaacat   4440
aaggtgaaat tagttgtgga cttcatcgat aatctgtcgt taaatcgttt gtagctaact   4500
aaaaatctat cgcgaaatag gattaacgac gaatttttct gtttaactag agaatttttt   4560
cgtcgctaat taatttttttt tttttgtagt gagtacataa tagaaagaaa aaaaaaaaaa   4620
aaaaggaaag tgttgaagtc gtaatgtgta caacatatga agtccataac ctgccaggta   4680
caattctttta aagaattaaa atggaagaag aaagtaaaa gcaaagattg acaacaattt   4740
ttttgtggct cgatgaaaat tattagtgtc aaagaaagaa ataaaggtaa aaaatggcag   4800
aggaaagaat cacctttggg aaatagcccc ttcacaaaga ctagagtcca aaattacaaa   4860
catcaaaaga tctttggtcg gttctactgt ttgcatctct tgttgttgct ttcgtcttgt   4920
gaaaaatcat tgaggtacta tgtaaattta taatcagttt tttaatctta ttgaaagttt   4980
catagtgaga aggaatttat                                              5000
```

SEQ ID NO: 104     moltype = DNA  length = 5000
FEATURE            Location/Qualifiers

```
source                  1..5000
                        mol_type = unassigned DNA
                        organism = Nicotiana tabacum
SEQUENCE: 104
gtactatcag aaaagattta aatctaacct tcgttataat ttgagtccaa atatacccct   60
gatgctatac tattggttca aatatatttct tttccattaa gtttgtccaa agtggacatc  120
caatcctacg ttgcactgac atttgatgat gtgggtgtca catggcttgc cacctcagcg  180
ccccaaatcc atatattaga gactaaaatt tgaaatacaa taattttttcg taatggtggc  240
aatagtgatg gaagggaaga aaattttagt ggtggaaaaa aaaaatagaa ggaaggggta   300
aaataggtta tgagcgctga ggtggcatgt cacctcatca aacgtcagtt tttcgtagga   360
ttggatgtcc accttggaca aacttaacag aagatgggta tatttaaacc aatagtatta   420
cggcaatgat atattttgac ccaaagtata acgaaagata tttactcata gtacaacgat   480
acatttcgtc atttaccgaa tttcgaattt acattctcaa agaactcata actttgatgt   540
taactaatta agtttaaact ttagatcacc ctacaattgt tgggagacat atcaaaccca   600
taccattgat atatataaga actttgtaaa actctttta atatgttagg gtatgtacta    660
gctagcacca tggatagtgc gtgtcaccat tttacagcaa ataatatgcc tcatgaattg   720
gtagggaaag ggtctttaaa gttgaagtgt ttttttcttt ttcttggtag gtagtggggg   780
aggggaaaat aaggggacaa aacacaaaat caatttgagt acaatttaca caagtctcca   840
tatattgata tagtgctgaa aagaaatata atgttctaag gcaaagggga taacacttag   900
aaattagcca acctcatgtt tcttacaagt ggatgagggt tcgactttgc atttagcatc   960
accttattct ctctaatttt caacaggaca tgttaataaa aggatgacaa tccagattga  1020
caaagttatg aaagtgaaag cactgtaaca tttcattcaa gtctcaagc atctcccgtt   1080
aattttttcta tcttttggaa tattacgaaa atcaaaccaa cctttttacg tataagtttc   1140
taatgacatc aggggggactc ctgagaaata ttctcactca aggtcgaaaa ggaccctta   1200
ataatgatca atataaattt ttttttataat ggtcctttaa tattcgaatc agctcgtaca  1260
catctcaatt tttgtaatga gtacatgtta tccccgacaa tatatatata agataacttt   1320
gccctcaaga atttatatcg acagataaga gatcacataa tatttttgtc tttgttggaa   1380
tgtaaactct actttttatga aattttatta actggtaggt cacatcctac agagcttta   1440
gtcaatgtta ctattattaa gaaggaaaaa aagaagaagc aaaaggaaga tattaacaat   1500
agtataacaa cattcataaa cgtgatttag gaaataaagt atggaaaaat gaatagtgaa   1560
aaaaagtcaa gtacttagga gttaaggttc gtaagttgat gggacagatc gcggtggaaa   1620
aggaagataa gcttcaaaga tacaaaagca aaggggggtt gggttgagat tctgagttgt   1680
gattaatacc actcatgaac aaaaagttat gtcatggcac cattcatgag attaagacaa   1740
cggtggaatt aagaattttta ttaaagggag tcaaatttta aaaaaataaa ttcatcaaaa   1800
agttaaagag tatcaatata tatcaatata tatatatata tatatatata tatatatata   1860
tatatattta tattaaatta tctaattaca cagtataatt tttaacgaaa gggtgtcgat   1920
cgacaccctt gaatgcatgt ggccccgcca ctgcattcag agccaactct cccccaaaag   1980
aaaaggcgca aaacaaaagg atttgaaaca gtagttgtgg aggtgattca gccatgcttt   2040
catgactcat caatacctac tttttatgtt tttctttttc cttttttattt tcaggatata   2100
aattttgttg taaactgata taaagaaata aatttactct cttcaaccta ttaagctttt   2160
aggtgaaatt agtaagtcgt acaatttaac atggtgtaga attgatagaa gtcgtagaca   2220
ctcataggtg cactttgtag tgaaaattag gagaaattag ggttcaaaat ccaactaaga   2280
taaaagatgc ttggtaattt cttcacatct gcttagaaat aatctgctta aatttggatg   2340
agcaaagtta tccaatacaa gtgttgctga gaaataatcg gtatctaata gaatagtcga   2400
gatgcacgca aataagtttt gactctactt taacaaaaaa aacaataggc agatgtatcc   2460
aaaattcata tcttatggtc actcgtcaac aaaaatattc cttatgttta gtccaagaaa   2520
aataaccata cccaaatata agggtttgtt gaagacggaa atataaaac aaataaacaa   2580
atatcatcat atctccgata gtttaaaatt ttagattgga tatttcacac aatttatcaa   2640
aattttcaaa aaaaaattct acttttttctt gcttggaact tggaagggga aggggtggtg   2700
gtggagatag ggcgggggcat cttctatcta gtctatgtga ttaatataac aaaacaaaaa   2760
gggcgaggca aaacatgga tgaatggtgg tcctttttca tatttatatg gattgttacg   2820
atacgtcgat ttcactttgc aaaataccaa ttagattcat ttagttatct tttttgatcac  2880
tctgctttta ctatcatata tatataggag tccttccacg tttcgcatgt gtcattgttt   2940
atattttcca tggtcttcct tccaaatggc taaaaaaatt tgacacagtg gtcccaaaag   3000
tttatagaaa tagaattcaa cagtgaggca tatacctatg aattctattt tacatcttca   3060
tcgtataaaa tagaatgtgt tataaacttt acctcgtgat gcttacaagg ggtgaaaata   3120
taaaagcact ttatagattt acaagagtca caccttgatt tatcctaaga tttttatttt   3180
ttacatgcca aacaatgaag tatgggagat ccaattggaa taacatcaaa tttaataaaa   3240
ttcgaaatag tcagagagct gtctactgag gtatattgaa acttatttt ttttaataga   3300
aaatatcaaa tacttagcaa tatattaaaa tgtttcataa attacattgt ttaaaccaag   3360
cgttgaaaca tatgctgata cgaggtaggc ttattgatga atttataagg gcctcattgg   3420
aaaagacgat ccaaagcaat gggctaaaaa ttggcccatt ttctgccacc cagtgtatgg   3480
ttattactag tttcacccac acagatttgc acttcattag aggacaatgt tgctgaattt   3540
gaaacataag tccatttatc tccactgtac agtccttcct cctgaccata   3600
tcttcatgat tttatgtaat gtggtgaata agcaaagttt catgttatgc tttgtctcat   3660
tttatagcaa attcatttcc tcataaaatt tacttcaaaa aagtttcgtt tgattttcag   3720
aaaatcaaaat atgcttttcg gtaaccaaat ggttttcaat tttgtttacg aagaacttaa   3780
aactttccaa caccctacat ctatgattgc aagttaaaat tgcagaaata tgacactttt   3840
tggagtggtc tttatcgttt aacttcactt gcactttaag ggcaaaagtt aaaagtgttt   3900
ccatgaagca agcgagggat aacacttatt aaacttgaaa ttctactcat agaccaaaac   3960
aaggacaaaa attcaagact atctatgtgg gtaaacgtac gaaaattggg cttctccaga   4020
ttagagccgg accttgtgga aagacagaga aattcgaggc ccacttccag tttctaagga   4080
gattaagcct atcaaacgat ggtccagaac gaaatatgtc tttctttatt ctctactata   4140
tagctgactc agaatcgtta gaatttgcaa tttcctcata ataaaatgtg aggcagtata   4200
gattcgaaaa cctttgttga agattattga ctcagctacg cgaaacaaac tgtagtatcc   4260
aatgtaccga ttaacaagcg actggttaac tatgaatttg ttagctcgac aaaatcaccg   4320
gttaataatg agtttgtgag ttcgataaaa tctaattttc tgatagaaat tttatatatt   4380
atgcagaaat ttaataaaag tagacttaac ttatatattt tagcattgac tcttttgaag   4440
taaaatccat tccatctaaa ttatgacttc cctcacatcga gtaagtaagt tgcgtctgta   4500
```

-continued

```
tcctcatttt acccactttt cgctatgcaa ttattcaagg atctttacac aaatagcaag  4560
ccaatattaa ttatttattt tttttagtca tatatataaa ttatacatat attatatacc  4620
cattaattat ttttaatttta agtgatagat tggacgacta tttggattaa ttcttcgtta  4680
ttcaagataa tagatgtcgt ctctaataca tgagctagaa gataataagg attactaggc  4740
cgaaaggctg atggaaatga acaagaagat aagctcctaa atggaaacag tacggaaaaa  4800
gtcaaagagc agtgcatggg aggaatcatc agtcagaaaa ggaagccacg tgtcaagtag  4860
aaacaagcac gtgtccatgc aaaagccacg taactccctt ccatcacatc ttccttcttc  4920
aaaacctcgt gttttactct ctcttttctc actgccagtg atcgtcagga ctgtgcatgt  4980
ttgtttaaaa actaaaggca                                              5000
```

```
SEQ ID NO: 105        moltype = DNA   length = 5000
FEATURE               Location/Qualifiers
source                1..5000
                      mol_type = unassigned DNA
                      organism = Nicotiana tabacum
SEQUENCE: 105
acatgacccg gttgtctcct ttgtggtgtc tttcagaaca tcgccagtag ttcgttgatg  60
tggtgttgag tgaatacttt ttcaatatat aagcaatttc gtgccttttt tggttcattt  120
tgaggcttat gtaatatatt tgatcatgta atcgtgaata cttcaataaa aggtaactct  180
tcctcagata atgtaaccaa gaataatttc attgaaggga agcggtataa gcataaaggt  240
aactttccct gtgatgaaga atgatgatat caagtaggcg ttgttgatca actttccaaa  300
tgggtggagg gtaagctact tcactgcctt acttcctcta agttcaagtt gggggaggta  360
tgatcgggga ttctctatct tcttgttgaa caagaaaaca gtactactac ttagcatata  420
tagtttcaat caataaatag gaactgtact aacaatcaga gcccttattt tcacttagca  480
tagttgtata ccagttagaa ctcatactgt ggaaacagag actcgtggac tagcaatgcc  540
cttattaaaa actatcatgg atgctctact cattgtctct ccaaacaaca gcactctttc  600
ataaaaaggt acttcatgcg acatccatta atacaagaag ttcaagatac ataacatgca  660
gtaacagaac tcgactcaac ttagacttat cccacatcta gcttgatttt ccatcaaacc  720
agtgtgcgta aaagtaaaac ataactatag aattgatccc atggttaatc acattcacat  780
aacaagcggt tgggataaaa agatggtcag ttctaaggct tcaaaattaa tatagccaat  840
tagtcgaacg gacggtgtgc aatcctagat gacttctatg aaagtgagac gaatcaatct  900
cccaaaagtt tagtacaaag aaataacagc aaccgttcaa acaatctaat acggctacac  960
atattaatct tcacaaatta aacattacaa caaaagcata ctaaattctg aactcagtaa  1020
agattcaaat caacagcacc atattataga cataacaaca ctagtgaatt ggtcatcaaa  1080
gcaacgaaga gcacagaaaa gttcgaaatt taaccaatca cgaacctgat cgaagctctt  1140
gtggaacatc tacacgcttc ctgacttgtg gagacaagag tctcgagtag attcggaaac  1200
tgcccagtct aattttgata cgtattctac aatttcctta ctaaagagaa aaagagaaag  1260
tgtgtgagaa tataaaattg gcgccttctt tcttttggcg ctatttatct agttttagcg  1320
accagttatc atgatttta aagatatttt tagattgcca ttttcgctg agaaaaaaag  1380
gaggtaaaag gggtggtagt taaaagtgat aatcaacttt atataagact agtcttaata  1440
tacgtgcgtt gcgcgtgtca taaaaaatat tttaaaaaat atatttgtgt tataatataa  1500
aaattaatac aaatttgcaa gcttcaaaat aatgaattaa tcatatttag gagtttgatc  1560
cactctagtg gttttggtt catcttgctt cattgtacaa aaaatttgag tatacttcca  1620
attctaagtc gttctattgt tcaaaggaaa aaaagtgtcc taattgctct tcaacttcta  1680
aaatattgcc tatctcttac cttaaatatg aattatcatt tctgcgtcca tattttttt  1740
ttaaatcaaa attgtctttt tcgttttttt tttttagaa aactatactc tatagcccac  1800
aaaattttaa tagctcatgt cttttctcac ttacacgaaa tggcccttg gcccaaacat  1860
aatagaccga aatgtctatt ttgtatattt tttgtatagt gacagtctat tttgaatatt  1920
tttttatata atgacagtct atttgtata tatattgtat agtgacggtg gggagtgggt  1980
tgctctagtg gtaagcaccc tccacttcca accaagaggt tgtgagttcg agtcacccca  2040
agagcaaggt ggggagttct tggagggagg gagccgaggt tctatcagaa aagcctctct  2100
accccagggt agaggtaagg tctgcgtaca cactaccctc cacataccct actagtggga  2160
ttatactgga tcgttgttgt tgttgttgtt gtattgtata gtgacggtct atttagtata  2220
taattgtata gtgtttgtat attttttgta tagtgacagt ctattgtata taaattgtac  2280
agtgacagac tattttatat attttttgta tactgacagt ctattttgta tatatgttgt  2340
atagtgacaa tctatttatt actccctccg ttccaattta tgtgaacatg tttgactggg  2400
catgaaattt aagaaaaaat aaagactttt ggaatttgtg gtcctaaaca agtcaaaagg  2460
aggtccagat tatttgtggg gttataaaag cttctcatta agggtacaat tgtaagttta  2520
agctaaatta ttatcaaatt tagaaaaggg tcattctttt tggaacagac caaaaaggaa  2580
ataggttcac ataaactgga acaaatggag tatattttt gtatagtgag agtctatttt  2640
tcatacttct atgctaagta ttgacttaa acactgttca aacttaaacg tgtctctttc  2700
gcgtgaaatt actctatatt gaactactac aactatttgt gccggatttt gtcaaaaaat  2760
tcaattttcc ggccaagttc gttctgcttc ctcctcccat ccttccaatc ttattctttc  2820
tgccactttt cagcaatagt gatacaacta agatatgttt taaggttttg aactatttgt  2880
gtggaagagt tttatggcat atactttttc tttggtcgtt gagaagagag gtcgacgtcg  2940
ctcatgaaga cattctgccg ccgacgaaac agatcttata gctagccgct agaattattt  3000
taggctataa aatgtatatt ataattttgg actactggat gatatatgtt ttgggccgat  3060
gggctataaa tgaattttgc tcatttttt aacgtgttct ttattagcat aaaaattgca  3120
ggatgagttt gttactttaa tttcattaat ttactcttt tttgcagaat atacatacat  3180
gaaaagtaac atgtagtaaa tattattatg ttacatatat agtttaaata aaggaaaaag  3240
ttaatgtaag gtagaatttt aattgacttt aaattcctaa attttaggac ttctcaccta  3300
gttcaaataa gtaaatattt aataatcagc atcttagtta atttcaaagt actaaatatt  3360
atgataataa ttaaatgact attttgtcta gtcgaaatct atttttaag ggtaaaaaaa  3420
gcgaacgata tttcgctaag aaccttcgtg cttttaatat aatactagtt tctatgtacg  3480
tgcgttgcac gtaaatcttt agtttatcat ttatatgaaa aaacaataca ttaaatttac  3540
tggaaaatca tatacaaaaa gaccgaataa agccattaat gtgggaacaa tgcaatagta  3600
tcgtcaatgg gaacatgcat tgcacatata ttccgtgtca atagttatct ttgtgaaata  3660
aaaaatgata catgtaattt tatactatca ttcatattat gaataaactt gtttgatttt  3720
taaaatagaa aataataaag agcacgaaaa gttactgcta gtcattaaaa tttgttatga  3780
```

```
acattgactc tattatagaa taactcatca agaagaattt taagtgcaat attgaaggat  3840
ttgctttagt ttctaatagt ataaatcgat gtctcttatc ggatcataaa accaaaagaa  3900
ctataatgtc catacaactc cctatgtatg tttacaattt gctttgtgtg tgtaaacatt  3960
agaactttc  acctaaatat ctcatacctc ttaagaaaga atccttgctg gatactttc   4020
ttttggagct tcacaattat aagttaccaa ttaactaatc tctccaagcc tctatttaac  4080
atatacacgt ttatctctgg acgaacaaac aatagatggc gtcgaagatc cactcttcat  4140
cttcctgatt ttcatcaact tccttatgcc tatttatttc ttgttttcag ttaattcgac  4200
aaattaaatt agaacaaaat ccattactgc tggttatcag acaaagaaaa actaaagtaa  4260
ctccttttgc caacaccaat gtagaacata aataagctta aaggtaattt cttttaaatt  4320
ttaggcaaaa cctttatgta aacgaacatt taagccgtgg ctttgccatt ggagttctaa  4380
tacaaatagg accttttagtt ttcaatgact tgaattctac aactaatgaa ctgtttttac  4440
gttttttggat attaatgttg aagacatgat ttaaatatga agggtaaaaa agtcggtcaa  4500
tatttcaggg acattttgt  cgttcaatat ttagcgtgta acattcgtgt tttataata   4560
atatagatat agatatagat ttctctcccc aaccccgaga tttttttaaa gtattttaaa  4620
atagggttac tgtgcacata taagaatcag aaatttccag gaccatagca atgagcatta  4680
ttgaacagta gtagtacgta tgtcctttct ggtataggat atgtagcttc attaaaagat  4740
agaaaatgaa aagcgtataa agtttgtgat acatttacta ataaatccaa cgaataaaag  4800
aaatactcgt atataaaagt agaaaagtaa gtgtttgtac tttttataaa aacacaatag  4860
gtggagttga gagggatatg gaaattgcct tggatattat gtaggcatca tgaaccaatt  4920
aatgggacct acaagattaa tgttttggct atccttatct tttattgaca ggcccttcaa  4980
tttaaatcgt tgctgcccaa                                              5000
```

```
SEQ ID NO: 106          moltype = DNA   length = 5000
FEATURE                 Location/Qualifiers
source                  1..5000
                        mol_type = unassigned DNA
                        organism = Nicotiana tabacum
SEQUENCE: 106
ccgactaaca aaggagtcaa acaatggcga aactagaaat ttacccaagg gtattcaaat  60
ttaaaaaaag tgaaaacaaa ttcctacaaa gggtgtttaa tatgtgttat atacttctaa  120
aacgtaatat ttatctataa acacaatgca atttttcaac gaagagtgat caactgacca  180
ccttataacc gccactggag tcaaaccta  gtttttctttt ttagcttctt tgtattattg  240
gtagaggtga accattttat acaaacatac atacatatat gtgtgtgtga gagagaaact  300
ttataaaaat agtactatga atattgaata tcgaatttcc attctcaaat aactcataac  360
tttaatgtta actcattgta aaaccttttt tttacatgtt agggtctgta ctagctagca  420
ccatggatag tgcgtgtcac cattttcag  caaataatat gcctcatgaa ttggtagggg  480
aagggtcttt aaagttagtg tgtttttttt tctttttctt ggtaggtggt gggggagggg  540
aaaatgaggg gacaaaaaaa atcaattgga gtacaattta cacaagactc cattgtatag  600
tgctgaaaag aaatataatg ttgtaaggca aagaggataa cactttagaa attatagcca  660
acctcatgtt tcttacaagt ggatgagggt tcgactttgc atttagcatc accttattcc  720
ctctaatttt caacaggaca tgttaataaa aggatgacaa tccagattga caaagttatg  780
aaagtgaaag cactgtaaca tttcattcaa tcatgaaaag catctcccat taatttttct  840
atcttttgga atattacgaa aatcaaacca actttttac  gtataaattt ctaatgatgt  900
cagggggaact cctgagaaat attctcactc aagttcgaaa aggacccttt aataatgatc  960
aataattttt tttaatggtc gtgtaatatt cgaatcagct cgtacacatt tcaattattg  1020
taacaagtac cttttatccc ccaacaatac atatataagg taacttatca cgtaatattt  1080
ttgtctttgt tggaatgtaa atcctgtttt tataattttt atccacttta ttgaccgcta  1140
ggtcacatct tatggagctt ttttagtcat gataaatatt actattatta agaagggaga  1200
aaaaagcaaa aggaagatat taacattagt ataacaccat tcataaacgt gatttaggaa  1260
ataaagtatg aagaaatgaa tagtgaaaaa agtcaagtac ttaggagtta aggttcgtaa  1320
gtagatggga cagatcgcgg tggaaaagga agagaagctt gaaagataca aaagcaaagg  1380
ggggttgggt tgagattctg agttgtgatt aataccactc atgaagaaaa agatatgtca  1440
tggcaccatt caggacatac agagccaact ctccccccaa aagaaaaggc gcaaaacaaa  1500
aggtttgaaa cagtacttgt ggaggtgatt cagccatgct ttcatgactc atcaatgcct  1560
actttttttt ctgtttttgt ttttcctttt tattttcagg atataaagtt tgttgttaac  1620
ttaaataaag aaataaaaatt actctcttca acctattaag ctttaggtga aattagtaac  1680
tcataaaatt taacatggta tgaattgata gaagtcgtag acaccatag  gtgcgctttg  1740
tagtgaaaat tagggttcaa ataagataaa acatgcttga tgatttcttc tcatcggttt  1800
aagtttggat gagcaaagtt atccaataca agtattgccg tgacctaata aaatactcga  1860
gatgcacgca aacaaatttt gacactactg ttaacaataa acaatatgca gctgtccaaa  1920
attaatacta tatcttattg tcactcagtc aacaaaaata ttccttatgt ttagtccaag  1980
aaaaataacc atacccaatt ataagggttt gttgaagaca gaaatatata aataaatgaa  2040
tcatcatatc tccaatagtt taaaatttca aatgggggta tttcacacaa tttatcaaaa  2100
ttttaaataa tttttatact ttttcttgct tggaagggga aggggtggtg gtgggagtag  2160
ggcggggcat cttctatcta gtctatgtga ttaatataac taaacaaaaa gggcaaggca  2220
aaaacatgga tgaatggtgg tccttttcta tatttatatg gattgttacg atacgtcgat  2280
ttcactttgc aaaataccca ctagattcat ttagtttttct ttttgatcac tctgctttttt 2340
ctatcatata tataggaagt ccttccacgt ttcgcatgtg tcattgttta tattttccat  2400
ggtcttcctt ccaaatggct aaataatttt gacacagtgg tcccgaaagt ttatagaaat  2460
agaattcaac agtgaggcat atacgtatga attatatttt acatcttcat cgtataaaat  2520
agaatgtgct ataaacttta cctcgtgatg cttacaaggg gtgaaaatat aaaagcactt  2580
tatagattta caagagtcac accttcttga tttatcctaa gattgtattt ttttacatgc  2640
caagcaatga agtatgggag atccaattgg aataacatca aaattaataa gattcgaaat  2700
tgtcagagag ctgtctactg agatacattg aaacttattt cttttgtaca acagaaaata  2760
tcaaatattt agcaacatat taaaatcttc ataaattaca ttgtttaaat cttacgctgt  2820
aacatatgtt gataggaggt aggcctattg atgaatttat aaggtgaaaa tacatggact  2880
agccagtttt cgaactagta attgaaaaaa ggtatattat cacttttagc ccgcgccaga  2940
aattatttat atttggtagt tgaaaaagtg tataaatttg taattttttg tatataacac  3000
acataatgtg tgtgtgagtg tatatatata cacacacaaa aactatatat attttttcta  3060
```

```
ttattttgag agtggttata cagtgtcatc tttctaatcg aaaatagcca gcgtttgcaa   3120
tgttattaaa aaaaaatagc cactatttta gctgaaacac ggaaagttcc agcataatat   3180
atcggatttc agagctcctg catataaact tccagcacat tatgaaattc catcacatta   3240
tgctgaaatt tttccggatt cttaaggtgt tttcattcag attttatctt tacataaaaa   3300
aatggctaaa tttcgattac ttttgaaatt atagctcttt ttcaattact aattataaat   3360
ctgactattt ctgatttttt gcctctggtc aaaatggcat ggcatagtca ttttttagggg  3420
tggttattga aaaatagcta gtattcacaa agttattgaa aatagtcatt atttacggcg   3480
aagattaaat cttaacaaat gtacctgagt taaaacacaa aaagttacaa cataatatgt   3540
tggatcatgg aactccttca tgtatgcttc tagcatatta tgttgaaact ccagcacatt   3600
atgaattcca acacattatg tcgaaatctc atatgtaaaa aattcgaact ctggcatatt   3660
atgctggaat tttttcgtat tttttatcag attttatttt cacataacaa agtgactaga   3720
tttcaataac ttttgaaact atgaccaatt ttcaattaat tgtaaatcaa attatttctg   3780
atttttttcc tccagggcaa taatgggact caactttagg caacaaaaaa ctgtttatgt   3840
aggtaaacgc acgaaaattg ggcttctcca gattagagcc gggccttgtg gaaagacaag   3900
aaattcgagg cccacttcta gtttctaagg agattaagcg taaaaatagc actggctagc   3960
cagttttcgg actgatcatt caaaaatagc cagtatttgc aaagtcattg aaaaaatagcc  4020
attagtattt tgctgcaaca cgaaaagttc caacataata tattggagat cagtgcacct   4080
atgtataac ttccagcata ttatgctgga actccaacac gcggaaagtt ccactataat   4140
atactggaga ttggagcacc ggtgtcaaca aatctatcat ttaataggat ttatggctat   4200
ttttaaatga ccacttgtaa atctgattat ttttaatt ctcccgctta agcctaacca   4260
acgatggtca tgaacgaaat gtctgttttt actctctact atatagctga cccagaatca   4320
ttacaatttg caatttcctc ataataaaat gtgatgtagt atagatttga aaacccttga   4380
agattattaa tttatctttc gcgaaacaaa ctgtagtatc caaggtaccg aatagtaagc   4440
gattggctca caatgagtct gtttgttcga taaaatcatt ggttaataat gagtctctga   4500
gttccataca atctaatgct ctgatagaaa tttatatat atgcagaaag taataaaaat   4560
agactatgac ttactatatt ttaacattca ctctttgaa gtaaaatcct ttccgtcaaa   4620
attatgactt cattcaccca aattgcgcct gtatactcat tttaccttct cttcactatg   4680
caattattga gataaaaaat ttcgtctcta agacatagct agaggataag gatcttaggc   4740
cgaaacactg atggaactga acaagaagat aatcacctaa atgggaacag tacggaaaaa   4800
gtcaaagagc agtgcatggg aggaatcatc agtcagagaa ggtagccacg tgtcaagtag   4860
aaacaagcac gtgtccatgc aaaagccacg taactccact ccctcatatc ttccttcttc   4920
aaaacctcgt gtttttactcc cccttttcctc actgccggtg atcgtcagga ctgtgcatgt   4980
ttgtttaaaa attaaaggcg                                              5000
```

SEQ ID NO: 107          moltype = DNA  length = 5000
FEATURE                 Location/Qualifiers
source                  1..5000
                        mol_type = unassigned DNA
                        organism = Nicotiana tabacum
SEQUENCE: 107

```
acatgacccg gttgtctcct tggtggtgtc attcaaaaaa tcgccagtag ttcgttgatg   60
tggtgttgag tgcatacttt ttcaatataa gcaatttcgt gccttttgtt tttccatttt   120
gaggcttatg tagtatattt gatcatgtaa tcgtgaatat ttcaataaaa ggtaactttt   180
ccttagataa tgtgaccaat gatgatctca ttgaagggta tacttttcct gtgaagaaga   240
atgatgatac tcctatcatg taggcgttgt tgatcaactt tcccaatggg tgaagggtaa   300
gctacttcac tgccttactt tttctaagtt caagttggtg gaggtgtgat tggggatcct   360
ttatcttctt gttgaacaag aaaacgctac taattagcaa tgaataggaa ctgtactaac   420
aatcagagcc cttattttca cttagtatag ttgtatgtat accagttaga acctatactc   480
tggaaacagg gactcgtcaa caataaccag aagggtggat tagaaactat catgaattcc   540
ctactcattg tctctccaaa caacaacact cttttataaa aagtgtactg caagaatcat   600
gttatgcttt taaggaatgt gcatcaagat tgaagtatca tgcgacatcc attaacacga   660
gaagttcaag atgcacaacg tgcactaact gaagtcgact caacgtagac ttattccaca   720
tctaacttga tctttcataa aaccggtgtg cgtaaaacat tactatagaa ttgatcccac   780
ggttactcat attcacacaa caagcaattg ggacaaaaag atggtcagtt ctaaggcttc   840
aaaattcata cagccaatta gtcgaacatg cggtgtgcaa tcctagatga cttctatgaa   900
aatgagacca atcaatcttc caaaagttca gtacaaagaa ataacagcaa cccttcaaac   960
aatctaatac aacgacacat attaatcttc acaaattaaa cacaacatca aaagcgtact   1020
agattttgaa ctcggtaaag aatccaaatc aacagcaccg aattatcgac ataataccac   1080
tagtgaatta gtcatcaaag caacgaagag cacagaaaaa gttaagaaat ttaaccaata   1140
acaaacctga tcgaagatct cttagacat ctacacgctt cccgacttgt ggcgacaaga   1200
gtctcaagta gactcggaag ctgctcagtc taattttaaa tatatattct acactttcct   1260
cgcaaaagag aaaaagagag tgtatgagaa tattaaattg gcgcctttt cttttggcgg   1320
aattgttcta gtttttagcga ccagttatca tgattttact actatgtaaa tcgcaagcat   1380
taaagttata gcaagaaatg agaccgagtg acctaaaaac aatcacattt gtatgtttcg   1440
gttccacgag cagctctggg cggacctagt aggagctcct ttgcactgtt gcaggagtgc   1500
tcaagtacct ttactctctt ggtgactcag acactactgc catatcaatg agaaaaaagg   1560
aggtaaagta gtagttaaaa gtgataatcc attttatata aaatccctcc ccccgccccc   1620
atacccccgg aattgtaaaa atatttttaa atagtgcata tactagtcag   1680
aaatttgtag gattacggga ggtagtacgt gcgggtgtac aaaccaaatc ggaaaatcgc   1740
accaaaccga aaagtcaaat caaaaccgat taaaagattc gactagattt ggtttggtat   1800
tgagtaaaac aacccgaatt aaaccgacat ataaatataa attttttatgt atacttttaa   1860
gattttttata tagaatttc tttaagaaaa tatctaaaaa tatttgggat tctcttacgg   1920
gatataatat ttaataaaat atgaagtgct ccatatttat taaccttaaa caatgggtcg   1980
tatgatcact ttcttatcaa gtgttactga aatgcgtcaa tctctttgtt cttccatagt   2040
caagatctat taaattctta tatctttttc gaatttgaag tggttattat tatttaagta   2100
tcatattgac ttttacgttt aattactaaa ttcggttaac cttgaaagtg tatatcaaca   2160
aaaattattg tcgacgacta aaaagactaa ctatcatgtg ttattaagta aattcacgca   2220
taagaatatt taatagataa tatattttc taatttttaa aattttttact aaatatattt   2280
acttataaaa aatttaacaa agtaagattg aaataatatt taagtaacga aaaaccagcc   2340
```

-continued

```
aaaaccgata tagtttgtgt agtttgattt aaataaaagt cgaacccaac ccgatccatg  2400
tacacccctta atagtacgta tgtcctttct ggcatactgg taggatttgt agctgcatta  2460
aagatagaaa gcgaaaatcg tacaaagttt gtaatactag tacattacta ataaatccaa  2520
cggataaaag aaatatataa aagtagaaaa gtaattggtc tagattttat gaaacacaat  2580
aggtggagtt gagaggggta tggaaattgg cttggatatt atgtaggcat catgaaccat  2640
taatggacc tacaagatta atgtttttgga tatccatatc ttttgttgac aggcccttca  2700
attgaaatct ttgttgccca aaatgattcc actgtcaacc aattataagt tttttgttaa  2760
aaggtttatt gcaccattgc tccactaact tcatgtgcat ttgcaactta ccacacaaga  2820
gagaagaaaa gtttccagta cacaggatta acatttgcta agttgattcg gagttttagt  2880
tagcaaagtt gaaattatca aagacagatt ttgaaactat aagccagtgg atcgctaagg  2940
ggttcctcgt tgataaaatac ttattttcat ctggtgttta tactaatcca ataaatatat  3000
aatatatgtc tttacaaata tggttataat taaatcataa ttaattagta cacattgtta  3060
cctcacgtta tcactttacc atgataagag tttggtataa atactggtgg gactaagttt  3120
tttaccttcc tcgtttagtg tctacaagcc taattaggtg aagatggtgc tggatttttt  3180
tttttttttg ttacaagtgt agactacaga aattaaatta ctggtcctat tgtgcaaaat  3240
ttgaattcaa atcttcgtgc atttcagtat gttatttggt acaaaaaaca tggcatttat  3300
ggcttcgcat tgaggaagaa cttgtatata gcttgaatgc tcttgttaca tccaccctcc  3360
ttaaataccc ctagttgatc aacaggcacc aaaaatgtct agacacaaac atgaaccagt  3420
tttatttcta ttctctttat tgtaggtaat tgtttgctgt catcatataa tataagctag  3480
gaagaaaata agtaaaaatc atcagatgtg ataggtcttg aatagagaag caaacctaat  3540
gtagcataat aagaaaggaa gattaggtgg gagaccatta tttatgacct catcccaatt  3600
ttaatcatat ttcattattc caggttacta ctaccaaaca aaataaacg acaagaataa  3660
tgcataaact tccacaatag ctcattattt atttatcagc cggagtgtat taaagtaatg  3720
atataattag aagacaattg agttgctact taaactgatg ctaacctgac gcgttttcgt  3780
tttccaggta cagtcttcca acatcagatg tcccaattgg agttccaagt caaagtggaa  3840
ttggaaaatg gtaagaaaac tctcagcctt agctgtgaca tagacatcaa taaagtagaa  3900
aaaaatcata agatttcaat gtttgaatgc taagcgacac aaaaatcact aaataatttt  3960
tttcatttct gactaagtct ttatgagcaa aactatttat tacttacaat tttgtgatga  4020
taggagatat caaatactcg tggaatactt gaggtaccca caaagtgatt gagaagttgc  4080
tgttaattaa aaaatccttg catcagatcc cttcagtttg aggtcaaaag cacaatcatg  4140
aaaagcccctc tcacagcaca ttcacttgat ccattctatt ttacgtcttt tctctaacta  4200
cgacttaagt tcttctaact tttaatcatt accaccctat taaaacttat ctaaagactg  4260
tttttctctg cttttctcca tatttacctc aacgtctcct tccatatcca agctttggta  4320
cttttttcccc ttgtggtatt gattcaggca tggtcccttc tccaatctta tcaatcaaac  4380
atatactaat aaagtataat ataccaccga ctttggtgtc aaccacgagt tcgggagctt  4440
gtgaaatatg gtggtattta gccaattttt ttcttttttaa taaaattgac aattaggaac  4500
caacttgccg gcttcataat aaagtatata gttgaaatgg ttcagaaata ttaaattcaa  4560
ttctataaat tacttggatt cggtccatcc taaaggtggt cacttctagg atcaagcccc  4620
attgttggct aaatttttggt tttaaataga ttaattagct tggagtcgaa cagcaagcat  4680
taagtttacc aggtctatga tttagttagg catgaattgt aatacaaaga tgatttatgc  4740
agtgattaat gatatcagga tatatatata taagtattgt tatactataa ataacaacaa  4800
caacaacgac ccagtaaagt cccactaagt gggggtttggg gaaggtagtg tgtacgcaga  4860
ccttatcctt accctgatag ggcagagagg ttgtttccga tagatcctca gctcaggaag  4920
atgaaaataa aacaagaaaa caagaaaaga cagtaaccat agaaataatg acagcatcct  4980
aaaaaccata aaatagatga                                                5000
```

```
SEQ ID NO: 108        moltype = DNA  length = 5000
FEATURE               Location/Qualifiers
source                1..5000
                      mol_type = unassigned DNA
                      organism = Nicotiana tabacum
SEQUENCE: 108
aagctagcac catagatagt gggtgtcacc attttacagc aaataatatg cctcaattgg  60
tggagaaagg gtctttaaag ttgaagtgtt tttcttttttt tctctttctt tttcttggta  120
ggtggtgggg aaggggaaaa tgaggggaca aaacacgaaa aatcaatttt gatgtataat  180
ttacacaaga ctcaagctaa gtgatagagt tgataaaagg ataacaataa tatgggacac  240
ataaattcat gacgtctccg tttatcggat attttctcaa attgatgtaa catatgtttc  300
aagaagttca aataatgtgt atatagattt atttctataa aatattattt cgaattataa  360
atcttcgact caagaaaaaa taaaaatgtt agatatggca aaggggatag cacttagaca  420
attaggcaac ctcatatttg ttacaagtgg gggtgagggt tcaactttgc attatttagc  480
atcactttgt tatttatttt ttttatataa aatttataga acaggagatg ttaatataag  540
gatgacaatc cagattgaca aagttgtgat agtgatacta ctgtaacatc ttattcaatc  600
atgcaaagca tctcccatta atttgtccat cttttcgaat attacgaaaa tcagacctac  660
tttttttaca tataattttc tctaatgaca tcacaggaac tactcctgag agaaatattc  720
tcactcaagt ttgaaaacga ctcttaaatt atgataaagt gataactaca atgaccggct  780
aactcttgcg tgcattatga gtgtatatag ttatatgtta tttactctcg tcgtaaatat  840
caagtgcgaa taatatgtat gaaatttaga gaaatgagag taaattagtc gatgttttta  900
atttacgttg tgatttattc gttacttttt gctttctcta aagtcaattt cagtagttcg  960
tggagataca ttagattaaa ttaatctaat ctgttaaata ctacacggta aaaaataaaa  1020
aatatttaaa acgacataaa attttattat caaaataagt aaatcacaaa ttgggggggg  1080
gtttggcttt tttttttttt gtccgaaaat tattatcatc ggtatatata actatgcttc  1140
ttatattata ttttttttagt gaaaattcta atttttcgtag gcatacattt aattaagata  1200
agtaaatatg atgaataaga acagattgat aaacgtgatt taagaaaaat aaagaaagga  1260
gaaatgaata gtagttccaa tttataaaaa aaagtcaagt acttaggagt taaggttcgt  1320
gagtagatgg gacatatcac ggtggaaaag gtagaagaag cttcaaagat acaaaagaaa  1380
aagagggggtt gagattctgt gttgtgatta atacaattca atcaaagaaa aagatgtgtc  1440
attttggaca tacaactctc cctaaaataa aatgccaata aacacagtac ttgtggacat  1500
catccaccca tcctttttatg actcatcaca caaaaaaaac acttttttcc ttcttatttt  1560
tgaagatatt ctatgaagtt tgttgtaaac ttaaacaaaa taaatcaaca aaattgtcct  1620
```

```
atctctaaat agaggagttt ttaaaagtta aaaatcaata gaatagatac atgaagtagt   1680
cgaaggagat ttgacatttt attatgtata tatataaaat tattttaatc atatataaaa   1740
aatataattt tctatcaaaa agtgaatcct ttcatatttg tatctccgcc ctatctccaa   1800
atattaagct cacacatgaa aagagcgaga gacgaatgta gcctattggc tatgggttcc   1860
ctcactttcg atatgatgtg tataaaaaaa ttaattgaaa tctcaataaa tattagattt   1920
taacaataag ttaaaaattc aaatcattaa gtggggtctt gatttatttt ctttttgtttt  1980
ctttctcaaa ctgatgtttt tattaaggat ttattagaaa aatatttcta tctctcggg   2040
taggaattaa atttgctatg tgtatatcct accttttgtt aaatttagtt tacagaatta   2100
tcggttaaat atgttagata tgttattatt gttgttacgt ccgaatagac acccataggt   2160
gtagtgtagt caaattaata aaaccatgga atacgatggg atatcaaagt tgataatttt   2220
taactaaaaa aaaatgtcac tagatgattt tttttttctct caattgtcta atcttgacag   2280
aaagatgtac ctaatgaaat aataaaagtg caacaaaaaa gaatagacaa atttccaaaa   2340
attgaatctt ttgttggtac tcgtcaacaa gttattcttc atgtctaaat cctaaaaaaa   2400
atatctcctc gtgtaaagac tggtatattg aaaatttaaa ataaattaat acatctaaac   2460
gtatcatatc ttctatataa tataaaattt ttagtgactc gtttcttaca attcaataat   2520
ttagtataaa taatttgtcg attgcgcgga tgaaagaaag gggtggtggt ggagatataa   2580
agtgtgatcg atagggtatc ttgtatgtga ttaatatagc taaacaaaaa ggtgaaaggc   2640
aaaaacatat atgaatggtg gtcctattcc atatttaaat ggattattag gatacgtcga   2700
tttcactttg caaaataccc tctatagatt catatatttt cttttctcat caacttttttt   2760
ttctatcata taactagcct tactctggct tctcacgttt cacatgtctc aatgtttatt   2820
tgtttttttt ccactcttgg gcgtctaaag ggtttagaaa aatttgacaa tgtggaccac   2880
ccaaagttta taaaattaga attaaacagt catgaaggca tacctagg agttccattt   2940
acatcttcac gtataaaatg tgtacttat attaattta tttatctcat gattcttatt   3000
agagatgata aatgtaacat tttttttttg tttttattaa attttagaag agataaactt   3060
cttgattaat tctatgattt tccttttttta ttacgaaact gaaacttaac aattaactga   3120
gacataacaa acatgaatgt agttcatatc taaattaaca tcaaagccat catatctaac   3180
tcaactaagt tagtcatggt actcttgtga ttgacataaa ttttacaata aactttctta   3240
gctagaacgg actcaccaac aaatataaaa ccacagaaaa aattatatcg aactcaatac   3300
taaacaaaga agtatggaag actaaatatg ttgatacgag gtaggcttat tggtgatttt   3360
acaagggctt atatagcaaa agttgataca aacaaatggg ctaaaaagta aatggcccat   3420
ttattttatt tattttttcc attatcaata cacagatttg cacttcgtta gcggacaatt   3480
ttgggtaaat tatgaaaatt gggcctcttc acaatttaga tcccgaccgt gtggatggat   3540
ggacaaggaa attttaggtc cagttccagt tatattgggg agataaaagg aaaaattacg   3600
tggttaagta atatatatat tagttaatta gttattaaa taattatttt agttaattat   3660
tattcgcgat taacattagt gataattatg taggctgaga ttttgagttt gtataatttg   3720
aaatttttaag atataatttc tataacttttt atatagtaca attttataaa atattatttg   3780
tataattgat aaaatttaga tgtttgtgtt tgtataaatt tatattttag atttatcaaa   3840
atataactca attattcaaa ctaaccataa tacgtacgaa ttcactcaca aattatacaa   3900
acaatacaat ttgaaccata gctgcaaccc ctaataatgc gagctacgac tataaagtat   3960
aattaaattt atttactata acggatattt gcaaaaattc tccttaggca taaccaataa   4020
tggccctga acgagttgct cgaaaaagct aattaaagat cattcatttt tggaaaacta   4080
tataaatcag aagactaaaa tatagctttt agctttttcac ttgaaataag ttatttttta   4140
tttaaataaa ttattttgat aattattaaa cactctaata attaaaaag atgattttta   4200
agtcagattg atcagctttt aagtccatct aaagatgctt taattacatc ttattttttta  4260
aaaaaaatta attattaaaa tttcaaagtt ttcattgctc tcgaagacat ttttttaaat   4320
gtccggtaca ttgtaataat atattattta atggaaggaa agtatagaag gattttttaa   4380
aaaaaataat taagtgataa acttttttag aaattataat atgttgtata tttacgttaa   4440
atttcttaat ttttttaattt aacatttccc aaaaatttttg tgttatccaa atgtccgaat   4500
aacaaccaat taactgacac tgaatttgtg aattttacga gacaaatgtt cttgttaaaa   4560
tttcatatta ggtttcaact gtgagttatt tttggaaatt taaattatgt gtgttgatca   4620
aaatacttta aatatttttt tttcattata tcatgaattt aaatagata tcatatattt   4680
ttaaaagatt tagatttaaa ttttactatt aatatactaa accgacatag ccttaagttg   4740
aaaaaaatatc aaattcatcg agggaaaacg aaaattgcaa gtatatttgg ccaaacgaag   4800
cacctgtcca tgaaatgcca cgtaaaaatt ctaagcaaaa atactacaat aagtgcatgg   4860
aatgagacga gcacgtgtca agttgaaaga agcacctgtc catgaaatgc cacgtaactc   4920
acaccttcaa aacctctcca ttgctacaaa tctccatatt tttgttttttt tttttttaaga  4980
aaaagataaa agtactagca                                               5000
```

```
SEQ ID NO: 109         moltype = DNA   length = 2400
FEATURE                Location/Qualifiers
source                 1..2400
                       mol_type = unassigned DNA
                       organism = Nicotiana tabacum
SEQUENCE: 109
ttagcactta aaaacatag gtttacatgc tctcattgtc acgccaggcc gctaattaaa   60
tggtacattt catcatcccc attttttggc ctcatagtta attatcacaa tttctgaaag   120
caacatcaga acaaccccac atttcttgtg gtcctataat tactgctaga tagtccaaac   180
ccatctgcct atttagggct tgtgaatgag gattgaaaat ggtagagaat atttgcaaag   240
gcatcatgca tatatggaaa agactaaaga gagagttagt gccttgcaaa gcggattctc   300
acagttgtag aaaaggactc accatttttca agaatactcc cggcatgaag atggacaatt   360
taatataaaa aacaaagaaa atagtaatta agtgcgttga gatgaatgaa atttatccgc   420
tcttaattga atatggggaa ttgaaagaaa tttctgataa taaattaatg agtcttacat   480
gacgtggatc cgacttaatc tagtctattt aaactaagaa tagataagaa tagagaatat   540
agacaaaaga gaggctcatt ggctagggtt tcaagggagt tccttgaaca taagtggcaa   600
gtacaagcac aaagccaatt tccatggact aaagatgaat aagatgtgtc gtgtggtatg   660
gtgggaaggt gaggaggtat ggggtaattg gagatgctaa acctctctaa aagctctttt   720
gctccaaata tctaaatcca tctctatcac ttttggcgac tgccccaaaa tttgcaactt   780
atgaattaaa gtttttaatat tttttaagtta ataaattctg aattaataat ttaacatatt   840
caataaactt tttaaaacaa attacgtata taccatcaaa ctggctgcac catgatcact   900
```

```
ttctaaactc acaatgacat atggatttaa tcaggcacaa agtcatgttg atagaaagag  960
atagtacgga gaatgaagaa aaaggtaggg gagagagatg gggtgagtgg ggaaaagata 1020
gggttctctt tttagtgaaa gcgacagggt ctgagaaccc taggtcaaaa gttgcataaa 1080
cctctataca ggcttcttca ctcccttact actaatatac tctcattaag gcttgaggtt 1140
taattcatta aaattgtggt ttaattattg tatcccctca aacgaaataa ttgtccttgt 1200
cgaggttaga caatgttgcg tactattttc aaacgcagtc agccattatt ctcctatcct 1260
ttacagtcga gattcaaaga cagaaagtag catgcaagct gttattaatt tactttgatt 1320
aggactttgc caagaaaatg aagaaccttt tctttttct tttaatttag ttatcttaca 1380
acatgtaatt tttcctagca agcaaatacg gtaacttttt tttttattct catttaattt 1440
gttggagcta ttgctacttt gatgacttca accaaatcct ggttggtagg cggagggtgc 1500
tgacgatgga aactacccct cttgtccaaa tacgataacc taaaaaatag aataatagct 1560
tattgtactg tgctgcaaaa attgcattgt cagtatacat aattaaaatc tattttgaat 1620
gtgtggaggg caaagagggg tgactggtct agggttgtag aaatcaggtg ggagagagaa 1680
tggtatttgt ctctgtgtca gctgatatca cgtgaagagg cacaataaga agtccttcgt 1740
atccattcac ttcccaaaaa taccggcatt actacaaata tagtactagc acttgctttc 1800
tctatcccca tctttgctat ttcctttccc tttccaactt tttggcttta gaattgcaaa 1860
gatggaggga attgtggttc tttgtatctg taaaattttt cctccaagct ccagttgtag 1920
ctagcttaat gcgtggacgc gcgcgcgcac acactagaaa tctgcaatct atatatatat 1980
tcacaaggca ctcacatatc aaaaaccaca tagacattgt atagagagag ctgtcgttct 2040
caagcagaaa aaatgatatg atttcatcag catgtggtca accaaatagt tcaattctag 2100
tctttgcttc ctctttctaa ttactgtata aatagagcca caaggacata gaattgagaa 2160
aataaaagac aataaaaaca aatctagcta cttaagcgaa tgatgatgac tctctctcag 2220
tagtcttaac tcttaatacc cttgtttcc ttcttgtgct gcagtttgat tggttaatta 2280
acctaatcaa aagatgtttt aactgtgttt tatccgtctt tctcaagatc tatcttagtc 2340
ccaccacata gctccctcaa gctacagctg caaaatatat actatatata tatataacaa 2400

SEQ ID NO: 110         moltype = AA   length = 7
FEATURE                Location/Qualifiers
REGION                 1..7
                       note = Description of Unknown:WRKY transcription factor
                        core domain sequence
source                 1..7
                       mol_type = protein
                       organism = unidentified
SEQUENCE: 110
WRKYGQK                                                            7

SEQ ID NO: 111         moltype = AA   length = 7
FEATURE                Location/Qualifiers
REGION                 1..7
                       note = Description of Unknown:WRKY transcription factor
                        core domain sequence
source                 1..7
                       mol_type = protein
                       organism = unidentified
SEQUENCE: 111
WRKYGKK                                                            7

SEQ ID NO: 112         moltype = AA   length = 5
FEATURE                Location/Qualifiers
REGION                 1..5
                       note = Description of Unknown:WRKY transcription factor
                        "PRSYY" motif sequence
source                 1..5
                       mol_type = protein
                       organism = unidentified
SEQUENCE: 112
PRSYY                                                              5

SEQ ID NO: 113         moltype = DNA   length = 777
FEATURE                Location/Qualifiers
source                 1..777
                       mol_type = unassigned DNA
                       organism = Nicotiana tabacum
SEQUENCE: 113
atggatacaa gttctcggga caagtctttt gctattgacc ttaacacaaa cccttcaccg  60
caaaacgtca atagtattcc gcatgagatg ttggatgaag agttgatcag gatgaaagag 120
gagaataaga agctaacgac aacgttaaca actttgtgtg agaactacaa ttacttgcaa 180
actcacctaa ttgaattgct gcaaaaacac aactctgagg agcagaattc caaattatta 240
tctagaaaaa gaaaggctga agatgatcac tgttgtgaaa attcagaaat cataattgaa 300
gaagcatcac ctaagaagcc aagggaaatc agaaccaacg tttcaactgt ttgtgtaaaa 360
actactccct ccgatcaaag cgcagtggtg aaagatggat atcactggag aaaatatggt 420
caaaaagtca caagagataa tccttcacct agagcctact ataagtgttc ttttgcacca 480
tcatgcccag tcaagaagaa ggtgcaaaga agtgttgaag atccatcagt tttagtagct 540
acatatgagg gggagcacaa ccatcctctc ccatccaag ctcaagtaac agtcccatta 600
attaaccaaa atgttacaac aaatcctagt tttctgaaca aattcatgca agacattgac 660
acaacttcgc tacagcaagt tttagtcgca caaatggcgt cttccttgac caagaaccct 720
agtttcacag ctgcagttgc tgcagccatc tccggaaaat tctttgaata tgattaa    777
```

-continued

```
SEQ ID NO: 114        moltype = AA  length = 258
FEATURE               Location/Qualifiers
source                1..258
                      mol_type = protein
                      organism = Nicotiana tabacum
SEQUENCE: 114
MDTSSRDKSF AIDLNTNPSP QNVNSIPHEM LDEELIRMKE ENKKLTTTLT TLCENYNYLQ    60
THLIELLQKH NSEEQNSKLL SRKRKAEDDH CCENSEIIIE EASPKKPREI RTNVSTVCVK   120
TTPSDQSAVV KDGYHWRKYG QKVTRDNPSP RAYYKCSFAP SCPVKKKVQR SVEDPSVLVA   180
TYEGEHNHPL PSQAQVTVPL INQNVTTNPS FLNKFMQDID TTSLQQVLVA QMASSLTKNP   240
SFTAAVAAAI SGKFFEYD                                                 258

SEQ ID NO: 115        moltype = AA  length = 33
FEATURE               Location/Qualifiers
REGION                1..33
                      note = Description of Unknown:WRKY transcription factor
                       zinc finger region sequence
MOD_RES               2..6
                      note = Any amino acid
REGION                2..6
                      note = MISC_FEATURE - This region may encompass 4-5 residues
MOD_RES               8..30
                      note = Any amino acid
REGION                8..30
                      note = MISC_FEATURE - This region may encompass 22-23
                       residues
MOD_RES               32
                      note = Any amino acid
source                1..33
                      mol_type = protein
                      organism = unidentified
SEQUENCE: 115
CXXXXXCXXX XXXXXXXXXX XXXXXXXXXX HXH                                 33

SEQ ID NO: 116        moltype = AA  length = 35
FEATURE               Location/Qualifiers
REGION                1..35
                      note = Description of Unknown:WRKY transcription factor
                       zinc finger region sequence
MOD_RES               2..8
                      note = Any amino acid
MOD_RES               10..32
                      note = Any amino acid
MOD_RES               34
                      note = Any amino acid
source                1..35
                      mol_type = protein
                      organism = unidentified
SEQUENCE: 116
CXXXXXXXCX XXXXXXXXXX XXXXXXXXXX XXHXC                               35

SEQ ID NO: 117        moltype = AA  length = 4
FEATURE               Location/Qualifiers
REGION                1..4
                      note = Description of Unknown:WRKY transcription factor
                       "WRKY" motif sequence
source                1..4
                      mol_type = protein
                      organism = unidentified
SEQUENCE: 117
WRKY                                                                 4

SEQ ID NO: 118        moltype = DNA  length = 204
FEATURE               Location/Qualifiers
misc_feature          1..204
                      note = Description of Artificial Sequence:
                       Syntheticpolynucleotide
source                1..204
                      mol_type = other DNA
                      organism = synthetic construct
SEQUENCE: 118
cctcttcctg gcataccagc agttgctaac atctatgttt ttgttgttct attttgcaca    60
tttgtccact aataggtcct gtgttcttac acttcatcac tatagtgtgt gtacagagaa   120
acaggacctt ttagtggaca aatgcctaaa atagggcaaa ggatggtcac gtcttaatgt   180
tatattaata tgatggtcag gttt                                          204

SEQ ID NO: 119        moltype = DNA  length = 204
FEATURE               Location/Qualifiers
misc_feature          1..204
```

-continued

```
                          note = Description of Artificial Sequence:
                          Syntheticpolynucleotide
source                    1..204
                          mol_type = other DNA
                          organism = synthetic construct
SEQUENCE: 119
cctcttcctg gcataccagc agttgctaac atctatgttt ttgttgttct attttgcaca    60
tcatttgcgc ggaaactacg atgttcttac acttcatcac tatagtgtgt gtacagagaa   120
atcgtagtta ccgcgcaaat gatgcctaaa atagggcaaa ggatggtcac gtcttaatgt   180
tatattaata tgatggtcag gttt                                          204

SEQ ID NO: 120           moltype = DNA   length = 204
FEATURE                  Location/Qualifiers
misc_feature             1..204
                          note = Description of Artificial Sequence:
                          Syntheticpolynucleotide
source                    1..204
                          mol_type = other DNA
                          organism = synthetic construct
SEQUENCE: 120
cctcttcctg gcataccagc agttgctaac atctatgttt ttgttgttct attttgcaca    60
tacattcgtc ttacggtcca gtgttcttac acttcatcac tatagtgtgt gtacagagaa   120
actggaccga aagacgaatg tatgcctaaa atagggcaaa ggatggtcac gtcttaatgt   180
tatattaata tgatggtcag gttt                                          204

SEQ ID NO: 121           moltype = DNA   length = 21
FEATURE                  Location/Qualifiers
misc_feature             1..21
                          note = Description of Artificial Sequence:
                          Syntheticoligonucleotide
source                    1..21
                          mol_type = other DNA
                          organism = synthetic construct
SEQUENCE: 121
tttgtccact aataggtcct g                                              21

SEQ ID NO: 122           moltype = DNA   length = 21
FEATURE                  Location/Qualifiers
misc_feature             1..21
                          note = Description of Artificial Sequence:
                          Syntheticoligonucleotide
source                    1..21
                          mol_type = other DNA
                          organism = synthetic construct
SEQUENCE: 122
tcatttgcgc ggaaactacg a                                              21

SEQ ID NO: 123           moltype = DNA   length = 21
FEATURE                  Location/Qualifiers
misc_feature             1..21
                          note = Description of Artificial Sequence:
                          Syntheticoligonucleotide
source                    1..21
                          mol_type = other DNA
                          organism = synthetic construct
SEQUENCE: 123
tacattcgtc ttacggtcca g                                              21

SEQ ID NO: 124           moltype = DNA   length = 21
FEATURE                  Location/Qualifiers
misc_feature             1..21
                          note = Description of Artificial Sequence:
                          Syntheticoligonucleotide
source                    1..21
                          mol_type = other DNA
                          organism = synthetic construct
SEQUENCE: 124
caggaccttt tagtggacaa a                                              21

SEQ ID NO: 125           moltype = DNA   length = 21
FEATURE                  Location/Qualifiers
misc_feature             1..21
                          note = Description of Artificial Sequence:
                          Syntheticoligonucleotide
source                    1..21
                          mol_type = other DNA
                          organism = synthetic construct
SEQUENCE: 125
tcgtagttac cgcgcaaatg a                                              21
```

-continued

```
SEQ ID NO: 126        moltype = DNA  length = 21
FEATURE               Location/Qualifiers
misc_feature          1..21
                      note = Description of Artificial Sequence:
                      Syntheticoligonucleotide
source                1..21
                      mol_type = other DNA
                      organism = synthetic construct
SEQUENCE: 126
ctggaccgaa agacgaatgt a                                          21
```

COMPOSITIONS AND METHODS FOR PRODUCING TOBACCO PLANTS AND PRODUCTS HAVING REDUCED OR ELIMINATED SUCKERS

CROSS-REFERENCE TO RELATED APPLICATIONS

This application is a continuation of U.S. patent application Ser. No. 16/886,118, filed May 28, 2020, which claims the benefit of U.S. Provisional Application No. 62/854,139, which was filed on May 29, 2019. The entire content of these applications are incorporated by reference in their entireties.

FIELD

The present disclosure provides methods and compositions for refining the expression of nucleic acids and proteins useful for the reduction or elimination of suckers in plants.

INCORPORATION OF SEQUENCE LISTING

The instant application contains a Sequence Listing which has been submitted electronically in XML format and is hereby incorporated by reference in its entirety. Said XML copy, created on Aug. 22, 2022, is named P34703US02_SL.XML and is 287,997 bytes in size.

BACKGROUND

Tobacco is a plant species that exhibits exceptionally strong apical dominance. Molecular signals from the shoot apical meristem (SAM) mediate a hormonal signal that effectively inhibits axillary bud growth. Upon removal of the SAM (also known as "topping"), physiological and molecular changes occur, enabling the growth of new shoots (or "suckers") from axillary meristems (buds). Sucker growth results in loss of yield and leaf quality. Suckers have been controlled by manual removal and through the application of chemicals. Maleic hydrazide and flumetralin are routinely used on topped plants to inhibit axillary bud growth ("suckering"). However, labor and chemical agents to control suckers are very expensive. Control of suckering in tobacco through conventional breeding, mutation breeding, and transgenic approaches have been a major objective for several decades but, to date, successful inhibition or elimination of suckering has not been achieved through these approaches. Recent molecular work has produced transgenic plants with reduced or eliminated suckers, but leaky expression of axillary bud-degrading genes can result in the death of seeds and embryos and prevents the production of successive generations of transgenic plants. Therefore, development of methods and compositions to prevent axillary bud-degrading genes from being expressed in non-desired tissues and/or organs would result in a reduction of the use of chemical agents and would reduce costs and labor associated with tobacco production.

SUMMARY

In one aspect, this disclosure provides a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to the control tobacco plant when grown under comparable growth conditions.

In one aspect, this disclosure provides a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety.

In one aspect, this disclosure provides a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, where the modified tobacco plant comprises no suckers or reduced suckers after topping as compared to a control tobacco plant when grown under comparable growth conditions.

In one aspect, this disclosure provides a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In one aspect, this disclosure provides a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, where the modified tobacco plant comprises no suckers or reduced suckers after topping as compared to a control tobacco plant when grown under comparable growth conditions.

In one aspect, this disclosure provides a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In one aspect, this disclosure provides a tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to the control tobacco plant when grown under comparable growth conditions.

In one aspect, this disclosure provides a tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety.

In one aspect, this disclosure provides a tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and where the modified tobacco plant comprises no suckers or reduced suckers after topping as compared to a control tobacco plant when grown under comparable growth conditions.

In one aspect, this disclosure provides a tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In one aspect, this disclosure provides a tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, where the modified tobacco plant comprises no suckers or reduced suckers after topping as compared to a control tobacco plant when grown under comparable growth conditions.

In one aspect, this disclosure provides a tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In one aspect, this disclosure provides a method for producing a modified tobacco plant comprising: (a) inducing a mutation in at least one tobacco cell at a genomic locus encoding a polypeptide selected from the group consisting of a cyclin, a cyclin-dependent kinase (CDK), a CDK inhibitor, a MYB, and a WRKY transcription factor; (b) selecting at least one tobacco cell comprising the mutation from step (a); and (c) regenerating a modified tobacco plant from the at least one tobacco cell selected in step (b), where the modified tobacco plant comprises no suckers or reduced suckers after topping as compared to a control tobacco plant lacking the mutation when grown under comparable growth conditions.

In one aspect, this disclosure provides a method for producing a modified tobacco plant comprising: (a) introducing a recombinant DNA construct to at least one tobacco cell, where the recombinant DNA construct comprises a heterologous promoter operably linked to a nucleic acid encoding a polypeptide selected from the group consisting of a cyclin, a cyclin-dependent kinase (CDK), a CDK inhibitor, a MYB, and a WRKY transcription factor; (b) selecting at least one tobacco cell comprising the recombinant DNA construct; and (c) regenerating a modified tobacco plant from the at least one tobacco cell selected in step (b), where the modified tobacco plant comprises no suckers or reduced suckers after topping as compared to a control tobacco plant lacking the recombinant DNA construct when grown under comparable growth conditions.

In one aspect, this disclosure provides a method for producing a modified tobacco plant comprising: (a) introducing a recombinant DNA construct to at least one tobacco cell, where the recombinant DNA construct comprises a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor; (b) selecting at least one tobacco cell comprising the recombinant DNA construct; and (c) regenerating a modified tobacco plant from the at least one tobacco cell selected in step (b), where the modified tobacco plant comprises no suckers or reduced suckers after topping as compared to a control tobacco plant lacking the recombinant DNA construct when grown under comparable growth conditions.

In one aspect, this disclosure provides a method comprising preparing a tobacco product using cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and where the modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and wherein said modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, wherein said modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In one aspect, this disclosure provides a method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions.

In one aspect, this disclosure provides a method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In one aspect, this disclosure provides a method comprising transforming a tobacco cell with a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor.

In one aspect, this disclosure provides a method comprising transforming a tobacco cell with a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In one aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the at least one tobacco plant comprises no suckers or reduced suckers after topping as compared to the control tobacco plant when grown under comparable growth conditions; and (b) selecting for progeny tobacco plants that exhibit no suckers or reduced suckers after topping compared to a control tobacco plant of the same cross grown under comparable growth conditions.

In one aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor, where the at least one tobacco plant comprises no suckers or reduced suckers after topping as compared to a control tobacco plant when grown under comparable growth conditions; and (b) selecting for progeny tobacco plants that exhibit no suckers or reduced suckers after topping compared to a control tobacco plant of the same cross grown under comparable growth conditions.

In one aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a recombinant DNA construct comprising a heterologous promoter operably linked to a nucleic acid encoding at least one small RNA molecule capable of reducing the expression of an endogenous genomic locus that encodes a polypeptide selected from the group consisting of a cyclin, a cyclin-dependent kinase (CDK), a CDK inhibitor, a MYB, and a WRKY transcription factor, where the at least one tobacco plant comprises no suckers or reduced suckers after topping as compared to a control tobacco plant when grown under comparable growth conditions; and (b) selecting for progeny tobacco plants that exhibit no suckers or reduced suckers after topping compared to a control tobacco plant of the same cross grown under comparable growth conditions.

BRIEF DESCRIPTION OF THE SEQUENCES

SEQ ID NOs: 1-44, 89-113, and 118-126 are nucleic acid sequences.

SEQ ID NOs: 45-88 and 114-117 are amino acid sequences.

Additional descriptions of the SEQ ID NOs provided herein can be found below in Table 1.

TABLE 1

| Description of sequences | | |
| --- | --- | --- |
| SEQ ID NO | Sequence Type | Sequence Description |
| 1 | Nucleic acid | Cyclin-dependent kinase |
| 2 | Nucleic acid | Cyclin-dependent kinase |
| 3 | Nucleic acid | Cyclin-dependent kinase |
| 4 | Nucleic acid | Cyclin-dependent kinase |
| 5 | Nucleic acid | Cyclin-dependent kinase inhibitor |
| 6 | Nucleic acid | Cyclin |
| 7 | Nucleic acid | Cyclin |
| 8 | Nucleic acid | Cyclin |
| 9 | Nucleic acid | Cyclin |
| 10 | Nucleic acid | Cyclin |
| 11 | Nucleic acid | Cyclin |
| 12 | Nucleic acid | Cyclin |
| 13 | Nucleic acid | Cyclin |
| 14 | Nucleic acid | Cyclin |
| 15 | Nucleic acid | Cyclin |
| 16 | Nucleic acid | Cyclin |
| 17 | Nucleic acid | Cyclin |
| 18 | Nucleic acid | Cyclin |
| 19 | Nucleic acid | Cyclin |
| 20 | Nucleic acid | Cyclin |
| 21 | Nucleic acid | Cyclin |
| 22 | Nucleic acid | Cyclin |
| 23 | Nucleic acid | Cyclin |
| 24 | Nucleic acid | Cyclin |
| 25 | Nucleic acid | Cyclin |
| 26 | Nucleic acid | Cyclin |
| 27 | Nucleic acid | Cyclin |
| 28 | Nucleic acid | Cyclin |
| 29 | Nucleic acid | Cyclin |
| 30 | Nucleic acid | Cyclin |
| 31 | Nucleic acid | Cyclin |
| 32 | Nucleic acid | Cyclin |
| 33 | Nucleic acid | MYB |
| 34 | Nucleic acid | MYB |
| 35 | Nucleic acid | MYB |
| 36 | Nucleic acid | MYB |

TABLE 1-continued

| SEQ ID NO | Sequence Type | Sequence Description |
|---|---|---|
| 37 | Nucleic acid | MYB |
| 38 | Nucleic acid | MYB |
| 39 | Nucleic acid | MYB |
| 40 | Nucleic acid | MYB |
| 41 | Nucleic acid | MYB |
| 42 | Nucleic acid | MYB |
| 43 | Nucleic acid | MYB |
| 44 | Nucleic acid | MYB |
| 45 | Amino acid | Cyclin-dependent kinase |
| 46 | Amino acid | Cyclin-dependent kinase |
| 47 | Amino acid | Cyclin-dependent kinase |
| 48 | Amino acid | Cyclin-dependent kinase |
| 49 | Amino acid | Cyclin-dependent kinase inhibitor |
| 50 | Amino acid | Cyclin |
| 51 | Amino acid | Cyclin |
| 52 | Amino acid | Cyclin |
| 53 | Amino acid | Cyclin |
| 54 | Amino acid | Cyclin |
| 55 | Amino acid | Cyclin |
| 56 | Amino acid | Cyclin |
| 57 | Amino acid | Cyclin |
| 58 | Amino acid | Cyclin |
| 59 | Amino acid | Cyclin |
| 60 | Amino acid | Cyclin |
| 61 | Amino acid | Cyclin |
| 62 | Amino acid | Cyclin |
| 63 | Amino acid | Cyclin |
| 64 | Amino acid | Cyclin |
| 65 | Amino acid | Cyclin |
| 66 | Amino acid | Cyclin |
| 67 | Amino acid | Cyclin |
| 68 | Amino acid | Cyclin |
| 69 | Amino acid | Cyclin |
| 70 | Amino acid | Cyclin |
| 71 | Amino acid | Cyclin |
| 72 | Amino acid | Cyclin |
| 73 | Amino acid | Cyclin |
| 74 | Amino acid | Cyclin |
| 75 | Amino acid | Cyclin |
| 76 | Amino acid | Cyclin |
| 77 | Amino acid | MYB |
| 78 | Amino acid | MYB |
| 79 | Amino acid | MYB |
| 80 | Amino acid | MYB |
| 81 | Amino acid | MYB |
| 82 | Amino acid | MYB |
| 83 | Amino acid | MYB |
| 84 | Amino acid | MYB |
| 85 | Amino acid | MYB |
| 86 | Amino acid | MYB |
| 87 | Amino acid | MYB |
| 88 | Amino acid | MYB |
| 89 | Nucleic acid | Promoter |
| 90 | Nucleic acid | Promoter |
| 91 | Nucleic acid | Promoter |
| 92 | Nucleic acid | Promoter |
| 93 | Nucleic acid | Promoter |
| 94 | Nucleic acid | Promoter |
| 95 | Nucleic acid | Promoter |
| 96 | Nucleic acid | Promoter |
| 97 | Nucleic acid | Promoter |
| 98 | Nucleic acid | Promoter |
| 99 | Nucleic acid | Promoter |
| 100 | Nucleic acid | Promoter |
| 101 | Nucleic acid | Promoter |
| 102 | Nucleic acid | Promoter |
| 103 | Nucleic acid | Promoter |
| 104 | Nucleic acid | Promoter |
| 105 | Nucleic acid | Promoter |
| 106 | Nucleic acid | Promoter |
| 107 | Nucleic acid | Promoter |
| 108 | Nucleic acid | Promoter |
| 109 | Nucleic acid | Promoter |
| 110 | Nucleic acid | WRKY core domain |
| 111 | Nucleic acid | WRKY core domain variant |

TABLE 1-continued

| SEQ ID NO | Sequence Type | Sequence Description |
|---|---|---|
| 112 | Nucleic acid | WRKY domain motif |
| 113 | Nucleic acid | WRKY transcription factor |
| 114 | Amino acid | WRKY transcription factor |
| 115 | Amino acid | WRKY transcription factor zinc finger region |
| 116 | Amino acid | WRKY transcription factor zinc finger region |
| 117 | Amino acid | WRKY domain |
| 118 | Nucleic acid | Artificial miRNA precursor |
| 119 | Nucleic acid | Artificial miRNA precursor |
| 120 | Nucleic acid | Artificial miRNA precursor |
| 121 | Nucleic acid | Mature artificial miRNA |
| 122 | Nucleic acid | Mature artificial miRNA |
| 123 | Nucleic acid | Mature artificial miRNA |
| 124 | Nucleic acid | Artificial miRNA* |
| 125 | Nucleic acid | Artificial miRNA* |
| 126 | Nucleic acid | Artificial miRNA* |

DETAILED DESCRIPTION

Figure 1:
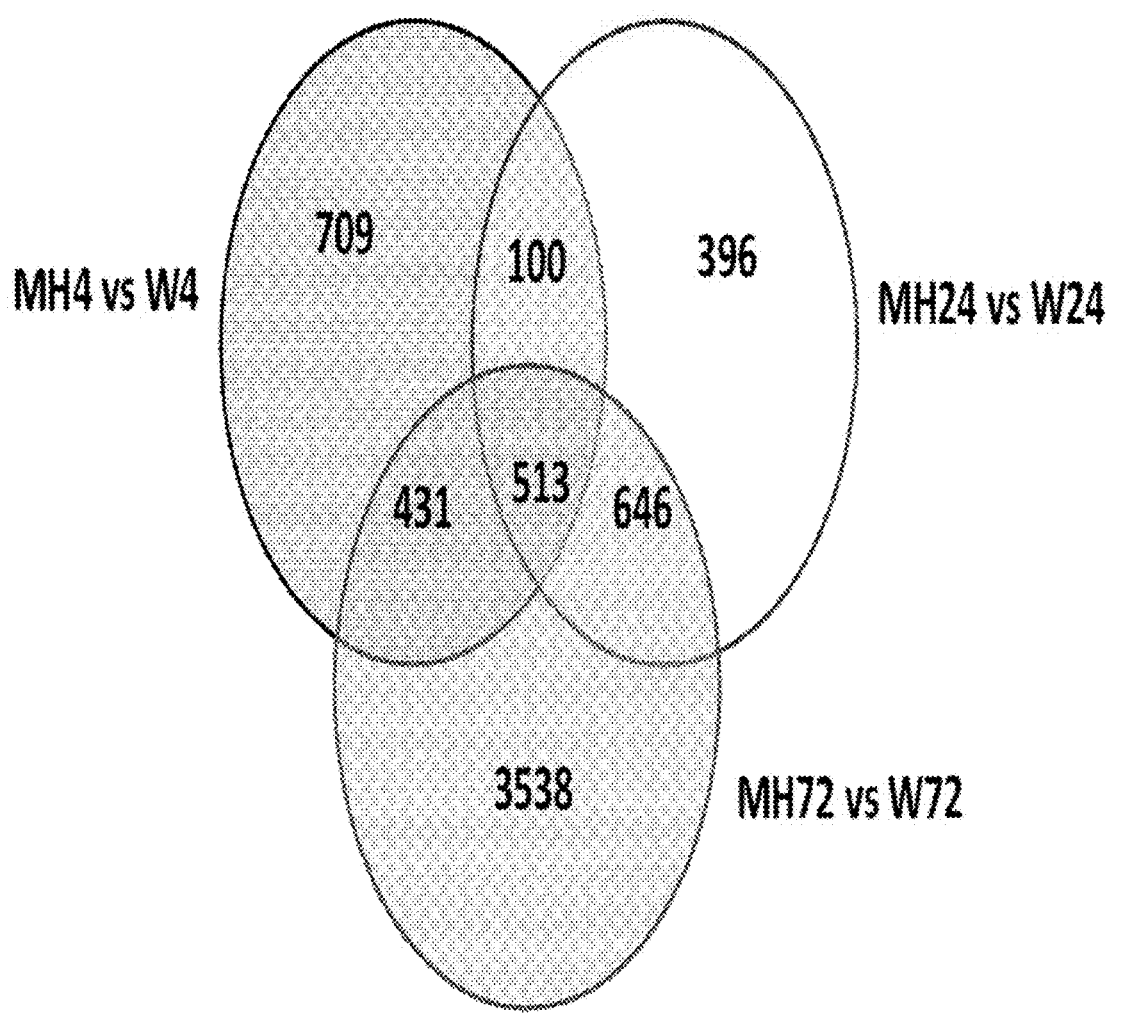
FIG. 1 is a Venn diagram depicting the overlap of differentially expressed genes in axillary buds between 4-hour, 24-hour, and 72-hour post-topping pairwise comparisons of water-treated and maleic hydrazine-treated tobacco plants. MH4 refers 4-hours after maleic hydrazide treatment; W4 refers to 4-hours after water treatment; MH24 refers to 24-hours after maleic hydrazide treatment; W24 refers to 24-hours after water treatment; MH72 refers to 72-hours after maleic hydrazide treatment; W72 refers to 72-hours after water treatment.

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc. The term "and/or" when used in a list of two or more items means any one of the listed items by itself or in combination with any one or more of the other listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

When a range of numbers is provided herein, the range is understood to inclusive of the edges of the range as well as any number between the defined edges of the range. For example, "between 1 and 10" includes any number between 1 and 10, as well as the number 1 and the number 10.

As used herein, the singular form "a," "an," and "the" include plural references unless the context clearly dictates otherwise. For example, the term "a compound" or "at least one compound" may include a plurality of compounds, including mixtures thereof.

In an aspect, a modified tobacco plant provided herein comprises reduced suckering or no suckering after topping as compared to a control tobacco plant when grown under comparable conditions.

As used herein, "suckering" refers to the development and/or growth of axillary (or lateral) buds ("suckers") from axillary meristems that grow between a leaf and the stalk. An axillary bud is an embryonic shoot that comprises an axillary meristem, surrounding leaf tissue, and surrounding stem tissue. See, for example, U.S. Patent Application Publication Nos. 2016/0281100; and 2017/0260535, which are incorporated by reference herein in their entireties.

As used herein, "topping" refers to the removal of the stalk apex, including the shoot apical meristem, flowers, and up to several adjacent leaves, when a plant is near maturity. Topping a tobacco plant results in the loss of apical dominance. Prior to topping, suckering is largely kept dormant by hormonal signals emanating from the shoot-apical meristem; topping removes the hormonal signals and can allow the outgrowth of suckers ("topping-induced suckering"). Provided suckering is sufficiently controlled, topping increases yield, increases value-per-acre, and results in desirable modifications to physical and chemical properties of tobacco leaves.

As used herein, "comparable growth conditions" refers to similar environmental conditions and/or agronomic practices for growing and making meaningful comparisons between two or more plant genotypes so that neither environmental conditions nor agronomic practices would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp. 70-103. It is appreciated in the art that "comparable growth conditions" does not require identical growth conditions.

As used herein, "modified" refers to plants, seeds, plant parts, plant cells, and plant genomes that have been subjected to mutagenesis, genome editing, genetic transformation, or a combination thereof.

In an aspect, this disclosure provides a modified tobacco plant that comprise no suckers or reduced suckers after topping as compared to a control tobacco plant when grown under comparable conditions. As used herein, a "reduction" in the number of suckers, the size of suckers, and/or the impact suckers have on agronomic performance refers to a statistically significant reduction. As used herein, "statistically significant" refers to a p-value of less than 0.05 when using an appropriate measure of statistical significance (e.g., a one-tailed two sample t-test).

In one aspect, a modified plant or method provided herein requires reduced management for controlling suckering compared to a control plant when grown under comparable conditions. As used herein, "management" refers to manually removing suckers, application of chemicals (e.g., maleic hydrazide, flumetralin) to inhibit or remove suckers, or both. In one aspect, a modified plant or method provided herein requires reduced frequency of manual sucker removal, reduced frequency of chemical application, reduced quantities of chemical application, or a combination thereof, as compared to a control plant grown under comparable conditions. See, for example, Fisher et al. "Topping, Managing Suckers, and Using Ethephon," pages 96-117 In: 2016 Flue-Cured Tobacco Information, North Carolina State University, which is herein incorporated by reference in its entirety.

In an aspect, a modified plant or method provided herein requires reduced frequency of maleic hydrazide application to reduce or eliminate suckers. In an aspect, a modified plant or method provided herein requires reduced quantities of maleic hydrazide application to reduce or eliminate suckers. In an aspect, a modified plant or method provided herein requires reduced frequency of flumetralin application to reduce or eliminate suckers. In an aspect, a modified plant or method provided herein requires reduced quantities of flumetralin application to reduce or eliminate suckers.

In one aspect, a modified plant or method provided herein requires manual removal of suckers 1% as frequently as a control plant when grown under comparable conditions. In one aspect, a modified plant or method provided herein requires manual removal of suckers 5% as frequently as a control plant when grown under comparable conditions. In one aspect, a modified plant or method provided herein requires manual removal of suckers 10% as frequently as a control plant when grown under comparable conditions. In one aspect, a modified plant or method provided herein requires manual removal of suckers 20% as frequently as a control plant when grown under comparable conditions. In one aspect, a modified plant or method provided herein requires manual removal of suckers 30% as frequently as a control plant when grown under comparable conditions. In one aspect, a modified plant or method provided herein requires manual removal of suckers 40% as frequently as a control plant when grown under comparable conditions. In one aspect, a modified plant or method provided herein requires manual removal of suckers 50% as frequently as a control plant when grown under comparable conditions. In one aspect, a modified plant or method provided herein requires manual removal of suckers 60% as frequently as a control plant when grown under comparable conditions. In one aspect, a modified plant or method provided herein requires manual removal of suckers 70% as frequently as a control plant when grown under comparable conditions. In one aspect, a modified plant or method provided herein requires manual removal of suckers 80% as frequently as a control plant when grown under comparable conditions. In one aspect, a modified plant or method provided herein requires manual removal of suckers 90% as frequently as a control plant when grown under comparable conditions. In one aspect, a modified plant or method provided herein requires manual removal of suckers 95% as frequently as a control plant when grown under comparable conditions.

In one aspect, a modified plant or method provided herein requires manual removal of suckers less than 1% as frequently as a control plant when grown under comparable conditions. In one aspect, a modified plant or method provided herein requires manual removal of suckers less than 5% as frequently as a control plant when grown under comparable conditions. In one aspect, a modified plant or method provided herein requires manual removal of suckers less than 10% as frequently as a control plant when grown under comparable conditions. In one aspect, a modified plant or method provided herein requires manual removal of suckers less than 20% as frequently as a control plant when grown under comparable conditions. In one aspect, a modified plant or method provided herein requires manual removal of suckers less than 30% as frequently as a control plant when grown under comparable conditions. In one aspect, a modified plant or method provided herein requires manual removal of suckers less than 40% as frequently as a control plant when grown under comparable conditions. In one aspect, a modified plant or method provided herein requires manual removal of suckers less than 50% as frequently as a control plant when grown under comparable conditions. In one aspect, a modified plant or method provided herein requires manual removal of suckers less than 60% as frequently as a control plant when grown under comparable conditions. In one aspect, a modified plant or method provided herein requires manual removal of suckers less than 70% as frequently as a control plant when grown under comparable conditions. In one aspect, a modified plant or method provided herein requires manual removal of suckers less than 80% as frequently as a control plant when grown under comparable conditions. In one aspect, a modified plant or method provided herein requires manual removal of suckers less than 90% as frequently as a control plant when grown under comparable conditions. In one aspect, a modified plant or method provided herein requires manual removal of suckers less than 95% as frequently as a control plant when grown under comparable conditions.

In one aspect, a modified plant provided herein requires manual removal of suckers between 10% and 95% as frequently as a control plant when grown under comparable conditions. In one aspect, a modified plant provided herein requires manual removal of suckers between 20% and 95% as frequently as a control plant when grown under comparable conditions. In one aspect, a modified plant provided herein requires manual removal of suckers between 30% and 95% as frequently as a control plant when grown under comparable conditions. In one aspect, a modified plant provided herein requires manual removal of suckers between 40% and 95% as frequently as a control plant when grown under comparable conditions. In one aspect, a modified plant provided herein requires manual removal of suckers between 50% and 95% as frequently as a control plant when grown under comparable conditions. In one aspect, a modified plant provided herein requires manual removal of suckers between 60% and 95% as frequently as a control plant when grown under comparable conditions. In one aspect, a modified plant provided herein requires manual removal of suckers between 70% and 95% as frequently as a control plant when grown under comparable conditions. In one aspect, a modified plant provided herein requires manual removal of suckers between 80% and 95% as frequently as a control plant when grown under comparable conditions. In one aspect, a modified plant provided herein requires manual removal of suckers between 90% and 95% as frequently as a control plant when grown under comparable conditions. In one aspect, a modified plant provided herein requires manual removal of suckers between 10% and 75% as frequently as a control plant when grown under comparable conditions. In one aspect, a modified plant provided herein requires manual removal of suckers between 10% and 50% as frequently as a control plant when grown under comparable conditions. In one aspect, a modified plant provided herein requires manual removal of suckers between 10% and 25% as frequently as a control plant when grown under comparable conditions. In one aspect, a modified plant provided herein requires manual removal of suckers between 50% and 75% as frequently as a control plant when grown under comparable conditions. In one aspect, a modified plant provided herein requires manual removal of suckers between 25% and 75% as frequently as a control plant when grown under comparable conditions. In one aspect, a modified plant provided herein requires manual removal of suckers between 25% and 50% as frequently as a control plant when grown under comparable conditions. In one aspect, a modified plant provided herein requires manual removal of suckers between 1% and 50% as frequently as a control plant when grown under comparable conditions. In one aspect, a modified plant provided herein requires manual removal of suckers between 1% and 25% as frequently as a control plant when grown under comparable conditions. In one aspect, a modified plant provided herein requires manual removal of suckers between 1% and 10% as frequently as a control plant when grown under comparable conditions.

In one aspect, a modified plant provided herein requires chemical application to control suckering 1% as frequently as a control plant when grown under comparable conditions. In one aspect, a modified plant provided herein requires chemical application to control suckering 5% as frequently as a control plant when grown under comparable conditions. In one aspect, a modified plant provided herein requires chemical application to control suckering 10% as frequently as a control plant when grown under comparable conditions. In one aspect, a modified plant provided herein requires chemical application to control suckering 20% as frequently as a control plant when grown under comparable conditions. In one aspect, a modified plant provided herein requires chemical application to control suckering 30% as frequently as a control plant when grown under comparable conditions. In one aspect, a modified plant provided herein requires chemical application to control suckering 40% as frequently as a control plant when grown under comparable conditions.

In one aspect, a modified plant provided herein requires chemical application to control suckering 50% as frequently as a control plant when grown under comparable conditions. In one aspect, a modified plant provided herein requires chemical application to control suckering 60% as frequently as a control plant when grown under comparable conditions. In one aspect, a modified plant provided herein requires chemical application to control suckering 70% as frequently as a control plant when grown under comparable conditions. In one aspect, a modified plant provided herein requires chemical application to control suckering 80% as frequently as a control plant when grown under comparable conditions. In one aspect, a modified plant provided herein requires chemical application to control suckering 90% as frequently as a control plant when grown under comparable conditions. In one aspect, a modified plant provided herein requires chemical application to control suckering 95% as frequently as a control plant when grown under comparable conditions.

In one aspect, a modified plant provided herein requires chemical application to control suckering less than 1% as frequently as a control plant when grown under comparable conditions. In one aspect, a modified plant provided herein requires chemical application to control suckering less than 5% as frequently as a control plant when grown under comparable conditions. In one aspect, a modified plant provided herein requires chemical application to control suckering less than 10% as frequently as a control plant when grown under comparable conditions. In one aspect, a modified plant provided herein requires chemical application to control suckering less than 20% as frequently as a control plant when grown under comparable conditions. In one aspect, a modified plant provided herein requires chemical application to control suckering less than 30% as frequently as a control plant when grown under comparable conditions. In one aspect, a modified plant provided herein requires chemical application to control suckering less than 40% as frequently as a control plant when grown under comparable conditions. In one aspect, a modified plant provided herein requires chemical application to control suckering less than 50% as frequently as a control plant when grown under comparable conditions. In one aspect, a modified plant provided herein requires chemical application to control suckering less than 60% as frequently as a control plant when grown under comparable conditions. In one aspect, a modified plant provided herein requires chemical application to control suckering less than 70% as frequently as a control plant when grown under comparable conditions. In one aspect, a modified plant provided herein requires chemical application to control suckering less than 80% as frequently as a control plant when grown under comparable conditions. In one aspect, a modified plant provided herein requires chemical application to control suckering less than 90% as frequently as a control plant when grown under comparable conditions. In one aspect, a modified plant provided herein requires chemical application to control suckering less than 95% as frequently as a control plant when grown under comparable conditions.

In one aspect, a modified plant provided herein requires chemical application to control suckering between 10% and 95% as frequently as a control plant when grown under comparable conditions. In one aspect, a modified plant provided herein requires chemical application to control suckering between 20% and 95% as frequently as a control plant when grown under comparable conditions. In one aspect, a modified plant provided herein requires chemical application to control suckering between 30% and 95% as frequently as a control plant when grown under comparable conditions. In one aspect, a modified plant provided herein requires chemical application to control suckering between 40% and 95% as frequently as a control plant when grown under comparable conditions. In one aspect, a modified plant provided herein requires chemical application to control suckering between 50% and 95% as frequently as a control plant when grown under comparable conditions. In one aspect, a modified plant provided herein requires chemical application to control suckering between 60% and 95% as frequently as a control plant when grown under comparable conditions. In one aspect, a modified plant provided herein requires chemical application to control suckering between 70% and 95% as frequently as a control plant when grown under comparable conditions. In one aspect, a modified plant provided herein requires chemical application to control suckering between 80% and 95% as frequently as a control plant when grown under comparable conditions. In one aspect, a modified plant provided herein requires chemical application to control suckering between 90% and 95% as frequently as a control plant when grown under comparable conditions. In one aspect, a modified plant provided herein requires chemical application to control suckering between 10% and 75% as frequently as a control plant when grown under comparable conditions. In one aspect, a modified plant provided herein requires chemical application to control suckering between 10% and 50% as frequently as a control plant when grown under comparable conditions. In one aspect, a modified plant provided herein requires chemical application to control suckering between 10% and 25% as frequently as a control plant when grown under comparable conditions. In one aspect, a modified plant provided herein requires chemical application to control suckering between 50% and 75% as frequently as a control plant when grown under comparable conditions. In one aspect, a modified plant provided herein requires chemical application to control suckering between 25% and 50% as frequently as a control plant when grown under comparable conditions. In one aspect, a modified plant provided herein requires chemical application to control suckering between 25% and 75% as frequently as a control plant when grown under comparable conditions. In one aspect, a modified plant provided herein requires chemical application to control suckering between 1% and 50% as frequently as a control plant when grown under comparable conditions. In one aspect, a modified plant provided herein requires chemical application to control suckering between 1% and 25% as frequently as a control plant when grown under comparable conditions. In one aspect, a modified plant provided herein requires chemical application to control suckering between 1% and 10% as frequently as a control plant when grown under comparable conditions.

In one aspect, a modified plant provided herein requires a chemical spray volume of 1% of the volume used to control suckering of a control plant when grown under comparable conditions. In one aspect, a modified plant provided herein requires a chemical spray volume of 5% of the volume used to control suckering of a control plant when grown under comparable conditions. In one aspect, a modified plant provided herein requires a chemical spray volume of 10% of the volume used to control suckering of a control plant when grown under comparable conditions. In one aspect, a modified plant provided herein requires a chemical spray volume of 20% of the volume used to control suckering of a control plant when grown under comparable conditions. In one aspect, a modified plant provided herein requires a chemical spray volume of 30% of the volume used to control suckering of a control plant when grown under comparable conditions. In one aspect, a modified plant provided herein requires a chemical spray volume of 40% of the volume used to control suckering of a control plant when grown under comparable conditions. In one aspect, a modified plant provided herein requires a chemical spray volume of 50% of the volume used to control suckering of a control plant when grown under comparable conditions. In one aspect, a modified plant provided herein requires a chemical spray volume of 60% of the volume used to control suckering of a control plant when grown under comparable conditions. In one aspect, a modified plant provided herein requires a chemical spray volume of 70% of the volume used to control suckering of a control plant when grown under comparable conditions. In one aspect, a modified plant provided herein requires a chemical spray volume of 80% of the volume used to control suckering of a control plant when grown under comparable conditions. In one aspect, a modified plant provided herein requires a chemical spray volume of 90% of the volume used to control suckering of a control plant when grown under comparable conditions. In one aspect, a modified plant provided herein requires a chemical spray volume of 95% of the volume used to control suckering of a control plant when grown under comparable conditions.

In one aspect, a modified plant provided herein requires a chemical spray volume of less than 1% of the volume used to control suckering of a control plant when grown under comparable conditions. In one aspect, a modified plant provided herein requires a chemical spray volume of less than 5% of the volume used to control suckering of a control plant when grown under comparable conditions. In one aspect, a modified plant provided herein requires a chemical spray volume of less than 10% of the volume used to control suckering of a control plant when grown under comparable conditions. In one aspect, a modified plant provided herein requires a chemical spray volume of less than 20% of the volume used to control suckering of a control plant when grown under comparable conditions. In one aspect, a modified plant provided herein requires a chemical spray volume of less than 30% of the volume used to control suckering of a control plant when grown under comparable conditions. In one aspect, a modified plant provided herein requires a chemical spray volume of less than 40% of the volume used to control suckering of a control plant when grown under comparable conditions. In one aspect, a modified plant provided herein requires a chemical spray volume of less than 50% of the volume used to control suckering of a control plant when grown under comparable conditions. In one aspect, a modified plant provided herein requires a chemical spray volume of less than 60% of the volume used to control suckering of a control plant when grown under comparable conditions. In one aspect, a modified plant provided herein requires a chemical spray volume of less than 70% of the volume used to control suckering of a control plant when grown under comparable conditions. In one aspect, a modified plant provided herein requires a chemical spray volume of less than 80% of the volume used to control suckering of a control plant when grown under comparable conditions. In one aspect, a modified plant provided herein requires a chemical spray volume of less than 90% of the volume used to control suckering of a control plant when grown under comparable conditions. In one aspect, a modified plant provided herein requires a chemical spray volume of less than 95% of the volume used to control suckering of a control plant when grown under comparable conditions.

In one aspect, a modified plant provided herein requires a chemical spray volume between 10% and 95% less than a control plant when grown under comparable conditions. In one aspect, a modified plant provided herein requires a chemical spray volume between 20% and 95% less than a control plant when grown under comparable conditions. In one aspect, a modified plant provided herein requires a chemical spray volume between 30% and 95% less than a control plant when grown under comparable conditions. In one aspect, a modified plant provided herein requires a chemical spray volume between 40% and 95% less than a control plant when grown under comparable conditions. In one aspect, a modified plant provided herein requires a chemical spray volume between 50% and 95% less than a control plant when grown under comparable conditions. In one aspect, a modified plant provided herein requires a chemical spray volume between 60% and 95% less than a control plant when grown under comparable conditions. In one aspect, a modified plant provided herein requires a chemical spray volume between 70% and 95% less than a control plant when grown under comparable conditions. In one aspect, a modified plant provided herein requires a chemical spray volume between 80% and 95% less than a control plant when grown under comparable conditions. In one aspect, a modified plant provided herein requires a chemical spray volume between 90% and 95% less than a control plant when grown under comparable conditions. In one aspect, a modified plant provided herein requires a chemical spray volume between 10% and 75% less than a control plant when grown under comparable conditions. In one aspect, a modified plant provided herein requires a chemical spray volume between 10% and 50% less than a control plant when grown under comparable conditions. In one aspect, a modified plant provided herein requires a chemical spray volume between 10% and 25% less than a control plant when grown under comparable conditions. In one aspect, a modified plant provided herein requires a chemical spray volume between 25% and 50% less than a control plant when grown under comparable conditions. In one aspect, a modified plant provided herein requires a chemical spray volume between 25% and 75% less than a control plant when grown under comparable conditions. In one aspect, a modified plant provided herein requires a chemical spray volume between 50% and 75% less than a control plant when grown under comparable conditions. In one aspect, a modified plant provided herein requires a chemical spray volume between 1% and 50% less than a control plant when grown under comparable conditions. In one aspect, a modified plant provided herein requires a chemical spray volume between 1% and 25% less than a control plant when grown under comparable conditions. In one aspect, a modified plant provided herein requires a chemical spray volume between 1% and 10% less than a control plant when grown under comparable conditions.

In an aspect, reduced suckers comprises fewer total suckers, smaller average sucker size, or both, as compared to a control tobacco plant when grown under comparable conditions. In another aspect, smaller average sucker size comprises a measurement selected from the group consisting of reduced average mass, reduced average length, reduced average diameter, or any combination thereof, as compared to suckers of a control tobacco plant when grown under comparable growth conditions. In another aspect, smaller average sucker size comprises reduced average mass of suckers. In a further aspect, smaller average sucker size comprises reduced average length of suckers. In a still further aspect, smaller average sucker size comprises reduced average diameter of suckers.

In an aspect, a modified tobacco plant comprises fewer total suckers as compared to a control tobacco plant when grown under comparable conditions. In an aspect, a modified tobacco plant comprises a smaller average sucker size as compared to a control tobacco plant when grown under comparable conditions. In an aspect, a modified tobacco plant comprises a shorter average sucker length as compared to a control tobacco plant when grown under comparable conditions. In an aspect, a modified tobacco plant comprises a lower average sucker mass as compared to a control tobacco plant when grown under comparable conditions. In an aspect, a modified tobacco plant comprises a shorter average sucker diameter as compared to a control tobacco plant when grown under comparable conditions.

In an aspect, a modified tobacco plant comprises at least 1 fewer sucker as compared to a control tobacco plant when grown under comparable conditions. In an aspect, a modified tobacco plant comprises at least 2 fewer suckers as compared to a control tobacco plant when grown under comparable conditions. In an aspect, a modified tobacco plant comprises at least 3 fewer suckers as compared to a control tobacco plant when grown under comparable conditions. In an aspect, a modified tobacco plant comprises at least 4 fewer suckers as compared to a control tobacco plant when grown under comparable conditions. In an aspect, a modified tobacco plant comprises at least 5 fewer suckers as compared to a control tobacco plant when grown under comparable conditions. In an aspect, a modified tobacco plant comprises at least 7 fewer suckers as compared to a control tobacco plant when grown under comparable conditions. In an aspect, a modified tobacco plant comprises at least 10 fewer suckers as compared to a control tobacco plant when grown under comparable conditions. In an aspect, a modified tobacco plant comprises at least 15 fewer suckers as compared to a control tobacco plant when grown under comparable conditions. In an aspect, a modified tobacco plant comprises at least 20 fewer suckers as compared to a control tobacco plant when grown under comparable conditions. In an aspect, a modified tobacco plant comprises at least 25 fewer suckers as compared to a control tobacco plant when grown under comparable conditions. In an aspect, a modified tobacco plant comprises at least 30 fewer suckers as compared to a control tobacco plant when grown under comparable conditions.

In an aspect, a modified tobacco plant comprises at least 5% fewer suckers as compared to a control tobacco plant when grown under comparable conditions. In an aspect, a modified tobacco plant comprises at least 10% fewer suckers as compared to a control tobacco plant when grown under comparable conditions. In an aspect, a modified tobacco plant comprises at least 15% fewer suckers as compared to a control tobacco plant when grown under comparable conditions. In an aspect, a modified tobacco plant comprises at least 20% fewer suckers as compared to a control tobacco plant when grown under comparable conditions. In an aspect, a modified tobacco plant comprises at least 25% fewer suckers as compared to a control tobacco plant when grown under comparable conditions. In an aspect, a modified tobacco plant comprises at least 30% fewer suckers as compared to a control tobacco plant when grown under comparable conditions. In an aspect, a modified tobacco plant comprises at least 40% fewer suckers as compared to a control tobacco plant when grown under comparable conditions. In an aspect, a modified tobacco plant comprises at least 50% fewer suckers as compared to a control tobacco plant when grown under comparable conditions. In an aspect, a modified tobacco plant comprises at least 60% fewer suckers as compared to a control tobacco plant when grown under comparable conditions. In an aspect, a modified tobacco plant comprises at least 70% fewer suckers as compared to a control tobacco plant when grown under comparable conditions. In an aspect, a modified tobacco plant comprises at least 80% fewer suckers as compared to a control tobacco plant when grown under comparable conditions. In an aspect, a modified tobacco plant comprises at least 90% fewer suckers as compared to a control tobacco plant when grown under comparable conditions. In an aspect, a modified tobacco plant comprises at least 95% fewer suckers as compared to a control tobacco plant when grown under comparable conditions.

In an aspect, average sucker mass is measured using fresh sucker weight. In another aspect, average sucker mass is measured using dry sucker weight.

In an aspect, a modified tobacco plant comprises an average sucker mass at least 5% lower as compared to the average sucker mass of a control tobacco plant when grown under comparable conditions. In an aspect, a modified tobacco plant comprises an average sucker mass at least 10% lower as compared to the average sucker mass of a control tobacco plant when grown under comparable conditions. In an aspect, a modified tobacco plant comprises an average sucker mass at least 15% lower as compared to the average sucker mass of a control tobacco plant when grown under comparable conditions. In an aspect, a modified tobacco plant comprises an average sucker mass at least 20% lower as compared to the average sucker mass of a control tobacco plant when grown under comparable conditions. In an aspect, a modified tobacco plant comprises an average sucker mass at least 25% lower as compared to the average sucker mass of a control tobacco plant when grown under comparable conditions. In an aspect, a modified tobacco plant comprises an average sucker mass at least 30% lower as compared to the average sucker mass of a control tobacco plant when grown under comparable conditions. In an aspect, a modified tobacco plant comprises an average sucker mass at least 40% lower as compared to the average sucker mass of a control tobacco plant when grown under comparable conditions. In an aspect, a modified tobacco plant comprises an average sucker mass at least 50% lower as compared to the average sucker mass of a control tobacco plant when grown under comparable conditions. In an aspect, a modified tobacco plant comprises an average sucker mass at least 60% lower as compared to the average sucker mass of a control tobacco plant when grown under comparable conditions. In an aspect, a modified tobacco plant comprises an average sucker mass at least 70% lower as compared to the average sucker mass of a control tobacco plant when grown under comparable conditions. In an aspect, a modified tobacco plant comprises an average sucker mass at least 80% lower as compared to the average sucker mass of a control tobacco plant when grown under comparable conditions. In an aspect, a modified tobacco plant comprises an average sucker mass at least 90% lower as compared to the average sucker mass of a control tobacco plant when grown under comparable conditions. In an aspect, a modified tobacco plant comprises an average sucker mass at least 95% lower as compared to the average sucker mass of a control tobacco plant when grown under comparable conditions.

In an aspect, average sucker length is measured from the base of the sucker where it joins the main tobacco stem to the distal tip of the sucker stem.

In an aspect, a modified tobacco plant comprises an average sucker length at least 1 centimeter shorter as compared to the average sucker length of a control tobacco plant when grown under comparable conditions. In an aspect, a modified tobacco plant comprises an average sucker length at least 2 centimeters shorter as compared to the average sucker length of a control tobacco plant when grown under comparable conditions. In an aspect, a modified tobacco plant comprises an average sucker length at least 3 centimeters shorter as compared to the average sucker length of a control tobacco plant when grown under comparable conditions. In an aspect, a modified tobacco plant comprises an average sucker length at least 4 centimeters shorter as compared to the average sucker length of a control tobacco plant when grown under comparable conditions. In an aspect, a modified tobacco plant comprises an average sucker length at least 5 centimeters shorter as compared to the average sucker length of a control tobacco plant when grown under comparable conditions. In an aspect, a modified tobacco plant comprises an average sucker length at least 10 centimeters shorter as compared to the average sucker length of a control tobacco plant when grown under comparable conditions. In an aspect, a modified tobacco plant comprises an average sucker length at least 15 centimeters shorter as compared to the average sucker length of a control tobacco plant when grown under comparable conditions. In an aspect, a modified tobacco plant comprises an average sucker length at least 20 centimeters shorter as compared to the average sucker length of a control tobacco plant when grown under comparable conditions.

In an aspect, a modified tobacco plant comprises an average sucker length between 0.5 centimeters and 30 centimeters shorter as compared to the average sucker length of a control tobacco plant when grown under comparable conditions. In an aspect, a modified tobacco plant comprises an average sucker length between 0.5 centimeters and 25 centimeters shorter as compared to the average sucker length of a control tobacco plant when grown under comparable conditions. In an aspect, a modified tobacco plant comprises an average sucker length between 0.5 centimeters and 20 centimeters shorter as compared to the average sucker length of a control tobacco plant when grown under comparable conditions. In an aspect, a modified tobacco plant comprises an average sucker length between 0.5 centimeters and 15 centimeters shorter as compared to the average sucker length of a control tobacco plant when grown under comparable conditions. In an aspect, a modified tobacco plant comprises an average sucker length between 0.5 centimeters and 10 centimeters shorter as compared to the average sucker length of a control tobacco plant when grown under comparable conditions. In an aspect, a modified tobacco plant comprises an average sucker length between 0.5 centimeters and 5 centimeters shorter as compared to the average sucker length of a control tobacco plant when grown under comparable conditions. In an aspect, a modified tobacco plant comprises an average sucker length between 1 centimeter and 30 centimeters shorter as compared to the average sucker length of a control tobacco plant when grown under comparable conditions. In an aspect, a modified tobacco plant comprises an average sucker length between 1 centimeter and 20 centimeters shorter as compared to the average sucker length of a control tobacco plant when grown under comparable conditions. In an aspect, a modified tobacco plant comprises an average sucker length between 1 centimeter and 10 centimeters shorter as compared to the average sucker length of a control tobacco plant when grown under comparable conditions.

In an aspect, a modified tobacco plant comprises an average sucker length at least 5% shorter as compared to the average sucker length of a control tobacco plant when grown under comparable conditions. In an aspect, a modified tobacco plant comprises an average sucker length at least 10% shorter as compared to the average sucker length of a control tobacco plant when grown under comparable conditions. In an aspect, a modified tobacco plant comprises an average sucker length at least 15% shorter as compared to the average sucker length of a control tobacco plant when grown under comparable conditions. In an aspect, a modified tobacco plant comprises an average sucker length at least 20% shorter as compared to the average sucker length of a control tobacco plant when grown under comparable conditions. In an aspect, a modified tobacco plant comprises an average sucker length at least 25% shorter as compared to the average sucker length of a control tobacco plant when grown under comparable conditions. In an aspect, a modified tobacco plant comprises an average sucker length at least 30% shorter as compared to the average sucker length of a control tobacco plant when grown under comparable conditions. In an aspect, a modified tobacco plant comprises an average sucker length at least 40% shorter as compared to the average sucker length of a control tobacco plant when grown under comparable conditions. In an aspect, a modified tobacco plant comprises an average sucker length at least 50% shorter as compared to the average sucker length of a control tobacco plant when grown under comparable conditions. In an aspect, a modified tobacco plant comprises an average sucker length at least 60% shorter as compared to the average sucker length of a control tobacco plant when grown under comparable conditions. In an aspect, a modified tobacco plant comprises an average sucker length at least 70% shorter as compared to the average sucker length of a control tobacco plant when grown under comparable conditions. In an aspect, a modified tobacco plant comprises an average sucker length at least 80% shorter as compared to the average sucker length of a control tobacco plant when grown under comparable conditions. In an aspect, a modified tobacco plant comprises an average sucker length at least 90% shorter as compared to the average sucker length of a control tobacco plant when grown under comparable conditions. In an aspect, a modified tobacco plant comprises an average sucker length at least 95% shorter as compared to the average sucker length of a control tobacco plant when grown under comparable conditions.

In an aspect, sucker diameter is measured at the base of the sucker where it adjoins the main stem of the plant.

In an aspect, a modified tobacco plant comprises an average sucker diameter at least 5% shorter as compared to the average sucker diameter of a control tobacco plant when grown under comparable conditions. In an aspect, a modified tobacco plant comprises an average sucker diameter at least 10% shorter as compared to the average sucker diameter of a control tobacco plant when grown under comparable conditions. In an aspect, a modified tobacco plant comprises an average sucker diameter at least 15% shorter as compared to the average sucker diameter of a control tobacco plant when grown under comparable conditions. In an aspect, a modified tobacco plant comprises an average sucker diameter at least 20% shorter as compared to the average sucker diameter of a control tobacco plant when grown under comparable conditions. In an aspect, a modified tobacco plant comprises an average sucker diameter at least 25% shorter as compared to the average sucker diameter of a control tobacco plant when grown under comparable conditions. In an aspect, a modified tobacco plant comprises an average sucker diameter at least 30% shorter as compared to the average sucker diameter of a control tobacco plant when grown under comparable conditions. In an aspect, a modified tobacco plant comprises an average sucker diameter at least 40% shorter as compared to the average sucker diameter of a control tobacco plant when grown under comparable conditions. In an aspect, a modified tobacco plant comprises an average sucker diameter at least 50% shorter as compared to the average sucker diameter of a control tobacco plant when grown under comparable conditions. In an aspect, a modified tobacco plant comprises an average sucker diameter at least 60% shorter as compared to the average sucker diameter of a control tobacco plant when grown under comparable conditions. In an aspect, a modified tobacco plant comprises an average sucker diameter at least 70% shorter as compared to the average sucker diameter of a control tobacco plant when grown under comparable conditions. In an aspect, a modified tobacco plant comprises an average sucker diameter at least 80% shorter as compared to the average sucker diameter of a control tobacco plant when grown under comparable conditions. In an aspect, a modified tobacco plant comprises an average sucker diameter at least 90% shorter as compared to the average sucker diameter of a control tobacco plant when grown under comparable conditions. In an aspect, a modified tobacco plant comprises an average sucker diameter at least 95% shorter as compared to the average sucker diameter of a control tobacco plant when grown under comparable conditions.

In an aspect, a modified tobacco plant comprises an average sucker diameter at least 1 millimeter shorter as compared to the average sucker diameter of a control tobacco plant when grown under comparable conditions. In an aspect, a modified tobacco plant comprises an average sucker diameter at least 2 millimeters shorter as compared to the average sucker diameter of a control tobacco plant when grown under comparable conditions. In an aspect, a modified tobacco plant comprises an average sucker diameter at least 3 millimeters shorter as compared to the average sucker diameter of a control tobacco plant when grown under comparable conditions. In an aspect, a modified tobacco plant comprises an average sucker diameter at least 4 millimeters shorter as compared to the average sucker diameter of a control tobacco plant when grown under comparable conditions. In an aspect, a modified tobacco plant comprises an average sucker diameter at least 5 millimeters shorter as compared to the average sucker diameter of a control tobacco plant when grown under comparable conditions. In an aspect, a modified tobacco plant comprises an average sucker diameter at least 6 millimeters shorter as compared to the average sucker diameter of a control tobacco plant when grown under comparable conditions. In an aspect, a modified tobacco plant comprises an average sucker diameter at least 7 millimeters shorter as compared to the average sucker diameter of a control tobacco plant when grown under comparable conditions. In an aspect, a modified tobacco plant comprises an average sucker diameter at least 8 millimeters shorter as compared to the average sucker diameter of a control tobacco plant when grown under comparable conditions. In an aspect, a modified tobacco plant comprises an average sucker diameter at least 9 millimeters shorter as compared to the average sucker diameter of a control tobacco plant when grown under comparable conditions. In an aspect, a modified tobacco plant comprises an average sucker diameter at least 1 centimeter shorter as compared to the average sucker diameter of a control tobacco plant when grown under comparable conditions. In an aspect, a modified tobacco plant comprises an average sucker diameter at least 1.5 centimeters shorter as compared to the average sucker diameter of a control tobacco plant when grown under comparable conditions. In an aspect, a modified tobacco plant comprises an average sucker diameter at least 2 centimeters shorter as compared to the average sucker diameter of a control tobacco plant when grown under comparable conditions. In an aspect, a modified tobacco plant comprises an average sucker diameter at least 3 centimeters shorter as compared to the average sucker diameter of a control tobacco plant when grown under comparable conditions. In an aspect, a modified tobacco plant comprises an average sucker diameter at least 4 centimeters shorter as compared to the average sucker diameter of a control tobacco plant when grown under comparable conditions. In an aspect, a modified tobacco plant comprises an average sucker diameter at least 5 centimeters shorter as compared to the average sucker diameter of a control tobacco plant when grown under comparable conditions.

Any nucleic acid molecule, protein, or polypeptide provided herein is envisioned for use with any method provided herein. Any nucleic acid molecule, protein, or polypeptide provided herein is envisioned for use with any plant, plant part, cell, or seed provided herein. Any nucleic acid molecule, protein, or polypeptide provided herein is envisioned for use with any tobacco plant, tobacco plant part, tobacco cell, or tobacco seed provided herein.

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded. A nucleic acid molecule can encode a polypeptide or a small RNA.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

In an aspect, an endogenous gene provided herein comprises a polynucleotide sequence at least 80% identical to a sequence selected from the group consisting of SEQ ID NOs: 1-44 and 113. In an aspect, an endogenous gene provided herein comprises a polynucleotide sequence at least 85% identical to a sequence selected from the group consisting of SEQ ID NOs: 1-44 and 113. In an aspect, an endogenous gene provided herein comprises a polynucleotide sequence at least 90% identical to a sequence selected from the group consisting of SEQ ID NOs: 1-44 and 113. In an aspect, an endogenous gene provided herein comprises a polynucleotide sequence at least 95% identical to a sequence selected from the group consisting of SEQ ID NOs: 1-44 and 113. In an aspect, an endogenous gene provided herein comprises a polynucleotide sequence at least 96% identical to a sequence selected from the group consisting of SEQ ID NOs: 1-44 and 113. In an aspect, an endogenous gene provided herein comprises a polynucleotide sequence at least 97% identical to a sequence selected from the group consisting of SEQ ID NOs: 1-44 and 113. In an aspect, an endogenous gene provided herein comprises a polynucleotide sequence at least 98% identical to a sequence selected from the group consisting of SEQ ID NOs: 1-44 and 113. In an aspect, an endogenous gene provided herein comprises a polynucleotide sequence at least 99% identical to a sequence selected from the group consisting of SEQ ID NOs: 1-44 and 113. In an aspect, an endogenous gene provided herein comprises a polynucleotide sequence 100% identical to a sequence selected from the group consisting of SEQ ID NOs: 1-44 and 113.

As used herein, the term "polypeptide" refers to a chain of at least two covalently linked amino acids. Polypeptides can be encoded by polynucleotides provided herein. Proteins provided herein can be encoded by nucleic acid molecules provided herein. Proteins can comprise polypeptides provided herein. As used herein, a "protein" refers to a chain of amino acid residues that is capable of providing structure or enzymatic activity to a cell.

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

In an aspect, an endogenous gene provided herein encodes a polypeptide comprising an amino acid sequence at least 70% identical or similar to an amino acid sequence selected from the group consisting of SEQ ID NOs: 45-88 and 114. In an aspect, an endogenous gene provided herein encodes a polypeptide comprising an amino acid sequence at least 75% identical or similar to an amino acid sequence selected from the group consisting of SEQ ID NOs: 45-88 and 114. In an aspect, an endogenous gene provided herein encodes a polypeptide comprising an amino acid sequence at least 80% identical or similar to an amino acid sequence selected from the group consisting of SEQ ID NOs: 45-88 and 114. In an aspect, an endogenous gene provided herein encodes a polypeptide comprising an amino acid sequence at least 85% identical or similar to an amino acid sequence selected from the group consisting of SEQ ID NOs: 45-88 and 114. In an aspect, an endogenous gene provided herein encodes a polypeptide comprising an amino acid sequence at least 90% identical or similar to an amino acid sequence selected from the group consisting of SEQ ID NOs: 45-88 and 114. In an aspect, an endogenous gene provided herein encodes a polypeptide comprising an amino acid sequence at least 95% identical or similar to an amino acid sequence selected from the group consisting of SEQ ID NOs: 45-88 and 114. In an aspect, an endogenous gene provided herein encodes a polypeptide comprising an amino acid sequence at least 96% identical or similar to an amino acid sequence selected from the group consisting of SEQ ID NOs: 45-88 and 114. In an aspect, an endogenous gene provided herein encodes a polypeptide comprising an amino acid sequence at least 97% identical or similar to an amino acid sequence selected from the group consisting of SEQ ID NOs: 45-88 and 114. In an aspect, an endogenous gene provided herein encodes a polypeptide comprising an amino acid sequence at least 98% identical or similar to an amino acid sequence selected from the group consisting of SEQ ID NOs: 45-88 and 114. In an aspect, an endogenous gene provided herein encodes a polypeptide comprising an amino acid sequence at least 99% identical or similar to an amino acid sequence selected from the group consisting of SEQ ID NOs: 45-88 and 114. In an aspect, an endogenous gene provided herein encodes a polypeptide comprising an amino acid sequence 100% identical or similar to an amino acid sequence selected from the group consisting of SEQ ID NOs: 45-88 and 114.

The terms "percent identity" or "percent identical" as used herein in reference to two or more nucleotide or amino acid sequences is calculated by (i) comparing two optimally aligned sequences (nucleotide or amino acid) over a window of comparison (the "alignable" region or regions), (ii) determining the number of positions at which the identical nucleic acid base (for nucleotide sequences) or amino acid residue (for proteins and polypeptides) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

When percentage of sequence identity is used in reference to amino acids it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST™), etc., that can be used to compare the sequence identity or similarity between two or more nucleotide or amino acid sequences. Although other alignment and comparison methods are known in the art, the alignment and percent identity between two sequences (including the percent identity ranges described above) can be as determined by the ClustalW algorithm, see, e.g., Chenna et al., "Multiple sequence alignment with the Clustal series of programs," *Nucleic Acids Research* 31:3497-3500 (2003); Thompson et al., "Clustal W: Improving the sensitivity of progressive multiple sequence alignment through sequence weighting, position-specific gap penalties and weight matrix choice," *Nucleic Acids Research* 22:4673-4680 (1994); Larkin M A et al., "Clustal W and Clustal X version 2.0," *Bioinformatics* 23:2947-48 (2007); and Altschul et al. "Basic local alignment search tool." *J. Mol. Biol.* 215:403-410 (1990), the entire contents and disclosures of which are incorporated herein by reference.

The terms "percent complementarity" or "percent complementary" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

In one aspect, this disclosure provides a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to the control tobacco plant when grown under comparable growth conditions.

In another aspect, this disclosure provides a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety.

In a further aspect, this disclosure provides a method for producing a modified tobacco plant comprising: (a) inducing a mutation in at least one tobacco cell at a genomic locus encoding a polypeptide selected from the group consisting of a cyclin, a cyclin-dependent kinase (CDK), a CDK inhibitor, a MYB, and a WRKY transcription factor; (b) selecting at least one tobacco cell comprising the mutation from step (a); and (c) regenerating a modified tobacco plant from the at least one tobacco cell selected in step (b), where the modified tobacco plant comprises no suckers or reduced suckers after topping as compared to a control tobacco plant lacking the mutation when grown under comparable growth conditions. In an aspect, this method further comprises (d) growing the modified tobacco plant regenerated in step (c). In another aspect, this method further comprises (e) crossing the modified tobacco plant grown in step (d) with a second tobacco plant; and (f) obtaining at least one seed from the crossing in step (e).

In an aspect, a modified tobacco plant, tobacco plant part, tobacco seed, tobacco cell, or tobacco genome provided herein comprises one or more mutations in an endogenous gene encoding a cyclin. In an aspect, a modified tobacco plant, tobacco plant part, tobacco seed, tobacco cell, or tobacco genome provided herein comprises one or more mutations in an endogenous gene encoding a cyclin-dependent kinase. In an aspect, a modified tobacco plant, tobacco plant part, tobacco seed, tobacco cell, or tobacco genome provided herein comprises one or more mutations in an endogenous gene encoding a cyclin-dependent kinase inhibitor. In an aspect, a modified tobacco plant, tobacco plant part, tobacco seed, tobacco cell, or tobacco genome provided herein comprises one or more mutations in an endogenous gene encoding a MYB. In an aspect, a modified tobacco plant, tobacco plant part, tobacco seed, tobacco cell, or tobacco genome provided herein comprises one or more mutations in an endogenous gene encoding a WRKY transcription factor.

Cyclins control the progression of cells through the cell cycle. They often play a role in the activation of CDKs. Cyclins are characterized as having a conserved cyclin box domain. Cyclin box domains typically comprise about 150 amino acids, which are organized into five alpha-helical regions. Cyclin box domains are important for binding other proteins, such as CDKs. See, for example, Noble et al., "The cyclin box fold: protein recognition in cell-cycle and transcription control," *Trends Biochem. Sci.* 22:482-487 (1997);

and Menges et al., "Genomic Organization and Evolutionary Conservation of Plant D-Type Cyclins," *Plant Physiology*, 145:1558-1576 (2007), which are incorporated herein by reference in their entireties.

$G_1$ (Gap 1 phase) is the first part of interphase during the cell cycle in eukaryotic cells. Cells synthesize mRNA and proteins during $G_1$ phase, which ends with the transition into S phase. S phase (Synthesis phase) is the second part of interphase during the cell cycle, in which DNA is replicated. S phase ends with the transition into $G_2$ phase. $G_2$ (Gap 2 phase) typically involves rapid cellular growth as the cell prepares for transition to M phase (Mitosis phase). Cyclins and CDKs are important regulators at the checkpoints between the transition from $G_1$ to S phase and from $G_2$ to M phase, as well as during $G_1$ phase, S phase, $G_2$ phase, and M phase.

There are two main groups of cyclins: $G_1$/S cyclins, which are required for control of the cell cycle through the $G_1$/S transition, and $G_2$/M cyclins, which are required for control of the cell cycle through the $G_2$/M transition. If the required cyclins or CDKs are unable to function correctly, the cell cycle can arrest at the $G_1$/S transition or the $G_2$/M transition and prevent the formation of daughter cells. In an aspect, a cyclin provided herein is a $G_1$/S cyclin. In another aspect, a cyclin provided herein is a $G_2$/M cyclin.

In an aspect, this disclosure provides a polynucleotide that encodes a cyclin. In another aspect, this disclosure provides a cyclin.

In an aspect, this disclosure provides a mutated polynucleotide comprising a mutation in an endogenous gene, where the mutated polynucleotide encodes a mutated cyclin as compared to a cyclin encoded by the endogenous gene lacking the mutation. In an aspect, this disclosure provides a mutated polynucleotide comprising a mutation in an endogenous gene, where the mutated polynucleotide encodes a truncated cyclin as compared to a cyclin encoded by the endogenous gene lacking the mutation. In another aspect, this disclosure provides a non-naturally occurring truncated cyclin. In an aspect, this disclosure provides a polynucleotide encoding a mutated mRNA of an endogenous gene comprising a premature stop codon, where the mutated mRNA encodes a truncated cyclin as compared to an mRNA of the endogenous gene lacking the premature stop codon.

In an aspect, this disclosure provides a polynucleotide comprising a non-naturally occurring mutation in a sequence encoding a cyclin box domain. In an aspect, this disclosure provides a mutated polynucleotide comprising a mutation in an endogenous gene encoding a cyclin, where the mutated polynucleotide encodes a cyclin lacking a cyclin box domain. In another aspect, this disclosure provides a mutated polynucleotide comprising a mutation in an endogenous gene encoding a cyclin, where the mutated polynucleotide encodes a cyclin comprising a truncated cyclin box domain as compared to a cyclin encoded by the endogenous gene lacking the mutation. In an aspect, this disclosure provides a mutated polynucleotide comprising a mutation in an endogenous gene encoding a cyclin, where the mutated polynucleotide encodes a cyclin that is incapable of binding a CDK. In an aspect, this disclosure provides a mutated polynucleotide comprising a mutation in an endogenous gene encoding a cyclin, where the mutated polynucleotide encodes a cyclin that exhibits reduced binding affinity for at least one CDK as compared to a cyclin encoded by the endogenous gene lacking the mutation.

In an aspect, a mutated polynucleotide encodes a dominant negative allele of a cyclin. In another aspect, a mutated polynucleotide encodes a dominant positive allele of a cyclin. In a further aspect, a mutated polynucleotide encodes a constitutively active cyclin. In another aspect, a mutated polynucleotide encodes an inactive cyclin.

In an aspect, an endogenous gene encoding a cyclin comprises a polynucleotide sequence at least 80% identical to a sequence selected from the group consisting of SEQ ID NOs: 6-32. In an aspect, an endogenous gene encoding a cyclin comprises a polynucleotide sequence at least 85% identical to a sequence selected from the group consisting of SEQ ID NOs: 6-32. In an aspect, an endogenous gene encoding a cyclin comprises a polynucleotide sequence at least 90% identical to a sequence selected from the group consisting of SEQ ID NOs: 6-32. In an aspect, an endogenous gene encoding a cyclin comprises a polynucleotide sequence at least 95% identical to a sequence selected from the group consisting of SEQ ID NOs: 6-32. In an aspect, an endogenous gene encoding a cyclin comprises a polynucleotide sequence at least 96% identical to a sequence selected from the group consisting of SEQ ID NOs: 6-32. In an aspect, an endogenous gene encoding a cyclin comprises a polynucleotide sequence at least 97% identical to a sequence selected from the group consisting of SEQ ID NOs: 6-32. In an aspect, an endogenous gene encoding a cyclin comprises a polynucleotide sequence at least 98% identical to a sequence selected from the group consisting of SEQ ID NOs: 6-32. In an aspect, an endogenous gene encoding a cyclin comprises a polynucleotide sequence at least 99% identical to a sequence selected from the group consisting of SEQ ID NOs: 6-32. In an aspect, an endogenous gene encoding a cyclin comprises a polynucleotide sequence 100% identical to a sequence selected from the group consisting of SEQ ID NOs: 6-32.

In an aspect, an endogenous cyclin comprises an amino acid sequence at least 70% identical to a sequence selected from the group consisting of SEQ ID NOs: 50-76. In an aspect, an endogenous cyclin comprises an amino acid sequence at least 75% identical to a sequence selected from the group consisting of SEQ ID NOs: 50-76. In an aspect, an endogenous cyclin comprises an amino acid sequence at least 80% identical to a sequence selected from the group consisting of SEQ ID NOs: 50-76. In an aspect, an endogenous cyclin comprises an amino acid sequence at least 85% identical to a sequence selected from the group consisting of SEQ ID NOs: 50-76. In an aspect, an endogenous cyclin comprises an amino acid sequence at least 90% identical to a sequence selected from the group consisting of SEQ ID NOs: 50-76. In an aspect, an endogenous cyclin comprises an amino acid sequence at least 95% identical to a sequence selected from the group consisting of SEQ ID NOs: 50-76. In an aspect, an endogenous cyclin comprises an amino acid sequence at least 96% identical to a sequence selected from the group consisting of SEQ ID NOs: 50-76. In an aspect, an endogenous cyclin comprises an amino acid sequence at least 97% identical to a sequence selected from the group consisting of SEQ ID NOs: 50-76. In an aspect, an endogenous cyclin comprises an amino acid sequence at least 98% identical to a sequence selected from the group consisting of SEQ ID NOs: 50-76. In an aspect, an endogenous cyclin comprises an amino acid sequence at least 99% identical to a sequence selected from the group consisting of SEQ ID NOs: 50-76. In an aspect, a cyclin comprises an amino acid sequence 100% identical to a sequence selected from the group consisting of SEQ ID NOs: 50-76.

In an aspect, an endogenous cyclin comprises an amino acid sequence at least 70% similar to a sequence selected from the group consisting of SEQ ID NOs: 50-76. In an aspect, an endogenous cyclin comprises an amino acid sequence at least 75% similar to a sequence selected from the group consisting of SEQ ID NOs: 50-76. In an aspect, an endogenous cyclin comprises an amino acid sequence at least 80% similar to a sequence selected from the group consisting of SEQ ID NOs: 50-76. In an aspect, an endogenous cyclin comprises an amino acid sequence at least 85% similar to a sequence selected from the group consisting of SEQ ID NOs: 50-76. In an aspect, an endogenous cyclin comprises an amino acid sequence at least 90% similar to a sequence selected from the group consisting of SEQ ID NOs: 50-76. In an aspect, an endogenous cyclin comprises an amino acid sequence at least 95% similar to a sequence selected from the group consisting of SEQ ID NOs: 50-76. In an aspect, an endogenous cyclin comprises an amino acid sequence at least 96% similar to a sequence selected from the group consisting of SEQ ID NOs: 50-76. In an aspect, an endogenous cyclin comprises an amino acid sequence at least 97% similar to a sequence selected from the group consisting of SEQ ID NOs: 50-76. In an aspect, an endogenous cyclin comprises an amino acid sequence at least 98% similar to a sequence selected from the group consisting of SEQ ID NOs: 50-76. In an aspect, an endogenous cyclin comprises an amino acid sequence at least 99% similar to a sequence selected from the group consisting of SEQ ID NOs: 50-76. In an aspect, a cyclin comprises an amino acid sequence 100% similar to a sequence selected from the group consisting of SEQ ID NOs: 50-76.

Cyclin dependent kinases (CDKs) are a family of protein kinases that are involved in regulating the cell cycle, regulating transcription, and regulating mRNA processing. CDKs are recognized as belonging to the Enzyme Commission class 2.7.11.22. CDKs comprise a kinase domain, and they interact with, or bind to, cyclins. CDKs phosphorylate substrates on serine and threonine, so they can also be referred to as serine-threonine kinases. CDKs, in conjunction with cyclins, are required for cells to progress through the cell cycle. See, for example, Mironov et al., "Cyclin-Dependent Kinases and Cell Division in Plants—The Nexus," Plant Cell, 11:509-521 (1999), which is herein incorporated by reference in its entirety.

In an aspect, this disclosure provides a polynucleotide that encodes a CDK. In another aspect, this disclosure provides a CDK.

In an aspect, this disclosure provides a mutated polynucleotide comprising a mutation in an endogenous gene, where the mutated polynucleotide encodes a mutated CDK as compared to a CDK encoded by the endogenous gene lacking the mutation. In an aspect, this disclosure provides a mutated polynucleotide comprising a mutation in an endogenous gene, where the mutated polynucleotide encodes a truncated CDK as compared to a CDK encoded by the endogenous gene lacking the mutation. In another aspect, this disclosure provides a non-naturally occurring truncated CDK. In an aspect, this disclosure provides a polynucleotide encoding a mutated mRNA of an endogenous gene comprising a premature stop codon, where the mutated mRNA encodes a truncated CDK as compared to an mRNA of the endogenous gene lacking the premature stop codon.

In an aspect, this disclosure provides a polynucleotide comprising a non-naturally occurring mutation in a sequence encoding a kinase domain. In an aspect, this disclosure provides a mutated polynucleotide comprising a mutation in an endogenous gene encoding a CDK, where the mutated polynucleotide encodes a CDK lacking a kinase domain. In another aspect, this disclosure provides a mutated poly-nucleotide comprising a mutation in an endogenous gene encoding a CDK, where the mutated polynucleotide encodes a CDK comprising a truncated kinase domain as compared to a CDK encoded by the endogenous gene lacking the mutation. In an aspect, this disclosure provides a mutated polynucleotide comprising a mutation in an endogenous gene encoding a CDK, where the mutated polynucleotide encodes a CDK that is incapable of binding a cyclin. In an aspect, this disclosure provides a mutated polynucleotide comprising a mutation in an endogenous gene encoding a CDK that exhibits reduced binding affinity for at least one cyclin as compared to a CDK encoded by the endogenous gene lacking the mutation.

In an aspect, a mutated polynucleotide encodes a dominant negative allele of a CDK. In another aspect, a mutated polynucleotide encodes a dominant positive allele of a CDK. In a further aspect, a mutated polynucleotide encodes a constitutively active CDK. In another aspect, a mutated polynucleotide encodes an inactive CDK.

In an aspect, an endogenous gene encoding a CDK comprises a polynucleotide sequence at least 80% identical to a sequence selected from the group consisting of SEQ ID NOs: 1-4. In an aspect, an endogenous gene encoding a CDK comprises a polynucleotide sequence at least 85% identical to a sequence selected from the group consisting of SEQ ID NOs: 1-4. In an aspect, an endogenous gene encoding a CDK comprises a polynucleotide sequence at least 90% identical to a sequence selected from the group consisting of SEQ ID NOs: 1-4. In an aspect, an endogenous gene encoding a CDK comprises a polynucleotide sequence at least 95% identical to a sequence selected from the group consisting of SEQ ID NOs: 1-4. In an aspect, an endogenous gene encoding a CDK comprises a polynucleotide sequence at least 96% identical to a sequence selected from the group consisting of SEQ ID NOs: 1-4. In an aspect, an endogenous gene encoding a CDK comprises a polynucleotide sequence at least 97% identical to a sequence selected from the group consisting of SEQ ID NOs: 1-4. In an aspect, an endogenous gene encoding a CDK comprises a polynucleotide sequence at least 98% identical to a sequence selected from the group consisting of SEQ ID NOs: 1-4. In an aspect, an endogenous gene encoding a CDK comprises a polynucleotide sequence at least 99% identical to a sequence selected from the group consisting of SEQ ID NOs: 1-4. In an aspect, an endogenous gene encoding a CDK comprises a polynucleotide sequence 100% identical to a sequence selected from the group consisting of SEQ ID NOs: 1-4.

In an aspect, an endogenous CDK comprises an amino acid sequence at least 70% identical to a sequence selected from the group consisting of SEQ ID NOs: 45-48. In an aspect, an endogenous CDK comprises an amino acid sequence at least 75% identical to a sequence selected from the group consisting of SEQ ID NOs: 45-48. In an aspect, an endogenous CDK comprises an amino acid sequence at least 80% identical to a sequence selected from the group consisting of SEQ ID NOs: 45-48. In an aspect, an endogenous CDK comprises an amino acid sequence at least 85% identical to a sequence selected from the group consisting of SEQ ID NOs: 45-48. In an aspect, an endogenous CDK comprises an amino acid sequence at least 90% identical to a sequence selected from the group consisting of SEQ ID NOs: 45-48. In an aspect, an endogenous CDK comprises an amino acid sequence at least 95% identical to a sequence selected from the group consisting of SEQ ID NOs: 45-48. In an aspect, an endogenous CDK comprises an amino acid sequence at least 96% identical to a sequence selected from the group consisting of SEQ ID NOs: 45-48. In an aspect, an endogenous CDK comprises an amino acid sequence at least 97% identical to a sequence selected from the group consisting of SEQ ID NOs: 45-48. In an aspect, an endogenous CDK comprises an amino acid sequence at least 98% identical to a sequence selected from the group consisting of SEQ ID NOs: 45-48. In an aspect, an endogenous CDK comprises an amino acid sequence at least 99% identical to a sequence selected from the group consisting of SEQ ID NOs: 45-48. In an aspect, a CDK comprises an amino acid sequence 100% identical to a sequence selected from the group consisting of SEQ ID NOs: 45-48.

In an aspect, an endogenous CDK comprises an amino acid sequence at least 70% similar to a sequence selected from the group consisting of SEQ ID NOs: 45-48. In an aspect, an endogenous CDK comprises an amino acid sequence at least 75% similar to a sequence selected from the group consisting of SEQ ID NOs: 45-48. In an aspect, an endogenous CDK comprises an amino acid sequence at least 80% similar to a sequence selected from the group consisting of SEQ ID NOs: 45-48. In an aspect, an endogenous CDK comprises an amino acid sequence at least 85% similar to a sequence selected from the group consisting of SEQ ID NOs: 45-48. In an aspect, an endogenous CDK comprises an amino acid sequence at least 90% similar to a sequence selected from the group consisting of SEQ ID NOs: 45-48. In an aspect, an endogenous CDK comprises an amino acid sequence at least 95% similar to a sequence selected from the group consisting of SEQ ID NOs: 45-48. In an aspect, an endogenous CDK comprises an amino acid sequence at least 96% similar to a sequence selected from the group consisting of SEQ ID NOs: 45-48. In an aspect, an endogenous CDK comprises an amino acid sequence at least 97% similar to a sequence selected from the group consisting of SEQ ID NOs: 45-48. In an aspect, an endogenous CDK comprises an amino acid sequence at least 98% similar to a sequence selected from the group consisting of SEQ ID NOs: 45-48. In an aspect, an endogenous CDK comprises an amino acid sequence at least 99% similar to a sequence selected from the group consisting of SEQ ID NOs: 45-48. In an aspect, a CDK comprises an amino acid sequence 100% similar to a sequence selected from the group consisting of SEQ ID NOs: 45-48.

Cyclin-dependent kinase inhibitors (CDKIs) are proteins that inhibit CDKs. CDKIs can bind to CDKs to prevent CDKs from binding to cyclins, thereby negatively regulating the cell cycle in eukaryotes. In plants, CDKIs are categorized into two families: KIP-RELATED PROTEINS (KRPs) and SIAMESE-RELATED PROTEINS (SMRs). See, for example, Kumar and Larkin, "Why do plants need so many cyclin-dependent kinase inhibitors?," *Plant Signaling & Behavior,* 12: e1282021 (2017), which is herein incorporated by reference in its entirety.

In an aspect, this disclosure provides a polynucleotide that encodes a CDKI. In another aspect, this disclosure provides a CDKI. In an aspect, a CDKI provided herein is a KRP. In another aspect, a CDKI provided herein is an SMR.

In an aspect, this disclosure provides a mutated polynucleotide comprising a mutation in an endogenous gene, where the mutated polynucleotide encodes a mutated CDKI as compared to a CDKI encoded by the endogenous gene lacking the mutation. In an aspect, this disclosure provides a mutated polynucleotide comprising a mutation in an endogenous gene, where the mutated polynucleotide encodes a truncated CDKI as compared to a CDKI encoded by the endogenous gene lacking the mutation. In another aspect, this disclosure provides a non-naturally occurring truncated CDKI. In an aspect, this disclosure provides a polynucleotide encoding a mutated mRNA of an endogenous gene comprising a premature stop codon, where the mutated mRNA encodes a truncated CDKI as compared to an mRNA of the endogenous gene lacking the premature stop codon.

In an aspect, this disclosure provides a mutated polynucleotide comprising a mutation in an endogenous gene encoding a CDKI, where the mutated polynucleotide encodes a CDKI that is incapable of binding a CDK. In an aspect, this disclosure provides a mutated polynucleotide comprising a mutation in an endogenous gene encoding a CDKI, where the mutated polynucleotide encodes a CDKI that exhibits reduced binding affinity for at least one CDK as compared to a CDKI encoded by the endogenous gene lacking the mutation.

In an aspect, a mutated polynucleotide encodes a dominant negative allele of a CDKI. In another aspect, a mutated polynucleotide encodes a dominant positive allele of a CDKI. In a further aspect, a mutated polynucleotide encodes a constitutively active CDKI. In another aspect, a mutated polynucleotide encodes an inactive CDKI.

In an aspect, an endogenous gene encoding a CDKI comprises a polynucleotide sequence at least 80% identical to SEQ ID NO: 5. In an aspect, an endogenous gene encoding a CDKI comprises a polynucleotide sequence at least 85% identical to SEQ ID NO: 5. In an aspect, an endogenous gene encoding a CDKI comprises a polynucleotide sequence at least 90% identical to SEQ ID NO: 5. In an aspect, an endogenous gene encoding a CDKI comprises a polynucleotide sequence at least 95% identical to SEQ ID NO: 5. In an aspect, an endogenous gene encoding a CDKI comprises a polynucleotide sequence at least 96% identical to SEQ ID NO: 5. In an aspect, an endogenous gene encoding a CDKI comprises a polynucleotide sequence at least 97% identical to SEQ ID NO: 5. In an aspect, an endogenous gene encoding a CDKI comprises a polynucleotide sequence at least 98% identical to SEQ ID NO: 5. In an aspect, an endogenous gene encoding a CDKI comprises a polynucleotide sequence at least 99% identical to SEQ ID NO: 5. In an aspect, an endogenous gene encoding a CDKI comprises a polynucleotide sequence 100% identical to SEQ ID NO: 5.

In an aspect, an endogenous CDKI comprises an amino acid sequence at least 70% identical to SEQ ID NO: 49. In an aspect, an endogenous CDKI comprises an amino acid sequence at least 75% identical to SEQ ID NO: 49. In an aspect, an endogenous CDKI comprises an amino acid sequence at least 80% identical to SEQ ID NO: 49. In an aspect, an endogenous CDKI comprises an amino acid sequence at least 85% identical to SEQ ID NO: 49. In an aspect, an endogenous CDKI comprises an amino acid sequence at least 90% identical to SEQ ID NO: 49. In an aspect, an endogenous CDKI comprises an amino acid sequence at least 95% identical to SEQ ID NO: 49. In an aspect, an endogenous CDKI comprises an amino acid sequence at least 96% identical to SEQ ID NO: 49. In an aspect, an endogenous CDKI comprises an amino acid sequence at least 97% identical to SEQ ID NO: 49. In an aspect, an endogenous CDKI comprises an amino acid sequence at least 98% identical to SEQ ID NO: 49. In an aspect, an endogenous CDKI comprises an amino acid sequence at least 99% identical to SEQ ID NO: 49. In an aspect, a CDKI comprises an amino acid sequence 100% identical to SEQ ID NO: 49.

In an aspect, an endogenous CDKI comprises an amino acid sequence at least 70% similar to SEQ ID NO: 49. In an aspect, an endogenous CDKI comprises an amino acid sequence at least 75% similar to SEQ ID NO: 49. In an aspect, an endogenous CDKI comprises an amino acid sequence at least 80% similar to SEQ ID NO: 49. In an aspect, an endogenous CDKI comprises an amino acid sequence at least 85% similar to SEQ ID NO: 49. In an aspect, an endogenous CDKI comprises an amino acid sequence at least 90 similar identical to SEQ ID NO: 49. In an aspect, an endogenous CDKI comprises an amino acid sequence at least 95% similar to SEQ ID NO: 49. In an aspect, an endogenous CDKI comprises an amino acid sequence at least 96% similar to SEQ ID NO: 49. In an aspect, an endogenous CDKI comprises an amino acid sequence at least 97% similar to SEQ ID NO: 49. In an aspect, an endogenous CDKI comprises an amino acid sequence at least 98% similar to SEQ ID NO: 49. In an aspect, an endogenous CDKI comprises an amino acid sequence at least 99% similar to SEQ ID NO: 49. In an aspect, a CDKI comprises an amino acid sequence 100% similar to SEQ ID NO: 49.

MYB proteins (MYBs) are part of a family of transcription factors. In plants, MYBs comprise a conserved MYB DNA-binding domain. The MYB DNA-binding domain contains up to three imperfect repeats of about 55 amino acids each, in a helix-turn-helix structure. These repeats are termed R1, R2, and R3, and the R2/R3 repeats have been shown to bind directly to the major groove of DNA. A subfamily of plant-specific MYBs contains an R2R3-type MYB domain and are termed R2R3-type MYBs. Other subfamilies of MYBs include R1-type, 3R-type, and 4R-type MYBs. See, for example, Ambawat et al., "MYB transcription factor genes as regulators for plant responses: an overview," *Physiol. Mol. Biol. Plants,* 19:307-321 (2013), which is herein incorporated by reference in its entirety.

In an aspect, a MYB provided herein is an R1-type MYB. In another aspect, a MYB provided herein is an R2R3-type MYB. In another aspect, a MYB provided herein is a 3R-type MYB. In another aspect, a MYB provided herein is a 4R-type MYB.

In an aspect, this disclosure provides a polynucleotide that encodes a MYB. In another aspect, this disclosure provides a MYB.

In an aspect, this disclosure provides a mutated polynucleotide comprising a mutation in an endogenous gene, where the mutated polynucleotide encodes a mutated MYB as compared to a MYB encoded by the endogenous gene lacking the mutation. In an aspect, this disclosure provides a mutated polynucleotide comprising a mutation in an endogenous gene, where the mutated polynucleotide encodes a truncated MYB as compared to a MYB encoded by the endogenous gene lacking the mutation. In another aspect, this disclosure provides a non-naturally occurring truncated MYB. In an aspect, this disclosure provides a polynucleotide encoding a mutated mRNA of an endogenous gene comprising a premature stop codon, where the mutated mRNA encodes a truncated MYB as compared to an mRNA of the endogenous gene lacking the premature stop codon.

In an aspect, this disclosure provides a polynucleotide comprising a non-naturally occurring mutation in a sequence encoding a MYB DNA-binding domain. In an aspect, this disclosure provides a mutated polynucleotide comprising a mutation in an endogenous gene encoding a MYB, where the mutated polynucleotide encodes a MYB lacking a MYB DNA-binding domain. In another aspect, this disclosure provides a mutated polynucleotide comprising a mutation in an endogenous gene encoding a MYB, where the mutated polynucleotide encodes a MYB comprising a truncated MYB DNA-binding domain as compared to a MYB encoded by the endogenous gene lacking the mutation.

In an aspect, this disclosure provides a mutated polynucleotide comprising a mutation in an endogenous gene encoding a MYB, where the mutated polynucleotide encodes a MYB that is incapable of binding DNA. In an aspect, this disclosure provides a mutated polynucleotide comprising a mutation in an endogenous gene encoding a MYB, where the mutated polynucleotide encodes a MYB that exhibits reduced binding affinity for DNA as compared to a MYB encoded by the endogenous gene lacking the mutation.

In another aspect, this disclosure provides a mutated polynucleotide comprising a mutation in an endogenous gene encoding a MYB, where the mutated polynucleotide encodes a MYB comprising a truncated R2R3-type MYB domain as compared to a MYB encoded by the endogenous gene lacking the mutation. In another aspect, this disclosure provides a mutated polynucleotide comprising a mutation in an endogenous gene encoding a MYB, where the mutated polynucleotide encodes a MYB comprising a truncated R1-type MYB domain as compared to a MYB encoded by the endogenous gene lacking the mutation. In another aspect, this disclosure provides a mutated polynucleotide comprising a mutation in an endogenous gene encoding a MYB, where the mutated polynucleotide encodes a MYB comprising a truncated 3R-type MYB domain as compared to a MYB encoded by the endogenous gene lacking the mutation. In another aspect, this disclosure provides a mutated polynucleotide comprising a mutation in an endogenous gene encoding a MYB, where the mutated polynucleotide encodes a MYB comprising a truncated 4R-type MYB domain as compared to a MYB encoded by the endogenous gene lacking the mutation.

In an aspect, a mutated polynucleotide encodes a dominant negative allele of a MYB. In another aspect, a mutated polynucleotide encodes a dominant positive allele of a MYB. In a further aspect, a mutated polynucleotide encodes a constitutively active MYB. In another aspect, a mutated polynucleotide encodes an inactive MYB.

In an aspect, an endogenous gene encoding a MYB comprises a polynucleotide sequence at least 80% identical to a sequence selected from the group consisting of SEQ ID NOs: 33-44. In an aspect, an endogenous gene encoding a MYB comprises a polynucleotide sequence at least 85% identical to a sequence selected from the group consisting of SEQ ID NOs: 33-44. In an aspect, an endogenous gene encoding a MYB comprises a polynucleotide sequence at least 90% identical to a sequence selected from the group consisting of SEQ ID NOs: 33-44. In an aspect, an endogenous gene encoding a MYB comprises a polynucleotide sequence at least 95% identical to a sequence selected from the group consisting of SEQ ID NOs: 33-44. In an aspect, an endogenous gene encoding a MYB comprises a polynucleotide sequence at least 96% identical to a sequence selected from the group consisting of SEQ ID NOs: 33-44. In an aspect, an endogenous gene encoding a MYB comprises a polynucleotide sequence at least 97% identical to a sequence selected from the group consisting of SEQ ID NOs: 33-44. In an aspect, an endogenous gene encoding a MYB comprises a polynucleotide sequence at least 98% identical to a sequence selected from the group consisting of SEQ ID NOs: 33-44. In an aspect, an endogenous gene encoding a MYB comprises a polynucleotide sequence at least 99% identical to a sequence selected from the group consisting of SEQ ID NOs: 33-44. In an aspect, an endogenous gene encoding a MYB comprises a polynucleotide sequence 100% identical to a sequence selected from the group consisting of SEQ ID NOs: 33-44.

In an aspect, an endogenous MYB comprises an amino acid sequence at least 70% identical to a sequence selected from the group consisting of SEQ ID NOs: 77-88. In an aspect, an endogenous MYB comprises an amino acid sequence at least 75% identical to a sequence selected from the group consisting of SEQ ID NOs: 77-88. In an aspect, an endogenous MYB comprises an amino acid sequence at least 80% identical to a sequence selected from the group consisting of SEQ ID NOs: 77-88. In an aspect, an endogenous MYB comprises an amino acid sequence at least 85% identical to a sequence selected from the group consisting of SEQ ID NOs: 77-88. In an aspect, an endogenous MYB comprises an amino acid sequence at least 90% identical to a sequence selected from the group consisting of SEQ ID NOs: 77-88. In an aspect, an endogenous MYB comprises an amino acid sequence at least 95% identical to a sequence selected from the group consisting of SEQ ID NOs: 77-88. In an aspect, an endogenous MYB comprises an amino acid sequence at least 96% identical to a sequence selected from the group consisting of SEQ ID NOs: 77-88. In an aspect, an endogenous MYB comprises an amino acid sequence at least 97% identical to a sequence selected from the group consisting of SEQ ID NOs: 77-88. In an aspect, an endogenous MYB comprises an amino acid sequence at least 98% identical to a sequence selected from the group consisting of SEQ ID NOs: 77-88. In an aspect, an endogenous MYB comprises an amino acid sequence at least 99% identical to a sequence selected from the group consisting of SEQ ID NOs: 77-88. In an aspect, a MYB comprises an amino acid sequence 100% identical to a sequence selected from the group consisting of SEQ ID NOs: 77-88.

In an aspect, an endogenous MYB comprises an amino acid sequence at least 70% similar to a sequence selected from the group consisting of SEQ ID NOs: 77-88. In an aspect, an endogenous MYB comprises an amino acid sequence at least 75% similar to a sequence selected from the group consisting of SEQ ID NOs: 77-88. In an aspect, an endogenous MYB comprises an amino acid sequence at least 80% similar to a sequence selected from the group consisting of SEQ ID NOs: 77-88. In an aspect, an endogenous MYB comprises an amino acid sequence at least 85% similar to a sequence selected from the group consisting of SEQ ID NOs: 77-88. In an aspect, an endogenous MYB comprises an amino acid sequence at least 90% similar to a sequence selected from the group consisting of SEQ ID NOs: 77-88. In an aspect, an endogenous MYB comprises an amino acid sequence at least 95% similar to a sequence selected from the group consisting of SEQ ID NOs: 77-88. In an aspect, an endogenous MYB comprises an amino acid sequence at least 96% similar to a sequence selected from the group consisting of SEQ ID NOs: 77-88. In an aspect, an endogenous MYB comprises an amino acid sequence at least 97% similar to a sequence selected from the group consisting of SEQ ID NOs: 77-88. In an aspect, an endogenous MYB comprises an amino acid sequence at least 98% similar to a sequence selected from the group consisting of SEQ ID NOs: 77-88. In an aspect, an endogenous MYB comprises an amino acid sequence at least 99% similar to a sequence selected from the group consisting of SEQ ID NOs: 77-88. In an aspect, a MYB comprises an amino acid sequence 100% similar to a sequence selected from the group consisting of SEQ ID NOs: 77-88.

WRKY transcription factors are one of the largest families of transcriptional regulators known in plants. A WRKY transcription factor is a protein that comprises a "WRKY domain." A WRKY domain comprises about 60 to 70 amino acids, and is involved in DNA binding. The WRKY domain contains a highly conserved "WRKY core domain" having an amino acid motif of WRKYGQK (SEQ ID NO: 110). The conserved core of the WRKY domain can vary, and the amino acid motif WRKYGKK (SEQ ID NO: 111) is a commonly observed "WRKY core variant domain." WRKY domains comprise a globular shape composed of five anti-parallel β-strands, and the conserved core is found on the second β-strand. The third β-strand also contains a highly conserved amino acid motif of PRSYY (SEQ ID NO: 112). In many WRKY transcription factors, the PR and SYY amino acids of the "PRSYY motif" (SEQ ID NO: 112) are encoded by different exons; the position of the intervening intron is highly conserved amongst WRKY transcription factors. WRKY domains also contain a "zinc finger region" comprising an amino acid motif of $CX_{4-5}CX_{22-23}HXH$ (SEQ ID NO: 115) or $CX_7CX_{23}HXC$ (SEQ ID NO: 116), where X can be any amino acid, C is a cysteine, and His a histidine. WRKY domains also contain a "DWK salt bridge" motif, where the conserved tryptophan (W) of the WRKY core (SEQ ID NO: 117) forms a triad with an aspartic acid (D) four amino acids upstream of the W, and a lysine (K) twenty-nine amino acids downstream of the W. It is believed that the DWK salt bridge is important for stabilizing the WRKY domain. See, for example, Rushton et al., "WRKY transcription factors," *Trends in Plant Science,* 15:247-258 (2010), which is incorporated herein by reference in its entirety.

In an aspect, this disclosure provides a polynucleotide that encodes a WRKY transcription factor. In another aspect, this disclosure provides a WRKY transcription factor.

In an aspect, this disclosure provides a polynucleotide comprising a non-naturally occurring mutation, where the polynucleotide encodes a WRKY transcription factor. In an aspect, this disclosure provides a polynucleotide encoding a truncated WRKY transcription factor. In another aspect, this disclosure provides a non-naturally occurring truncated WRKY transcription factor. In an aspect, this disclosure provides a polynucleotide encoding an mRNA comprising a premature stop codon, where the mRNA encodes a truncated WRKY transcription factor.

In an aspect, this disclosure provides a mutated poly-nucleotide comprising a mutation in an endogenous gene, where the mutated polynucleotide encodes a mutated WRKY transcription factor as compared to a WRKY tran-scription factor encoded by the endogenous gene lacking the mutation. In an aspect, this disclosure provides a mutated polynucleotide comprising a mutation in an endogenous gene, where the mutated polynucleotide encodes a truncated WRKY transcription factor as compared to a WRKY tran-scription factor encoded by the endogenous gene lacking the mutation. In another aspect, this disclosure provides a non-naturally occurring truncated WRKY transcription factor. In an aspect, this disclosure provides a polynucleotide encod-ing a mutated mRNA of an endogenous gene comprising a premature stop codon, where the mutated mRNA encodes a truncated WRKY transcription factor as compared to an mRNA of the endogenous gene lacking the premature stop codon.

In an aspect, this disclosure provides a polynucleotide comprising a non-naturally occurring mutation in a sequence encoding a WRKY domain. In an aspect, this disclosure provides a mutated polynucleotide comprising a mutation in an endogenous gene encoding a WRKY transcription factor, where the mutated polynucleotide encodes a WRKY transcription factor lacking a WRKY domain. In another aspect, this disclosure provides a mutated polynucleotide comprising a mutation in an endogenous gene encoding a WRKY transcription factor, where the mutated polynucleotide encodes a WRKY transcription factor comprising a truncated WRKY domain as compared to a WRKY transcription factor encoded by the endogenous gene lacking the mutation.

In an aspect, this disclosure provides a polynucleotide comprising a non-naturally occurring mutation in a sequence encoding a WRKY core domain. In an aspect, this disclosure provides a mutated polynucleotide comprising a mutation in an endogenous gene encoding a WRKY transcription factor, where the mutated polynucleotide encodes a WRKY transcription factor lacking a WRKY core domain. In another aspect, this disclosure provides a mutated polynucleotide comprising a mutation in an endogenous gene encoding a WRKY transcription factor, where the mutated polynucleotide encodes a WRKY transcription factor comprising a truncated WRKY core domain as compared to a WRKY transcription factor encoded by the endogenous gene lacking the mutation.

In an aspect, this disclosure provides a polynucleotide comprising a non-naturally occurring mutation in a sequence encoding a WRKY core variant domain. In an aspect, this disclosure provides a mutated polynucleotide comprising a mutation in an endogenous gene encoding a WRKY transcription factor, where the mutated polynucleotide encodes a WRKY transcription factor lacking a WRKY core variant domain. In another aspect, this disclosure provides a mutated polynucleotide comprising a mutation in an endogenous gene encoding a WRKY transcription factor, where the mutated polynucleotide encodes a WRKY transcription factor comprising a truncated WRKY core variant domain as compared to a WRKY transcription factor encoded by the endogenous gene lacking the mutation.

In an aspect, this disclosure provides a polynucleotide comprising a non-naturally occurring mutation in a sequence encoding a PRSYY motif (SEQ ID NO: 112). In an aspect, this disclosure provides a mutated polynucleotide comprising a mutation in an endogenous gene encoding a WRKY transcription factor, where the mutated polynucleotide encodes a WRKY transcription factor lacking a PRSYY motif (SEQ ID NO: 112). In another aspect, this disclosure provides a mutated polynucleotide comprising a mutation in an endogenous gene encoding a WRKY transcription factor, where the mutated polynucleotide encodes a WRKY transcription factor comprising a truncated PRSYY motif (SEQ ID NO: 112) as compared to a WRKY transcription factor encoded by the endogenous gene lacking the mutation.

In an aspect, this disclosure provides a polynucleotide comprising a non-naturally occurring mutation in a sequence encoding a zinc finger region. In an aspect, this disclosure provides a mutated polynucleotide comprising a mutation in an endogenous gene encoding a WRKY transcription factor, where the mutated polynucleotide encodes a WRKY transcription factor lacking a zinc finger region. In another aspect, this disclosure provides a mutated polynucleotide comprising a mutation in an endogenous gene encoding a WRKY transcription factor, where the mutated polynucleotide encodes a WRKY transcription factor comprising a truncated zinc finger region as compared to a WRKY transcription factor encoded by the endogenous gene lacking the mutation.

In an aspect, this disclosure provides a polynucleotide comprising a non-naturally occurring mutation in a sequence encoding a DWK salt bridge motif. In an aspect, this disclosure provides a mutated polynucleotide comprising a mutation in an endogenous gene encoding a WRKY transcription factor, where the mutated polynucleotide encodes a WRKY transcription factor lacking a DWK salt bridge motif. In another aspect, this disclosure provides a mutated polynucleotide comprising a mutation in an endogenous gene encoding a WRKY transcription factor, where the mutated polynucleotide encodes a WRKY transcription factor comprising a truncated DWK salt bridge motif as compared to a WRKY transcription factor encoded by the endogenous gene lacking the mutation.

In an aspect, this disclosure provides a mutated polynucleotide comprising a mutation in an endogenous gene encoding a WRKY transcription factor, where the mutated polynucleotide encodes a WRKY transcription factor that is incapable of binding DNA. In an aspect, this disclosure provides a mutated polynucleotide comprising a mutation in an endogenous gene encoding a WRKY transcription factor, where the mutated polynucleotide encodes a WRKY transcription factor that exhibits reduced binding affinity for DNA as compared to a WRKY transcription factor encoded by the endogenous gene lacking the mutation.

In an aspect, a mutated polynucleotide encodes a dominant negative allele of a WRKY transcription factor. In another aspect, a mutated polynucleotide encodes a dominant positive allele of a WRKY transcription factor. In a further aspect, a mutated polynucleotide encodes a constitutively active WRKY transcription factor. In another aspect, a mutated polynucleotide encodes an inactive WRKY transcription factor.

In an aspect, an endogenous gene encoding a WRKY transcription factor comprises a polynucleotide sequence at least 80% identical to SEQ ID NO: 113. In an aspect, an endogenous gene encoding a WRKY transcription factor comprises a polynucleotide sequence at least 85% identical to SEQ ID NO: 113. In an aspect, an endogenous gene encoding a WRKY transcription factor comprises a polynucleotide sequence at least 90% identical to SEQ ID NO: 113. In an aspect, an endogenous gene encoding a WRKY transcription factor comprises a polynucleotide sequence at least 95% identical to SEQ ID NO: 113. In an aspect, an endogenous gene encoding a WRKY transcription factor comprises a polynucleotide sequence at least 96% identical to SEQ ID NO: 113. In an aspect, an endogenous gene encoding a WRKY transcription factor comprises a polynucleotide sequence at least 97% identical to SEQ ID NO: 113. In an aspect, an endogenous gene encoding a WRKY transcription factor comprises a polynucleotide sequence at least 98% identical to SEQ ID NO: 113. In an aspect, an endogenous gene encoding a WRKY transcription factor comprises a polynucleotide sequence at least 99% identical to SEQ ID NO: 113. In an aspect, an endogenous gene encoding a WRKY transcription factor comprises a polynucleotide sequence 100% identical to SEQ ID NO: 113.

In an aspect, an endogenous WRKY transcription factor comprises an amino acid sequence at least 70% identical to SEQ ID NO: 114. In an aspect, an endogenous WRKY transcription factor comprises an amino acid sequence at least 75% identical to SEQ ID NO: 114. In an aspect, an endogenous WRKY transcription factor comprises an amino acid sequence at least 80% identical to SEQ ID NO: 114. In an aspect, an endogenous WRKY transcription factor comprises an amino acid sequence at least 85% identical to SEQ ID NO: 114. In an aspect, an endogenous WRKY transcription factor comprises an amino acid sequence at least 90% identical to SEQ ID NO: 114. In an aspect, an endogenous WRKY transcription factor comprises an amino acid sequence at least 95% identical to SEQ ID NO: 114. In an aspect, an endogenous WRKY transcription factor comprises an amino acid sequence at least 96% identical to SEQ ID NO: 114. In an aspect, an endogenous WRKY transcription factor comprises an amino acid sequence at least 97% identical to SEQ ID NO: 114. In an aspect, an endogenous WRKY transcription factor comprises an amino acid sequence at least 98% identical to SEQ ID NO: 114. In an aspect, an endogenous WRKY transcription factor comprises an amino acid sequence at least 99% identical to SEQ ID NO: 114. In an aspect, a WRKY transcription factor comprises an amino acid sequence 100% identical to SEQ ID NO: 114.

In an aspect, an endogenous WRKY transcription factor comprises an amino acid sequence at least 70% similar to SEQ ID NO: 114. In an aspect, an endogenous WRKY transcription factor comprises an amino acid sequence at least 75% similar to SEQ ID NO: 114. In an aspect, an endogenous WRKY transcription factor comprises an amino acid sequence at least 80% similar to SEQ ID NO: 114. In an aspect, an endogenous WRKY transcription factor comprises an amino acid sequence at least 85% similar to SEQ ID NO: 114. In an aspect, an endogenous WRKY transcription factor comprises an amino acid sequence at least 90% similar to SEQ ID NO: 114. In an aspect, an endogenous WRKY transcription factor comprises an amino acid sequence at least 95% similar to SEQ ID NO: 114. In an aspect, an endogenous WRKY transcription factor comprises an amino acid sequence at least 96% similar to SEQ ID NO: 114. In an aspect, an endogenous WRKY transcription factor comprises an amino acid sequence at least 97% similar to SEQ ID NO: 114. In an aspect, an endogenous WRKY transcription factor comprises an amino acid sequence at least 98% similar to SEQ ID NO: 114. In an aspect, an endogenous WRKY transcription factor comprises an amino acid sequence at least 99% similar to SEQ ID NO: 114. In an aspect, a WRKY transcription factor comprises an amino acid sequence 100% similar to SEQ ID NO: 114.

In an aspect, a modified tobacco plant, tobacco plant part, tobacco seed, tobacco cell, or tobacco genome provided herein comprises one or more mutations. As used herein, a "mutation" refers to a non-naturally occurring alteration to DNA as compared to an endogenous reference DNA sequence. It will be appreciated that, when identifying a mutation, the endogenous reference DNA sequence should be from the same variety of tobacco. For example, if a modified tobacco plant comprising a mutation is from the variety TN90, then the endogenous reference sequence must be the endogenous TN90 sequence, not a homologous sequence from a different tobacco variety (e.g., K326). Similarly, if a modified tobacco cell comprising a mutation is a TN90 cell, then the endogenous reference sequence must be the endogenous TN90 sequence, not a homologous sequence from a tobacco cell from a different tobacco variety (e.g., K326).

In an aspect, a mutation provided herein creates a dominant allele of the mutated locus. Dominant alleles are alleles that mask the contribution of a second allele at the same locus. A dominant allele can be a "dominant negative allele" or a "dominant positive allele." Dominant negative alleles, or antimorphs, are alleles that act in opposition to normal allelic function. A dominant negative allele typically does not function normally and either directly inhibits the activity of a wild-type protein (e.g., through dimerization) or inhibits the activity of a second protein that is required for the normal function of the wild-type protein (e.g., an activator or a downstream component of a pathway). For example, a dominant negative allele abrogates or reduces the normal function of an allele in a heterozygous or homozygous state. Dominant positive alleles can increase normal gene function (e.g., a hypermorph) or provide new functions for a gene (e.g., a neomorph). A semi-dominant allele occurs when penetrance of a linked phenotype in individuals heterozygous for the allele is less than that which is observed in individuals homozygous for the allele.

In an aspect, a mutation provided herein creates a dominant negative allele of the mutated locus. In another aspect, a mutation provided herein creates a dominant positive allele of a mutated locus.

As used herein, "inducing" a mutation refers to generating a mutation in a polynucleotide sequence via human intervention. Many suitable methods for inducing mutations in tobacco are known in the art. Non-limiting examples of such methods include use of chemical mutagens, use of radiation, and use of nucleases. In an aspect, inducing a mutation comprises the use of an agent selected from the group consisting of a chemical mutagen, irradiation, a transposon, *Agrobacterium*, and a nuclease.

In an aspect, inducing a mutation comprises the use of a chemical mutagen. In an aspect, a chemical mutagen comprises ethyl methanesulfonate (EMS).

In another aspect, inducing a mutation comprises the use of irradiation. In an aspect, irradiation comprises gamma rays, X-rays, or ionizing radiation. In another aspect, irradiation comprises the use of fast neutrons.

In an aspect, inducing a mutation comprises the use of a transposon. In another aspect, inducing a mutation comprises the use of *Agrobacterium*.

In a further aspect, inducing a mutation comprises the use of a nuclease. In an aspect, a nuclease is selected from the group consisting of a meganuclease, a zinc-finger nuclease, a transcription activator-like effector nuclease, a CRISPR/Cas9 nuclease, a CRISPR/Cpf1 nuclease, a CRISPR/CasX nuclease, a CRISPR/CasY nuclease, and a Csm1 nuclease. In an aspect, inducing a mutation comprises the use of a CRISPR/Cas9 nuclease. In an aspect, inducing a mutation comprises the use of a CRISPR/Cpf1 nuclease. In an aspect, inducing a mutation comprises the use of a CRISPR/CasX nuclease. In an aspect, inducing a mutation comprises the use of a CRISPR/CasY nuclease. In an aspect, inducing a mutation comprises the use of a Csm1 nuclease.

Several types of mutations are known in the art. In an aspect, a mutation comprises an insertion. An "insertion" refers to the addition of one or more nucleotides or amino acids to a given polynucleotide or amino acid sequence, respectively, as compared to an endogenous reference polynucleotide or amino acid sequence. In another aspect, a mutation comprises a deletion. A "deletion" refers to the removal of one or more nucleotides or amino acids to a given polynucleotide or amino acid sequence, respectively, as compared to an endogenous reference polynucleotide or amino acid sequence. In another aspect, a mutation comprises a substitution. A "substitution" refers to the replacement of one or more nucleotides or amino acids to a given polynucleotide or amino acid sequence, respectively, as compared to an endogenous reference polynucleotide or amino acid sequence. In another aspect, a mutation comprises an inversion. An "inversion" refers to when a segment of a polynucleotide or amino acid sequence is reversed end-to-end. In an aspect, a mutation provided herein comprises a mutation selected from the group consisting of an insertion, a deletion, a substitution, and an inversion.

Mutations in coding regions of genes (e.g., exonic mutations) can result in a truncated protein or polypeptide when a mutated messenger RNA (mRNA) is translated into a protein or polypeptide. In an aspect, this disclosure provides a mutation that results in the truncation of a protein or polypeptide. As used herein, a "truncated" protein or polypeptide comprises at least one fewer amino acid as compared to an endogenous control protein or polypeptide. For example, if endogenous Protein A comprises 100 amino acids, a truncated version of Protein A can comprise between 1 and 99 amino acids.

Without being limited by any scientific theory, one way to cause a protein or polypeptide truncation is by the introduction of a premature stop codon in an mRNA transcript of an endogenous gene. In an aspect, this disclosure provides a mutation that results in a premature stop codon in an mRNA transcript of an endogenous gene. As used herein, a "stop codon" refers to a nucleotide triplet within an mRNA transcript that signals a termination of protein translation. A "premature stop codon" refers to a stop codon positioned earlier (e.g., on the 5'-side) than the normal stop codon position in an endogenous mRNA transcript. Without being limiting, several stop codons are known in the art, including "UAG," "UAA," "UGA," "TAG," "TAA," and "TGA."

In an aspect, a mutation provided herein comprises a null mutation. As used herein, a "null mutation" refers to a mutation that confers a complete loss-of-function for a protein encoded by a gene comprising the mutation, or, alternatively, a mutation that confers a complete loss-of-function for a small RNA encoded by a genomic locus. A null mutation can cause lack of mRNA transcript production, a lack of small RNA transcript production, a lack of protein function, or a combination thereof.

A mutation provided herein can be positioned in any part of an endogenous gene. In an aspect, a mutation provided herein is positioned within an exon of an endogenous gene. In another aspect, a mutation provided herein is positioned within an intron of an endogenous gene. In a further aspect, a mutation provided herein is positioned within a 5'-untranslated region of an endogenous gene. In still another aspect, a mutation provided herein is positioned within a 3'-untranslated region of an endogenous gene. In yet another aspect, a mutation provided herein is positioned within a promoter of an endogenous gene.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In an aspect, a mutation in an endogenous gene results in a reduced level of expression as compared to the endogenous gene lacking the mutation. In another aspect, a mutation in an endogenous gene results in an increased level of expression as compared to the endogenous gene lacking the mutation. In a further aspect, a mutation in an endogenous gene results in a reduced level of activity by a protein or polypeptide encoded by the endogenous gene having the mutation as compared to a protein or polypeptide encoded by the endogenous gene lacking the mutation. In a further aspect, a mutation in an endogenous gene results in an increased level of activity by a protein or polypeptide encoded by the endogenous gene having the mutation as compared to a protein or polypeptide encoded by the endogenous gene lacking the mutation.

In an aspect, a mutation in a genomic locus results in a reduced level of expression as compared to the genomic locus lacking the mutation. In another aspect, a mutation in a genomic locus results in an increased level of expression as compared to the genomic locus lacking the mutation. In a further aspect, a mutation in a genomic locus results in a reduced level of activity by a protein or polypeptide encoded by the genomic locus having the mutation as compared to a protein or polypeptide encoded by the genomic locus lacking the mutation. In a further aspect, a mutation in a genomic locus results in an increased level of activity by a protein or polypeptide encoded by the genomic locus having the mutation as compared to a protein or polypeptide encoded by the genomic locus lacking the mutation.

Levels of gene expression are routinely investigated in the art. As non-limiting examples, gene expression can be measured using quantitative reverse transcriptase PCR (qRT-PCR), RNA sequencing, or Northern blots. In an aspect, gene expression is measured using qRT-PCR. In another aspect, gene expression is measured using a Northern blot. In another aspect, gene expression is measured using RNA sequencing.

Levels of protein activity are also routinely investigated in the art. For example, CDK activity can be measured using phosphorylation assays.

As used herein, the term "heterologous" refers to a combination of two or more DNA molecules or sequences, such as a promoter and an associated transcribable DNA sequence, coding sequence or gene, when such a combination is man-made and not normally found in nature.

In one aspect, the level of expression of an endogenous gene comprising a mutation is reduced by at least 1% as compared to the level of expression of the endogenous gene lacking the mutation. In one aspect, the level of expression of an endogenous gene comprising a mutation is reduced by at least 5% as compared to the level of expression of the endogenous gene lacking the mutation. In one aspect, the level of expression of an endogenous gene comprising a mutation is reduced by at least 10% as compared to the level of expression of the endogenous gene lacking the mutation. In one aspect, the level of expression of an endogenous gene comprising a mutation is reduced by at least 15% as compared to the level of expression of the endogenous gene lacking the mutation. In one aspect, the level of expression of an endogenous gene comprising a mutation is reduced by at least 20% as compared to the level of expression of the endogenous gene lacking the mutation. In one aspect, the level of expression of an endogenous gene comprising a mutation is reduced by at least 25% as compared to the level of expression of the endogenous gene lacking the mutation. In one aspect, the level of expression of an endogenous gene comprising a mutation is reduced by at least 50% as compared to the level of expression of the endogenous gene lacking the mutation. In one aspect, the level of expression of an endogenous gene comprising a mutation is reduced by at least 75% as compared to the level of expression of the endogenous gene lacking the mutation. In one aspect, the level of expression of an endogenous gene comprising a mutation is reduced by at least 90% as compared to the level of expression of the endogenous gene lacking the mutation. In one aspect, the level of expression of an endogenous gene comprising a mutation is reduced by at least 95% as compared to the level of expression of the endogenous gene lacking the mutation.

In one aspect, the level of expression of an endogenous gene comprising a mutation is reduced by between 1% and 99% as compared to the level of expression of the endogenous gene lacking the mutation. In one aspect, the level of expression of an endogenous gene comprising a mutation is reduced by between 1% and 90% as compared to the level of expression of the endogenous gene lacking the mutation. In one aspect, the level of expression of an endogenous gene comprising a mutation is reduced by between 1% and 75% as compared to the level of expression of the endogenous gene lacking the mutation. In one aspect, the level of expression of an endogenous gene comprising a mutation is reduced by between 1% and 50% as compared to the level of expression of the endogenous gene lacking the mutation. In one aspect, the level of expression of an endogenous gene comprising a mutation is reduced by between 1% and 25% as compared to the level of expression of the endogenous gene lacking the mutation. In one aspect, the level of expression of an endogenous gene comprising a mutation is reduced by between 1% and 10% as compared to the level of expression of the endogenous gene lacking the mutation. In one aspect, the level of expression of an endogenous gene comprising a mutation is reduced by between 75% and 99% as compared to the level of expression of the endogenous gene lacking the mutation. In one aspect, the level of expression of an endogenous gene comprising a mutation is reduced by between 50% and 99% as compared to the level of expression of the endogenous gene lacking the mutation. In one aspect, the level of expression of an endogenous gene comprising a mutation is reduced by between 25% and 99% as compared to the level of expression of the endogenous gene lacking the mutation. In one aspect, the level of expression of an endogenous gene comprising a mutation is reduced by between 10% and 99% as compared to the level of expression of the endogenous gene lacking the mutation. In one aspect, the level of expression of an endogenous gene comprising a mutation is reduced by between 50% and 75% as compared to the level of expression of the endogenous gene lacking the mutation. In one aspect, the level of expression of an endogenous gene comprising a mutation is reduced by between 25% and 75% as compared to the level of expression of the endogenous gene lacking the mutation. In one aspect, the level of expression of an endogenous gene comprising a mutation is reduced by between 10% and 50% as compared to the level of expression of the endogenous gene lacking the mutation.

In one aspect, the level of expression of an endogenous gene comprising a mutation is increased by at least 1% as compared to the level of expression of the endogenous gene lacking the mutation. In one aspect, the level of expression of an endogenous gene comprising a mutation is increased by at least 5% as compared to the level of expression of the endogenous gene lacking the mutation. In one aspect, the level of expression of an endogenous gene comprising a mutation is increased by at least 10% as compared to the level of expression of the endogenous gene lacking the mutation. In one aspect, the level of expression of an endogenous gene comprising a mutation is increased by at least 15% as compared to the level of expression of the endogenous gene lacking the mutation. In one aspect, the level of expression of an endogenous gene comprising a mutation is increased by at least 20% as compared to the level of expression of the endogenous gene lacking the mutation. In one aspect, the level of expression of an endogenous gene comprising a mutation is increased by at least 25% as compared to the level of expression of the endogenous gene lacking the mutation. In one aspect, the level of expression of an endogenous gene comprising a mutation is increased by at least 50% as compared to the level of expression of the endogenous gene lacking the mutation. In one aspect, the level of expression of an endogenous gene comprising a mutation is increased by at least 75% as compared to the level of expression of the endogenous gene lacking the mutation. In one aspect, the level of expression of an endogenous gene comprising a mutation is increased by at least 90% as compared to the level of expression of the endogenous gene lacking the mutation. In one aspect, the level of expression of an endogenous gene comprising a mutation is increased by at least 95% as compared to the level of expression of the endogenous gene lacking the mutation. In one aspect, the level of expression of an endogenous gene comprising a mutation is increased by at least 100% as compared to the level of expression of the endogenous gene lacking the mutation. In one aspect, the level of expression of an endogenous gene comprising a mutation is increased by at least 150% as compared to the level of expression of the endogenous gene lacking the mutation. In one aspect, the level of expression of an endogenous gene comprising a mutation is increased by at least 200% as compared to the level of expression of the endogenous gene lacking the mutation. In one aspect, the level of expression of an endogenous gene comprising a mutation is increased by at least 250% as compared to the level of expression of the endogenous gene lacking the mutation. In one aspect, the level of expression of an endogenous gene comprising a mutation is increased by at least 300% as compared to the level of expression of the endogenous gene lacking the mutation. In one aspect, the level of expression of an endogenous gene comprising a mutation is increased by at least 400% as compared to the level of expression of the endogenous gene lacking the mutation. In one aspect, the level of expression of an endogenous gene comprising a mutation is increased by at least 500% as compared to the level of expression of the endogenous gene lacking the mutation. In one aspect, the level of expression of an endogenous gene comprising a mutation is increased by at least 750% as compared to the level of expression of the endogenous gene lacking the mutation. In one aspect, the level of expression of an endogenous gene comprising a mutation is increased by at least 1000% as compared to the level of expression of the endogenous gene lacking the mutation.

In one aspect, the level of expression of an endogenous gene comprising a mutation is increased by between 1% and 1000% as compared to the level of expression of the endogenous gene lacking the mutation. In one aspect, the level of expression of an endogenous gene comprising a mutation is increased by between 1% and 750% as compared to the level of expression of the endogenous gene lacking the mutation. In one aspect, the level of expression of an endogenous gene comprising a mutation is increased by between 1% and 500% as compared to the level of expression of the endogenous gene lacking the mutation. In one aspect, the level of expression of an endogenous gene comprising a mutation is increased by between 1% and 400% as compared to the level of expression of the endogenous gene lacking the mutation. In one aspect, the level of expression of an endogenous gene comprising a mutation is increased by between 1% and 300% as compared to the level of expression of the endogenous gene lacking the mutation. In one aspect, the level of expression of an endogenous gene comprising a mutation is increased by between 1% and 200% as compared to the level of expression of the endogenous gene lacking the mutation. In one aspect, the level of expression of an endogenous gene comprising a mutation is increased by between 1% and 100% as compared to the level of expression of the endogenous gene lacking the mutation. In one aspect, the level of expression of an endogenous gene comprising a mutation is increased by between 1% and 75% as compared to the level of expression of the endogenous gene lacking the mutation. In one aspect, the level of expression of an endogenous gene comprising a mutation is increased by between 1% and 50% as compared to the level of expression of the endogenous gene lacking the mutation. In one aspect, the level of expression of an endogenous gene comprising a mutation is increased by between 1% and 25% as compared to the level of expression of the endogenous gene lacking the mutation. In one aspect, the level of expression of an endogenous gene comprising a mutation is increased by between 1% and 10% as compared to the level of expression of the endogenous gene lacking the mutation. In one aspect, the level of expression of an endogenous gene comprising a mutation is increased by between 100% and 1000% as compared to the level of expression of the endogenous gene lacking the mutation. In one aspect, the level of expression of an endogenous gene comprising a mutation is increased by between 100% and 750% as compared to the level of expression of the endogenous gene lacking the mutation. In one aspect, the level of expression of an endogenous gene comprising a mutation is increased by between 100% and 500% as compared to the level of expression of the endogenous gene lacking the mutation. In one aspect, the level of expression of an endogenous gene comprising a mutation is increased by between 100% and 250% as compared to the level of expression of the endogenous gene lacking the mutation. In one aspect, the level of expression of an endogenous gene comprising a mutation is increased by between 750% and 1000% as compared to the level of expression of the endogenous gene lacking the mutation. In one aspect, the level of expression of an endogenous gene comprising a mutation is increased by between 500% and 1000% as compared to the level of expression of the endogenous gene lacking the mutation. In one aspect, the level of expression of an endogenous gene comprising a mutation is increased by between 250% and 1000% as compared to the level of expression of the endogenous gene lacking the mutation. In one aspect, the level of expression of an endogenous gene comprising a mutation is increased by between 1% and 100% as compared to the level of expression of the endogenous gene lacking the mutation. In one aspect, the level of expression of an endogenous gene comprising a mutation is increased by between 50% and 100% as compared to the level of expression of the endogenous gene lacking the mutation.

As used herein, the term "endogenous gene" or "native gene" refers to a gene that originates within a tobacco genome. An "endogenous gene" is a gene that was not previously modified by human action. In an aspect, an endogenous gene is a nuclear gene. In another aspect, an endogenous gene is a mitochondrial gene. In a further aspect, an endogenous gene is a chloroplast gene.

As used herein, a "gene" refers to a polynucleotide that can produce a functional unit (e.g., without being limiting, for example, a protein, or a small RNA molecule). A gene can comprise a promoter, an enhancer sequence, a leader sequence, a transcriptional start site, a transcriptional stop site, a polyadenylation site, one or more exons, one or more introns, a 5'-untranslated region (UTR), a 3'-UTR, or any combination thereof. A "gene sequence" can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a gene encodes a small RNA molecule or a precursor thereof. In another aspect, a gene encodes a protein or polypeptide.

As used herein, a "genomic locus" refers to a fixed position on a chromosome. In an aspect, a genomic locus comprises a polynucleotide encoding a gene. In an aspect, a genomic locus comprises a polynucleotide encoding an endogenous gene. In another aspect, a genomic locus comprises a polynucleotide encoding a transgene. In an aspect, a genomic locus can be transcribed from DNA to RNA. In an aspect, a genomic locus encodes a messenger RNA. In another aspect, a genomic locus encodes a small RNA molecule.

As commonly understood in the art, the term "promoter" refers to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied, or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein.

Promoters that drive expression in all or most tissues of the plant are referred to as "constitutive" promoters. Promoters that drive expression during certain periods or stages of development are referred to as "developmental" promoters. Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. As a non-limiting example, an "axillary bud-preferred promoter" causes relatively higher or preferential expression in axillary bud tissues, but can have lower levels of expression in other parts of a plant (e.g., roots, leaves, stem). Promoters that express within a specific tissue(s) of an organism, with little or no expression in other tissues, are referred to as "tissue-specific" promoters. As a non-limited example, an "axillary bud-specific promoter" drives expression in axillary bud tissues, with little to no detectable expression in other plant tissue types. An "inducible" promoter is a promoter that initiates transcription in response to an environmental stimulus such as heat, cold, drought, light, or other stimuli, such as wounding or chemical application.

In an aspect, a promoter provided herein is an axillary bud-specific promoter. In another aspect, a promoter provided herein is an axillary bud-preferred promoter. In an aspect, a promoter provided herein is a constitutive promoter. In another aspect, a promoter provided herein is an inducible promoter. In a further aspect, a promoter provided herein is a developmental promoter.

In an aspect, this disclosure provides a heterologous promoter. In another aspect, this disclosure provides a promoter that is operably linked to a heterologous polynucleotide. In another aspect, this disclosure provides a polynucleotide sequence that is operably linked to a heterologous promoter.

In an aspect, a heterologous promoter comprises an axillary bud-specific promoter. In another aspect, a heterologous promoter comprises an axillary bud-preferred promoter. In an aspect, a heterologous promoter comprises a constitutive promoter. In an aspect, a heterologous promoter comprises an inducible promoter. In an aspect, a heterologous promoter comprises a developmental promoter.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. In an aspect, a promoter provided herein is operably linked to a heterologous nucleic acid molecule.

In an aspect, a heterologous promoter comprises a polynucleotide sequence at least 90% identical to a polynucleotide selected from the group consisting of SEQ ID NOs: 89-109. In an aspect, a heterologous promoter comprises a polynucleotide sequence at least 91% identical to a polynucleotide selected from the group consisting of SEQ ID NOs: 89-109. In an aspect, a heterologous promoter comprises a polynucleotide sequence at least 92% identical to a polynucleotide selected from the group consisting of SEQ ID NOs: 89-109. In an aspect, a heterologous promoter comprises a polynucleotide sequence at least 93% identical to a polynucleotide selected from the group consisting of SEQ ID NOs: 89-109. In an aspect, a heterologous promoter comprises a polynucleotide sequence at least 94% identical to a polynucleotide selected from the group consisting of SEQ ID NOs: 89-109. In an aspect, a heterologous promoter comprises a polynucleotide sequence at least 95% identical to a polynucleotide selected from the group consisting of SEQ ID NOs: 89-109. In an aspect, a heterologous promoter comprises a polynucleotide sequence at least 96% identical to a polynucleotide selected from the group consisting of SEQ ID NOs: 89-109. In an aspect, a heterologous promoter comprises a polynucleotide sequence at least 97% identical to a polynucleotide selected from the group consisting of SEQ ID NOs: 89-109. In an aspect, a heterologous promoter comprises a polynucleotide sequence at least 98% identical to a polynucleotide selected from the group consisting of SEQ ID NOs: 89-109. In an aspect, a heterologous promoter comprises a polynucleotide sequence at least 99% identical to a polynucleotide selected from the group consisting of SEQ ID NOs: 89-109. In an aspect, a heterologous promoter comprises a polynucleotide sequence 100% identical to a polynucleotide selected from the group consisting of SEQ ID NOs: 89-109.

In an aspect, an axillary bud-preferred promoter comprises a polynucleotide sequence at least 90% identical to a polynucleotide selected from the group consisting of SEQ ID NOs: 89-109. In an aspect, an axillary bud-preferred promoter comprises a polynucleotide sequence at least 95% identical to a polynucleotide selected from the group consisting of SEQ ID NOs: 89-109. In an aspect, an axillary bud-preferred promoter comprises a polynucleotide sequence at least 96% identical to a polynucleotide selected from the group consisting of SEQ ID NOs: 89-109. In an aspect, an axillary bud-preferred promoter comprises a polynucleotide sequence at least 97% identical to a polynucleotide selected from the group consisting of SEQ ID NOs: 89-109. In an aspect, an axillary bud-preferred promoter comprises a polynucleotide sequence at least 98% identical to a polynucleotide selected from the group consisting of SEQ ID NOs: 89-109. In an aspect, an axillary bud-preferred promoter comprises a polynucleotide sequence at least 99% identical to a polynucleotide selected from the group consisting of SEQ ID NOs: 89-109. In an aspect, an axillary bud-preferred promoter comprises a polynucleotide sequence 100% identical to a polynucleotide selected from the group consisting of SEQ ID NOs: 89-109.

In an aspect, an axillary bud-specific promoter comprises a polynucleotide sequence at least 90% identical to a polynucleotide selected from the group consisting of SEQ ID NOs: 89-109. In an aspect, an axillary bud-specific promoter comprises a polynucleotide sequence at least 95% identical to a polynucleotide selected from the group consisting of SEQ ID NOs: 89-109. In an aspect, an axillary bud-specific promoter comprises a polynucleotide sequence at least 96% identical to a polynucleotide selected from the group consisting of SEQ ID NOs: 89-109. In an aspect, an axillary bud-specific promoter comprises a polynucleotide sequence at least 97% identical to a polynucleotide selected from the group consisting of SEQ ID NOs: 89-109. In an aspect, an axillary bud-specific promoter comprises a polynucleotide sequence at least 98% identical to a polynucleotide selected from the group consisting of SEQ ID NOs: 89-109. In an aspect, an axillary bud-specific promoter comprises a polynucleotide sequence at least 99% identical to a polynucleotide selected from the group consisting of SEQ ID NOs: 89-109. In an aspect, an axillary bud-specific promoter comprises a polynucleotide sequence 100% identical to a polynucleotide selected from the group consisting of SEQ ID NOs: 89-109.

In one aspect, this disclosure provides a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, where the modified tobacco plant comprises no suckers or reduced suckers after topping as compared to a control tobacco plant when grown under comparable growth conditions.

In another aspect, this disclosure provides a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In a further aspect, this disclosure provides a method for producing a modified tobacco plant comprising: (a) introducing a recombinant DNA construct to at least one tobacco cell, where the recombinant DNA construct comprises a heterologous promoter operably linked to a nucleic acid encoding a polypeptide selected from the group consisting of a cyclin, a cyclin-dependent kinase (CDK), a CDK inhibitor, a MYB, and a WRKY transcription factor; (b) selecting at least one tobacco cell comprising the recombinant DNA construct; and (c) regenerating a modified tobacco plant from the at least one tobacco cell selected in step (b), where the modified tobacco plant comprises no suckers or reduced suckers after topping as compared to a control tobacco plant lacking the recombinant DNA construct when grown under comparable growth conditions. In an aspect, this method further comprises (d) growing the modified tobacco plant regenerated in step (c). In another aspect, this method further comprises (e) crossing the modified tobacco plant grown in step (d) with a second tobacco plant; and (f) obtaining at least one seed from the crossing in step (e).

In an aspect, this disclosure provides a method comprising transforming a tobacco cell with a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor. In in aspect, this method further comprises regenerating a modified tobacco plant from said tobacco cell, wherein said modified tobacco plant comprises said recombinant DNA construct.

In one aspect, this disclosure provides recombinant DNA constructs comprising polynucleotides provided herein. As used herein, the term "recombinant DNA construct" refers to a construct formed by laboratory methods of genetic recombination, such as molecular cloning. In an aspect, a recombinant DNA construct is synthetically produced. In another aspect, a recombinant DNA construct comprises a promoter operably linked to a heterologous polynucleotide sequence. In an aspect, a recombinant DNA construct comprises a polynucleotide sequence that encodes an amino acid sequence. In another aspect, a recombinant DNA construct comprises a polynucleotide sequence encoding a small RNA or a prescursor thereof. In an aspect, a recombinant DNA construct comprises a plasmid. In another aspect, a recombinant DNA construct comprises a vector.

As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In an aspect, a vector provided herein comprises a promoter. In an aspect, a vector provided herein comprises an axillary bud-specific promoter. In an aspect, a vector provided herein comprises an axillary bud-preferred promoter. In another aspect, a vector provided herein comprises a small RNA. In another aspect, a vector provided herein comprises a small RNA precursor. In an aspect, a vector provided herein comprises an artificial miRNA. In another aspect, a vector provided herein comprises an artificial miRNA precursor. In another aspect, a vector provided herein comprises a sequence at least 80% identical to a sequence selected from the group consisting of SEQ ID NOs: 1-44 and 89-113, or fragments thereof. In another aspect, a vector provided herein comprises a sequence at least 85% identical to a sequence selected from the group consisting of SEQ ID NOs: 1-44 and 89-113, or fragments thereof. In another aspect, a vector provided herein comprises a sequence at least 90% identical to a sequence selected from the group consisting of SEQ ID NOs: 1-44 and 89-113, or fragments thereof. In another aspect, a vector provided herein comprises a sequence at least 95% identical to a sequence selected from the group consisting of SEQ ID NOs: 1-44 and 89-113, or fragments thereof. In another aspect, a vector provided herein comprises a sequence at least 96% identical to a sequence selected from the group consisting of SEQ ID NOs: 1-44 and 89-113, or fragments thereof. In another aspect, a vector provided herein comprises a sequence at least 97% identical to a sequence selected from the group consisting of SEQ ID NOs: 1-44 and 89-113, or fragments thereof. In another aspect, a vector provided herein comprises a sequence at least 98% identical to a sequence selected from the group consisting of SEQ ID NOs: 1-44 and 89-113, or fragments thereof. In another aspect, a vector provided herein comprises a sequence at least 99% identical to a sequence selected from the group consisting of SEQ ID NOs: 1-44 and 89-113, or fragments thereof. In another aspect, a vector provided herein comprises a sequence 100% identical to a sequence selected from the group consisting of SEQ ID NOs: 1-44 and 89-113, or fragments thereof.

As used herein, a "fragment" of a nucleic acid sequence or amino acid sequence comprises a contiguous segment of sequence comprising between 1% to 99.99% of the total length of a reference sequence. For example, if a nucleic acid sequence comprises 1000 nucleotides, a fragment of the nucleic acid sequence could comprise any number between 10 and 999 contiguous nucleotides of the reference sequence. This disclosure explicitly provides fragments of each of SEQ ID NOs: 1-114 where ever SEQ ID NOs 1-114 are referenced.

Numerous methods for introducing a recombinant DNA construct to a plant cell are known in the art, which can be used according to methods of the present application to produce a transgenic plant cell and plant. Any suitable method or technique for transformation of a plant cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, polyethylene glycol (PEG)-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a tobacco cell with any of the nucleic acid molecules provided herein.

In an aspect, a method of providing a nucleic acid molecule to a tobacco cell comprises *Agrobacterium*-mediated transformation. In another aspect, a method of providing a nucleic acid molecule to a cell comprises PEG-mediated transformation. In another aspect, a method of providing a nucleic acid molecule to a cell comprises biolistic transformation. In another aspect, a method of providing a nucleic acid molecule to a cell comprises liposome-mediated transfection (lipofection). In another aspect, a method of providing a nucleic acid molecule to a cell comprises lentiviral transfection.

Lipofection is described in e.g., U.S. Pat. Nos. 5,049,386, 4,946,787; and 4,897,355) and lipofection reagents are sold commercially (e.g., Transfectam™, which is the cationic lipid dioctadecylamidoglycylspermine (DOGS), and Lipofectin™, which is a 1:1 (w/w) liposome formulation of the cationic lipid N-[1-(2,3-dioleyloxy) propyl]-n,n,n-trimethyl-ammonium chloride (DOTMA) and dioleoyl phophotidyle-thanolamine (DOPE) in membrane-filtered water). Cationic and neutral lipids that are suitable for efficient receptor-recognition lipofection of polynucleotides include those of WO 91/17424 and WO 91/16024. Delivery can be to cells (e.g. in vitro or ex vivo administration) or target tissues (e.g. in vivo administration).

Any tobacco cell from which a fertile tobacco plant can be regenerated is contemplated as a useful recipient cell for practice of this disclosure. In an aspect, a recombinant DNA construct is introduced to a tobacco cell. In an aspect, a recombinant DNA construct is introduced to a tobacco protoplast cell. In another aspect, a recombinant DNA construct is introduced to a tobacco callus cell. In an aspect, a recombinant DNA construct is introduced to a tobacco cell selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference.

In one aspect, this disclosure provides a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, where the modified tobacco plant comprises no suckers or reduced suckers after topping as compared to a control tobacco plant when grown under comparable growth conditions.

In another aspect, this disclosure provides a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In a further aspect, this disclosure provides a method for producing a modified tobacco plant comprising: (a) introducing a recombinant DNA construct to at least one tobacco cell, where the recombinant DNA construct comprises a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor; (b) selecting at least one tobacco cell comprising the recombinant DNA construct; and (c) regenerating a modified tobacco plant from the at least one tobacco cell selected in step (b), where the modified tobacco plant comprises no suckers or reduced suckers after topping as compared to a control tobacco plant lacking the recombinant DNA construct when grown under comparable growth conditions. In an aspect, this method further comprises (d) growing the modified tobacco plant regenerated in step (c). In another aspect, this method further comprises (e) crossing the modified tobacco plant grown in step (d) with a second tobacco plant; and (f) obtaining at least one seed from the crossing in step (e).

In another aspect, this disclosure provides a method comprising transforming a tobacco cell with a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor. In an aspect, this method further comprises regenerating a modified tobacco plant from said tobacco cell, wherein said modified tobacco plant comprises said recombinant DNA construct.

As used herein, the term "small RNA molecule" refers to any non-coding RNA molecule. In addition to providing small RNA molecules, this disclosure also provides a small RNA precursor molecule for each small RNA molecule.

In an aspect, a small RNA molecule comprises between 18 nucleotides and 30 nucleotides in length. In another aspect, a small RNA molecule comprises between 18 nucleotides and 24 nucleotides in length. In another aspect, a small RNA molecule comprises between 18 nucleotides and 22 nucleotides in length.

In another aspect, a small RNA molecule is 18 nucleotides in length. In another aspect, a small RNA molecule is 19 nucleotides in length. In another aspect, a small RNA molecule is 20 nucleotides in length. In another aspect, a small RNA molecule is 21 nucleotides in length. In another aspect, a small RNA molecule is 22 nucleotides in length. In another aspect, a small RNA molecule is 23 nucleotides in length. In another aspect, a small RNA molecule is 24 nucleotides in length. In another aspect, a small RNA molecule is 25 nucleotides in length. In another aspect, a small RNA molecule is 26 nucleotides in length. In another aspect, a small RNA molecule is 27 nucleotides in length. In another aspect, a small RNA molecule is 28 nucleotides in length.

In another aspect, a small RNA molecule is at least 18 nucleotides in length. In another aspect, a small RNA molecule is at least 19 nucleotides in length. In another aspect, a small RNA molecule is at least 20 nucleotides in length. In another aspect, a small RNA molecule is at least 21 nucleotides in length. In another aspect, a small RNA molecule is at least 22 nucleotides in length. In another aspect, a small RNA molecule is at least 23 nucleotides in length. In another aspect, a small RNA molecule is at least 24 nucleotides in length. In another aspect, a small RNA molecule is at least 25 nucleotides in length. In another aspect, a small RNA molecule is at least 26 nucleotides in length. In another aspect, a small RNA molecule is at least 27 nucleotides in length. In another aspect, a small RNA molecule is at least 28 nucleotides in length.

In an aspect, a small RNA molecule comprises between 18 nucleotides and 30 nucleotides. In another aspect, a small RNA molecule comprises between 18 nucleotides and 24 nucleotides. In another aspect, a small RNA molecule comprises between 18 nucleotides and 21 nucleotides. In another aspect, a small RNA molecule comprises between 21 nucleotides and 24 nucleotides. In another aspect, a small RNA molecule comprises between 21 nucleotides and 30 nucleotides.

In an aspect, a small RNA molecule provided herein is a microRNA (miRNA). In an aspect, a small RNA molecule provided herein is an artificial miRNA. In another aspect, a small RNA molecule provided herein is a small interfering RNA (siRNA). In another aspect, a small RNA molecule provided herein is a heterochromatic siRNA (hc-siRNA). In another aspect, a small RNA molecule provided herein is a Piwi-interacting RNA (piRNA). In an aspect, a small RNA molecule provided herein is a double-stranded RNA (dsRNA). In another aspect, a small RNA molecule provided herein is a hairpin double-stranded RNA (hp-dsRNA). In another aspect, a small RNA molecule provided herein is a trans-acting siRNA (ta-siRNA). In another aspect, a small RNA molecule provided herein is a naturally occurring antisense siRNA (nat-siRNA). In another aspect, a small RNA molecule provided herein is a Cas9-guide RNA (gRNA). In another aspect, a small RNA molecule provided herein is a Cpf1-gRNA. In another aspect, a small RNA molecule provided herein is a CasX-gRNA. In another aspect, a small RNA molecule provided herein is a Csm1-gRNA.

In an aspect, a small RNA molecule is selected from the group consisting of a dsRNA, a siRNA, a ta-siRNA, and a miRNA. In another aspect, a small RNA molecule is selected from the group consisting of a miRNA, an siRNA, a hc-siRNA, a piRNA, a dsRNA, a hp-dsRNA, a ta-siRNA, a nat-siRNA, a Cas9-gRNA, a Cpf1-gRNA, a CasX-gRNA, and a Csm1-gRNA.

In an aspect, a small RNA molecule provided herein comprises a polynucleotide sequence having at least 90% identity or complementarity with an endogenous mRNA. In an aspect, a small RNA molecule provided herein comprises a polynucleotide sequence having at least 91% identity or complementarity with an endogenous mRNA. In an aspect, a small RNA molecule provided herein comprises a polynucleotide sequence having at least 92% identity or complementarity with an endogenous mRNA. In an aspect, a small RNA molecule provided herein comprises a polynucleotide sequence having at least 93% identity or complementarity with an endogenous mRNA. In an aspect, a small RNA molecule provided herein comprises a polynucleotide sequence having at least 94% identity or complementarity with an endogenous mRNA. In an aspect, a small RNA molecule provided herein comprises a polynucleotide sequence having at least 95% identity or complementarity with an endogenous mRNA. In an aspect, a small RNA molecule provided herein comprises a polynucleotide sequence having at least 96% identity or complementarity with an endogenous mRNA. In an aspect, a small RNA molecule provided herein comprises a polynucleotide sequence having at least 97% identity or complementarity with an endogenous mRNA. In an aspect, a small RNA molecule provided herein comprises a polynucleotide sequence having at least 98% identity or complementarity with an endogenous mRNA. In an aspect, a small RNA molecule provided herein comprises a polynucleotide sequence having at least 99% identity or complementarity with an endogenous mRNA. In an aspect, a small RNA molecule provided herein comprises a polynucleotide sequence having 100% identity or complementarity with an endogenous mRNA.

In an aspect, a small RNA molecule comprises a polynucleotide sequence having at least 85% identity or complementarity with a polynucleotide sequence selected from the group consisting of SEQ ID NOs: 1-44 and 113. In an aspect, a small RNA molecule comprises a polynucleotide sequence having at least 90% identity or complementarity with a polynucleotide sequence selected from the group consisting of SEQ ID NOs: 1-44 and 113. In an aspect, a small RNA molecule comprises a polynucleotide sequence having at least 91% identity or complementarity with a polynucleotide sequence selected from the group consisting of SEQ ID NOs: 1-44 and 113. In an aspect, a small RNA molecule comprises a polynucleotide sequence having at least 92% identity or complementarity with a polynucleotide sequence selected from the group consisting of SEQ ID NOs: 1-44 and 113. In an aspect, a small RNA molecule comprises a polynucleotide sequence having at least 93% identity or complementarity with a polynucleotide sequence selected from the group consisting of SEQ ID NOs: 1-44 and 113. In an aspect, a small RNA molecule comprises a polynucleotide sequence having at least 94% identity or complementarity with a polynucleotide sequence selected from the group consisting of SEQ ID NOs: 1-44 and 113. In an aspect, a small RNA molecule comprises a polynucleotide sequence having at least 95% identity or complementarity with a polynucleotide sequence selected from the group consisting of SEQ ID NOs: 1-44 and 113. In an aspect, a small RNA molecule comprises a polynucleotide sequence having at least 96% identity or complementarity with a polynucleotide sequence selected from the group consisting of SEQ ID NOs: 1-44 and 113. In an aspect, a small RNA molecule comprises a polynucleotide sequence having at least 97% identity or complementarity with a polynucleotide sequence selected from the group consisting of SEQ ID NOs: 1-44 and 113. In an aspect, a small RNA molecule comprises a polynucleotide sequence having at least 98% identity or complementarity with a polynucleotide sequence selected from the group consisting of SEQ ID NOs: 1-44 and 113. In an aspect, a small RNA molecule comprises a polynucleotide sequence having at least 99% identity or complementarity with a polynucleotide sequence selected from the group consisting of SEQ ID NOs: 1-44 and 113. In an aspect, a small RNA molecule comprises a polynucleotide sequence having 100% identity or complementarity with a polynucleotide sequence selected from the group consisting of SEQ ID NOs: 1-44 and 113.

In an aspect, a small RNA molecule comprises a polynucleotide sequence identical to, or complementary to, at least 16 contiguous nucleotides of a polynucleotide sequence selected from the group consisting of SEQ ID NOs: 1-44 and 113. In an aspect, a small RNA molecule comprises a polynucleotide sequence identical to, or complementary to, at least 17 contiguous nucleotides of a polynucleotide sequence selected from the group consisting of SEQ ID NOs: 1-44 and 113. In an aspect, a small RNA molecule comprises a polynucleotide sequence identical to, or complementary to, at least 18 contiguous nucleotides of a polynucleotide sequence selected from the group consisting of SEQ ID NOs: 1-44 and 113. In an aspect, a small RNA molecule comprises a polynucleotide sequence identical to, or complementary to, at least 19 contiguous nucleotides of a polynucleotide sequence selected from the group consisting of SEQ ID NOs: 1-44 and 113. In an aspect, a small RNA molecule comprises a polynucleotide sequence identical to, or complementary to, at least 20 contiguous nucleotides of a polynucleotide sequence selected from the group consisting of SEQ ID NOs: 1-44 and 113. In an aspect, a small RNA molecule comprises a polynucleotide sequence identical to, or complementary to, at least 21 contiguous nucleotides of a polynucleotide sequence selected from the group consisting of SEQ ID NOs: 1-44 and 113. In an aspect, a small RNA molecule comprises a polynucleotide sequence identical to, or complementary to, at least 22 contiguous nucleotides of a polynucleotide sequence selected from the group consisting of SEQ ID NOs: 1-44 and 113. In an aspect, a small RNA molecule comprises a polynucleotide sequence identical to, or complementary to, at least 23 contiguous nucleotides of a polynucleotide sequence selected from the group consisting of SEQ ID NOs: 1-44 and 113. In an aspect, a small RNA molecule comprises a polynucleotide sequence identical to, or complementary to, at least 24 contiguous nucleotides of a polynucleotide sequence selected from the group consisting of SEQ ID NOs: 1-44 and 113. In an aspect, a small RNA molecule comprises a polynucleotide sequence identical to, or complementary to, at least 25 contiguous nucleotides of a polynucleotide sequence selected from the group consisting of SEQ ID NOs: 1-44 and 113. In an aspect, a small RNA molecule comprises a polynucleotide sequence identical to, or complementary to, at least 26 contiguous nucleotides of a polynucleotide sequence selected from the group consisting of SEQ ID NOs: 1-44 and 113. In an aspect, a small RNA molecule comprises a polynucleotide sequence identical to, or complementary to, at least 27 contiguous nucleotides of a polynucleotide sequence selected from the group consisting of SEQ ID NOs: 1-44 and 113. In an aspect, a small RNA molecule comprises a polynucleotide sequence identical to, or complementary to, at least 28 contiguous nucleotides of a polynucleotide sequence selected from the group consisting of SEQ ID NOs: 1-44 and 113. In an aspect, a small RNA molecule comprises a polynucleotide sequence identical to, or complementary to, at least 29 contiguous nucleotides of a polynucleotide sequence selected from the group consisting of SEQ ID NOs: 1-44 and 113. In an aspect, a small RNA molecule comprises a polynucleotide sequence identical to, or complementary to, at least 30 contiguous nucleotides of a polynucleotide sequence selected from the group consisting of SEQ ID NOs: 1-44 and 113.

In an aspect, this disclosure provides a small RNA capable of reducing the expression of a polynucleotide encoding a cyclin. In an aspect, this disclosure provides a small RNA capable of reducing the translation of a polynucleotide encoding a cyclin. In an aspect, this disclosure provides a small RNA capable of reducing the expression of a polynucleotide encoding a CDK. In an aspect, this disclosure provides a small RNA capable of reducing the translation of a polynucleotide encoding a CDK. In an aspect, this disclosure provides a small RNA capable of reducing the expression of a polynucleotide encoding a CDKI. In an aspect, this disclosure provides a small RNA capable of reducing the translation of a polynucleotide encoding a CDKI. In an aspect, this disclosure provides a small RNA capable of reducing the expression of a polynucleotide encoding a MYB. In an aspect, this disclosure provides a small RNA capable of reducing the translation of a polynucleotide encoding a MYB. In an aspect, this disclosure provides a small RNA capable of reducing the expression of a polynucleotide encoding a WRKY transcription factor. In an aspect, this disclosure provides a small RNA capable of reducing the translation of a polynucleotide encoding a WRKY transcription factor.

MicroRNAs (miRNAs) are non-protein coding RNAs, generally of between about 19 to about 25 nucleotides (commonly about 20-24 nucleotides in plants), that guide cleavage in trans of target transcripts, negatively regulating the expression of genes involved in various regulation and development pathways. In some cases, miRNAs serve to guide in-phase processing of siRNA primary transcripts.

Many microRNA genes (MIR genes) have been identified and made publicly available in a database ("miRBase", available on line at microrna (dot) sanger (dot) ac (dot) uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA.

Transgenic expression of miRNAs (whether a naturally occurring sequence or an artificial sequence) can be employed to regulate expression of the miRNA's target gene or genes. Inclusion of a miRNA recognition site in a transgenically expressed transcript is also useful in regulating expression of the transcript. Recognition sites of miRNAs have been validated in all regions of an mRNA, including the 5' untranslated region, coding region, and 3' untranslated region, indicating that the position of the miRNA target site relative to the coding sequence may not necessarily affect suppression.

Because miRNAs are important regulatory elements in eukaryotes, transgenic suppression of miRNAs is useful for manipulating biological pathways and responses. Various utilities of miRNAs, their precursors, their recognition sites, and their promoters are described in detail in U.S. Patent Application Publication 2006/0200878 A1, incorporated by reference herein. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor, as demonstrated by Zeng et al. (2002) Mol. Cell, 9:1327-1333. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA . . . DELTA.G" or "ΔΔG") (see Khvorova et al. (2003) Cell, 114:209-216). Preferably 19-mers are selected that have all or most of the following characteristics: (1) a Reynolds score>4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at rna (dot) chem (dot) t (dot) u-tokyo (dot) ac (dot) jp/siexplorer.htm (see Katoh and Suzuki (2007) Nucleic Acids Res., 10.1093/nar/gkl1120); (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

In one aspect, an artificial miRNA provided herein is complementary to at least 18 contiguous nucleotides of a nucleic acid sequence selected from the group consisting of SEQ ID NOs: 1-44 and 113. In one aspect, an artificial miRNA provided herein is complementary to at least 19 contiguous nucleotides of a nucleic acid sequence selected from the group consisting of SEQ ID NOs: 1-44 and 113. In one aspect, an artificial miRNA provided herein is complementary to at least 20 contiguous nucleotides of a nucleic acid sequence selected from the group consisting of SEQ ID NOs: 1-44 and 113. In one aspect, an artificial miRNA provided herein is complementary to at least 21 contiguous nucleotides of a nucleic acid sequence selected from the group consisting of SEQ ID NOs: 1-44 and 113. In one aspect, an artificial miRNA provided herein is complementary to at least 22 contiguous nucleotides of a nucleic acid sequence selected from the group consisting of SEQ ID NOs: 1-44 and 113. In one aspect, an artificial miRNA provided herein is complementary to at least 23 contiguous nucleotides of a nucleic acid sequence selected from the group consisting of SEQ ID NOs: 1-44 and 113. In one aspect, an artificial miRNA provided herein is complementary to at least 24 contiguous nucleotides of a nucleic acid sequence selected from the group consisting of SEQ ID NOs: 1-44 and 113. In one aspect, an artificial miRNA provided herein is complementary to at least 25 contiguous nucleotides of a nucleic acid sequence selected from the group consisting of SEQ ID NOs: 1-44 and 113. In one aspect, an artificial miRNA provided herein is complementary to at least 26 contiguous nucleotides of a nucleic acid sequence selected from the group consisting of SEQ ID NOs: 1-44 and 113.

In one aspect, an artificial miRNA provided herein is at least 75% complementary to a nucleic acid sequence selected from the group consisting of SEQ ID NOs: 1-44 and 113. In one aspect, an artificial miRNA provided herein is at least 80% complementary to a nucleic acid sequence selected from the group consisting of SEQ ID NOs: 1-44 and 113. In one aspect, an artificial miRNA provided herein is at least 85% complementary to a nucleic acid sequence selected from the group consisting of SEQ ID NOs: 1-44 and 113. In one aspect, an artificial miRNA provided herein is at least 90% complementary to a nucleic acid sequence selected from the group consisting of SEQ ID NOs: 1-44 and 113. In one aspect, an artificial miRNA provided herein is at least 91% complementary to a nucleic acid sequence selected from the group consisting of SEQ ID NOs: 1-44 and 113. In one aspect, an artificial miRNA provided herein is at least 92% complementary to a nucleic acid sequence selected from the group consisting of SEQ ID NOs: 1-44 and 113. In one aspect, an artificial miRNA provided herein is at least 93% complementary to a nucleic acid sequence selected from the group consisting of SEQ ID NOs: 1-44 and 113. In one aspect, an artificial miRNA provided herein is at least 94% complementary to a nucleic acid sequence selected from the group consisting of SEQ ID NOs: 1-44 and 113. In one aspect, an artificial miRNA provided herein is at least 95% complementary to a nucleic acid sequence selected from the group consisting of SEQ ID NOs: 1-44 and 113. In one aspect, an artificial miRNA provided herein is at least 96% complementary to a nucleic acid sequence selected from the group consisting of SEQ ID NOs: 1-44 and 113. In one aspect, an artificial miRNA provided herein is at least 97% complementary to a nucleic acid sequence selected from the group consisting of SEQ ID NOs: 1-44 and 113. In one aspect, an artificial miRNA provided herein is at least 98% complementary to a nucleic acid sequence selected from the group consisting of SEQ ID NOs: 1-44 and 113. In one aspect, an artificial miRNA provided herein is at least 99% complementary to a nucleic acid sequence selected from the group consisting of SEQ ID NOs: 1-44 and 113. In one aspect, an artificial miRNA provided herein is 100% complementary to a nucleic acid sequence selected from the group consisting of SEQ ID NOs: 1-44 and 113.

In one aspect, an artificial miRNA provided herein reduces or eliminates RNA transcription or protein translation of a target gene.

In one aspect, an artificial miRNA, or a precursor thereof, is operably linked to an axillary bud-specific promoter. In another aspect, an artificial miRNA, or a precursor thereof, is operably linked to an axillary bud-preferred promoter. In another aspect, an artificial miRNA, or a precursor thereof, is operably linked to a promoter comprising a sequence selected from the group consisting of SEQ ID NOs: 89-109 and fragments thereof.

Tobacco is known in the art as a plant from the family Solanaceae. As used herein, a tobacco plant can be from any plant from the Nicotiana genus including, but not limited to Nicotiana tabacum, Nicotiana amplexicaulis PI 271989; Nicotiana benthamiana PI 555478; Nicotiana bigelovii PI 555485; Nicotiana debneyi; Nicotiana excelsior PI 224063; Nicotiana glutinosa PI 555507; Nicotiana goodspeedii PI 241012; Nicotiana gossei PI 230953; Nicotiana hesperis PI 271991; Nicotiana knightiana PI 555527; Nicotiana maritima PI 555535; Nicotiana megalosiphon PI 555536; Nicotiana nudicaulis PI 555540; Nicotiana paniculata PI 555545; Nicotiana plumbaginifolia PI 555548; Nicotiana repanda PI 555552; Nicotiana rustica; Nicotiana suaveolens PI 230960; Nicotiana sylvestris PI 555569; Nicotiana tomentosa PI 266379; Nicotiana tomentosiformis; and Nicotiana trigonophylla PI 555572. In an aspect, a tobacco plant described here is a Nicotiana tabacum plant.

In one aspect, modified tobacco plants, seeds, cells, hybrids, varieties, or lines provided herein are essentially derived from or in the genetic background of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, VA 359, or any commercial tobacco variety according to standard tobacco breeding techniques known in the art.

In an aspect, a modified tobacco plant is selected from the group consisting of a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a *Galpao* plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.

In another aspect, a modified tobacco cell is selected from the group consisting of a BU 64 cell, a CC 101 cell, a CC 200 cell, a CC 13 cell, a CC 27 cell, a CC 33 cell, a CC 35 cell, a CC 37 cell, a CC 65 cell, a CC 67 cell, a CC 301 cell, a CC 400 cell, a CC 500 cell, CC 600 cell, a CC 700 cell, a CC 800 cell, a CC 900 cell, a CC 1063 cell, a Coker 176 cell, a Coker 319 cell, a Coker 371 Gold cell, a Coker 48 cell, a CU 263 cell, a DF911 cell, a *Galpao* cell, a GL 26H cell, a GL 338 cell, a GL 350 cell, a GL 395 cell, a GL 600 cell, a GL 737 cell, a GL 939 cell, a GL 973 cell, a GF 157 cell, a GF 318 cell, an RJR 901 cell, an HB 04P cell, a K 149 cell, a K 326 cell, a K 346 cell, a K 358 cell, a K394 cell, a K 399 cell, a K 730 cell, an NC 196 cell, an NC 37NF cell, an NC 471 cell, an NC 55 cell, an NC 92 cell, an NC2326 cell, an NC 95 cell, an NC 925 cell, a PVH 1118 cell, a PVH 1452 cell, a PVH 2110 cell, a PVH 2254 cell, a PVH 2275 cell, a VA 116 cell, a VA 119 cell, a KDH 959 cell, a KT 200 cell, a KT204LC cell, a KY 10 cell, a KY 14 cell, a KY 160 cell, a KY 17 cell, a KY 171 cell, a KY 907 cell, a KY 907LC cell, a KTY14×L8 LC cell, a Little Crittenden cell, a McNair 373 cell, a McNair 944 cell, a male sterile KY 14×L8 cell, a Narrow Leaf Madole cell, a MS KY171 cell, a Narrow Leaf Madole (phph) cell, a MS Narrow Leaf Madole cell, a MS TND950 cell, a PD 7302LC cell, a PD 7305LC cell, a PD 7309LC cell, a PD 7312LC cell, a PD 7318LC cell, a PD 7319LC cell, a MSTKS 2002 cell, a TKF 2002 cell, a TKF 6400 cell, a TKF 4028 cell, a TKF 4024 cell, a KT206LC cell, a KT209LC cell, a KT210LC cell, a KT212LC cell, an NC 100 cell, an NC 102 cell, an NC 2000 cell, an NC 291 cell, an NC 297 cell, an NC 299 cell, an NC 3 cell, an NC 4 cell, an NC 5 cell, an NC 6 cell, an NC7 cell, an NC 606 cell, an NC 71 cell, an NC 72 cell, an NC 810 cell, an NC BH 129 cell, an NC 2002 cell, a Neal Smith Madole cell, an OXFORD 207 cell, a 'Perique' cell, a PVH03 cell, a PVH09 cell, a PVH19 cell, a PVH50 cell, a PVH51 cell, an R 610 cell, an R 630 cell, an R 7-11 cell, an R 7-12 cell, an RG 17 cell, an RG 81 cell, an RG H51 cell, an RGH 4 cell, an RGH 51 cell, an RS 1410 cell, a Speight 168 cell, a Speight 172 cell, a Speight 179 cell, a Speight 210 cell, a Speight 220 cell, a Speight 225 cell, a Speight 227 cell, a Speight 234 cell, a Speight G-28 cell, a Speight G-70 cell, a Speight H-6 cell, a Speight H20 cell, a Speight NF3 cell, a TI 1406 cell, a TI 1269 cell, a TN 86 cell, a TN86LC cell, a TN 90 cell, a TN90LC cell, a TN 97 cell, a TN97LC cell, a TN D94 cell, a TN D950 cell, a TR (Tom Rosson) Madole cell, a VA 309 cell, and a VA 359 cell.

In another aspect, a modified tobacco seed is selected from the group consisting of a BU 64 seed, a CC 101 seed, a CC 200 seed, a CC 13 seed, a CC 27 seed, a CC 33 seed, a CC 35 seed, a CC 37 seed, a CC 65 seed, a CC 67 seed, a CC 301 seed, a CC 400 seed, a CC 500 seed, CC 600 seed, a CC 700 seed, a CC 800 seed, a CC 900 seed, a CC 1063 seed, a Coker 176 seed, a Coker 319 seed, a Coker 371 Gold seed, a Coker 48 seed, a CU 263 seed, a DF911 seed, a *Galpao* seed, a GL 26H seed, a GL 338 seed, a GL 350 seed, a GL 395 seed, a GL 600 seed, a GL 737 seed, a GL 939 seed, a GL 973 seed, a GF 157 seed, a GF 318 seed, an RJR 901 seed, an HB 04P seed, a K 149 seed, a K 326 seed, a K 346 seed, a K 358 seed, a K394 seed, a K 399 seed, a K 730 seed, an NC 196 seed, an NC 37NF seed, an NC 471 seed, an NC 55 seed, an NC 92 seed, an NC2326 seed, an NC 95 seed, an NC 925 seed, a PVH 1118 seed, a PVH 1452 seed, a PVH 2110 seed, a PVH 2254 seed, a PVH 2275 seed, a VA 116 seed, a VA 119 seed, a KDH 959 seed, a KT 200 seed, a KT204LC seed, a KY 10 seed, a KY 14 seed, a KY 160 seed, a KY 17 seed, a KY 171 seed, a KY 907 seed, a KY 907LC seed, a KTY 14×L8 LC seed, a Little Crittenden seed, a McNair 373 seed, a McNair 944 seed, a male sterile KY 14×L8 seed, a Narrow Leaf Madole seed, a MS KY171 seed, a Narrow Leaf Madole (phph) seed, a MS Narrow Leaf Madole seed, a MS TND950 seed, a PD 7302LC seed, a PD 7305LC seed, a PD 7309LC seed, a PD 7312LC seed, a PD 7318LC seed, a PD 7319LC seed, a MSTKS 2002 seed, a TKF 2002 seed, a TKF 6400 seed, a TKF 4028 seed, a TKF 4024 seed, a KT206LC seed, a KT209LC seed, a KT210LC seed, a KT212LC seed, an NC 100 seed, an NC 102 seed, an NC 2000 seed, an NC 291 seed, an NC 297 seed, an NC 299 seed, an NC 3 seed, an NC 4 seed, an NC 5 seed, an NC 6 seed, an NC7 seed, an NC 606 seed, an NC 71 seed, an NC 72 seed, an NC 810 seed, an NC BH 129 seed, an NC 2002 seed, a Neal Smith Madole seed, an OXFORD 207 seed, a 'Perique' seed, a PVH03 seed, a PVH09 seed, a PVH19 seed, a PVH50 seed, a PVH51 seed, an R 610 seed, an R 630 seed, an R 7-11 seed, an R 7-12 seed, an RG 17 seed, an RG 81 seed, an RG H51 seed, an RGH 4 seed, an RGH 51 seed, an RS 1410 seed, a Speight 168 seed, a Speight 172 seed, a Speight 179 seed, a Speight 210 seed, a Speight 220 seed, a Speight 225 seed, a Speight 227 seed, a Speight 234 seed, a Speight G-28 seed, a Speight G-70 seed, a Speight H-6 seed, a Speight H20 seed, a Speight NF3 seed, a TI 1406 seed, a TI 1269 seed, a TN 86 seed, a TN86LC seed, a TN 90 seed, a TN90LC seed, a TN 97 seed, a TN97LC seed, a TN D94 seed, a TN D950 seed, a TR (Tom Rosson) Madole seed, a VA 309 seed, and a VA 359 seed.

As used herein, "tobacco plant" refers to a whole tobacco plant. A tobacco cell or tobacco tissue culture derived from a tobacco plant can comprise any tobacco plant parts or tobacco plant organs (e.g., leaves, stems, roots, etc.), tobacco plant tissues, tobacco seeds, tobacco plant cells, and/or progeny of the same. A progeny plant can be from any filial generation, e.g., $F_1$, $F_2$, $F_3$, $F_4$, $F_5$, $F_6$, $F_7$, etc. A tobacco plant cell is a biological cell of a tobacco plant, taken from a tobacco plant or derived through culture from a cell taken from a tobacco plant. As used herein, "seedling" refers to a tobacco plant that is equal to, or less than, 14 days post-germination.

In one aspect, a tobacco plant part provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic plant cells. Somatic cells, contrary to germline cells, do not mediate plant reproduction.

Provided tobacco cells, tobacco tissues and tobacco organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a trichome cell, a root hair, or a storage root.

In an aspect, this disclosure provides a tobacco protoplast cell. In another aspect, this disclosure provides a tobacco callus cell. In another aspect, this disclosure provides a tobacco seed cell. In another aspect, this disclosure provides a tobacco fruit cell. In another aspect, this disclosure provides a tobacco leaf cell. In another aspect, this disclosure provides a tobacco cotyledon cell. In another aspect, this disclosure provides a tobacco hypocotyl cell. In another aspect, this disclosure provides a tobacco meristem cell. In another aspect, this disclosure provides a tobacco embryo cell. In another aspect, this disclosure provides a tobacco root cell. In another aspect, this disclosure provides a tobacco shoot cell. In another aspect, this disclosure provides a tobacco stem cell. In another aspect, this disclosure provides a tobacco flower cell. In another aspect, this disclosure provides a tobacco inflorescence cell. In another aspect, this disclosure provides a tobacco stalk cell. In another aspect, this disclosure provides a tobacco pedicel cell. In another aspect, this disclosure provides a tobacco style cell. In another aspect, this disclosure provides a tobacco stigma cell. In another aspect, this disclosure provides a tobacco receptacle cell. In another aspect, this disclosure provides a tobacco petal cell. In another aspect, this disclosure provides a tobacco sepal cell. In another aspect, this disclosure provides a tobacco pollen cell. In another aspect, this disclosure provides a tobacco anther cell. In another aspect, this disclosure provides a tobacco filament cell. In another aspect, this disclosure provides a tobacco ovary cell. In another aspect, this disclosure provides a tobacco ovule cell. In another aspect, this disclosure provides a tobacco pericarp cell. In another aspect, this disclosure provides a tobacco phloem cell.

This disclosure provides modified tobacco plants, modified tobacco plant parts, modified tobacco seeds, and modified tobacco cells and methods of making the same. In an aspect, this disclosure provides a tobacco leaf of a modified tobacco plant. In another aspect, this disclosure provides a tobacco seed of a modified tobacco plant. In another aspect, this disclosure provides a tobacco stem of a modified tobacco plant. In a further aspect, this disclosure provides a tobacco plant part of a modified tobacco plant. In another aspect, this disclosure provides a tobacco cell of a modified tobacco plant. In a further aspect, this disclosure provides a dried tobacco leaf of a modified tobacco plant. In still a further aspect, this disclosure provides a cured tobacco leaf of a modified tobacco plant. In yet another aspect, this disclosure provides a fermented tobacco leaf of a modified tobacco plant.

In another aspect, this disclosure provides an alkaloid extracted from a modified tobacco plant. In another aspect, this disclosure provides nicotine extracted from a modified tobacco plant. In another aspect, this disclosure provides anatabine extracted from a modified tobacco plant. In another aspect, this disclosure provides anabasine extracted from a modified tobacco plant. In another aspect, this disclosure provides nornicotine extracted from a modified tobacco plant.

In an aspect, a modified tobacco plant, plant part, seed, cell, or genome is cisgenic. As used herein, "cisgenic" refers to genetic modification of a plant, plant cell, or plant genome in which all parts (e.g., promoter, donor nucleic acid, selection gene) have only plant origins (i.e., no non-plant origin parts are used). Cisgenic plants, plant cells, and plant genomes provided herein can lead to ready-to-use tobacco lines. In another aspect, a modified tobacco plant provided herein comprises no non-tobacco genetic material or sequences.

In an aspect, a modified plant comprises an increased leaf yield mass as compared to a control tobacco plant when grown under comparable conditions. In an aspect, leaf yield is selected from the group consisting of fresh leaf yield mass, dry leaf yield mass, and cured leaf yield mass.

In an aspect, a modified plant comprises at least 0.5% increased leaf yield mass as compared to a control tobacco plant when grown under comparable conditions. In an aspect, a modified plant comprises at least 0.5% increased fresh leaf yield mass as compared to a control tobacco plant when grown under comparable conditions. In an aspect, a modified plant comprises at least 0.5% increased dry leaf yield mass as compared to a control tobacco plant when grown under comparable conditions. In an aspect, a modified plant comprises at least 0.5% increased cured leaf yield mass as compared to a control tobacco plant when grown under comparable conditions. In an aspect, a modified plant comprises at least 1% increased leaf yield mass as compared to a control tobacco plant when grown under comparable conditions. In an aspect, a modified plant comprises at least 1% increased fresh leaf yield mass as compared to a control tobacco plant when grown under comparable conditions. In an aspect, a modified plant comprises at least 1% increased dry leaf yield mass as compared to a control tobacco plant when grown under comparable conditions. In an aspect, a modified plant comprises at least 1% increased cured leaf yield mass as compared to a control tobacco plant when grown under comparable conditions. In an aspect, a modified plant comprises at least 2% increased leaf yield mass as compared to a control tobacco plant when grown under comparable conditions. In an aspect, a modified plant comprises at least 2% increased fresh leaf yield mass as compared to a control tobacco plant when grown under comparable conditions. In an aspect, a modified plant comprises at least 2% increased dry leaf yield mass as compared to a control tobacco plant when grown under comparable conditions. In an aspect, a modified plant comprises at least 2% increased cured leaf yield mass as compared to a control tobacco plant when grown under comparable conditions. In an aspect, a modified plant comprises at least 3% increased leaf yield mass as compared to a control tobacco plant when grown under comparable conditions. In an aspect, a modified plant comprises at least 3% increased fresh leaf yield mass as compared to a control tobacco plant when grown under comparable conditions. In an aspect, a modified plant comprises at least 3% increased dry leaf yield mass as compared to a control tobacco plant when grown under comparable conditions. In an aspect, a modified plant comprises at least 3% increased cured leaf yield mass as compared to a control tobacco plant when grown under comparable conditions. In an aspect, a modified plant comprises at least 4% increased leaf yield mass as compared to a control tobacco plant when grown under comparable conditions. In an aspect, a modified plant comprises at least 4% increased fresh leaf yield mass as compared to a control tobacco plant when grown under comparable conditions. In an aspect, a modified plant comprises at least 4% increased dry leaf yield mass as compared to a control tobacco plant when grown under comparable conditions. In an aspect, a modified plant comprises at least 4% increased cured leaf yield mass as compared to a control tobacco plant when grown under comparable conditions. In an aspect, a modified plant comprises at least 5% increased leaf yield mass as compared to a control tobacco plant when grown under comparable conditions. In an aspect, a modified plant comprises at least 5% increased fresh leaf yield mass as compared to a control tobacco plant when grown under comparable conditions. In an aspect, a modified plant comprises at least 5% increased dry leaf yield mass as compared to a control tobacco plant when grown under comparable conditions. In an aspect, a modified plant comprises at least 5% increased cured leaf yield mass as compared to a control tobacco plant when grown under comparable conditions. In an aspect, a modified plant comprises at least 250% increased leaf yield mass as compared to a control tobacco plant when grown under comparable conditions. In an aspect, a modified plant comprises at least 250% increased fresh leaf yield mass as compared to a control tobacco plant when grown under comparable conditions. In an aspect, a modified plant comprises at least 250% increased dry leaf yield mass as compared to a control tobacco plant when grown under comparable conditions. In an aspect, a modified plant comprises at least 250% increased cured leaf yield mass as compared to a control tobacco plant when grown under comparable conditions. In an aspect, a modified plant comprises at least 25% increased leaf yield mass as compared to a control tobacco plant when grown under comparable conditions. In an aspect, a modified plant comprises at least 25% increased fresh leaf yield mass as compared to a control tobacco plant when grown under comparable conditions. In an aspect, a modified plant comprises at least 25% increased dry leaf yield mass as compared to a control tobacco plant when grown under comparable conditions. In an aspect, a modified plant comprises at least 25% increased cured leaf yield mass as compared to a control tobacco plant when grown under comparable conditions. In an aspect, a modified plant comprises at least 50% increased leaf yield mass as compared to a control tobacco plant when grown under comparable conditions. In an aspect, a modified plant comprises at least 50% increased fresh leaf yield mass as compared to a control tobacco plant when grown under comparable conditions. In an aspect, a modified plant comprises at least 50% increased dry leaf yield mass as compared to a control tobacco plant when grown under comparable conditions. In an aspect, a modified plant comprises at least 50% increased cured leaf yield mass as compared to a control tobacco plant when grown under comparable conditions. In an aspect, a modified plant comprises at least 75% increased leaf yield mass as compared to a control tobacco plant when grown under comparable conditions. In an aspect, a modified plant comprises at least 75% increased fresh leaf yield mass as compared to a control tobacco plant when grown under comparable conditions. In an aspect, a modified plant comprises at least 75% increased dry leaf yield mass as compared to a control tobacco plant when grown under comparable conditions. In an aspect, a modified plant comprises at least 75% increased cured leaf yield mass as compared to a control tobacco plant when grown under comparable conditions. In an aspect, a modified plant comprises at least 100% increased leaf yield mass as compared to a control tobacco plant when grown under comparable conditions. In an aspect, a modified plant comprises at least 100% increased fresh leaf yield mass as compared to a control tobacco plant when grown under comparable conditions. In an aspect, a modified plant comprises at least 100% increased dry leaf yield mass as compared to a control tobacco plant when grown under comparable conditions. In an aspect, a modified plant comprises at least 100% increased cured leaf yield mass as compared to a control tobacco plant when grown under comparable conditions.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation.

In an aspect, cured tobacco leaf provided herein is selected from the group consisting of air-cured tobacco leaf, fire-cured tobacco leaf, sun-cured tobacco leaf, and flue-cured tobacco leaf. In another aspect, cured tobacco material provided herein is selected from the group consisting of air-cured tobacco material, fire-cured tobacco material, sun-cured tobacco material, and flue-cured tobacco material. In an aspect, cured tobacco leaf is from a tobacco variety selected from the group consisting of a flue-cured variety, a bright variety, a Burley variety, a Virginia variety, a Maryland variety, a dark variety, an Oriental variety, and a Turkish variety. In another aspect, cured tobacco material is from a tobacco variety selected from the group consisting of a flue-cured variety, a bright variety, a Burley variety, a Virginia variety, a Maryland variety, a dark variety, an Oriental variety, and a Turkish variety.

Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is flue-cured, sun-cured, air-cured, or fire-cured.

In one aspect, tobacco plants, seeds, plant parts, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant parts, plant cells, and plant genomes provided herein are from a tobacco type selected from the group consisting of Burley tobacco, Maryland tobacco, bright tobacco, Virginia tobacco, Oriental tobacco, Turkish tobacco, and Galpão tobacco.

In one aspect, a modified tobacco plant provided herein is of a tobacco variety selected from the group consisting of a flue-cured variety, a bright variety, a Burley variety, a Virginia variety, a Maryland variety, a Galpão variety, a dark variety, an Oriental variety, and a Turkish variety.

In one aspect, a modified tobacco plant provided herein is selected from the group consisting of a flue-cured variety tobacco plant, a bright variety tobacco plant, a Burley variety tobacco plant, a Virginia variety tobacco plant, a Maryland variety tobacco plant, a Galpão variety tobacco plant, a dark variety tobacco plant, an Oriental variety tobacco plant, and a Turkish variety tobacco plant. In one aspect, a modified tobacco cell provided herein is selected from the group consisting of a flue-cured variety tobacco cell, a bright variety tobacco cell, a Burley variety tobacco cell, a Virginia variety tobacco cell, a Maryland variety tobacco cell, a Galpão variety tobacco cell, a dark variety tobacco cell, an Oriental variety tobacco cell, and a Turkish variety tobacco cell. In one aspect, a modified tobacco plant part provided herein is selected from the group consisting of a flue-cured variety tobacco plant part, a bright variety tobacco plant part, a Burley variety tobacco plant part, a Virginia variety tobacco plant part, a Maryland variety tobacco plant part, a Galpão variety tobacco plant part, a dark variety tobacco plant part, an Oriental variety tobacco plant part, and a Turkish variety tobacco plant part. In one aspect, a modified tobacco seed provided herein is selected from the group consisting of a flue-cured variety tobacco seed, a bright variety tobacco seed, a Burley variety tobacco seed, a Virginia variety tobacco seed, a Maryland variety tobacco seed, a Galpão variety tobacco seed, a dark variety tobacco seed, an Oriental variety tobacco seed, and a Turkish variety tobacco seed.

As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties. In an aspect, a modified tobacco plant provided herein is a hybrid tobacco plant. In another aspect, a modified tobacco seed provided herein is a hybrid tobacco seed.

As used herein, the term "crossing" refers to the deliberate mating of two plants. In an aspect, crossing comprises pollination and/or fertilization of a first tobacco plant by a second tobacco plant. The two tobacco plants being crossed can be distantly related, closely related, or identical. In an aspect, the two tobacco plants being crossed are both modified tobacco plants. In an aspect, the two tobacco plants being crossed are of the same tobacco variety. In an aspect, the two tobacco plants being crossed are of two different tobacco varieties. In an aspect, one of the two tobacco plants being crossed is male sterile. In an aspect, one of the two tobacco plants being crossed is female sterile. In an aspect, at least one of the two tobacco plants being crossed is a hybrid tobacco plant. In an aspect, at least one of the two tobacco plants being crossed is a modified tobacco plant.

In an aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the at least one tobacco plant comprises no suckers or reduced suckers after topping as compared to the control tobacco plant when grown under comparable growth conditions; and (b) selecting for progeny tobacco plants that exhibit no suckers or reduced suckers after topping compared to a control tobacco plant of the same cross grown under comparable growth conditions.

In another aspect, this disclosure provides a method for producing a modified tobacco plant comprising: (a) crossing at least one tobacco plant of a first tobacco variety with at least one tobacco plant of a second tobacco variety, where the at least one tobacco plant of the first tobacco variety comprises a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor, where the at least one tobacco plant comprises no suckers or reduced suckers after topping as compared to a control tobacco plant when grown under comparable growth conditions; and (b) selecting for progeny tobacco plants that exhibit no suckers or reduced suckers after topping compared to a control tobacco plant of the same cross grown under comparable growth conditions.

In a further aspect, this disclosure provides a method for producing a modified tobacco plant comprising: (a) crossing at least one tobacco plant of a first tobacco variety with at least one tobacco plant of a second tobacco variety, where the at least one tobacco plant of said first tobacco variety comprises a recombinant DNA construct comprising a heterologous promoter operably linked to a nucleic acid encoding at least one small RNA molecule capable of reducing the expression of an endogenous genomic locus that encodes a polypeptide selected from the group consisting of a cyclin, a cyclin-dependent kinase (CDK), a CDK inhibitor, a MYB, and a WRKY transcription factor, where the at least one tobacco plant comprises no suckers or reduced suckers after topping as compared to a control tobacco plant when grown under comparable growth conditions; and (b) selecting for progeny tobacco plants that exhibit no suckers or reduced suckers after topping compared to a control tobacco plant of the same cross grown under comparable growth conditions.

In one aspect, a tobacco variety provided herein is male sterile. In another aspect, a tobacco variety provided herein is cytoplasmic male sterile (CMS). In an aspect, a modified tobacco plant provided herein is male sterile. In another aspect, a modified tobacco plant provided herein is cytoplasmic male sterile. Male sterile tobacco plants can be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N. Y. 761 pp.

In another aspect, a tobacco variety provided herein is female sterile. As a non-limiting example, female sterile plants can be made by mutating the STIGI gene. See, for example, Goldman et al. 1994, *EMBO Journal* 13:2976-2984. In an aspect, a modified tobacco plant provided herein is female sterile.

Flue-cured tobaccos (also called "Virginia" or "bright" tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the United States of America. In one aspect, modified tobacco plants or seeds provided herein are of a flue-cured tobacco variety selected from the group consisting of CC 13, CC 27, CC 33, CC35, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, modified tobacco plants or seeds provided herein are in a flue-cured tobacco variety selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In a further aspect, modified tobacco plants or seeds provided herein are in a flue-cured variety selected from the group consisting of K326, K346, and NC196.

Air-cured tobaccos include "Burley," "Maryland," and "dark" tobaccos. The common factor linking air-cured tobaccos is that curing occurs primarily without artificial sources of heat and humidity. Burley tobaccos are light to dark brown in color, high in oil, and low in sugar. Burley tobaccos are typically air-cured in barns. Major Burley growing countries include Argentina, Brazil, Italy, Malawi, and the United States of America.

Maryland tobaccos are extremely fluffy, have good burning properties, low nicotine and a neutral aroma. Major Maryland growing countries include the United States of America and Italy.

In one aspect, modified tobacco plants or seeds provided herein are of a Burley tobacco variety selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, HB4488PLC, PD 7319LC, Bu 21×Ky 10, HB04P, Ky 14×L 8, Kt 200, Newton 98, Pedigo 561, Pf561 and Va 509. In a further aspect, modified tobacco plants or seeds provided herein are in a Burley variety selected from the group consisting of TN 90, KT 209, KT 206, KT212, and HB 4488. In another aspect, modified tobacco plants or seeds provided herein are of a Maryland tobacco variety selected from the group consisting of Md 10, Md 40, Md 201, Md 609, Md 872 and Md 341.

Dark air-cured tobaccos are distinguished from other tobacco types primarily by its curing process, which gives dark air-cured tobacco its medium-brown to dark-brown color and a distinct aroma. Dark air-cured tobaccos are mainly used in the production of chewing tobacco and snuff. In one aspect, modified tobacco plants or seeds provided herein are of a dark air-cured tobacco variety selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Dark fire-cured tobaccos are typically used for making pipe blends, cigarettes, chewing tobacco, snuff, and strong-tasting cigars. Major growing regions for dark fire-cured tobaccos are Tennessee, Kentucky, and Virginia in the United States of America. In one aspect, modified tobacco plants or seeds provided herein are of a dark fire-cured tobacco variety selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant size, small leaf size, and unique aroma properties of Oriental tobacco varieties are a result of their adaptation to the poor soil and stressful climatic conditions in which they have been developed. In one aspect, modified tobacco plants or seeds provided herein are of an Oriental tobacco variety selected from the group consisting of Izmir, Katerini, Samsun, Basma, Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

The tobacco plants, plant parts, and tobacco material provided herein can be used in any tobacco product. As used herein, "tobacco product" is defined as any product made or derived from tobacco that is intended for human use or consumption. In an aspect, a tobacco product provided herein comprises cured components from a tobacco plant provided herein. In another aspect, a tobacco product provided herein comprises cured tobacco leaves from a tobacco plant provided herein. In an aspect, this disclosure provides a tobacco product comprising cured tobacco material from any tobacco plant provided herein.

In an aspect, this disclosure provides a tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety, and where the modified tobacco plant comprises no suckers or reduced suckers after topping as compared to the control tobacco plant when grown under comparable growth conditions. In another aspect, this disclosure provides a tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, where the mutation is not present in the endogenous gene in a control tobacco plant of the same variety.

In an aspect, this disclosure provides a method comprising preparing a tobacco product using cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said modified tobacco plant comprises no suckers or reduced suckers after topping as compared to a control tobacco plant when grown under comparable growth conditions. In another aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and wherein said modified tobacco plant comprises no suckers or reduced suckers after topping as compared to a control tobacco plant when grown under comparable growth conditions.

In an aspect, this disclosure provides a tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and where the modified tobacco plant comprises no suckers or reduced suckers after topping as compared to a control tobacco plant when grown under comparable growth conditions. In another aspect, this disclosure provides a tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In an aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, wherein said modified tobacco plant comprises no suckers or reduced suckers after topping as compared to a control tobacco plant when grown under comparable growth conditions. In another aspect, this disclosure provides a method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

In an aspect, this disclosure provides a tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, where the modified tobacco plant comprises no suckers or reduced suckers after topping as compared to a control tobacco plant when grown under comparable growth conditions. In another aspect, this disclosure provides a tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

In an aspect, this disclosure provides a method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions. In another aspect, this disclosure provides a method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

Alkaloid compounds can be extracted, or isolated, from any tobacco plant or plant part provided herein. In an aspect, a tobacco product provided herein comprises an alkaloid extracted from a modified tobacco plant or part thereof. In another aspect, a tobacco product provided herein comprises nicotine extracted from a tobacco plant or tobacco plant part. In another aspect, a tobacco product provided herein comprises anatabine extracted from a tobacco plant or tobacco plant part. In another aspect, a tobacco product provided herein comprises anabasine extracted from a tobacco plant or tobacco plant part. In an aspect, a tobacco product provided herein comprises nornicotine extracted from a tobacco plant or plant part. In an aspect, a tobacco product provided herein comprises an alkaloid extracted from a modified tobacco plant, where the alkaloid is selected from the group consisting of nicotine, nornicotine, anatabine, and anabasine.

Alkaloid compounds extracted from tobacco plants or tobacco plant parts provided herein can be used to produce compositions suitable for use with non-combustible products. Exemplary non-combustible products include electronic cigarettes ("e-cigarettes"), electronic smoking articles, e-vapor products, aerosolized vapor products, and heated tobacco products. In an aspect, a non-combustible product provided herein comprises an alkaloid extracted from a tobacco plant or tobacco plant part provided herein. In an aspect, a non-combustible product provided herein comprises nicotine extracted from a tobacco plant or tobacco plant part provided herein. In an aspect, a non-combustible product provided herein comprises anabasine extracted from a tobacco plant or tobacco plant part provided herein. In an aspect, a non-combustible product provided herein comprises anatabine extracted from a tobacco plant or tobacco plant part provided herein. In an aspect, a non-combustible product provided herein comprises nornicotine extracted from a tobacco plant or tobacco plant part provided herein.

In one aspect, a non-combustible product provided herein is an e-cigarette. In another aspect, a non-combustible product provided herein is an electronic smoking article. In another aspect, a non-combustible product provided herein is an aerosolized vapor product. In another aspect, a non-combustible product provided herein is a heated tobacco product. In another aspect, a non-combustible product provided herein is an e-vapor product.

Tobacco products provided herein include, without limitation, cigarette products (e.g., cigarettes, bidi cigarettes, kreteks), cigar products (e.g., cigars, cigar wrapping tobacco, cigarillos), pipe tobacco products, products derived from tobacco, tobacco-derived nicotine products, smokeless tobacco products (e.g., moist snuff, dry snuff, chewing tobacco, moist smokeless tobacco, fine cut chewing tobacco, long cut chewing tobacco, pouched chewing tobacco, snus), films, chewables (e.g., gum), lozenges, dissolving strips, tabs, tablets, shaped parts, gels, consumable units, insoluble matrices, hollow shapes, reconstituted tobacco, expanded tobacco, and the like. See, for example, U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In one aspect, this disclosure provides nicotine derived from and a method of producing nicotine from a modified tobacco plant provided herein for use in a product.

In one aspect, a method provided herein comprises preparing a tobacco product using a cured tobacco leaf from a modified tobacco plant provided herein.

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars. In an aspect, a tobacco product provided herein comprises reconstituted tobacco derived from a modified tobacco plant.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokeable material includes cured tobacco within a tobacco blend. In an aspect, a tobacco product of the present disclosure is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, and pouched chewing tobacco product. In another aspect, a tobacco product of the present disclosure is selected from the group consisting of a gum, a tablet, a lozenge, and a dissolving strip.

In an aspect, a tobacco product provided herein comprises cured tobacco material from a modified tobacco plant. In another aspect, a tobacco product provided herein comprises cured tobacco leaf material from a modified tobacco plant.

In another aspect, a tobacco product provided herein comprises cured tobacco stem material from a modified tobacco plant.

In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff.

The present disclosure further provides a method manufacturing a tobacco product comprising tobacco material from modified tobacco plants provided herein. In one aspect, methods provided herein comprise conditioning aged tobacco material made from modified tobacco plants provided herein to increase its moisture content from between about 12.5% and about 13.5% to about 21%, blending the conditioned tobacco material to produce a desirable blend. In one aspect, the method of manufacturing a tobacco product provided herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

This disclosure provides tobacco material from modified tobacco plants or parts thereof. Tobacco material obtained from tobacco plants, cells, lines, varieties, or hybrids of the present disclosure can be used to make tobacco products. In an aspect, tobacco material comprises leaf material. In an aspect, tobacco material comprises stem material. In an aspect, tobacco material comprises fresh tobacco material. In another aspect, tobacco material comprises dried tobacco material. In a further aspect, tobacco material comprises cured tobacco material. In still another aspect, tobacco material comprises fermented tobacco material. In an aspect, tobacco material provided herein can be used in any tobacco product provided herein. In an aspect, cured tobacco material provided herein comprises air-cured tobacco material. In another aspect, cured tobacco material provided herein comprises fire-cured tobacco material. In another aspect, cured tobacco material provided herein comprises sun-cured tobacco material. In another aspect, cured tobacco material provided herein comprises flue-cured tobacco material. In another aspect, cured tobacco material provided herein is selected from the group consisting of air-cured tobacco material, fire-cured tobacco material, sun-cured tobacco material, and flue-cured tobacco material.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In one aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with a copolymer and, optionally, flavorants and other additives.

In one aspect, tobacco material provided herein can be processed to a desired size. In certain aspects, tobacco fibers can be processed to have an average fiber size of less than 200 micrometers. In one aspect, tobacco fibers are between 75 and 125 micrometers. In another aspect, tobacco fibers are processed to have a size of 75 micrometers or less. In one aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided herein can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. An oral product can have a different overall oven volatiles content than the oven volatiles content of the tobacco fibers used to make the oral product. The processing steps described herein can reduce or increase the oven volatiles content.

The following exemplary, non-limiting embodiments are envisioned:

1. A modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said modified tobacco plant comprises no suckers or reduced suckers after topping as compared to said control tobacco plant when grown under comparable growth conditions.

2. A modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety.

3. A modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, wherein said modified tobacco plant comprises no suckers or reduced suckers after topping as compared to a control tobacco plant when grown under comparable growth conditions.

4. A modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

5. A modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions.

6. A modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

7. The modified tobacco plant of embodiment 1 or 2, wherein said mutation comprises a mutation selected from the group consisting of an insertion, a deletion, a substitution, and an inversion.

8. The modified tobacco plant of any one of embodiments 1, 2, or 7, wherein said mutation comprises a null mutation.

9. The modified tobacco plant of any one of embodiments 1, 2, 7, or 8, wherein said mutation results in a premature stop codon in an mRNA transcript of said endogenous gene.

10. The modified tobacco plant of any one of embodiments 1, 2, or 7-9, wherein said mutation results in a truncation of said polypeptide.

11. The modified tobacco plant of any one of embodiments 1, 2, or 7-10, wherein said mutation is positioned within an exon of said endogenous gene.

12. The modified tobacco plant of any one of embodiments 1, 2, or 7-10, wherein said mutation is positioned within an intron of said endogenous gene.

13. The modified tobacco plant of any one of embodiments 1, 2, or 7, wherein said mutation is positioned within a 5'-untranslated region (UTR) or a 3'-UTR of said endogenous gene.

14. The modified tobacco plant of any one of embodiments 1, 2, or 7, wherein said mutation is positioned within a promoter of said endogenous gene.

15. The modified tobacco plant of any one of embodiments 1, 2, or 7-14, wherein said endogenous gene comprises a polynucleotide sequence at least 80% identical to a polynucleotide sequence selected from the group consisting of SEQ ID NOs: 1-44 and 113.

16. The modified tobacco plant of any one of embodiments 1, 2, or 7-15, wherein said endogenous gene encodes a polypeptide comprising an amino acid sequence at least 80% identical or similar to an amino acid sequence selected from the group consisting of SEQ ID NOs: 45-88 and 114.

17. The modified tobacco plant of any one of embodiments 1, 2, or 7-16, wherein said mutation results in reduced level of expression of said endogenous gene as compared to said control tobacco plant.

18. The modified tobacco plant of any one of embodiments 1, 2, or 7-16, wherein said mutation results in increased level of expression of said endogenous gene as compared to said control tobacco plant.

19. The modified tobacco plant of any one of embodiments 1, 2, or 7-16, wherein said mutation results in reduced level of activity of said polypeptide as compared to said control tobacco plant.

20. The modified tobacco plant of any one of embodiments 1, 2, or 7-16, wherein said mutation results in increased level of activity of said polypeptide as compared to said control tobacco plant.

21. The modified tobacco plant of any one of embodiments 3-6, wherein said heterologous promoter comprises an axillary meristem-specific promoter.

22. The modified tobacco plant of any one of embodiments 3-6, wherein said heterologous promoter comprises an axillary meristem-preferred promoter.

23. The modified tobacco plant of any one of embodiments 3-6, wherein said heterologous promoter comprises a polynucleotide sequence at least 90% identical to a polynucleotide sequence selected from the group consisting of SEQ ID NOs: 89-109.

24 The modified tobacco plant of any one of embodiments 3-6, wherein said small RNA molecule is selected from the group consisting of a double-stranded RNA, a small interfering RNA (siRNA), a trans-acting siRNA, and a microRNA.

25. The modified tobacco plant of embodiments 5 or 6, wherein said small RNA molecule comprises between 18 nucleotides and 30 nucleotides.

26. The modified tobacco plant of embodiments 5 or 6, wherein said small RNA molecule comprises a polynucleotide sequence having at least 90% identity or complementarity with said endogenous mRNA.

27. The modified tobacco plant of embodiments 5 or 6, wherein said small RNA molecule comprises between 18 nucleotides and 30 nucleotides.

28. The modified tobacco plant of embodiments 5 or 6, wherein said small RNA molecule comprises a polynucleotide sequence having at least 90% identity or complementarity with a polynucleotide sequence selected from the group consisting of SEQ ID NOs: 1-44 and 113.

29. The modified tobacco plant of embodiments 5 or 6, wherein said small RNA molecule comprises a polynucleotide sequence identical to, or complementary to, at least 18 contiguous nucleotides of a polynucleotide sequence selected from the group consisting of SEQ ID NOs: 1-44 and 113.

30. The modified tobacco plant of any one of embodiments 1-29, wherein said polypeptide is a cyclin.

31 The modified tobacco plant of any one of embodiments 1-29, wherein said polypeptide is a CDK.

32. The modified tobacco plant of any one of embodiments 1-29, wherein said polypeptide is a CDK inhibitor.

33. The modified tobacco plant of any one of embodiments 1-29, wherein said polypeptide is a MYB.

34 The modified tobacco plant of any one of embodiments 1-29, wherein said polypeptide is a WRKY transcription factor.

35. The modified tobacco plant of embodiment 30, wherein said cyclin is encoded by a polynucleotide sequence at least 80% identical to SEQ ID NOs: 6-32.

36 The modified tobacco plant of embodiment 30, wherein said cyclin comprises an amino acid sequence at least 80% identical or similar to an amino acid sequence selected from the group consisting of SEQ ID NOs: 50-76.

37. The modified tobacco plant of embodiment 31, wherein said CDK is encoded by a polynucleotide sequence at least 80% identical to SEQ ID NOs: 1-4.

38 The modified tobacco plant of embodiment 31, wherein said CDK comprises an amino acid sequence at least 80% identical or similar to an amino acid sequence at least 80% identical or similar to an amino acid sequence selected from the group consisting of SEQ ID NOs: 45-48.

39. The modified tobacco plant of embodiment 32, wherein said CDK inhibitor is encoded by a polynucleotide sequence at least 80% identical to SEQ ID NO: 5.

40 The modified tobacco plant of embodiment 32, wherein said CDK inhibitor comprises an amino acid sequence at least 80% identical or similar to an amino acid sequence selected from the group consisting of SEQ ID NO: 49.

41. The modified tobacco plant of embodiment 33, wherein said MYB is encoded by a polynucleotide sequence at least 80% identical to SEQ ID NOs: 33-44.

42. The modified tobacco plant of embodiment 33, wherein said MYB comprises an amino acid sequence at least 80% identical or similar to an amino acid sequence at least 80% identical or similar to an amino acid sequence selected from the group consisting of SEQ ID NOs: 77-88.

43 The modified tobacco plant of embodiment 34, wherein said WRKY transcription factor is encoded by a polynucleotide sequence at least 80% identical to SEQ ID NO: 113.

44. The modified tobacco plant of embodiment 34, wherein said WRKY transcription factor comprises an amino acid sequence at least 80% identical or similar to an amino acid sequence at least 80% identical or similar to SEQ ID NO: 114.

45. The modified tobacco plant of any one of embodiments 1-44, wherein said modified tobacco plant is of a tobacco variety selected from the group consisting of a flue-cured variety, a bright variety, a Burley variety, a Virginia variety, a Maryland variety, a dark variety, a Galpão variety, an Oriental variety, and a Turkish variety.

46. The modified tobacco plant of any one of embodiments 1-45, wherein said modified tobacco plant is selected from the group consisting of a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a *Galpao* plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.

47. The modified tobacco plant of any one of embodiments 1-46, wherein said modified tobacco plant is a hybrid.

48. The modified tobacco plant of any one of embodiments 1-47, wherein said modified tobacco plant is male sterile or cytoplasmically male sterile.

49 The modified tobacco plant of any one of embodiments 1-47, wherein said modified tobacco plant is female sterile.

50. The modified tobacco plant of any one of embodiments 1, 3 or, wherein said reduced suckers comprises fewer total suckers, smaller average sucker size, or both, as compared to suckers of said control tobacco plant when grown under comparable growth conditions.

51. The modified tobacco plant of embodiment 50, wherein said smaller average sucker size comprises a measurement selected from the group consisting of reduced average mass, reduced average length, reduced average diameter, or any combination thereof, as compared to suckers of said control tobacco plant when grown under comparable growth conditions.

52. The modified tobacco plant of any one of embodiments 1-51, wherein said modified plant has increased leaf yield mass as compared to said control tobacco plant when grown under comparable growth conditions.

53. The modified tobacco plant of embodiment 52, wherein said increased leaf yield mass comprises an increase of at least 0.5%.

54. A tobacco leaf of the modified tobacco plant of any one of embodiments 1-53.

55. A tobacco seed of the modified tobacco plant of any one of c embodiments 1-53.

56. The tobacco leaf of embodiment 54, wherein said tobacco leaf is a cured tobacco leaf.

57. The tobacco leaf of embodiment 56, wherein said cured tobacco leaf is selected from the group consisting of is air-cured tobacco leaf, fire-cured tobacco leaf, sun-cured tobacco leaf, and flue-cured tobacco leaf.

58. A tobacco product comprising an alkaloid extracted from the modified tobacco plant, or a part thereof, of any one of embodiments 1-53.

59. The tobacco product of embodiment 58, wherein said alkaloid is selected from the group consisting of nicotine, nornicotine, anatabine, and anabasine.

60 The tobacco product of embodiment 58 or 59, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, and pouched chewing tobacco product.

61. The tobacco product of embodiment 58 or 59, wherein said tobacco product is selected from the group consisting of a gum, a tablet, a lozenge, and a dissolving strip.

62. The tobacco product of embodiment 58 or 59, wherein said tobacco product is a non-combustible product.

63. The tobacco product of embodiment 62, wherein said non-combustible product is selected from the group consisting of an electronic cigarette, an electronic smoking article, an aerosolized vapor product, and a heated tobacco product.

64. A tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said modified tobacco plant comprises no suckers or reduced suckers after topping as compared to said control tobacco plant when grown under comparable growth conditions.

65. A tobacco product comprising cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety.

66. A tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and wherein said modified tobacco plant comprises no suckers or reduced suckers after topping as compared to a control tobacco plant when grown under comparable growth conditions.

67. A tobacco product comprising cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

68. A tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions.

69. A tobacco product comprising cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

70. The tobacco product of any one of embodiments 64-69, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, and a pouched chewing tobacco product.

71. The tobacco product of any one of embodiments 64-69, wherein said cured tobacco material is from a tobacco variety selected from the group consisting of a flue-cured variety, a bright variety, a Burley variety, a Virginia variety, a Maryland variety, a dark variety, an Oriental variety, and a Turkish variety.

72. The tobacco product of any one of embodiments 64-69, wherein said cured tobacco material is selected from the group consisting of air-cured tobacco material, fire-cured tobacco material, sun-cured tobacco material, and flue-cured tobacco material.

73. The tobacco product of any one of embodiments 64-69, wherein said cured tobacco material comprises cured tobacco leaf material.

74. The tobacco product of any one of embodiments 64-69, wherein said cured tobacco material comprises cured tobacco stem material.

75. A method for producing a modified tobacco plant comprising:
   (a) inducing a mutation in at least one tobacco cell at a genomic locus encoding a polypeptide selected from the group consisting of a cyclin, a cyclin-dependent kinase (CDK), a CDK inhibitor, a MYB, and a WRKY transcription factor;
   (b) selecting at least one tobacco cell comprising said mutation from step (a); and
   (c) regenerating a modified tobacco plant from said at least one tobacco cell selected in step (b), wherein said modified tobacco plant comprises no suckers or reduced suckers after topping as compared to a control tobacco plant lacking said mutation when grown under comparable growth conditions.

76. A method for producing a modified tobacco plant comprising:
   (a) introducing a recombinant DNA construct to at least one tobacco cell, wherein said recombinant DNA construct comprises a heterologous promoter operably linked to a nucleic acid encoding a polypeptide selected from the group consisting of a cyclin, a cyclin-dependent kinase (CDK), a CDK inhibitor, a MYB, and a WRKY transcription factor;
   (b) selecting at least one tobacco cell comprising said recombinant DNA construct; and
   (c) regenerating a modified tobacco plant from said at least one tobacco cell selected in step (b), wherein said modified tobacco plant comprises no suckers or reduced suckers after topping as compared to a control tobacco plant lacking said recombinant DNA construct when grown under comparable growth conditions.

77. A method for producing a modified tobacco plant comprising:
   (a) introducing a recombinant DNA construct to at least one tobacco cell, wherein said recombinant DNA construct comprises a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor;
   (b) selecting at least one tobacco cell comprising said recombinant DNA construct; and
   (c) regenerating a modified tobacco plant from said at least one tobacco cell selected in step (b), wherein said modified tobacco plant comprises no suckers or reduced suckers after topping as compared to a control tobacco plant lacking said recombinant DNA construct when grown under comparable growth conditions.

78. The method of embodiment 75, wherein said inducing comprises the use of an agent selected from the group consisting of: a chemical mutagen, irradiation, a transposon, *Agrobacterium*, and a nuclease.

79. The method of embodiment 78, wherein said nuclease is selected from the group consisting of a meganuclease, a zinc-finger nuclease, a transcription activator-like effector nuclease, a CRISPR/Cas9 nuclease, a CRISPR/Cpf1 nuclease, a CRISPR/CasX nuclease, a CRISPR/CasY nuclease, a Csm1 nuclease, or any combination thereof.

80. The method of embodiment 78, wherein said chemical mutagen comprises ethyl methanesulfonate.

81. The method of embodiment 78, wherein said irradiation comprises gamma rays, X-rays, or ionizing radiation.

82. The method of embodiment 77, wherein said small RNA molecule is selected from the group consisting of a double-stranded RNA, a small interfering RNA (siRNA), a trans-acting siRNA, and a microRNA.

83. The method of embodiment 77 or 82, wherein said small RNA molecule comprises at least 18 nucleotides.

84. The method of any one of embodiments 77, 82, or 83, wherein said small RNA molecule comprises at least 90% identity or complementarity with said endogenous mRNA.

85. The method of any one of embodiments 77, 82, or 84, wherein said small RNA molecule comprises between 18 nucleotides and 30 nucleotides.

86 The method of any one of embodiments 77 or 82-85, wherein said small RNA molecule comprises at least 90% identity or complementarity with a polynucleotide sequence selected from the group consisting of SEQ ID NOs: 1-44 and 113.

87. The method of any one of embodiments 77 or 82-86, wherein said endogenous mRNA comprises a sequence identical to, or complementary to, at least 18 contiguous nucleotides of a polynucleotide sequence selected from the group consisting of SEQ ID NOs: 1-44 and 113.

88 The method of any one of embodiments 75-87, wherein said at least one tobacco cell is a tobacco protoplast cell.

89. The method of any one of embodiments 75-87, wherein said at least one tobacco cell is a tobacco callus cell.

90. The method of any one of embodiments 75-87, wherein said at least one tobacco cell is selected from the group consisting of a seed cell, a fruit cell, a leaf cell, a cotyledon cell, a hypocotyl cell, a meristem cell, an embryo cell, an endosperm cell, a root cell, a shoot cell, a stem cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, and a phloem cell.

91. The method of any one of embodiments 75-77, wherein said method further comprises:
   (d) growing said modified tobacco plant regenerated in step (c).

92. The method of embodiment 91, wherein said method further comprises:
   (e) crossing said modified tobacco plant grown in step (d) with a second tobacco plant; and
   (f) obtaining at least one seed from said crossing in step (e).

93. The method of embodiments 76 or 77, wherein said heterologous promoter comprises an axillary meristem-specific promoter.

94. The modified tobacco plant of embodiment 93, wherein said heterologous promoter comprises a polynucleotide sequence at least 90% identical to a poly-nucleotide sequence selected from the group consisting of SEQ ID NOs: 89-109.

95. The method of embodiment 75, wherein said genomic locus comprises a polynucleotide sequence at least 80% identical to a polynucleotide sequence selected from the group consisting of SEQ ID NOs: 1-44 and 113.

96. The method of embodiment 75, wherein said genomic locus encodes a polypeptide comprising an amino acid sequence at least 80% identical or similar to an amino acid sequence selected from the group consisting of SEQ ID NOs: 45-88 and 114.

97. The method of embodiment 75, wherein said mutation results in reduced expression of said genomic locus as compared to said control tobacco plant.

98 The method of embodiment 75, wherein said mutation results in increased expression of said genomic locus as compared to said control tobacco plant.

99 The method of embodiment 75, wherein said mutation results in reduced activity of said polypeptide as compared to said control tobacco plant.

100. The method of embodiment 75, wherein said mutation results in increased activity of said polypeptide as compared to said control tobacco plant.

101. The method of any one of embodiments 75-100, wherein said polypeptide is a cyclin.

102. The method of any one of embodiments 75-100, wherein said polypeptide is a CDK.

103. The method of any one of embodiments 75-100, wherein said polypeptide is a CDK inhibitor.

104. The method of any one of embodiments 75-100, wherein said polypeptide is a MYB.

105. The method of any one of embodiments 75-100, wherein said polypeptide is a WRKY transcription factor.

106. The method of embodiment 101, wherein said cyclin is encoded by a polynucleotide sequence at least 80% identical to SEQ ID NOs: 6-32.

107. The method of embodiment 101, wherein said cyclin comprises an amino acid sequence at least 80% identical or similar to an amino acid sequence selected from the group consisting of SEQ ID NOs: 50-76.

108. The method of embodiment 102, wherein said CDK is encoded by a polynucleotide sequence at least 80% identical to SEQ ID NOs: 1-4.

109. The method of embodiment 102, wherein said CDK comprises an amino acid sequence at least 80% identical or similar to an amino acid sequence selected from the group consisting of SEQ ID NOs: 45-48.

110. The method of embodiment 103, wherein said CDK inhibitor is encoded by a polynucleotide sequence at least 80% identical to SEQ ID NO: 5.

111. The method of embodiment 103, wherein said CDK inhibitor comprises an amino acid sequence at least 80% identical or similar to an amino acid sequence selected from the group consisting of SEQ ID NO: 49.

112. The method of embodiment 104, wherein said MYB is encoded by a polynucleotide sequence at least 80% identical to SEQ ID NOs: 33-44.

113. The method of embodiment 104, wherein said MYB comprises an amino acid sequence at least 80% identical or similar to an amino acid sequence selected from the group consisting of SEQ ID NOs: 77-88.

114. The method of embodiment 105, wherein said WRKY transcription factor is encoded by a polynucleotide sequence at least 80% identical to SEQ ID NO: 113.

115. The method of embodiment 105, wherein said WRKY transcription factor comprises an amino acid sequence at least 80% identical or similar to SEQ ID NO: 114.

116. The method of any one of embodiments 75-114, wherein said modified tobacco plant is of a tobacco variety selected from the group consisting of a flue-cured variety, a bright variety, a Burley variety, a Virginia variety, a Maryland variety, a dark variety, an Oriental variety, and a Turkish variety.

117. The method of any one of embodiments 75-114, wherein said modified tobacco plant is selected from the group consisting of a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a *Galpao* plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.

118. The method of any one of embodiments 75-117, wherein said modified tobacco plant is a hybrid.

119. The method of any one of embodiments 75-118, wherein said modified tobacco plant is male sterile or cytoplasmically male sterile.

120. The method of any one of embodiments 75-118, wherein said modified tobacco plant is female sterile.

121. The method of any one of embodiments 75-120, wherein said reduced suckers comprises fewer total suckers, smaller suckers, or both, as compared to suckers of said control tobacco plant when grown under comparable growth conditions.

122. The method of embodiment 121, wherein said smaller suckers comprise reduced average mass, reduced average length, reduced average diameter, or any combination thereof, as compared to suckers of said control tobacco plant when grown under comparable growth conditions.

123. The method of any one of embodiments 75-122, wherein said modified plant has increased leaf yield mass as compared to said control tobacco plant when grown under comparable growth conditions.

124. The method of embodiment 123, wherein said increased leaf yield mass comprises an increase of at least 0.5%.

125. A method comprising preparing a tobacco product using cured tobacco material from a modified tobacco plant comprising a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said modified tobacco plant comprises no suckers or reduced suckers after topping as compared to a control tobacco plant when grown under comparable growth conditions.

126. A method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, and wherein said modified tobacco plant comprises no suckers or reduced suckers after topping as compared to a control tobacco plant when grown under comparable growth conditions.

127. A method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter, wherein said modified tobacco plant comprises no suckers or reduced suckers after topping as compared to a control tobacco plant when grown under comparable growth conditions.

128. A method comprising preparing a tobacco product using cured tobacco material from a modified tobacco plant comprising a polynucleotide sequence encoding a polypeptide selected from the group consisting of a cyclin, a cyclin-dependent kinase (CDK), a CDK inhibitor, a MYB, and a WRKY transcription factor operably linked to a heterologous promoter.

129. A method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor, wherein said modified tobacco plant comprises no suckers or reduced suckers after topping as compared to a control tobacco plant when grown under comparable growth conditions.

130. A method comprising preparing a tobacco product using cured tobacco material from a modified tobacco plant comprising a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

131. The method of any one of embodiments 125-130, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, pouched chewing tobacco product, gum, a tablet, a lozenge, and a dissolving strip.

132. The method of any one of embodiments 125-131, wherein said cured tobacco material is from a tobacco variety selected from the group consisting of a flue-cured variety, a bright variety, a Burley variety, a Virginia variety, a Maryland variety, a dark variety, an Oriental variety, and a Turkish variety.

133. The method of any one of embodiments 125-132, wherein said cured tobacco material is selected from the group consisting of air-cured tobacco material, fire-cured tobacco material, sun-cured tobacco material, and flue-cured tobacco material.

134. The method of any one of embodiments 125-133, wherein said cured tobacco material comprises cured tobacco leaf material.

135. The method of any one of embodiments 125-133, wherein said cured tobacco material comprises cured tobacco stem material.

136. A method comprising transforming a tobacco cell with a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor.

137. A method comprising transforming a tobacco cell with a recombinant DNA construct comprising a heterologous promoter operably linked to a nucleic acid encoding at least one small RNA molecule capable of reducing the expression of an endogenous mRNA that encodes a polypeptide selected from the group consisting of a cyclin, a cyclin-dependent kinase (CDK), a CDK inhibitor, a MYB, and a WRKY transcription factor.

138. The method of embodiments 136 or 137, wherein said method further comprises regenerating a modified tobacco plant from said tobacco cell, wherein said modified tobacco plant comprises said recombinant DNA construct.

139. The method of embodiment 138, wherein said modified tobacco plant comprises no or reduced suckers after topping as compared to a control tobacco plant lacking said recombinant DNA construct when grown under comparable conditions.

140. A method for producing a modified tobacco plant comprising:
   (a) crossing at least one tobacco plant of a first tobacco variety with at least one tobacco plant of a second tobacco variety, wherein said at least one tobacco plant of said first tobacco variety comprises a mutation in an endogenous gene encoding a polypeptide selected from the group consisting of a cyclin, a cyclin-dependent kinase (CDK), a CDK inhibitor, a MYB, and a WRKY transcription factor, wherein said mutation is not present in said endogenous gene in a control tobacco plant of the same variety, and wherein said at least one tobacco plant comprises no suckers or reduced suckers after topping as compared to said control tobacco plant when grown under comparable growth conditions; and
   (b) selecting for progeny tobacco plants that exhibit no suckers or reduced suckers after topping compared to a control tobacco plant of the same cross grown under comparable growth conditions.

141. A method for producing a modified tobacco plant comprising:
   (a) crossing at least one tobacco plant of a first tobacco variety with at least one tobacco plant of a second tobacco variety, wherein said at least one tobacco plant of said first tobacco variety comprises a recombinant DNA construct comprising a heterologous promoter operably linked to a nucleic acid encoding a polypeptide selected from the group consisting of a cyclin, a cyclin-dependent kinase (CDK), a CDK inhibitor, a MYB, and a WRKY transcription factor, wherein said at least one tobacco plant comprises no suckers or reduced suckers after topping as compared to a control tobacco plant when grown under comparable growth conditions; and
   (b) selecting for progeny tobacco plants that exhibit no suckers or reduced suckers after topping compared to a control tobacco plant of the same cross grown under comparable growth conditions.

142. A method for producing a modified tobacco plant comprising:
   (a) crossing at least one tobacco plant of a first tobacco variety with at least one tobacco plant of a second tobacco variety, wherein said at least one tobacco plant of said first tobacco variety comprises a recombinant DNA construct comprising a heterologous promoter operably linked to a nucleic acid encoding at least one small RNA molecule capable of reducing the expression of an endogenous genomic locus that encodes a polypeptide selected from the group consisting of a cyclin, a cyclin-dependent kinase (CDK), a CDK inhibitor, a MYB, and a WRKY transcription factor, wherein said at least one tobacco plant comprises no suckers or reduced suckers after topping as compared to a control tobacco plant when grown under comparable growth conditions; and
   (b) selecting for progeny tobacco plants that exhibit no suckers or reduced suckers after topping compared to a control tobacco plant of the same cross grown under comparable growth conditions.

Having now generally described the disclosure, the same will be more readily understood through reference to the following examples that are provided by way of illustration, and are not intended to be limiting of the present disclosure, unless specified.

EXAMPLES

Example 1. Identification of Differentially Expressed Genes

Two hundred ten TN90 tobacco plants are grown to layby stage (eight to ten fully expanded leaves). At this stage, axillary buds are collected from 30 plants to form three replicates, each containing the pooled axillary buds from ten plants. The remaining 180 plants are topped. Ninety of the plants are sprayed with water, and ninety of the plants are sprayed with maleic hydrazide (MH) per the manufacturer's dosing instructions (Arysta LifeScience Royal MH-30® XTRA). Axillary buds from water-treated (control) and MH-treated plants are collected four hours after spraying, 24 hours after spraying, and 72 hours after spraying. See Table 2. RNA is extracted from each collection and sequenced using Hiseq (Illumina).

TABLE 2

| Experimental groups | | |
|---|---|---|
| Treatment | Description | Number of replicates |
| Control | Un-topped plants; no water or maleic hydrazide (MH) treatment | 3 |
| 4 hour-water | Plants topped and treated with water; axillary bud samples were collected 4 hours after treatment. | 3 |
| 4 hour-MH | Plants topped and treated with MH; axillary bud samples were collected 4 hours after treatment. | 3 |
| 24 hour-water | Plants topped and treated with water; axillary bud samples were collected 24 hours after treatment. | 3 |
| 24 hour-MH | Plants topped and treated with MH; axillary bud samples were collected 24 hours after treatment. | 3 |
| 72 hour-water | Plants topped and treated with water; axillary bud samples were collected 72 hours after treatment. | 3 |
| 72 hour-MH | Plants topped and treated with MH; axillary bud samples were collected 72 hours after treatment. | 3 |
| Total samples | | 21 |

The RNA sequences are mapped to a proprietary tobacco reference genome using CLC Genomics Workbench (version 11.0.1; QIAGEN) using default parameters. A read count matrix including all samples was generated by aggregating the raw counts of the mapped reads for a given gene in each sample against a total of 98,751 genes using the Expression Browser Tool in CLC Genomics Workbench. The read count matrix was subjected to differential gene expression analysis using the R package edgeR (version 3.0.8). See Robinson et al. "edgeR: a Bioconductor package for differential expression analysis of digital gene expression data," *Bioinformatics*, 26:139-140 (2010).

Genes with no expression or ubiquitously low expression were filtered out of the read count matrix in order to improve sensitivity of differential gene expression detection. Only genes having read counts per million reads of >1 in at least three RNA sequencing libraries were retained. These filters result in a filtered read count matrix containing 39,980 expressed genes.

The filtered read count matrix was normalized for compositional bias between libraries using the trimmed means of M (TMM) values method. See, for example, Robinson and Oshlack, "A scaling normalization method for differential expression analysis of RNA-seq data," Genome Biology, 11: R25 (2010). Differentially expressed genes were detected between three pairwise comparisons: control samples at 4 hours, 24 hours, and 72 hours post-topping vs. MH-treated samples at 4 hours, 24 hours, and 72 hours post-topping, respectively. Genes having a p-value of ≤0.05 and an absolute value of $\log_2$ fold changes of ≥1 or ≤1 are considered to be differentially expressed. In total, over 6300 genes are differentially expressed between the control and MH-treated samples. Gene expression values (reads per kilobase of transcript per million mapped reads (RPKM)) from the differentially expressed genes are used to perform downstream analysis and identify candidate genes.

Seven hundred nine differentially expressed genes are identified only in the 4-hour post-topping pairwise comparison. Three hundred ninety-six differentially expressed genes are identified only in the 24-hour post-topping pairwise comparison. Three thousand five hundred thirty-eight differentially expressed genes are identified only in the 72-hour post-topping pairwise comparison. One hundred differentially expressed genes are identified in both the 4-hour and 24-hour post-topping pairwise comparisons. Four hundred thirty-one differentially expressed genes are identified in both the 4-hour and 72-hour pairwise comparisons. Six hundred forty-six differentially expressed genes are identified in both the 24-hour and 72-hour pairwise comparisons. Five hundred thirteen differentially expressed genes are identified in all three pairwise comparisons. FIG. 1 provides a Venn diagram depicting the overlap of differentially expressed genes between the different comparisons.

Differentially expressed genes that are predicted to play a role in cell proliferation (e.g., cyclins, cyclin-dependent kinases, MYBs, WRKY transcription factors) are identified as candidate genes.

Example 2. Transformation and Regeneration of Modified Tobacco Plants

An expression vector is used as a backbone to generate multiple transformation vectors comprising recombinant DNA constructs (See Examples 5-6). The expression vector contains an axillary meristem-preferred promoter (e.g., SEQ ID NOs: 89-109), a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via Agrobacterium transformation. See, for example, Mayo et al., 2006, Nat Protoc. 1:1105-11 and Horsch et al., 1985, Science 227:1229-1231.

Narrow Leaf Madole (NLM) tobacco plants are grown in Magenta™ GA-7 boxes (77 mm×77 mm×97 mm clear polycarbonate boxes with polypropylene lids) and leaf discs are cut and placed into Petri plates. Agrobacterium tumefaciens cells comprising a transformation vector are collected by centrifuging a 20 mL cell suspension in a 50 mL centrifuge tube at 3500 RPM for 10 minutes. The supernatant is removed and the Agrobacterium tumefaciens cell pellet is re-suspended in 40 mL liquid re-suspension medium. Tobacco leaves, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. About 25 mL of the Agrobacterium tumefaciens suspension is added to the Petri plate and the leaf discs are incubated in the suspension for 10 minutes.

Leaf discs are transferred to co-cultivation Petri plates (½ MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaves are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

Example 3. Phenotypic Screening

When plantlets regenerated in Example 2 containing both shoots and roots grow large enough (e.g., reach approximately half the height of a Magenta™ GA-7 box), they are transferred to soil. Established seedlings are transferred to a greenhouse for further analysis and to set seed. Evaluation of suckering phenotypes is conducted by growing modified plants (T0, T1, T2, or later generations) and control plants to layby stage. Control plants are either NLM plants that have not been transformed or NLM plants that have been transformed with an empty p45-2-7 vector. Plants that have reached layby stage are manually topped (the shoot apical meristem and surrounding tissue is removed), and axillary bud growth is evaluated at specific time points after topping. Observations are typically performed at the time of topping (i.e., 0 hours), 24 hours (i.e., 1 day) after topping, 7-8 days after topping (i.e., one week), and/or 14-15 days (i.e., two weeks) after topping. Observations comprise qualitatively examining the presence or absence of axillary bud growth and overall plant appearance. Observations also comprise quantitatively measuring the fresh weight of all axillary buds at a specific time point after topping and/or measuring the length of all axillary bud outgrowths at a specific time point after topping.

Example 4. Development of Modified Tobacco Plants Via Induced Mutation

Mutations are produced in CDK, CDK inhibitor, cyclin, MYB, and WRKY genes by specifically editing SEQ ID NOs: 1-44 and 113. Tobacco protoplasts are transfected using polyethylene glycol (PEG) with plasmids encoding a CRISPR protein or a CRISPR protein and specific guide RNA (gRNA) targeting individual genes at desired positions.

Transfected protoplasts are then immobilized in 1% agarose beads and subjected to tissue culture. When calli grow to approximately 1 millimeter in diameter, they are spread on TOM2 plates. Calli are screened for mutations (e.g., insertions or deletions (indels)) at the target positions using fragment analysis. Candidates, showing size shifts compared to wildtype control, are selected for further culture and the consequent shoots are tested by fragment analysis again to confirm the presence of mutations.

Modified tobacco plants (TO generation) comprising the targeted mutations and control tobacco plants lacking the mutations are grown to the layby stage as described in Example 2. Then, plants are topped to remove the shoot apical meristem and modified and control tobacco plants are phenotypically evaluated as described in Example 3.

Example 5. Development of Modified Tobacco Plants Via Targeted Expression

Targeted over-expression of genes comprising SEQ ID NOs: 1-44 and 113 in axillary bud tissues can be used to reduce or eliminate sucker outgrowth in tobacco when operably linked to an axillary bud-preferred promoter (e.g. SEQ ID NOs: 83-109).

Six separate transformation vectors comprising SEQ ID NOs: 5, 33, or 36 driven by a promoter comprising SEQ ID NOs: 89 or 93 are constructed as described above in Example 2.

Modified tobacco plants (TO generation) comprising one the transformation vectors and control tobacco plants are grown to the layby stage as described in Example 2. Then, plants are topped to remove the shoot apical meristem and modified and control tobacco plants are phenotypically evaluated as described in Example 3.

Figure 2:
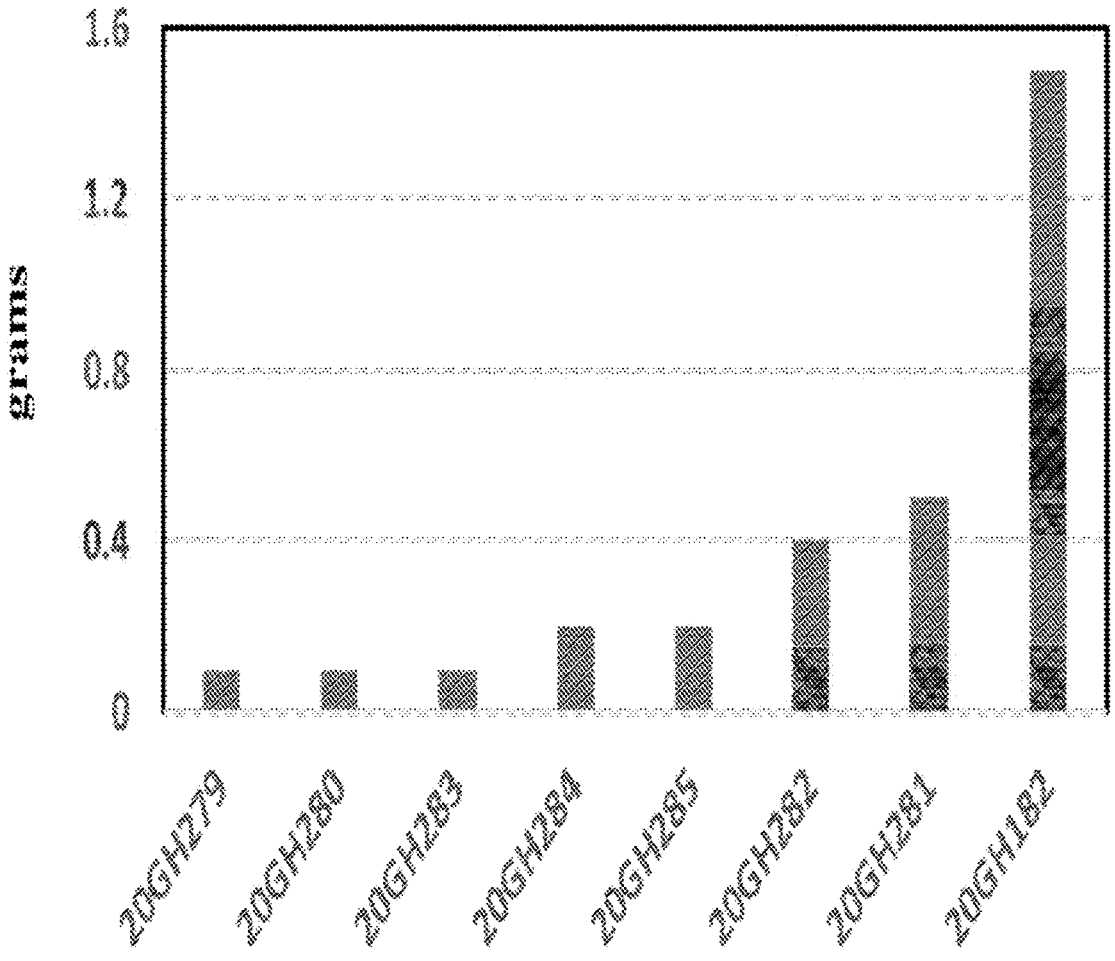
FIG. 2 depicts the collective mass of suckers from individual P1_2.4::MYB plants (20GH729; 20GH280; 20GH283; 20GH284; 20GH285; 20GH282; 20GH281; and 20GH182) one week after topping.
Figure 3:
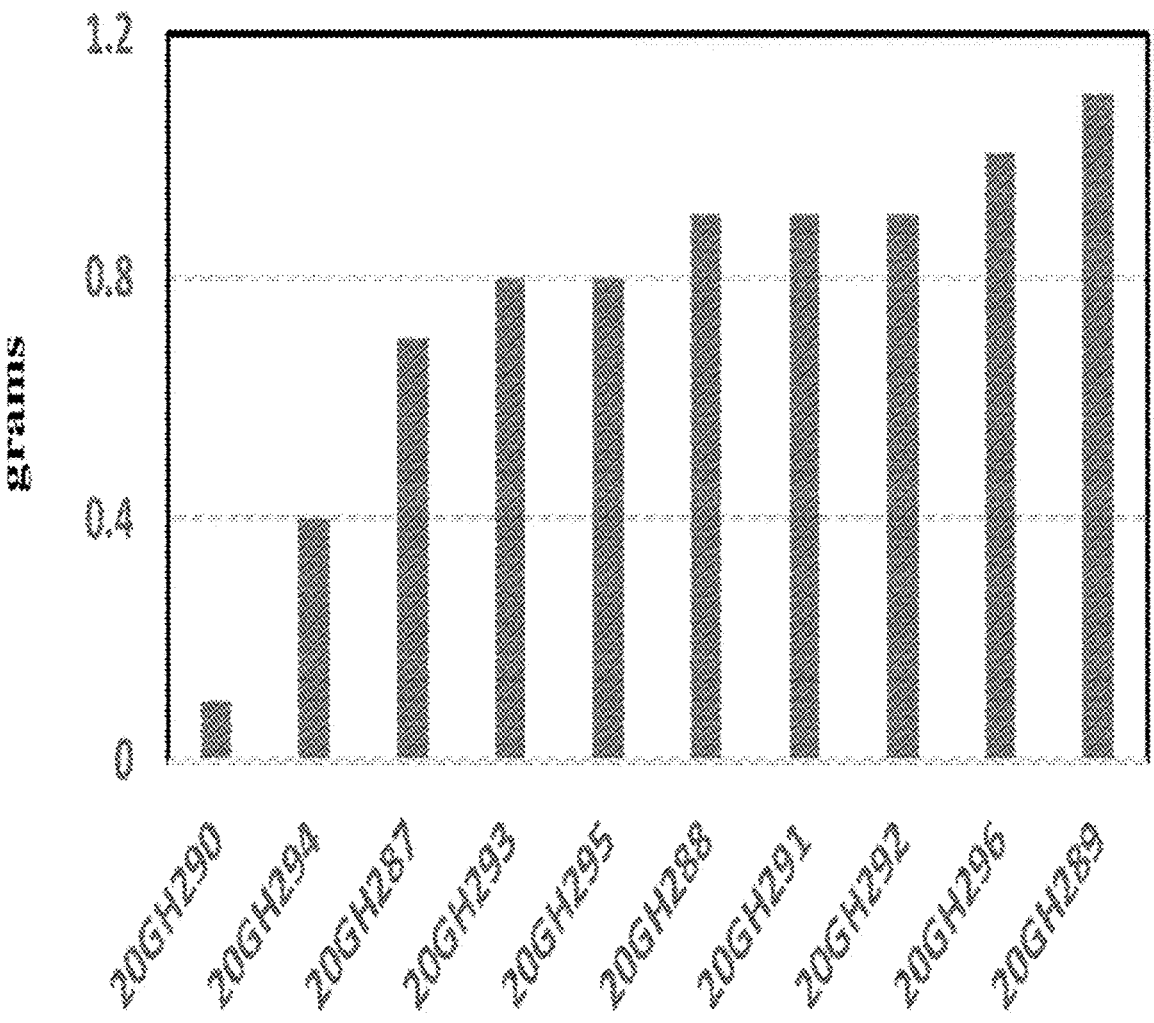
FIG. 3 depicts the collective mass of suckers from individual P1_2.4::CDKI plants (20GH290; 20GH294; 20GH287; 20GH293; 20GH295; 20GH288; 20GH291; 20GH292; 20GH296; and 20GH289) one week after topping.

Additional transformation vectors comprising SEQ ID NO: 109 driving the expression of SEQ ID NO: 36 (P1_2.4:: MYB) and SEQ ID NO: 109 driving the expression of SEQ ID NO: 5 (P1_2.4::CDKI) are also constructed and transformed into tobacco as described above in Example 2. Resulting modified tobacco plants are grown and phenotypically screened as described above in Example 3. FIG. 2 depicts the collective mass of suckers from individual P1_2.4::MYB plants one week after topping. FIG. 3 depicts the collective mass of suckers from individual P1_2.4:: CDKI plants one week after topping.

Example 6. Development of Modified Tobacco Plants Via Small RNA Molecules

Targeted suppression of genes comprising SEQ ID NOs: 1-44 and 113 in axillary bud tissues can be used to reduce or eliminate sucker outgrowth in tobacco. Transformation vectors comprising an axillary bud-preferred promoter (e.g., SEQ ID NOs: 89-109) driving the expression of an artificial miRNA designed to reduce the transcription or translation of SEQ ID NOs: 1-44 or 113 are created by modifying the Nt-miR6147 pre-miRNA and inserting the modified pre-miRNA into the transformation vector described in Example 2.

Additional transformation vectors are constructed to generate artificial miRNAs capable of suppressing the expression of CDKs in axillary buds. Each artificial miRNA construct is capable of suppressing two CDK genes. See Table 3.

TABLE 3

| Artificial miRNA vectors. | | | | | |
|---|---|---|---|---|---|
| Vector Name | Promoter SEQ ID NO. | First Targeted CDK SEQ ID NO | Second Targeted CDK SEQ ID NO | Artificial miRNA precursor SEQ ID NO | Artificial Mature miRNA SEQ ID NO | Artificial miRNA* SEQ ID NO |
| amiRNA-1 | 109 | 1 | 4 | 118 | 121 | 124 |
| amiRNA-2 | 109 | 2 | 3 | 119 | 122 | 125 |
| amiRNA-3 | 109 | 2 | 3 | 120 | 123 | 126 |

Figure 4:
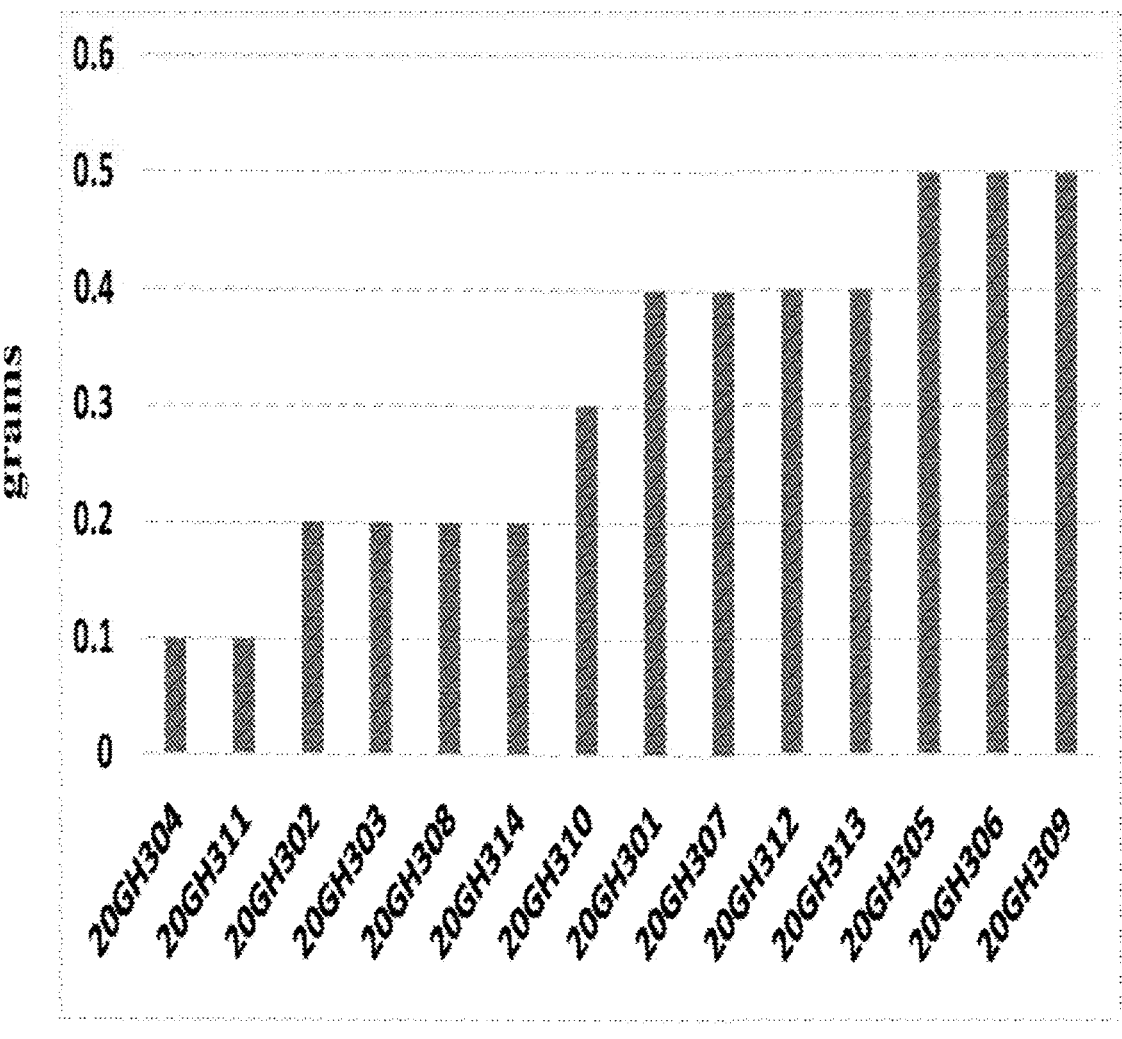
FIG. 4 depicts the collective mass of suckers from individual plants (20GH304; 20GH311; 20GH302; 20GH303; 20GH308; 20GH314; 20GH310; 20GH301, 20GH307; 20GH312; 20GH313; 20GH305; 20GH306; and 20GH309) comprising the amiRNA-1 construct one week after topping.
Figure 5:
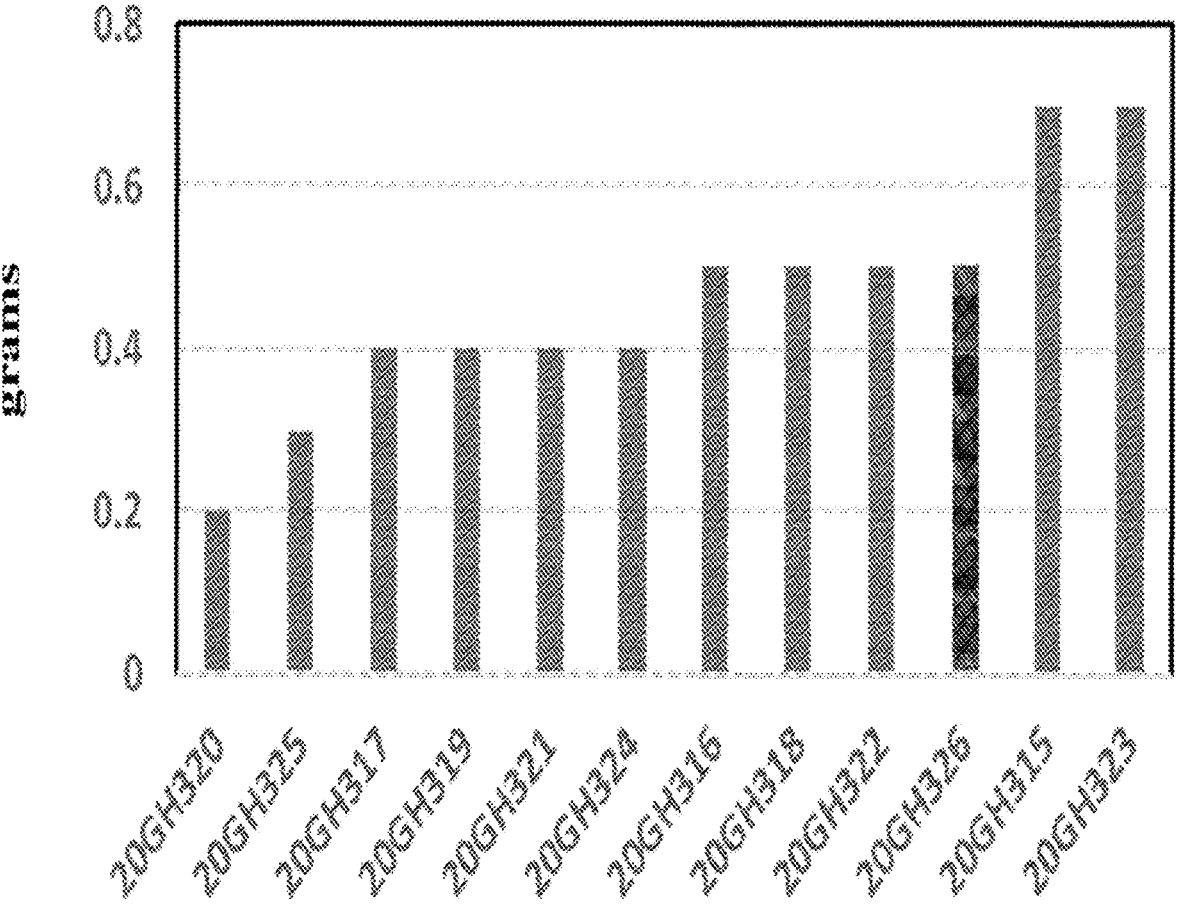
FIG. 5 depicts the collective mass of suckers from individual plants (20GH320; 20GH325; 20GH317; 20GH319; 20GH321; 20GH324; 20GH316; 20GH318; 20GH322; 20GH326; 20GH315; and 20GH323) comprising the amiRNA-2 construct one week after topping.
Figure 6:
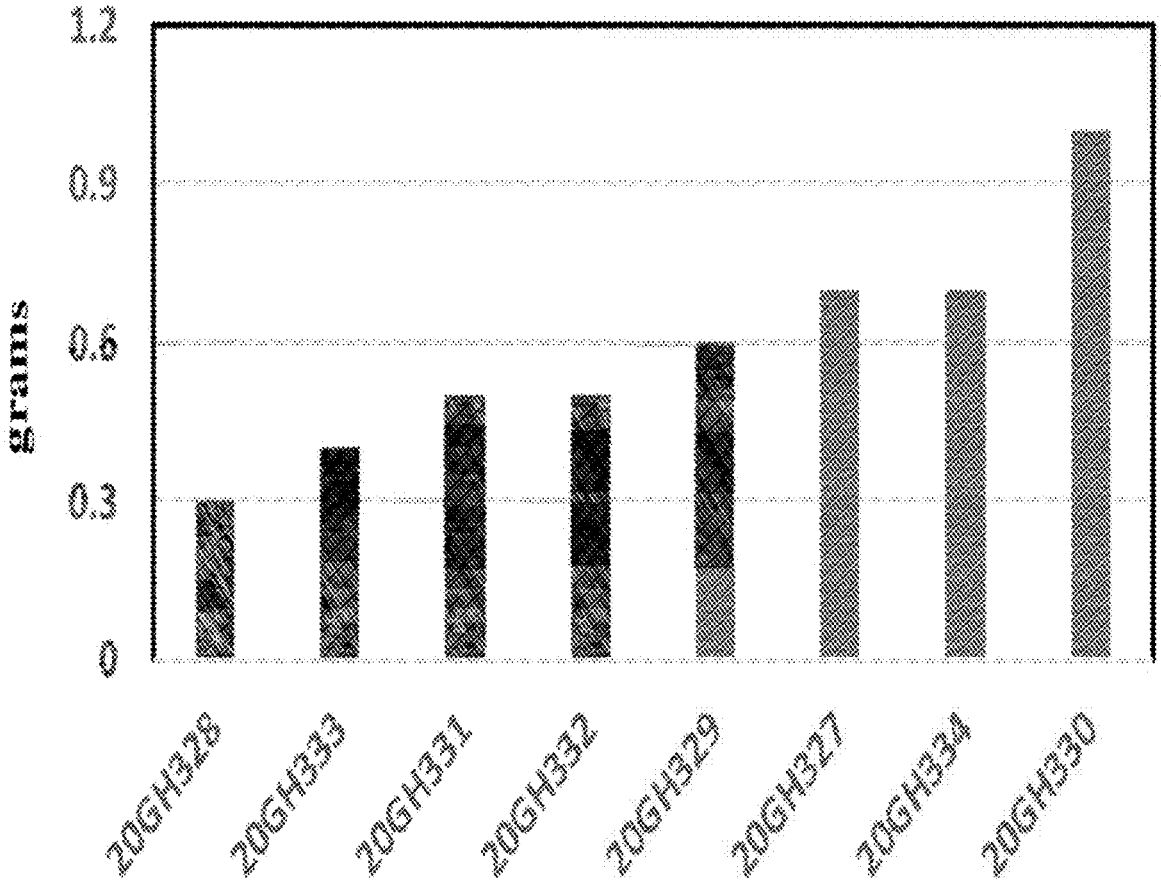
FIG. 6 depicts the collective mass of suckers from individual plants (20GH328; 20GH333; 20GH331; 20GH332; 20GH329; 20GH327; 20GH334; and 20GH330) comprising the amiRNA-3 construct one week after topping.

Modified tobacco plants (TO generation) comprising the transformation vectors and control tobacco plants are grown to the layby stage as described in Example 3. Then, plants are topped to remove the shoot apical meristem and modified and control tobacco plants are phenotypically evaluated as described in Example 4. FIGS. 4, 5, and 6 depict the collective mass of suckers from individual plants comprising amiRNA-1, amiRNA-2, and amiRNA-3, respectively, one week after topping.

The invention claimed is:

1. A tobacco product comprising cured tobacco material from a modified tobacco plant, said modified tobacco plant comprising a polynucleotide encoding a cyclin-dependent kinase inhibitor (CDKI) polypeptide, wherein said CDKI polypeptide comprises the amino acid sequence of SEQ ID NO: 49, wherein said polynucleotide is operably linked to a heterologous axillary bud-preferred promoter, and wherein said modified tobacco plant comprises reduced suckers after topping as compared to a control tobacco plant when grown under comparable growth conditions.

2. The tobacco product of claim 1, wherein said tobacco product is selected from the group consisting of a cigarette, a kretek, a bidi cigarette, a cigar, a cigarillo, a non-ventilated cigarette, a vented recess filter cigarette, pipe tobacco, snuff, snus, chewing tobacco, moist smokeless tobacco, fine cut chewing tobacco, long cut chewing tobacco, and a pouched chewing tobacco product.

3. The tobacco product of claim 1, wherein said tobacco product is a smokeless tobacco product.

4. The tobacco product of claim 1, wherein said polynucleotide comprises a nucleic acid sequence at least 98% identical to the nucleic acid sequence of SEQ ID NO: 5.

5. The tobacco product of claim 1, wherein said polynucleotide comprises a nucleic acid sequence at least 95% identical to the nucleic acid sequence of SEQ ID NO: 5.

6. The tobacco product of claim 1, wherein said polynucleotide comprises a nucleic acid sequence 100% identical to the nucleic acid sequence of SEQ ID NO: 5.

7. The tobacco product of claim 1, wherein said heterologous axillary bud-preferred promoter comprises a nucleic acid sequence at least 98% identical to a nucleic acid sequence selected from the group consisting of SEQ ID NOs: 89 to 96, 98, 100, 102, 104, 106, 108, and 109.

8. Cured tobacco material from a modified tobacco plant comprising a polynucleotide encoding a cyclin-dependent kinase inhibitor (CDKI) polypeptide, wherein said CDKI polypeptide comprises the amino acid sequence of SEQ ID NO: 49, wherein said polynucleotide is operably linked to a heterologous axillary bud-preferred promoter, and wherein said modified tobacco plant comprises reduced suckers after topping as compared to a control tobacco plant when grown under comparable growth conditions.

9. The cured tobacco material of claim 8, wherein said cured tobacco material is from a tobacco plant from a tobacco variety selected from the group consisting of a flue-cured variety, a bright variety, a Burley variety, a Virginia variety, a Maryland variety, a dark variety, an Oriental variety, and a Turkish variety.

10. The cured tobacco material of claim 8, wherein said cured tobacco material is selected from the group consisting of air-cured tobacco material, fire-cured tobacco material, sun-cured tobacco material, and flue-cured tobacco material.

11. The cured tobacco material of claim 8, wherein said polynucleotide comprises a nucleic acid sequence at least 95% identical to the nucleic acid sequence of SEQ ID NO: 5.

12. The cured tobacco material of claim 8, wherein said polynucleotide comprises a nucleic acid sequence 100% identical to the nucleic acid sequence of SEQ ID NO: 5.

13. The cured tobacco material of claim 8, wherein said heterologous axillary bud-preferred promoter comprises a polynucleotide sequence at least 98% identical to a nucleic acid sequence selected from the group consisting of SEQ ID NOs: 89 to 96, 98, 100, 102, 104, 106, 108, and 109.

14. The tobacco product of claim 1, wherein said heterologous axillary bud-preferred promoter comprises a polynucleotide sequence 100% identical to a nucleic acid sequence selected from the group consisting of SEQ ID NOs: 89 to 96, 98, 100, 102, 104, 106, 108, and 109.

15. The cured tobacco material of claim 8, wherein said heterologous axillary bud-preferred promoter comprises a polynucleotide sequence 100% identical to a nucleic acid sequence selected from the group consisting of SEQ ID NOs: 89 to 96, 98, 100, 102, 104, 106, 108, and 109.

16. The cured tobacco material of claim 8, wherein said polynucleotide comprises a nucleic acid sequence at least 98% identical to the nucleic acid sequence of SEQ ID NO: 5.

* * * * *